United States Patent
Ebert et al.

(10) Patent No.: US 11,459,613 B2
(45) Date of Patent: Oct. 4, 2022

(54) METHODS OF CHARACTERIZING RESISTANCE TO MODULATORS OF CEREBLON

(71) Applicant: THE BRIGHAM AND WOMEN'S HOSPITAL, INC., Boston, MA (US)

(72) Inventors: Benjamin Levine Ebert, Boston, MA (US); Quinlan Sievers, Boston, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 656 days.

(21) Appl. No.: 15/759,159

(22) PCT Filed: Sep. 9, 2016

(86) PCT No.: PCT/US2016/051019
§ 371 (c)(1),
(2) Date: Mar. 9, 2018

(87) PCT Pub. No.: WO2017/044793
PCT Pub. Date: Mar. 16, 2017

(65) Prior Publication Data
US 2022/0251651 A1 Aug. 11, 2022

Related U.S. Application Data

(60) Provisional application No. 62/217,455, filed on Sep. 11, 2015.

(51) Int. Cl.
*C12Q 1/6881* (2018.01)
*A61K 31/45* (2006.01)

(52) U.S. Cl.
CPC ............ *C12Q 1/6881* (2013.01); *A61K 31/45* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | |
|---|---|---|
| 6,358,683 B1 | 3/2002 | Collins |
| 6,740,495 B1 | 5/2004 | Issakani et al. |
| 9,611,465 B2 | 4/2017 | Handa et al. |
| 9,974,289 B2 | 5/2018 | Ebert et al. |
| 10,334,829 B2 | 7/2019 | Ebert et al. |
| 11,168,345 B2 | 11/2021 | Mikkelsen et al. |
| 2010/0240057 A1 | 9/2010 | Downing et al. |
| 2011/0223157 A1 | 9/2011 | Schafer et al. |
| 2012/0192297 A1 | 7/2012 | Handa et al. |
| 2012/0322073 A1 | 12/2012 | Lopez-Girona et al. |
| 2013/0020590 A1 | 1/2013 | Lin et al. |
| 2013/0115309 A1 | 5/2013 | Grandori et al. |
| 2013/0345091 A1 | 12/2013 | Downing et al. |
| 2014/0127690 A1 | 5/2014 | Bejar et al. |
| 2014/0162282 A1 | 6/2014 | Schafer et al. |
| 2015/0126538 A1 | 5/2015 | Muller et al. |
| 2015/0152511 A1 | 6/2015 | Thakurta et al. |
| 2016/0282354 A1 | 9/2016 | Ebert et al. |
| 2016/0338326 A1 | 11/2016 | Ebert et al. |
| 2018/0343839 A1 | 12/2018 | Ebert et al. |
| 2019/0071731 A1 | 3/2019 | Mikkelsen et al. |
| 2019/0274292 A1 | 9/2019 | Ebert et al. |

FOREIGN PATENT DOCUMENTS

| | | | |
|---|---|---|---|
| WO | 2012/125405 A2 | 9/2012 | |
| WO | WO-2012125405 A2 * | 9/2012 | ........... A61K 31/198 |
| WO | 2015077058 A2 | 5/2015 | |
| WO | 2015085160 A2 | 6/2015 | |
| WO | 2017/044801 A2 | 3/2017 | |
| WO | 2017044793 A1 | 3/2017 | |

OTHER PUBLICATIONS

Sardnal (Leukemia (2013) 27 pp. 1610-1613).*
Syvanen (Nature Reviews Genetics Dec. 2001 vol. 2 pp. 930-942).*
Evans (Science 1999 vol. 286 pp. 487-491).*
Dermer (Biotechnology 1994 vol. 12 p. 320).*
Menard (Blood 2013 122(21) 3107).*
International Search Report and Written Opinion for corresponding PCT Patent Application No. PCT/US16/51019, dated Feb. 2, 2017 (15 pages).
Office Action dated Sep. 10, 2020 as received in corresponding European Patent Application No. 16845149.0 (12 pages).
Extended European Search Report in corresponding European application No. 16845149.0, dated Jan. 22, 2019, (7 pages).
Extended European Search Report, dated May 6, 2019, as received in corresponding European Application No. 16845149.0 (12 pages).
Ball et al., "Cell type- and estrogen receptor-subtype specific regulation of selective estrogen receptor modulator regulatory elements," Molecular and Cellular Endocrinology, Feb. 27, 2009, vol. 299, No. 2, pp. 204-211.
Baxevanis, Constantin N., "Antibody-based cancer therapy," Expert Opinion on Drug Discovery, 2008, vol. 3, No. 4, pp. 441-452.
Bendall et al., "Prevention of Amino Acid Conversion in SILAC Experiments with Embryonic Stem Cells," Molecular & Cellular Proteomics, 2008, vol. 7, No. 9, pp. 1587-1597.
Chamberlain et al., "Structure of the human Cereblon-DDB1-lenalidomide complex reveals basis for responsiveness to thalidomide analogs," Nature Structural & Molecular Biology, Aug. 2014, vol. 21, pp. 803-809.

(Continued)

*Primary Examiner* — Amanda Haney
(74) *Attorney, Agent, or Firm* — Melissa Hunter-Ensor; Leslie Serunian; Greenberg Traurig, LLP

(57) ABSTRACT

In one aspect, the present invention features method of identifying a cell resistant to a modulator of Cereblon (CRBN). In another aspect, the present invention features a method of characterizing sensitivity of a subject to a modulator of CRBN. In yet another aspect, the present invention features a method of monitoring sensitivity of a subject to a modulator of CRBN.

15 Claims, 4 Drawing Sheets

Specification includes a Sequence Listing.

(56) References Cited

OTHER PUBLICATIONS

Doench et al., "Rational design of highly active sgRNAs for CRISPR-Cas9-mediated gene inactivation," Nature Biotechnology, Dec. 2014, vol. 32, No. 12, pp. 1262-1267.
Egan et al., "Extramedullary Myeloma whole genome sequencing reveals novel mutations in Cereblon, proteasome subunit G2 and the glucocorticoid receptor in multi drug resistant disease," British Journal of Haematology, Jun. 2013, vol. 161, No. 5, pp. 748-751.
Gandhi et al., "Immunomodulatory agents lenalidomide and pomalidomide co-stimulate T cells by inducing degradation of T cell repressors Ikaros and Aiolos via modulation of the E3 ubiquitin ligase complex CRL4CRBN," British Journal of Haematology, 2014, vol. 164, pp. 811-821.
Gouri et al., "Cereblon as a Predictive Biomarker for Imid Therapy Sensitivity," Journal of Hematology and Thromboembolic Diseases, 2014, vol. 2, No. 3, p. 1000112.
He et al., "Ikaros is degraded by proteasome-dependent mechanism in the early phase of apoptosis induction," Biochemical and Biophysical Research Communications, 2011, vol. 406, pp. 430-434.
Holmfeldt, et al., "The genomic landscape of hypodiploid acute lymphoblastic leukemia," Nature Genetics, Mar. 2013, vol. 45, No. 3, pp. 242-252.
Ito et al., "Identification of a Primary Target of Thalidomide Teratogenicity," Science, Mar. 12, 2010, vol. 327, pp. 1345-1350.
Kim et al., "Inhibition of cereblon by fenofibrate ameliorates alcoholic liver disease by enhancing AMPK," Biochimica et Biophysica Acta, 2015, vol. 1852, pp. 2662-2670.
Klein et al., "BCR-ABL1 induces aberrant splicing of IKAROS and lineage infidelity in pre-B lymphoblastic leukemia cells," Oncogene, 2006, vol. 25, pp. 1118-1124.
Krönke et al., "Lenalidomide Causes Selective Degradation of IKZF1 and IKZF3 in Multiple Myeloma Cells," Science, Jan. 17, 2014, vol. 343, No. 6168, pp. 301-305.
Krönke et al., "Lenalidomide induces degradation of IKZF1 and IKZF3," OncoImmunology, 2014, vol. 3, No. 7, pp. e941742-1-6941742-3.
Krönke et al., "Lenalidomide induces ubiquitination and degradation of CK1α in del(5q) MDS," Nature, Jul. 9, 2015, vol. 523, No. 7559, pp. 183-188.
Lee et al., "Depletion of the cereblon gene activates the unfolded protein response and protects cells from ER stress-induced cell death," Biochemical and Biophysical Research Communications, 2015, vol. 458, pp. 34-39.
Lee et al., "Disruption of the Cereblon Gene Enhances Hepatic AMPK Activity and Prevents High-Fat Diet-Induced Obesity and Insulin Resistance in Mice," Diabetes, Jun. 2013, vol. 62, pp. 1855-1864.
List et al., "Efficacy of Lenalidomide in Myelodysplastic Syndromes," The New England Journal of Medicine, Feb. 10, 2005, vol. 352, No. 6, pp. 549-557.
Lopez-Girona et al., "Cereblon is a direct protein target for immunomodulatory and antiproliferative activities of lenalidomide and pomalidomide," Leukemia, 2012, vol. 26, pp. 2326-2335.
Lu et al., "The Myeloma Drug Lenalidomide Promotes the Cereblon-Dependent Destruction of Ikaros Proteins," Science, Jan. 17, 2014, vol. 343, No. 6168, pp. 305-309.
Maity et al., "Cereblon (CRBN) Splice Isoform Lacking Exon 10 Attenuates Lenalidomide-Mediated Degradation of Aiolos and Is Upregulated in Immunomodulatory Drugs (IMiDs) Resistant Myeloma (MM) Patients," Blood, Dec. 6, 2014, vol. 124, No. 21, p. 639.
Melnikov et al., "Massively Parallel Reporter Assays in Cultured Mammalian Cells," Journal of Visualized Experiments (joVE), Aug. 2014, vol. 90, e51719, pp. 1-8.
Mertins et al., "Integrated proteomic analysis of post-translational modifications by serial enrichment," Nature Methods, Jul. 2013, vol. 10, No. 7, pp. 634-637.
Mullighan et al., "Genome-wide analysis of genetic alterations in acute lymphoblastic leukaemia," Nature, Apr. 12, 2007, vol. 446, pp. 758-764.
Nash et al., "Multisite phosphorylation of a CDK inhibitor sets a threshold for the onset of DNA replication," Nature, Nov. 29, 2001, vol. 414, pp. 514-521.
Neri et al., "Cereblon Splicing of Exon 10 Mediates IMiDs Resistance in Multiple Myeloma: Clinical Validation in the CoMMpass Trial," Blood, Dec. 2, 2016, vol. 128, No. 22, p. 120.
Ong et al., "A practical recipe for stable isotope labeling by amino acids in cell culture (SILAC)," Nature Protocols, 2006, vol. 1, No. 6, pp. 2650-2660.
Rajadhyaksha et al., "Behavioral characterization of cereblon forebrain-specific conditional null mice: A model for human non-syndromic intellectual disability," Behavioural Brain Research, Jan. 15, 2012, vol. 226, No. 2, pp. 428-434.
Rajkumar et al., "Combination therapy with lenalidomide plus dexamethasone (Rev/Dex) for newly diagnosed myeloma," Blood, Dec. 15, 2005, vol. 106, No. 13, pp. 4050-4053.
Rappsilber et al., "Protocol for micro-purification, enrichment, pre-fractionation and storage of peptides for proteomics using StageTips," Nature Protocols, 2007, vol. 2, No. 8, pp. 1896-1906.
Rudikoff et al., "Single amino acid substitution altering antigen-binding specificity," Proceedings of the National Academy of Sciences of the United States of America, Mar. 1982, vol. 79, pp. 1979-1983.
Sanjana et al., "Improved vectors and genome-wide libraries for CRISPR screening," Nature Methods, Aug. 2014, vol. 11, No. 8, pp. 783-784.
Sawamura et al., "Cereblon is recruited to aggresome and shows cytoprotective effect against ubiquitin-proteasome system dysfunction," Biochemical and Biophysical Research Communications, 2015, vol. 464, No. 4, pp. 1054-1059.
Schafer et al., "2689: The CUL4CRBNE3 Ubiquitin Ligase Modulator CC-220 Induces Degradation of the Transcription Factors Ikaros and Aiolos: Immunomodulation in Healthy Volunteers and Relevance to Systemic Lupus Erythematosus," Arthritis & Rheumatology, Oct. 2014, vol. 66, Suppl. 10, pp. S1176-S1177.
Shaffer et al., "IRF4 Addiction in Multiple Myeloma," Nature, Jul. 10, 2008, vol. 454, No. 7201, pp. 226-231.
Thakurta et al., "Absence of Mutation in Cereblon (CRBN) and DNA Damage Binding Protein 1 (DDB1) Genes in Myeloma Cells and Patients and Its Clinical Significance," Blood, Nov. 15, 2013, vol. 122, No. 21, p. 3139.
Thakurta et al., "Absence of mutations in cereblon (CRBN) and DNA damage-binding protein 1 (DDB1) genes and significance for IMiD therapy," Leukemia, 2014, vol. 28, pp. 1129-1131.
Winandy et al., "A Dominant Mutation in the Ikaros Gene Leads to Rapid Development of Leukemia and Lymphoma," Cell, Oct. 20, 1995, vol. 83, pp. 289-299.
Yang et al., "Exploiting Synthetic Lethality for the Therapy of ABC Diffuse Large B Cell Lymphoma," Cancer Cell, Jun. 12, 2012, vol. 21, pp. 723-737.
Zhu et al., "Cereblon Binding IMiD Small Molecules Mediate Myeloma Cell Death via IRF4," Blood, 2012, vol. 120, p. 1807.
Zhu et al., "Cereblon expression is required for the antimyeloma activity of lenalidomide and pomalidomide," Blood, Nov. 3, 2011, vol. 118, No. 18, pp. 4771-4779.
Zhu et al., "Identification of cereblon-binding proteins and relationship with response and survival after IMiDs in multiple myeloma," Blood, Jul. 24, 2014, vol. 124, No. 4, pp. 536-545.

* cited by examiner

METHODS OF CHARACTERIZING RESISTANCE TO MODULATORS OF CEREBLON

CROSS-REFERENCE TO RELATED APPLICATION

This application is the U.S. national phase application, pursuant to 35 U.S.C. § 371, of PCT international application Ser. No.: PCT/US2016/051019, filed Sep. 9, 2016, designating the United States and published in English, which claims the benefit of the following U.S. Provisional Application No. 62/217,455, filed Sep. 11, 2015, the entire content of which is incorporated herein by reference.

STATEMENT OF RIGHTS TO INVENTIONS MADE UNDER FEDERALLY SPONSORED RESEARCH

This invention was made with government support under Grant No. P01 CA066996 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 22, 2021, is named 167741_010602_US_SL.txt and is 299,728 bytes in size.

BACKGROUND OF THE INVENTION

Thalidomide, lenalidomide, and pomalidomide are effective therapies for a number of disorders, most notably 5q– myelodysplastic syndrome and the plasma cell malignancy multiple myeloma. The drug thalidomide became infamous in the early 1960s when its use during the first trimester of pregnancy was linked to profound birth defects, most commonly a malformation of the upper limbs known as phocomelia. The discovery of thalidomide's teratogenic property was a major setback for the compound. However, thalidomide was later repurposed and is currently an FDA-approved therapy for a number of disorders, including erythema nodosum leparum, 5q– myelodysplastic syndrome (MDS), and several mature B-cell malignancies, most notably the plasma cell malignancy multiple myeloma. Thalidomide's success as a treatment for these disorders motivated the synthesis of lenalidomide and pomalidomide, which are more potent derivatives that have largely replaced thalidomide in the clinic today. It is therefore important to identify additional potentially therapeutically relevant targets of thalidomide, lenalidomide, and pomalidomide to improve clinical use of these drugs. These drugs are known to bind to the Cereblon protein product CRBN (GeneCards identifier GCID: GC03M003166) and change its substrate specificity, and thus it is important to identify additional drug related substrates of CRBN. Further, it is important to detect resistance to these drugs in patients, particularly at an early stage of a disease, so that alternate forms of therapy can be provided.

SUMMARY OF THE INVENTION

As described below, the present invention features methods of characterizing the sensitivity in a subject to lenalidomide and other molecules that bind CRBN.

In one aspect, the invention provides a method of identifying a cell resistant to one or more modulators of CRBN, the method comprising detecting the polynucleotide sequence of at least one gene in Table 1 in the cell relative to a reference sequence, wherein detection of a mutation in the polynucleotide sequence of at least one gene in Table 1 indicates a cell resistant to one or more modulators of CRBN. In one aspect, the modulator of CRBN is lenalidomide. In one aspect, the modulator of CRBN is thalidomide. In one aspect, the modulator of CRBN is pomalidomide.

In another aspect, the invention provides a method of characterizing the sensitivity of a subject to a modulator of CRBN, the method comprising detecting the sequence of a polynucleotide of at least one gene in Table 1 in a biological sample obtained from the subject relative to a reference sequence, wherein detection of a mutation in the polynucleotide sequence of at least one gene in Table 1 is indicative of resistance to a modulator of CRBN and failure to detect a mutation is indicative of sensitivity to a modulator of CRBN.

In yet another aspect, the invention provides a method of monitoring sensitivity of a subject to a modulator of CRBN, the method comprising detecting the sequence of a polynucleotide of at least one gene in Table 1 in a biological sample obtained from the subject relative to a reference sequence, wherein detection of a mutation in the polynucleotide sequence of at least one gene in Table 1 is indicative of resistance to a modulator of CRBN and failure to detect a mutation is indicative of sensitivity to a modulator of CRBN.

In another aspect, the invention provides a method of monitoring sensitivity of a subject to a modulator of CRBN, the method comprising administering an amount of a modulator of CRBN to the subject; and detecting the sequence of a polynucleotide of at least one gene in Table 1 in a biological sample obtained from the subject relative to a reference sequence, wherein detection of a mutation in the polynucleotide sequence of at least one gene in Table 1 is indicative of resistance to a modulator of CRBN and failure to detect a mutation is indicative of sensitivity to a modulator of CRBN.

In another aspect, the invention provides a method of selecting a subject for treatment with an alternative to a modulator of CRBN, the method comprising detecting the sequence of a polynucleotide of at least one gene in Table 1 in a biological sample obtained from the subject relative to a reference sequence, wherein a subject having a mutation in the polynucleotide sequence of at least one gene in Table 1 is selected for treatment with an alternative to a modulator of CRBN.

In various embodiments of any of the aspects delineated herein, the mutation confers loss of at least one gene. In various embodiments of any of the aspects delineated herein, the subject has a B cell neoplasia or related condition. In various embodiments, the B cell neoplasia or related condition is a plasma cell malignancy multiple myeloma or a myelodysplastic syndrome.

In various embodiments of any of the aspects delineated herein, the polynucleotide sequence of at least one gene in Table 1 is detected by sequencing or probe hybridization. In various embodiments of any of the aspects delineated herein, the biological sample is a blood sample.

In another aspect, the invention provides a kit comprising a reagent detecting the sequence of a polynucleotide of at least one gene in Table 1. In various embodiments, the reagent is a sequencing primer or hybridization probe. In various embodiments of any of the aspects delineated herein, the modulator of CRBN is lenalidomide, thalidomide, or pomalidomide.

Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression or activity levels, preferably a 25% change, more preferably a 40% change, and most preferably a 50% or greater change in expression or activity levels.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid. Lenalidomide analogs include, but are not limited to, thalidomide or pomalidomide.

By "biological sample" is meant any liquid, cell, or tissue obtained from a subject.

By "biomarker" or "marker" is meant any protein or polynucleotide having an alteration in expression level or activity that is associated with a disease or disorder.

By "B cell neoplasia" is meant any neoplasia arising from a B-cell progenitor or other cell of B cell lineage, for example, plasma cell malignancy, multiple myeloma, or a myelodysplastic syndrome. In particular embodiments, a B cell neoplasia arises from a cell type undergoing B cell differentiation. In other embodiments, a B cell neoplasia includes plasma cells.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "CRBN polypeptide" or "Cereblon" is meant a polypeptide or fragment thereof having at least 85% amino acid sequence identity to NCBI Accession No. AAH67811.1 or NP_001166953.1 and having IKZF3 binding activity. Exemplary CRBN polypeptide sequences are provided below:

```
AAH67811.1
                                                                  (SEQ ID NO: 1)
  1 magegdqqda ahnmgnhlpl lpeseeedem evedqdskea kkpniinfdt slptshtylg 61 admeefhgrt lhdddscqvi pvlpqvmmil ipgqtlplql fhpqevsmvr nliqkdrtfa 121 vlaysnvqer eaqfgttaei yayreeqdfg ieivkvkaig rqrfkvlelr tqsdgiqqak 181 vqilpecvlp stmsavqles lnkcqifpsk pvsredqcsy kwwqkyqrrk fhcanltswp 241 rwlyslydae tlmdrikkql rewdenlkdd slpsnpidfs yrvaaclpid dvlriqllki 301 gsaiqrlrce ldimnkctsl cckqcqetei ttkneifsls lcgpmaayvn phgyvhetlt 361 vykacnlnli grpstehswf pgyawtvaqc kicashigwk ftatkkdmsp qkfwgltrsa 421 llptipdted eispdkvilc l NP_001166953.1
                                                                  (SEQ ID NO: 2)
  1 magegdqqda ahnmgnhlpl lpeseeedem evedqdskea kkpniinfdt slptshtylg 61 admeefhgrt lhdddscqvi pvlpqvmmil ipgqtlplql fhpqevsmvr nliqkdrtfa 121 vlaysnvqer eaqfgttaei yayreeqdfg ieivkvkaig rqrfkvlelr tqsdgiqqak 181 vqilpecvlp stmsavqles lnkcqifpsk pvsredqcsy kwwqkyqkrk fhcanltswp 241 rwlyslydae tlmdrikkql rewdenlkdd slpsnpidfs yrvaaclpid dvlriqllki 301 gsaiqrlrce ldimnkctsl cckqcqetei ttkneifsls lcgpmaayvn phgyvhetlt
```

-continued
```
361 vykacnlnli grpstehswf pgyawtvaqc kicashigwk ftatkkdmsp qkfwgltrsa 421 llptipdted eispdkvilc l
```

By "CRBN polynucleotide" is meant a nucleic acid molecule encoding a CRBN polypeptide. An exemplary CRBN polynucleotide sequence is provided at NCBI Accession No. BC067811, which is reproduced below (SEQ ID NO: 3):

```
   1 gcgtgtaaac agacatggcc ggcgaaggag atcagcagga cgctgcgcac aacatgggca 61 accacctgcc gctcctgcct gagagtgagg aagaagatga aatggaagtt gaagaccagg 121 atagtaaaga agccaaaaaa ccaaacatca taaattttga caccagtctg ccgacatcac 181 atacatacct aggtgctgat atggaagaat tcatggcag  gactttgcac gatgacgaca 241 gctgtcaggt gattccagtt cttccacaag tgatgatgat cctgattccc ggacagacat 301 tacctcttca gcttttttcac cctcaagaag tcagtatggt gcggaattta attcagaaag 361 atagaaccttt tgctgttctt gcatacagca atgtacagga aagggaagca cagtttggaa 421 caacagcaga gatatatgcc tatcgagaag aacaggattt tggaattgag atagtgaaag 481 tgaaagcaat tggaagacaa aggttcaaag tccttgagct aagaacacag tcagatggaa 541 tccagcaagc taaagtgcaa attcttcccg aatgtgtgtt gccttcaacc atgtctgcag 601 ttcaattaga atccctcaat aagtgccaga tatttccttc aaaacctgtc tcaagagaag 661 accaatgttc atataaatgg tggcagaaat accagaggag aaagtttcat tgtgcaaatc 721 taacttcatg gcctcgctgg ctgtattcct tatatgatgc tgagacctta atggacagaa 781 tcaagaaaca gctacgtgaa tgggatgaaa atctaaaaga tgattctctt ccttcaaatc 841 caatagattt ttcttacaga gtagctgctt gtcttcctat tgatgatgta ttgagaattc 901 agctccttaa aattggcagt gctatccagc gacttcgctg tgaattagac attatgaata 961 aatgtacttc cctttgctgt aaacaatgtc aagaaacaga ataacaacc aaaaatgaaa 1021 tattcagttt atccttatgt gggccgatgg cagcttatgt gaatcctcat ggatatgtgc 1081 atgagacact tactgtgtat aaggcttgca acttgaatct gataggccgg ccttctacag 1141 aacacagctg gttttcctggg tatgcctgga ctgttgccca gtgtaagatc tgtgcaagcc 1201 atattggatg gaagtttacg gccaccaaaa aagacatgtc acctcaaaaa ttttggggct 1261 taacgcgatc tgctctgttg cccacgatcc cagacactga agatgaaata agtccagaca 1321 aagtaatact ttgcttgtaa acagatgtga tagagataaa gttagttatc taacaaattg 1381 gttatattct aagatctgct ttggaaatta ttgcctctga tacataccta agtaaacata 1441 acattaatac ctaagtaaac ataacattac ttggagggtt gcagtttcta agtgaaactg 1501 tatttgaaac ttttaagtat actttaggaa acaagcatga acggcagtct agaataccag 1561 aaacatctac ttgggtagct tggtgccatt atcctgtgga atctgatatg tctggtagcg 1621 tgtcattgat gggacatgaa gacatctttg gaaatgatga gattatttcc tgtgttaaaa 1681 aaaaaaaaaa aatcttaaat tcctacaatg tgaaactgaa actaataatt tgatcctgat 1741 gtatgggaca gcgtatctgt accagtgctc taaataacaa aagctagggt gacaagtaca 1801 tgttcctttt ggaagaagc  aaggcaatgt atattaatta ttctaaaagg gctttgttcc 1861 tttccatttt ctttaacttc tctgagatac tgatttgtaa attttgaaaa ttagttaaaa 1921 tatgcagttt tttgagccca cgaatagttg tcatttcctt tatgtgcctg ttagtaaaaa 1981 gtagtattgt gtatttgctc agtatctgaa ctataagccc atttatactg ttccatacaa
```

```
-continued
2041 aagctatttt tcaaaaatta atttgaacca aaactactac tatagggaaa agatgccaaa 2101 acatgtcccc tcacccaggc taaacttgat actgtattat tttgttcaat gtaaattgaa 2161 gaaaatctgt aagtaagtaa accttaagtg tgaaactaaa aaaaaaaaaa aaa
```

By "COPS2 polypeptide" is meant a polypeptide or fragment thereof having at least 85% amino acid sequence identity to NCBI Accession No. NP_004227.1 and having activity that regulates the activity of the ubiquitin conjugation pathway for example, signal transduction activity and transcription corepressor activity. An exemplary COPS2 polypeptide sequence is provided below (SEQ ID NO: 4):

```
  1 msdmeddfmc ddeedydley sedsnsepnv dlenqyynsk alkeddpkaa lssfqkvlel 61 egekgewgfk alkqmikinf kltnfpemmn rykqlltyir savtrnysek sinsildyis 121 tskqmdllqe fyettlealk dakndrlwfk tntklgklyl ereeygklqk ilrqlhqscq 181 tddgeddlkk gtqlleiyal eiqmytaqkn nkklkalyeq slhiksaiph plimgvirec 241 ggkmhlrege fekahtdffe afknydesgs prrttclkyl vlanmlmksg inpfdsgeak 301 pykndpeila mtnlvsayqn nditefekil ktnhsnimdd pfirehieel lrnirtqvli 361 klikpytrih ipfiskelni dvadvesllv qcildntihg ridqvnqlle ldhqkrggar 421 ytaldkwtnq lnslnqavvs kla
```

By "COPS2 polynucleotide" is meant a nucleic acid molecule encoding a COPS2 polypeptide. An exemplary COPS2 polynucleotide sequence is provided at NCBI Accession No. NM_004236.3, which is reproduced below (SEQ ID NO: 5):

```
   1 agctgagagt gacgcctctg agccgcggag gattgtggga ggaggttgtc tccaatttct 61 cctcccccctc ccggccaaga tgtctgacat ggaggatgat ttcatgtgcg atgatgagga 121 ggactacgac ctggaatact ctgaagatag taactccgag ccaaatgtgg atttggaaaa 181 tcagtactat aattccaaag cattaaaaga agatgaccca aaagcggcat taagcagttt 241 ccaaaaggtt ttggaacttg aaggtgaaaa aggagaatgg ggatttaaag cactgaaaca 301 aatgattaag attaacttca agttgacaaa ctttccagaa atgatgaata gatataagca 361 gctattgacc tatattcgga gtgcagtcac aagaaattat tctgaaaaat ccattaattc 421 tattcttgat tatatctcta cttctaaaca gatggattta ctgcaggaat tctatgaaac 481 aacactggaa gctttgaaag atgctaagaa tgatagactg tggtttaaga caaacacaaa 541 gcttggaaaa ttatatttag aacgagagga atatggaaag cttcaaaaaa ttttacgcca 601 gttacatcag tcgtgccaga ctgatgatgg agaagatgat ctgaaaaaag gtacacagtt 661 attagaaata tatgctttgg aaattcaaat gtacacagca cagaaaaata caaaaaact 721 taaagcactc tatgaacagt cacttcacat caagtctgcc atccctcatc cactgattat 781 gggagttatc agagaatgtg gtggtaaaat gcacttgagg gaaggtgaat tgaaaaggc 841 acacactgat ttttttgaag ccttcaagaa ttatgatgaa tctggaagtc caagacgaac 901 cacttgctta aaatatttgg tcttagcaaa tatgcttatg aaatcgggaa taaatccatt 961 tgactcacag gaggccaagc cgtacaaaaa tgatccagaa attttagcaa tgacgaattt 1021 agtaagtgcc tatcagaata atgacatcac tgaatttgaa aagattctaa aaacaaatca 1081 cagcaacatc atggatgatc ctttcataag agaacacatt gaagagcttt tgcgaaacat
```

-continued

```
1141 cagaacacaa gtgcttataa aattaattaa gccttacaca agaatacata ttccttttat
1201 ttctaaggag ttaaacatag atgtagctga tgtggagagc ttgctggtgc agtgcatatt
1261 ggataacact attcatggcc gaattgatca agtcaaccaa ctccttgaac tggatcatca
1321 gaagaggggt ggtgcacgat atactgcact agataaatgg accaaccaac taaattctct
1381 caaccaggct gtagtcagta aactggctta acagagaaca agcttttaca gacgtcctta
1441 aggcaacagt gcagagatgt aatccttaaa agaactggga atggcaaaac tactgtcggt
1501 tgatgtgtcc tgaaaattat tggagttatg gcagaagtgc ttttttgatc aactggtttg
1561 tgttttgctg ctgcatttat cccaagaaaa acagctttaa tctccagaag aaaaccaaaa
1621 taccatggga tttatgctgt attgacatct tgccctaaac gtacaacatc atagtaattt
1681 gtcatgggca acatgaccag agagaagatt tttgtcatga ttttaaatac actgacacgc
1741 tactgttggt taaatttaaa catgttttac ctgcagaaat tctctcacaa ataacctgca
1801 ataacttgaa atgcataccc ttttgaacac ttccttttct catgtataaa ttaaaatgtt
1861 tgctgcattt tgcaaaatgt caattctcta aaaatgtgtc cgtatatttc tgtacctgca
1921 gtgtagtaaa ggtttagacg aaaccccata attatagtgg catactgtca cttaggtttc
1981 aagcagcaaa ataaacagtg cagctcagaa attgtagttt ggttcttgat gtgtttttat
2041 tacatttgga gttgttttgt tttttagtac cttcgaaatt tcaaattatt ttatcttcag
2101 ttaatgattt taaaaagcct gggggcaaat aagttggtta tttgctttca agttttaaa
2161 agtagtcttt attgatagag taaggagaac tactttctaa caaaacacgt gcatagttat
2221 gacagtgatg cttaaaagga ataaaattct ttttttttaa agagtgatat tcctttcaa
2281 aagaatacta actctcagaa tgttcacttt aaacgaatat gccagaacat agacagctaa
2341 atgaatgtta ctctgcatag tgatcatgct ggaaggttat ttcctaatgc cagcaatcta
2401 ccattgccca aaacctgctg agtttactct tttagaattg cattcaaagt taatttgtca
2461 cacacactaa actttatgat tatacattgt tttaaaaaat atagtattag gaagcttgat
2521 tatttttagt taccattact tggcaccaaa tgaaagtttc caaaacttcc acctaactt
2581 gaggtaatgc agaaagtata taactggctt tgaaggcaat cccaaaagag ttttaaaggt
2641 tttttgagca gtggcagtat acttaggaga atgaactgtg gccttccaag gtaactacct
2701 taaaggaact cagctcattt gaatgtattg agttttggat gtatttgttt catttttaa
2761 aaagttcaca ttattttata gtgtcgaaag gaagaactag gattaacata atttctttgg
2821 ttttctatt gcttgttatt attatgtaaa aactgggtgg cagttcagaa ggaagattgt
2881 ggttacagaa gagtgacaac caagaatttt ttgatcatta aatcagattt tataaacagt
2941 ggaaggagca tggacttaaa acaaggcatg cttattcggt tttgtcaaaa ttttacgaaa
3001 atatgtgata tatatttata ctaaaaatat ataatcctta gatttagaaa agcaatcagt
3061 taatgtcttt agcagactaa agcagtatta aacacaggta caagtggaa attgtagaaa
3121 acggaaagaa aacaaaagac aaaatgtcta tggtagggaa taaaagttta agatattata
3181 aaattatgtg tattttctct tttacataaa tcatttgtga aaagtgtgct aaacttttt
3241 tacaagagtg atattaatta ggatttattt ttcaataaa tttggagacc ctttgttatc
3301 caaataaaaa tgatgagttt ttgtgcctgt attcaaatat gtatgcatgt gataacccctt
3361 gaaagctaaa gcccttctta acttttgagt tgatggaatt agaattcaaa gatttgaatg
3421 aaaatgattta accttatcc tccaattctt acagtgccca gttctcctgt gctatctttg
3481 ctttgtacaa tagtgcatct tccactttct agagagaaag catgcacttg ttatttggaa
3541 aactgggcta aatatataac agtatccaaa gttataccat aataattta tgtaattgtg
```

```
3601 tattacatag ctttgtttac ccagatatag gtgcgttctt ttttttctgt tagtcatctg 3661 tgacttttgt tctggaatac aggtttttaa atatatctta acagtctgac taacttaaaa 3721 taatttattc ttcccttaaa acatttttct gtgtttttgt gcatcaaata ttgtagagtt 3781 gaaatcttag agattgctta tcgaaatata aatttagggg aagttaaaaa tcgattggca 3841 aatttgtagc atttattcac tgattaaatc ttttccactt ttgtgaaaac cataccagtg 3901 gtttacatca tattgtaatg tgttcatctc attcttcttt ttatccctaa acctagctaa 3961 aagttactgc aaagaaatct ttggctgcca caagtagatg ctctctacta caagagctgg 4021 atttccatta ctcactcttg ctcttacatt aaagttgttg attaaatact ttttctctac 4081 atcttaaaaa aaaaaaaaaa aaa
```

By "COPS3 polypeptide" is meant a polypeptide or fragment thereof having at least 85% amino acid sequence identity to NCBI Accession No. NP_003644.2 and having intracellular regulatory activity, for example, kinase activity and/or regulation of the ubiquitin (Ubl) pathway. An exemplary COPS3 polypeptide sequence is provided below (SEQ ID NO: 6):

```
  1 masaleqfvn svrqlsaqgq mtqlcelink sgellaknls hldtvlgald vqehslgvla 61 vlfvkfsmps vpdfetlfsq vqlfistcng ehiryatdtf aglchqltna lverkqplrg 121 igilkqaidk mqmntnqlts ihadlcqlcl lakcfkpalp yldvdmmdic kengaydakh 181 flcyyyyggm iytglknfer alyfyeqait tpamayshim lesykkyilv slillgkvqq 241 lpkytsgivg rfikplsnay helaqvystn npselrnlvn khsetftrdn nmglvkqcls 301 slykkniqrl tktfltlslq dmasrvqlsg pqeaekyvlh miedgeifas inqkdgmvsf 361 hdnpekynnp amlhnidqem lkcielderl kamdgeitvn pqfvqksmgs qeddsgnkps 421 sys
```

By "COPS3 polynucleotide" is meant a nucleic acid molecule encoding a COPS3 polypeptide. An exemplary COPS3 polynucleotide sequence is provided at NCBI Accession No. NM_003653.3, which is reproduced below (SEQ ID NO: 7):

```
  1 ggaagtgacg tcgccgctcg cgaggacctc aggtggatcg ccgcggcccc tcctcccaga 61 gcggcagcct tttcccgcgc gtgctgcctt cgccgctcgg gccgcccggg ggaaaacatg 121 gcgtctgccc tggagcagtt cgtgaacagt gtccgacagc tctcagctca agggcaaatg 181 acacagcttt gtgaactgat caacaagagt ggggaactcc ttgcgaagaa cttatcccat 241 ctggacactg tgctcggggc tctggatgta caagaacact ccttgggcgt ccttgctgtt 301 ttgtttgtga agttttctat gcccagtgtt cctgacttcg aaacgctatt ctcacaggtt 361 cagctcttca tcagcacttg taatggggag cacattcgat atgcaacaga cacttttgct 421 gggctttgcc atcagctaac aaatgcactt gtggaaagaa acagcccct gcgaggaatt 481 ggcatcctta gcaagccat agacaagatg cagatgaata caaaccagct gacctcaata 541 catgctgatc tctgccagct ttgtttgcta gcaaaatgct ttaagcctgc ccttccatat 601 cttgacgtgg atatgatgga tatctgtaaa gagaatggag cctatgatgc aaaacacttt 661 ttatgttact attattatgg agggatgatc tatactgggc tgaagaactt tgaaagagct 721 ctctactttt atgaacaggc tataactact cctgccatgg cggtcagtca tatcatgttg
```

-continued

```
 781 gaatcatata aaaagtatat tttagtgtct tgatattac ttggcaaagt acaacagcta 841 ccaaaatata catctcaaat tgtgggtaga ttcattaagc ctcttagcaa tgcataccac 901 gagttagcac aagtgtattc aaccaacaac ccctcagaac tccgaaacct ggtgaataag 961 cacagtgaaa ccttcactcg cgataacaac atggggctgg tgaagcaatg cttgtcatct 1021 ctttataaga agaatattca gaggctaaca aagacctttt taactctatc attacaagat 1081 atggcaagtc gtgtgcagtt gtctggacct caggaggcag agaaatacgt tctgcacatg 1141 atagaagatg gtgagatttt tgcaagtatt aaccagaagg acggtatggt cagtttccat 1201 gataaccctg aaaaatataa taacccagcc atgcttcata acattgatca ggagatgctg 1261 aagtgcattg agctggatga gcggctgaaa gccatggacc aggagatcac agtgaaccct 1321 cagtttgtac aaaagagtat gggctcacaa gaagatgatt caggaaacaa accatccagt 1381 tattcttgaa actaacatcc atcctgagct aaacaagaga aactaccatc ttggccagtg 1441 acaagtgttc ggagggcagc agagaggacc aagcctgtgt cacctggaga ctaagaaatt 1501 aagtttgtt ttgacatctt cagtcctgtg tgctttcaga aaaccatttt ctctgcaaag 1561 aaaggaaaca gatttgcaaa ctttaaagtc tgtcgtggat ttatttatcc tcagattatt 1621 gttactgcat taaatctacc tttttgtttt aagttgcttg aacattaatg tgtcttctgt 1681 atcacttttt tctcctctga agtttttaat aagcacattc attgtgaaca gaaatagctg 1741 gattttagga attttggaa gatttggatc tgaaaggttt ttatttattg acaaatttgt 1801 atctacaaaa aaatctaaaa gttgtaatca ttgtcttcag aaaataaaag aaaagaaagg 1861 ccaaa
```

By "COPS4 polypeptide" is meant a polypeptide or fragment thereof having at least 85% amino acid sequence identity to NCBI Accession No. NP_057213.2 and having intracellular regulatory activity, for example, regulation of the ubiquitin (Ubl) conjugation pathway, transcription-coupled nucleotide excision repair (TC-NER) and DNA double-strand break repair. An exemplary COPS4 polypeptide sequence is provided below (SEQ ID NO: 8):

```
  1 maaavrqdla qlmnssgshk dlagkyrqil ekaiqlsgae qlealkafve amvnenvslv 61 isrqlltdfc thlpnlpdst akeiyhftle kiqprvisfe eqvasirqhl asiyekeedw 121 rnaaqvlvgi pletgqkqyn vdykletylk iarlyleddd pvqaeayinr asllqnestn 181 eqlqihykvc yarvldyrrk fieaaqryne lsyktivhes erlealkhal hctilasagq 241 qrsrmlatlf kdercqqlaa ygilekmyld riirgnqlqe faamlmphqk attadgssil 301 draviehnll sasklynnit feelgallei paakaekias qmitegrmng fidqidgivh 361 fetrealptw dkqiqslcfq vnnllekisq tapewtaqam eaqmaq
```

By "COPS4 polynucleotide" is meant a nucleic acid molecule encoding a COPS4 polypeptide. An exemplary COPS4 polynucleotide sequence is provided at NCBI Accession No. NM_016129.2, which is reproduced below (SEQ ID NO: 9):

```
  1 tcccacaccc gacgctctgg cccacacaga cgctactctg tagcatctca ggttccctct 61 ggctgcactc tggaggacca cactcgtttt ctttttggct gccagaggcc cccgcatcca 121 ccgctgagct gggagaaaga tggcggcagc cgtgcgacag gatttggccc agctcatgaa 181 ttcgagcggc tctcataaag atctggctgg caagtatcgt cagatcctgg aaaaagccat 241 tcagttatct ggagcagaac aactagaagc tttgaaagct tttgtggaag caatggtaaa 301 tgagaatgtc agtctcgtga tctcgcggca gttgctgact gattttgca cacatcttcc
```

-continued

```
 361 taacttgcct gatagcacag ccaaagaaat ctatcacttc accttggaaa agatccagcc
 421 tagagtcatt tcatttgagg agcaggttgc ttccataaga cagcatcttg catctatata
 481 tgagaaagaa gaagattgga gaaatgcagc ccaagtgttg gtgggaattc ctttggaaac
 541 aggacaaaaa cagtacaatg tagattataa actggagact tacttgaaga ttgctaggct
 601 atatctggag gatgatgatc cagtccaggc agaggcttac ataaatcgag catcgttgct
 661 tcagaatgaa tcaaccaatg aacaattaca gatacattat aaggtatgct atgcacgtgt
 721 tcttgattat agaagaaaat tcattgaagc tgcacaaagg tacaatgagc tctcttacaa
 781 gacaatagtc cacgaaagtg aaagactaga ggccttaaaa catgctttgc actgtacgat
 841 cttagcatca gcagggcagc agcgttctcg gatgctagct actctttta aggatgaaag
 901 gtgccagcaa cttgctgcct atgggatcct agagaaaatg tatctagata ggatcatcag
 961 aggaaatcaa cttcaagaat ttgctgccat gctgatgcct caccaaaaag caactacagc
1021 tgatggttcc agcatcttgg acagagctgt tattgaacac aatttgttgt ctgcaagcaa
1081 attatataat aatattacct tcgaagaact tggagctctt ttagagatcc ctgcagctaa
1141 ggcggaaaag atagcatctc aaatgataac cgaaggacgt atgaatggat ttattgacca
1201 gattgatgga atagttcatt ttgaaacacg agaagccctg ccaacgtggg ataagcagat
1261 ccaatcactt tgtttccaag tgaataacct tttggagaaa attagtcaaa cagcaccaga
1321 atggacagca caagccatgg aagcccagat ggctcagtga atccttgcag aacttctgtg
1381 cacatgacat ctttttccat gttgtgcaga tcagtttcac tatctccaaa gcatttgcat
1441 catgacctta tacatttcaa tccctttat gctggattcc gtttaaagaa gacattatta
1501 gagcaggaag tacaagcatt taaaatatgt agttcccata tatttcaggg tctctgtgta
1561 ttaagctaac tcagatgttt tgaaagcttt ttctttaaac agaggtgaaa tatctgtggc
1621 taaaaagttt gagatttgtg ataactttgt agtcatgtaa aacttaagtg cttcatgcct
1681 ctccaaatgt ggttattcta ataaatggag aaatgagcca ataaaagta gtactttgtt
1741 tttagttaaa aaaaaaaaa aaa
```

By "COPS5 polypeptide" is meant a polypeptide or fragment thereof having at least 85% amino acid sequence identity to NCBI Accession No. NP_006828.2 and having intracellular signaling regulatory activity, for example, regulation of the ubiquitin (Ubl) conjugation pathway, transcription coactivator activity and thiol-dependent ubiquitin-specific protease activity. An exemplary COPS5 polypeptide sequence is provided below (SEQ ID NO: 10):

```
  1 maasgsgmaq ktwelannmq eaqsideiyk ydkkqqqeil aakpwtkdhh yfkyckisal 61 allkmvmhar sggnlevmgl mlgkvdgetm iimdsfalpv egtetrvnaq aaayeymaay 121 ienakqvgrl enaigwyhsh pgygcwlsgi dvstqmlnqq fqepfvavvi dptrtisagk 181 vnlgafrtyp kgykppdegp seyqtipink iedfgvhckq yyalevsyfk ssldrkllel 241 lwnkywvntl sssslltnad yttgqvfdls ekleqseaql grgsfmlgle thdrksedkl 301 akatrdsckt tieaihglms qvikdklfnq inis
```

By "COPS5 polynucleotide" is meant a nucleic acid molecule encoding a COPS5 polypeptide. An exemplary COPS5 polynucleotide sequence is provided at NCBI Accession No. NM_006837.2, which is reproduced below (SEQ ID NO: 11):

```
   1 gactatacca ctcccatacc ctataacttt gtttgttcta tttcacacat ataattttcc
  61 gagacaagat gttctcattt aagcaacaag aagattcgtc tctcgctatt actgtaactg
 121 ctgtttatat cgtcatgtcc cggaaaggtc cctgtcttcc ctgaatggtc tctaccaact
 181 tcacctccgg ttctaggtgt catggctgcc ccaagagtct aggtaagagt ttgttcccgt
 241 ggtgcggagg gtcaaggccc acacccggaa acctagcgag gtaaagttgc gtcttggttg
 301 tagagacgac aacttctccg cttcctcggc gatggcggcg tccgggagcg gtatggccca
 361 gaaaacctgg gaactggcca acaacatgca ggaagctcag agtatcgatg aaatctacaa
 421 atacgacaag aaacagcagc aagaaatcct ggcggcgaag ccctggacta aggatcacca
 481 ttactttaag tactgcaaaa tctcagcatt ggctctgctg aagatggtga tgcatgccag
 541 atcgggaggc aacttggaag tgatgggtct gatgctagga aaggtggatg gtgaaaccat
 601 gatcattatg gacagttttg ctttgcctgt ggagggcact gaaacccgag taaatgctca
 661 ggctgctgca tatgaataca tggctgcata catagaaaat gcaaacagg ttggccgcct
 721 tgaaaatgca atcgggtggt atcatagcca ccctggctat ggctgctggc tttctgggat
 781 tgatgttagt actcagatgc tcaatcagca gttccaggaa ccatttgtag cagtggtgat
 841 tgatccaaca agaacaatat ccgcagggaa agtgaatctt ggcgccttta ggacataccc
 901 aaagggctac aaacctcctg atgaaggacc ttctgagtac cagactattc cacttaataa
 961 aatagaagat tttggtgtac actgcaaaca atattatgcc ttagaagtct catatttcaa
1021 atcctctttg gatcgcaaat tgcttgagct gttgtggaat aaatactggg tgaatacgtt
1081 gagttcttct agcttgctta ctaatgcaga ctataccact ggtcaggtct ttgatttgtc
1141 tgaaaagtta gagcagtcag aagcccagct gggacgaggg agtttcatgt tgggtttaga
1201 aacgcatgac cgaaaatcag aagacaaact tgccaaagct acaagagaca gctgtaaaac
1261 taccatagaa gctatccatg gattgatgtc tcaggttatt aaggataaac tgtttaatca
1321 aattaacatc tcttaaacag tctctgagaa gtactttacc tgaaagacag tatgagaaaa
1381 atattcaagt aacactttaa aaccagttac ccaaaatctg attagaagta taaggtgctc
1441 tgaagtgtcc taaatattaa tatcctgtaa taaagctctt taaaatgaaa aaaaaaaaa
1501 aaaaaaaaaa
```

By "COPS6 polypeptide" is meant a polypeptide or fragment thereof having at least 85% amino acid sequence identity to NCBI Accession No. NP_006824.2 and having intracellular regulatory activity, for example, regulation of the ubiquitin (Ubl) conjugation pathway, transcription-coupled nucleotide excision repair (TC-NER) and DNA double-strand break repair. An exemplary COPS6 polypeptide sequence is provided below (SEQ ID NO: 12):

```
  1 maaaaaaaaa tngtggssgm evdaavvpsv macgvtgsvs valhplviln isdhwirmrs
 61 qegrpvqvig aligkqegrn ievmnsfell shtveekiii dkeyyytkee qfkqvfkele
121 flgwyttggp pdpsdihvhk qvceiiespl flklnpmtkh tdlpvsvfes vidiingeat
181 mlfaeltytl ateeaerigv dhvarmtatg sgenstvaeh liaqhsaikm lhsrvklile
241 yvkaseagev pfnheilrea yalchclpvl stdkfktdfy dqcndvglma ylgtitktcn
301 tmnqfvnkfn vlydrqgigr rmrglff
```

By "COPS6 polynucleotide" is meant a nucleic acid molecule encoding a COPS6 polypeptide. An exemplary COPS6 polynucleotide sequence is provided at NCBI Accession No. NM_006833.4, which is reproduced below (SEQ ID NO: 13):

```
   1 ggcggggccg aggctggcgg gcgcggggaa aatggcggcg gcggcggcgg cggctgcagc
  61 tacgaacggg accggaggaa gcagcgggat ggaggtggat gcagcagtag tccccagcgt
 121 gatggcctgc ggagtgactg ggagtgtttc cgtcgctctc catccccttg tcattctcaa
 181 catctcagac cactggatcc gcatgcgctc ccaggagggg cggcctgtgc aggtgattgg
 241 ggctctgatt ggcaagcagg agggccgaaa tatcgaggtg atgaactcct ttgagctgct
 301 gtcccacacc gtggaagaga agattatcat tgacaaggaa tattattaca ccaaggagga
 361 gcagtttaaa caggtgttca aggagctgga gtttctgggt tggtatacca caggggggcc
 421 acctgacccc tcggacatcc acgtccataa gcaggtgtgt gagatcatcg agagccccct
 481 ctttctgaag ttgaaccctg tgaccaagca cacagatctt cctgtcagcg tttttgagtc
 541 tgtcattgat ataatcaatg gagaggccac aatgctgttt gctgagctga cctacactct
 601 ggccacagag gaagcggaac gcattggtgt agaccacgta gcccgaatga cagcaacagg
 661 cagtggagag aactccactg tggctgaaca cctgatagca cagcacagcg ccatcaagat
 721 gctgcacagc cgcgtcaagc tcatcttgga gtacgtcaag gcctctgaag cgggagaggt
 781 cccctttaat catgagatcc tgcgggaggc ctatgctctg tgtcactgtc tcccggtgct
 841 cagcacagac aagttcaaga cagatttta tgatcaatgc aacgacgtgg ggctcatggc
 901 ctacctcggc accatcacca aaacgtgcaa caccatgaac cagtttgtga acaagttcaa
 961 tgtcctctac gaccgacaag gcatcggcag gagaatgcgc gggctctttt tctgatgagg
1021 gtacttgaag ggctgatgga caggggtcag gcaactatcc caaggggag ggcactacac
1081 ttccttgaga gaaaccgctg tcattaataa aaggggagca gcccctgagc acccctgctg
1141 gtggctctgt cctctgttag gcaccacact ggttggtcaa cttggatgtt catcgaggct
1201 cattctggcc ttgctcagaa gcccttctga tgctcttcag tgagggaggc actaccattt
1261 gaagtgaccc catgtcagtc acatggactg gtctttagca aagtccaagg ctgcctgctt
1321 ccacctaagt ggtctctgtt ctacacttta atgtcaccct ctacatcatc ttacctagcc
1381 cacccaacct tataaacatg ataattgact actttcctga gctaaaaaaa aaaaaaaaaa
1441 a
```

By "COPS7A polypeptide" is meant a polypeptide or fragment thereof having at least 85% amino acid sequence identity to NCBI Accession No. AAH11789.1 and having intracellular regulatory activity, for example, regulation of the ubiquitin (Ubl) conjugation pathway, transcription-coupled nucleotide excision repair (TC-NER) and DNA double-strand break repair. An exemplary COPS7A polypeptide sequence is provided below (SEQ ID NO: 14):

```
   1 msaevkvtgq nqeqflllak sakgaalatl ihqvleapgv yvfgelldmp nvrelaesdf
  61 astfrlltvf aygtyadyla earnlpplte aqknklrhls vvtlaakvkc ipyavlleal
 121 alrnvrqled lvieavyadv lrgsldqrnq rlevdysigr diqrqdlsai artlqewcvg
 181 cevvlsgiee qvsranqhke qqlglkqqie sevanlkkti kvttaaaaaa tsqdpeqhlt
 241 elrepapgtn qrqpskkask gkglrgsaki wsksn
```

By "COPS7A polynucleotide" is meant a nucleic acid molecule encoding a COPS7A polypeptide. An exemplary COPS7A polynucleotide sequence is provided at NCBI Accession No., NM_001164093.1 which is reproduced below (SEQ ID NO: 15):

```
   1 gtgggcgcgt gcggggcagc aatggagagc tgagggagcg tcgtcagggt ggacaccatg
  61 cgacacccat ttctcctttg catcctgtgt cttggggttc aatggggtgc acgtgatggg
 121 gcttggggtt aggcccaggg gaggggtgg gtgtggcagc cttgcgaagt ggctgacttt
 181 aggattccta gatcagaatt ttagaccgct ccatgtctga ttcctcaccg cagaaccgac
 241 ttagtgcctt tacaatccag tccctcagcc ttgtgcttcc catccgacca gccatcgggg
 301 acctctagct tcacatcctc tttccttgca gctctggaca tcctgagccc aagtccccca
 361 cactcagtgc agtgatgagt gcggaagtga aggtgacagg gcagaaccag gagcaatttc
 421 tgctcctagc caagtcggcc aaggggggcag cgctggccac actcatccat caggtgctgg
 481 aggcccctgg tgtctacgtg tttggagaac tgctggacat gcccaatgtt agagagctgg
 541 ctgagagtga ctttgcctct accttccggc tgctcacagt gtttgcttat gggacatacg
 601 ctgactactt agctgaagcc cggaatcttc ctccactaac agaggctcag aagaataagc
 661 ttcgacacct ctcagttgtc accctggctg ctaaagtaaa gtgtatccca tatgcagtgt
 721 tgctggaggc tcttgccctg cgtaatgtgc ggcagctgga agaccttgtg attgaggctg
 781 tgtatgctga cgtgcttcgt ggctccctgg accagcgcaa ccagcggctc gaggttgact
 841 acagcatcgg gcgggacatc cagcgccagg acctcagtgc cattgcccga accctgcagg
 901 aatggtgtgt gggctgtgag gtcgtgctgt caggcattga ggagcaggtg agccgtgcca
 961 accaacacaa ggagcagcag ctgggcctga agcagcagat tgagagtgag gttgccaacc
1021 ttaaaaaaac cattaaagtt acgacggcag cagcagccgc agccacatct caggaccctg
1081 agcaacacct gactgagctg agggaaccag ctcctggcac caaccagcgc cagcccagca
1141 agaaagcctc aaagggcaag gggctccgag ggagcgccaa gatttggtcc aagtcgaatt
1201 gaaaggactg tcgtttcctc cctggggatg tggggtccca gctgcctgcc tgcctcttag
1261 gagtcctcag agagccttct gtgcccctgg ccagctgata atcctaggtt catgaccctt
1321 cacctcccct aaccccaaac atagatcaca ccttctctag ggaggaggca aatgtaggtc
1381 atgtttttgt tggtactttc tgttttttgt gacttcatgt gttccattgc tccccgctgc
1441 catgctctct cccttgtttc cttaagagct cagcatctgt ccctgttcat tacatgtcat
1501 tgagtaggtg ggtagccctg atggggtcg ctctgtctgg agcataaccc acaggcgttt
1561 tttctgccac cccatccctg catgctgat ccccagttcc tataccctac ccctgaccta
1621 ttgagcagcc tctgaagagc catagggccc ccacctttac tcacaccctg agaattctgg
1681 gagccagtct gccatgccag gagtcactgg acatgttcat cctagaatcc tgtcacacta
1741 cagtcatttc ttttcctctc tctggccctt gggtcctggg aatgctgctg cttcaacccc
1801 agagcctaag aatggcagcc gtttcttaac atgttgagag atgattcttt cttggccctg
1861 gccatctcgg gaagcttgat ggcaatcctg gaagggttta atctcctttt gtgagtttgg
1921 tggggaaggg aagggtatat agattgtatt aaaaaaaaaa aggtatatat gcatatatct
1981 atatataata tgacgcagaa ataaatctat gagaaatcta tctacaaact accctgaaaa
2041 aaaaaaaaaa aaa
```

By "COPS7B polypeptide" is meant a polypeptide or fragment thereof having at least 85% amino acid sequence identity to NCBI Accession No. AAH91493.1 and having intracellular regulatory activity, for example, regulation of the ubiquitin (Ubl) conjugation pathway, transcription-coupled nucleotide excision repair (TC-NER) and DNA double-strand break repair. An exemplary COPS7B polypeptide sequence is provided below (SEQ ID NO: 16):

```
  1 mageqkpssn lleqfillak gtsgsaltal isqvleapgv yvfgellela nvqelaegan
 61 aaylqllnlf aygtypdyia nkeslpelst aqqnklkhlt ivslasrmkc ipysvllkdl
121 emrnlreled liieavytdi iqgkldqrnq llevdfcigr dirkkdinni vktlhewcdg
181 ceavllgieq qvlranqyke nhnrtqqqve aerekrdvpl lnlittaffw lptsrrhskp
241 phpprlrrws sswingsvpl tlsrgspprr cpk
```

By "COPS7B polynucleotide" is meant a nucleic acid molecule encoding a COPS7B polypeptide. An exemplary COPS7B polynucleotide sequence is provided at NCBI Accession No. NM_001282950.2, which is reproduced below (SEQ ID NO: 17):

```
   1 agcggtggga ggcttccggg ggagctgcac gggcgacggg tcggcggaga cagaaaagcg
  61 ccggacgccg gggtgatcat ggacgcttga caacctgcgg gcaggcgccg ggaggccgag
 121 ccagcgacta agaggaccga gaggtggcgt ggacagattt caaggccaga gaatggcagg
 181 ggaacagaaa ccctcaagta atctcctgga gcagtttatt ttactagcca aaggtaccag
 241 tggctcagcc ctcactgctc tcataagcca ggtcttagag gctcccggag tgtatgtctt
 301 tggagaactt ctggagctgg ccaacgtgca ggagcttgcg gaaggagcta atgctgctta
 361 tttgcagttg ttgaacctgt ttgcctatgg gacataccca gattacatag ccaacaagga
 421 gagcctgcca gaactgagca cagctcagca gaacaagctg aagcatctta ccatcgtgag
 481 cttggcatca agaatgaagt gtatccccta ctccgtgttg ctgaaagacc tggagatgcg
 541 gaatctccgg gaactagaag accttatcat tgaggctgtc tacactgaca tcatccaggg
 601 caagctggac cagcgaaacc agctgctgga agtggatttc tgcattggcc gtgacatccg
 661 aaagaaggat atcaataata ttgtcaagac cctgcatgaa tggtgtgatg gctgtgaagc
 721 agttctactg ggcatcgagc agcaagttct gagagccaac cagtacaaag agaaccacaa
 781 ccgaactcag cagcaggtag aagcagagag ggaaaaacgt gatgtccccc tcctgaatct
 841 tataacaaca gctttcttct ggttaccaac atcaagaaga cactcaaagc caccgcatcc
 901 tcctcggctc aggagatgga gcagcagctg gctgaacggg agtgtccccc tcacgctgag
 961 cagaggcagc ccaccaagaa gatgtccaaa gtgaaaggtc tggtctccag ccgccactag
1021 ggccggctgg ggcagctggc actcaccagg cctgggtcag gtggggaggg gacaccaagg
1081 gcccatttcc tccctctct acctgcagtg agttccagac ctgcccgtcc cctcaccagc
1141 gcctccccac cctgttggta ctgttccaga aaaactgtta ctcccccctca cccactccct
1201 ccttccccag ttgttccctt cagactcagg ggctccacca atgccatccc aaaacagggt
1261 cagacactgc ccagcttccc tccaggaggt tcttgtctct gtgtaagggc ttgtctccct
1321 cccagttttt cttttgctcc acgtcatttt gtcaggctgg ttataagcct gaggcagctt
1381 taaccagccc cagggatga ttgtgaagga ggccctccc cttgtgagga gggggcactc
1441 ctctccagcc cctggtacca cagtcctcac gatggtgcag tgatttctag ccaggcgtca
1501 agatgcgctg ctttccctct cctgcctcat cccttgttgg cagctccagt tcaggccgtg
1561 gagggacgtg atgctgggct gtgtttacta aacccacggg ttttcagcct cttaagccca
1621 gctccgatct ccaattagtt gagagcgctg ggttgactaa cctctggtat ctgagcacag
```

```
1681 acagagggtg ctgtgggtct gctgggtggc agaaatggtt ccttccggct tggcgttctc 1741 tcctggccac tcttcctgct gcctctgact actcagcctt gttttcggtg tgtaggcccc 1801 agctgcccac tggaactgcc ggctaatgct tgctctccca agatctttaa ctcctcctgg 1861 ctgcacctgg gtagggatgg tggcatcgat gcccctctgt ctgctgaagg acctgttgct 1921 gcttctgtct tttcacccct ccttggctga tgacccagag ccctctgatg atggcattct 1981 cctggcaaga gaaaaagact taactagact tctgaacttg aacagtttca ggttatattt 2041 taattttttt tttttgtac aggttctgat tctaatacat ttcaacatgc ttttgtcccc 2101 cctcgtgtca atatttgtta tagactaatc gccggggatt tttcacctgg ttggagggtg 2161 ggggtggggt ggggtgtgtg tgtgtgtgtg tgtgtgtgtg tgtgtgtgtg tgtgtgtttg 2221 taggtcctgg actgattaaa gttcattgag gaaaaagcac attttacaac aaaaaaataa 2281 aagtgtagat ttaatgtatg tgactggggt ttggggttgc atacctggtg gatcttgagg 2341 ggctgggatt agggtggttc aggaaaatgt gatgctgttt ccccatgttt agccatggtc 2401 aaaaaatgga tttctccttt ttctaaaatg tccagcaact gcctactgtt gatcaaatgt 2461 tgaagtattc ttgtttccct tttaagccaa tccatgtgcc cacataacat tatgcccaag 2521 tggagagttc actttaattt ccaaagtatg tttcatgcag cccctgtca gctgctctgt 2581 ggaaaagggg ttctgttatg aaataaatgt tgcactccct gcatcccaaa aaaaa
```

By "COPS8 polypeptide" is meant a polypeptide or fragment thereof having at least 85% amino acid sequence identity to NCBI Accession No. CAG33275.1 and having intracellular regulatory activity, for example, regulation of the ubiquitin (Ubl) conjugation pathway, transcription-coupled nucleotide excision repair (TC-NER) and DNA double-strand break repair. An exemplary COPS8 polypeptide sequence is provided below (SEQ ID NO: 18):

```
  1 mpvavmaesa fsfkklldqc engeleapgg iatppvygql lalyllhndm nnarylwkri 61 ppaiksanse lggiwsvgqr iwqrdfpgiy ttinahqwse tvqpimealr datrrrafal 121 vsqaytsiia ddfaafvglp veeavkgile qgwqadsttr mvlprkpvag aldvsfnkfi 181 plsepapvpp ipneqqlarl tdyvaflen
```

By "COPS8 polynucleotide" is meant a nucleic acid molecule encoding a COPS8 polypeptide. An exemplary COPS8 polynucleotide sequence is provided at NCBI Accession No. NM_006710.4, which is reproduced below (SEQ ID NO: 19):

```
  1 ggagactcac accttagatt ctgagttttt aagcttgttt cctcagagca gggaactcac 61 gaacgtttcg tgagcaccta cggtatgcag ggtacggtgc ggagccctag cgtcactgac 121 gaccgggaca gccgagcagc tgcaggatcc gtcgtgttcc ccagcaattt taatatttaa 181 aaattcgtta ctgttgctgt tacttgtttt ctatgtattg gatgtcttcg tgaagaaccc 241 tcaaaagtgc aacgaactcc tccctgccag agggcggccg cgcgctctga gtacagcttc 301 ccgcggagcc ggccaggtcc tccagggcac cgagaaagcc ggccagaacg gcggcgccct 361 atcccggccg cagcgatgtc tgacggcgcc ccggaactga cggtctggta cgcaggggcg 421 ctcggcggca acggcggctt taaacgtcat cgcgggcgcg acgcctgagg gacagtctgg 481 ggtttggctg tccgacggt gcagcggcga ggccggccgc gaagatgcca gtggcggtga 541 tggcggaaag cgcctttagt ttcaaaaagt tgctggatca gtgcgagaac caggagctcg
```

```
 601 aggcccctgg aggaattgct acaccccag tgtatggtca gcttctagct ttatatttgc 661 tccataatga catgaataat gcaagatatc tttggaaaag aataccacct gctataaaat 721 ctgcaaattc tgaacttggg ggaatttggt cagtaggaca agaatctgg cagagagatt 781 tccctgggat ctatacaacc atcaacgctc accagtggtc tgagacggtc cagccaatta 841 tggaagcact tagagatgca acaaggagac gcgcctttgc cctggtctct caagcgtata 901 cttcaatcat cgccgatgat tttgcagcct tgttggact tcctgtagaa gaggctgtga 961 aaggcatatt agaacaagga tggcaagctg attccaccac aagaatggtt ctgcccagaa 1021 agccagttgc aggggccctg gatgtttcct ttaacaagtt tattcccta tcagagcctg 1081 ctccagttcc cccaataccc aatgaacagc agttagccag actgacggat tatgtggctt 1141 tccttgaaaa ctgatttatc actctgagtt caagattcat cttcagaatc ctgtatactg 1201 acaaacgtag aaatgtaaag tttgtatttt caatttattg gatggcttaa gcacctcagc 1261 attccttact atgtgataaa atacatatag aatataagat atactatata cattttgtcc 1321 ataaacgtta tgctgaatag ttgttgaaac agttctcatt ttgtagtatt taataatctg 1381 gatggagcct gtcagtatta cagttagttt tctagtgact cataaaataa gatttcctgt 1441 ttcatgtaga atagtgtttg tcaactgtct tttctctgtc ccagcacatg ccgtactctt 1501 atatgtacca ttggttgata attataatga ttcatttgga cttgaagaaa gattgtcccc 1561 aggcacagta tctgaatcac tggggattat gattcaccct ctttggagaa catgctctct 1621 tttcaccccc cacctcctga gagccactaa tgtaagatac agaaacatag ctgaggaaca 1681 aatagaccat ttccatacta aaccagtttg ttaactttag attttttcca atagtgtgag 1741 tatatccatt gctggcagtg gagggcttgc catgaaaatg caacttattt aagacattta 1801 tgagacatat taacttgtgc tgtcgccttt tagaaggaga aacttaagtg tggaatgcat 1861 tatatgggca agaagctat gaagatacat gatacacttt gtacaactat cctgcagccc 1921 attggttgct tatatttatc gcttggctca agttctgccc tttggagaaa tactgagcaa 1981 gtctttcatt ctctgtgtga cagccctctg aatatttgaa gttgtttgtt gtaacttaag 2041 gttataacag cccttagttc atttactctg catttgttca ataaatattt aactgaattc 2101 ttcaattatt tcatctaaga tagtttctgg aaatttcact ctcgatcttt ctgtggacac 2161 aatctatttt gtcattgtgt ctatatgaat ctcttaagta gaaatgagtt gtatggtgaa 2221 tctgtgtagt gataattata taatttattt attttgaaaa aaaaaaaaa aaa
```

By "CAND1 polypeptide" is meant a polypeptide or fragment thereof having at least 85% amino acid sequence identity to NCBI Accession No. AAH26220.1 and having regulatory activity, for example, enhancing transcription from various types of promoters. An exemplary CAND1 polypeptide sequence is provided below (SEQ ID NO: 20):

```
  1 lgplvskvke yqvetivdtl ctnmlsdkeq lrdissiglk tvigelppas sgsalaanvc 61 kkitgrltsa iakqedvsvq lealdimadm lsrqggllvn fhpsiltcll pqltsprlav 121 rkrtiialgh lvmscgnivf vdliehllse lskndsmstt rtyiqciaai srqaghrige 181 ylekiiplvv kfcnvdddel reyciqafes fvrrcpkevy phvstiinic lkyltydpny 241 nyddededen amdadggddd dqgsddeysd dddmswkvrr aaakcldavv strhemlpef 301 yktvspalis rfkereenvk advfhaylsl lkqtrpvqsw lcdpdameqg etpltmlqsq 361 vpnivkalhk qmkeksvktr qccfnmltel vnvlpgaltq hipvlvpgii fslndkssss
```

-continued

```
 421  nlkidalscl yvilcnhspq vfhphvgalv ppvvacvgdp fykitseall vtqqlvkvir
 481  pldqpssfda tpyikdlftc tikrlkaadi dqevkerais cmgqiicnlg dnlgsdlpnt
 541  lqiflerlkn eitrlttvka ltliagsplk idlrpvlgeg vpilasflrk nqralklgtl
 601  saldilikny sdsltaamid avldelppli sesdmhvsqm aisflttlak vypsslskis
 661  gsilneligl vrspllqgga lsamldffqa lvvtgtnnlg ymdllrmltg pvysqstalt
 721  hkqsyysiak cvaaltracp kegpavvgqf iqdvknsrst dsirllalls lgevghhidl
 781  sgqlelksvi leafsspsee vksaasyalg sisvgnlpey lpfvlqeits qpkrqylllh
 841  slkeiissas vvglkpyven iwalllkhce caeegtrnvv aeclgkltli dpetllprlk
 901  gylisgssya rssvvtavkf tisdhpqpid pllkncigdf lktledpdln vrrvalvtfn
 961  saahnkpsli rdlldtvlph lynetkvrke lirevemgpf khtvddgldi rkaafecmyt
1021  lldscldrld ifeflnhved glkdhydikm ltflmlvrls ticpsavlqr ldrlveplra
1081  tcttkvkans vkqefekqde lkrsamrava alltipeaek splmsefqsq issnpelaai
1141  fesiqkdsss tnlesmdts
```

By "CAND1 polynucleotide" is meant a nucleic acid molecule encoding a CAND1 polypeptide. An exemplary CAND1 polynucleotide sequence is provided at NCBI Accession No. NM_018448.4, which is reproduced below (SEQ ID NO: 21):

```
   1  gtgaactctg accttagctt tccgtagcgc ccgcgtctgc cgccccgcc cccggagcga
  61  aggaggcggg ctttggcctt ttgccctagg gagcgagtgc ggagcgagtg ggagcgagac
 121  ggccctgagt ggaagtgtct ggctccccgt agaggccctt ctgtacgccc cgccgcccat
 181  gagctcgttc tcacgcgaac agcgccgtcg ttaggctggc tctgtagcct cggcttaccc
 241  cgggacaggc ccacgcctcg ccaggagggg ggcagcccgt cgaggcgcct ccctagtcag
 301  cgtcggcgtc gcgctgcgac cctggaagcg ggagccgccg cgagcgagag gaggagctcc
 361  agtggcggcg gcggcggcgg cagcggcagc gggcagcagc tccagcagcg ccagcaggcg
 421  ggatcgaggc cgtcaacatg cgcagcgcct cgtaccacat ttccaatttg ctggaaaaaa
 481  tgacatccag cgacaaggac tttaggttta tggctacaaa tgatttgatg acggaactgc
 541  agaaagattc catccagttg gatgatgata gtgaaaggaa agtagtgaaa atgattttga
 601  agttattgga agataaaaat ggagaggtac agaatttagc tgtcaaatgt cttggtcctt
 661  tagtgagtaa agtgaaagaa taccaagtag agacaattgt agataccctc tgcactaaca
 721  tgctttctga taagaacaa cttcgagaca tttcaagtat tggtcttaaa acagtaattg
 781  gagaacttcc tccagcttcc agtggctctg cattagctgc taatgtatgt aaaaagatta
 841  ctggacgtct tacaagtgca atagcaaaac aggaagatgt ctctgttcag ctagaagcct
 901  tggatattat ggctgatatt tgagcaggc aaggaggact tcttgttaat ttccatcctt
 961  caattctgac ctgtctactt ccccagttga ccagccctag acttgcagtg aggaaaagaa
1021  ccattatcgc tcttggccat ctggttatga gctgtggaaa tatagttttt gtagatctta
1081  ttgaacatct gttgtcagag ttgtccaaaa atgattctat gtcaacaaca agaacctaca
1141  tacaatgtat tgctgctatt agtaggcaag ctggtcatag aataggtgaa taccttgaga
1201  agataattcc tttggtggta aaattttgca atgtagatga tgatgaatta agagagtact
1261  gtattcaagc ctttgaatca tttgtaagaa gatgtcctaa ggaagtatat cctcatgttt
1321  ctaccattat aaatatttgt cttaaatatc ttacctatga tccaaattat aattacgatg
```

-continued

```
1381 atgaagatga agatgaaaat gcaatggatg ctgatggtgg tgatgatgat gatcaaggga 1441 gtgatgatga atacagtgat gatgatgaca tgagttggaa agtgagacgt gcagctgcga 1501 agtgcttgga tgctgtagtt agcacaaggc atgaaatgct tccagaattc tacaagaccg 1561 tctctcctgc actaatatcc agatttaaag agcgtgaaga gaatgtaaag gcagatgttt 1621 ttcacgcata cctttctctt ttgaagcaaa ctcgtcctgt acaaagttgg ctatgtgacc 1681 ctgatgcaat ggagcaggga gaaacacctt taacaatgct tcagagtcag gttcccaaca 1741 ttgttaaagc tcttcacaaa cagatgaaag aaaaaagtgt gaagacccga cagtgttgtt 1801 ttaacatgtt aactgagctg gtaaatgtat tacctggggc cctaactcaa cacattcctg 1861 tacttgtacc aggaatcatt ttctcactga atgataaatc aagctcatcg aatttgaaga 1921 tcgatgcttt gtcatgtcta tacgtaatcc tctgtaacca ttctcctcaa gtcttccatc 1981 ctcacgttca ggctttggtt cctccagtgg tggcttgtgt tggagaccca ttttacaaaa 2041 ttacatctga agcacttctt gttactcaac agcttgtcaa agtaattcgt cctttagatc 2101 agccttcctc gtttgatgca actccttata tcaaagatct atttacctgt accattaaga 2161 gattaaaagc agctgacatt gatcaggaag tcaaggaaag ggctatttcc tgtatgggac 2221 aaattatttg caaccttgga gacaatttgg gttctgactt gcctaataca cttcagattt 2281 tcttggagag actaagaat gaaattacca ggttaactac agtaaaggca ttgacactga 2341 ttgctgggtc acctttgaag atagatttga ggcctgttct gggagaaggg gttcctatcc 2401 ttgcttcatt tcttagaaaa aaccagagag ctttgaaact gggtactctt tctgcccttg 2461 atattctaat aaaaaactat agtgacagct tgacagctgc catgattgat gcagttctag 2521 atgagctccc acctcttatc agcgaaagtg atatgcatgt ttcacaaatg gccatcagtt 2581 ttcttaccac tttggcaaaa gtatatccct cctcccttc aaagataagt ggatccattc 2641 tcaatgaact tattggactt gtgagatcac ccttattgca gggggagct cttagtgcca 2701 tgctagactt tttccaagct ctggttgtca ctggaacaaa taatttagga tacatggatt 2761 tgttgcgcat gctgactggt ccagtttact ctcagagcac agctcttact cataagcagt 2821 cttattattc cattgccaaa tgtgtagctg cccttactcg agcatgccct aaagagggac 2881 cagctgtagt aggtcagttt attcaagatg tcaagaactc aaggtctaca gattccattc 2941 gtctcttagc tctactttct cttggagaag ttgggcatca tattgactta agtggacagt 3001 tggaactaaa atctgtaata ctagaagctt tctcatctcc tagtgaagaa gtcaaatcag 3061 ctgcatccta tgcattaggc agcattagtg tgggcaacct tcctgaatat ctgccgtttg 3121 tcctgcaaga ataactagt caacccaaaa ggcagtatct tttacttcat tccttgaagg 3181 aaattattag ctctgcatca gtggtgggcc ttaaaccata tgttgaaaac atctgggcct 3241 tattactaaa gcactgtgag tgtgcagagg aaggaaccag aaatgttgtt gctgaatgtc 3301 taggaaaact cactctaatt gatccagaaa ctctccttcc acggcttaag gggtacttga 3361 tatcaggctc atcatatgcc cgaagctcag tggttacggc tgtgaaattt acaatttctg 3421 accatccaca acctattgat ccactgttaa gaactgcat aggtgatttc ctaaaaactt 3481 tggaagaccc agatttgaat gtgagaagag tagccttggt cacatttaat tcagcagcac 3541 ataacaagcc atcattaata agggatctat tggatactgt tcttccacat ctttacaatg 3601 aaacaaaagt tagaaaggag cttataagag aggtagaaat gggtccattt aaacatacgg 3661 ttgatgatgg tctggatatt agaaaggcag catttgagtg tatgtacaca cttctagaca 3721 gttgtcttga tagacttgat atctttgaat ttctaaatca tgttgaagat ggtttgaagg 3781 accattatga tattaagatg ctgacatttt taatgttggt gagactgtct acccttgtc
```

-continued

```
3841 caagtgcagt actgcagagg ttggaccgac ttgttgagcc attacgtgca acatgtacaa
3901 ctaaggtaaa ggcaaactca gtaaagcagg agtttgaaaa acaagatgaa ttaaagcgat
3961 ctgccatgag agcagtagca gcactgctaa ccattccaga agcagagaag agtccactga
4021 tgagtgaatt ccagtcacag atcagttcta accctgagct ggcggctatc tttgaaagta
4081 tccagaaaga ttcatcatct actaacttgg aatcaatgga cactagttag atgtttgttc
4141 accatgggga ccattacata tgaccataca atgcactgaa ttgacaggtt aatcataaga
4201 catggaaaga gaagtgtcta aaagcttcaa aatgttccac ttttttttcc ttcatggaga
4261 ctgtttgttt ggctttcttc cattgttgtt tttgtagcat ttatttcaga aatgtgtatt
4321 tccataatcc agaggttgta aaaccactag tgttttagtg gttacagcaa catttgaaat
4381 ggaaactaaa agttaggatt ttatgtgagta tggagatagg gtccagtatc tatttaccct
4441 gtaatgttta ggattaaaat gttaaaattt tgtgaccatg aatttctttc ttttataaat
4501 tttctcattt aaaaatcaaa aatcttgcaa aacaaaaacc atgtttcttt tcttgtata
4561 actttttgtt ttcagcaaca taaattgatt tttagctggc agacaagaat atccatataa
4621 gatttgttaa ccatttcaga gagtttggca atttttaaaa gataataagg tatcattttt
4681 aagtatgaaa attaacaata tccctgttgc gcacactaat tttgcatgag taagtttaca
4741 aatatgtatc gtctgtaaag cagcatgtgc agattattca taatatagaa gttaaaataa
4801 gtattagtgc aattttcaga tatttatttt tgcacagaaa acacattatc tggagagaaa
4861 gaaaggagaa ttttttgagac ttgggttttc ttaatgccag tgtgaatttg cagatgtttt
4921 cagaaaatca agtcacagta acaatttgcc acttttttct attataaatc ttcttactta
4981 aattttgaat atttagtttt tctcagttac ccatttgtgt gtgtgtgatt ccacttagaa
5041 attcttaaaa ccagattttt ctttcattcc gtttggatgt ctacattcct tatcaaagga
5101 tataaatact gtgtatgctt ttgaatttta tttttaggaa aattctgaag ccagctatca
5161 caggtttgtt agctaataat agtattttct tttagttgag ttaggttttt ccccatctcc
5221 tgtagagcga atttacatat tgtattgggt aagtgttcac tacttttcct gattaaggga
5281 tctgtgctgg ggaacaaagc ttttgcagta ccttatattg tagttaaaat tttatttaac
5341 atatccttca gtgagctcat ttcacactgt agcctcttcc ttaaaatttg tggtgctcct
5401 gtaacagtaa gaactaattc tgaaataaaa gacatctcct aatgctgtgc aaacatagtt
5461 tacatgtatt gaaggaggca gttgttaaat tgagtgacca atttaagcaa tcagatattt
5521 gaaaactgca ccctttagtt ttgaaactgt gaattagaaa cactttttcct gctgtattac
5581 tacctgcttt aacatccaaa tatacagtga ttttaaatga taacatactg tggttattag
5641 attaacagct tgattttgaa tgttcagatg ataatgcaga agacatcact tctagtaagg
5701 attttgacta gtgcattgat gttgaagttg gtgccatttc aaaatgtggc aggtgataat
5761 cttttaccat aatttgcata aaactgtaat agaagtttat tttgagatgt tagtatatta
5821 tgtactatgc atttctgtgg tatagatgtt gtggatatat ttaagtattt ggttacatgg
5881 ttttacaata aattacaata ctgcaggctc taggactgaa caggagactg acatgcatat
5941 gttgtgtgaa tgtcttagtt gggtaaagtt aaatccaaat acttcaactg gcaaaaaaaa
6001 aaaaaaaaaa
```

By "DDB1 (DNA damage-binding protein 1) polypeptide" is meant a polypeptide or fragment thereof having at least 85% amino acid sequence identity to NCBI Accession No. NP_001914.3 and having regulatory activity of CUL4A- and CUL4B-based E3 ubiquitin ligase complexes and nucleotide excision repair activity. An exemplary DDB1 polypeptide sequence is provided below (SEQ ID NO: 22):

```
   1 msynyvvtaq kptavngcvt ghftsaedln lliakntrle iyvvtaeglr pvkevgmygk
  61 iavmelfrpk geskdllfil takynacile ykqsgesidi itrahgnvqd rigrpsetgi
 121 igiidpecrm iglrlydglf kvipldrdnk elkafnirle elhvidvkfl ygcqapticf
 181 vyqdpqgrhv ktyevslrek efnkgpwkqe nveaeasmvi avpepfggai iigqesityh
 241 ngdkylaiap piikqstivc hnrvdpngsr yllgdmegrl fmlllekeeq mdgtvtlkdl
 301 rvellgetsi aecltyldng vvfvgsrlgd sqlvklnvds necosyvvam etftnlgpiv
 361 dmcvvdlerq gqgqlvtcsg afkegslrii rngigiheha sidlpgikgl wpirsdpnre
 421 tddtivlsfv gqtrvlmlng eeveetelmg fvddqqtffc gnvahqqliq itsasvrlvs
 481 qepkalvsew kepqaknisv ascnssqvvv avgralyylq ihpqelrqis htemehevac
 541 lditplgdsn glsplcaigl wtdisarilk lpsfellhke mlggeiiprs ilmttfessh
 601 yllcalgdga lfyfglniet gllsdrkkvt lgtqptvlrt frslsttnvf acsdrptviy
 661 ssnhklvfsn vnlkevnymc pinsdgypds lalannstlt igtideiqkl hirtvplyes
 721 prkicyqevs qcfgvlssri evqdtsggtt alrpsastqa lsssyssskl fssstaphet
 781 sfgeevevhn lliidqhtfe vlhahqflqn eyalslvsck lgkdpntyfi vgtamvypee
 841 aepkqgrivv fqysdgklqt vaekevkgav ysmvefngkl lasinstvrl yewttekelr
 901 tecnhynnim alylktkgdf ilvgdlmrsv lllaykpmeg nfeeiardfn pnwmsaveil
 961 dddnflgaen afnlfvcqkd saattdeerq hlqevglfhl gefvnvfchg slvmqnlget
1021 stptqgsvlf gtvngmiglv tslseswynl lldmqnrink viksvgkieh sfwrsfhter
1081 ktepatgfid gdliesfldi srpkmqevva nlqyddgsgm kreataddli kvveeltrih
```

By "DDB1 polynucleotide" is meant a nucleic acid molecule encoding a DDB1 polypeptide. An exemplary DDB1 polynucleotide sequence is provided at NCBI Accession No. NM_001923.4, which is reproduced below (SEQ ID NO: 23):

```
   1 ggtgcctccg ggggcggggc ctccttcggt tggcggcctc gggcttcggg agtcctccaa
  61 gaggccaggt gaggccgtcc cgtgatgccc cgcgccccgg ccgctctggc ctgcaacgtg
 121 tctctggggc ggaggcagcg gcagtggagt tcgctgcgcg ctgttggggg ccacctgtct
 181 tttcgcttgt gtccctcttt ctagtgtcgc gctcgagtcc cgacgggccg ctccaagcct
 241 cgacatgtcg tacaactacg tggtaacggc ccagaagccc accgccgtga acggctgcgt
 301 gaccggacac tttacttcgg ccgaagactt aaacctgttg attgccaaaa acacgagatt
 361 agagatctat gtggtcaccg ccgaggggct tcggcccgtc aaagaggtgg gcatgtatgg
 421 gaagattgcg gtcatggagc ttttcaggcc caaggggggag agcaaggacc tgctgtttat
 481 cttgacagcg aagtacaatg cctgcatcct ggagtataaa cagagtggcg agagcattga
 541 catcattacg cgagcccatg gcaatgtcca ggaccgcatt ggccgcccct cagagaccgg
 601 cattattggc atcattgacc ctgagtgccg gatgattggc ctgcgtctct atgatggcct
 661 tttcaaggtt attccactag atcgcgataa taagaactc aaggccttca acatccgcct
 721 ggaggagctg catgtcattg atgtcaagtt cctatatggt tgccaagcac ctactatttg
```

```
 781 ctttgtctac caggaccctc aggggcggca cgtaaaaacc tatgaggtgt ctctccgaga
 841 aaaggaattc aataagggcc cttggaaaca ggaaaatgtc gaagctgaag cttccatggt
 901 gatcgcagtc ccagagccct ttgggggggc catcatcatt ggacaggagt caatcaccta
 961 tcacaatggt gacaaatacc tggctattgc ccctcctatc atcaagcaaa gcacgattgt
1021 gtgccacaat cgagtggacc ctaatggctc aagatacctg ctgggagaca tggaaggccg
1081 gctcttcatg ctgcttttgg agaaggagga acagatggat ggcaccgtca ctctcaagga
1141 tctccgtgta gaactccttg gagagacctc tattgctgag tgcttgacat accttgataa
1201 tggtgttgtg tttgtcgggt ctcgcctggg tgactcccag cttgtgaagc tcaacgttga
1261 cagtaatgaa caaggctcct atgtagtggc catggaaacc tttaccaact taggacccat
1321 tgtcgatatg tgcgtggtgg acctgagag gcaggggcag gggcagctgg tcacttgctc
1381 tggggctttc aaggaaggtt cttttgcggat catccggaat ggaattggaa tccacgagca
1441 tgccagcatt gacttaccag gcatcaaagg attatggcca ctgcggtctg accctaatcg
1501 tgagactgat gacactttgg tgctctcttt tgtgggccag acaagagttc tcatgttaaa
1561 tggagaggag gtagaagaaa ccgaactgat gggtttcgtg gatgatcagc agactttctt
1621 ctgtggcaac gtggctcatc agcagcttat ccagatcact tcagcatcgg tgaggttggt
1681 ctctcaagaa cccaaagctc tggtcagtga atggaaggag cctcaggcca agaacatcag
1741 tgtggcctcc tgcaatagca gccaggtggt ggtggctgta ggcagggccc tctactatct
1801 gcagatccat cctcaggagc tccggcagat cagccacaca gagatggaac atgaagtggc
1861 ttgcttggac atcaccccat aggagacag caatggactg tcccctcttt gtgccattgg
1921 cctctggacg gacatctcgg ctcgtatctt gaagttgccc tcttttgaac tactgcacaa
1981 ggagatgctg ggtggagaga tcattcctcg ctccatcctg atgaccacct ttgagagtag
2041 ccattacctc ctttgtgcct tgggagatgg agcgcttttc tactttgggc tcaacattga
2101 gacaggtctg ttgagcgacc gtaagaaggt gactttgggc acccagccca ccgtattgag
2161 gacttttcgt tctcttttcta ccaccaacgt ctttgcttgt tctgaccgcc ccactgtcat
2221 ctatagcagc aaccacaaat tggtcttctc aaatgtcaac ctcaaggaag tgaactacat
2281 gtgtcccctc aattcagatg ctatcctga cagcctggcg ctggccaaca atagcaccct
2341 caccattggc accatcgatg agatccagaa gctgcacatt cgcacagttc ccctctatga
2401 gtctccaagg aagatctgct accaggaagt gtcccagtgt ttcggggtcc tctccagccg
2461 cattgaagtc caagacacga gtgggggcac gacagccttg aggcccagcg ctagcaccca
2521 ggctctgtcc agcagtgtaa gctccagcaa gctgttctcc agcagcactg ctcctcatga
2581 gacctccttt ggagaagagg tggaggtgca caacctactt atcattgacc aacacacctt
2641 tgaagtgctt catgcccacc agtttctgca gaatgaatat gccctcagtc tggtttcctg
2701 caagctgggc aaagacccca acacttactt cattgtgggc acagcaatgg tgtatcctga
2761 agaggcagag cccaagcagg gtcgcattgt ggtctttcag tattcggatg gaaaactaca
2821 gactgtggct gaaaaggaag tgaaaggggc cgtgtactct atggtggaat taacgggaa
2881 gctgttagcc agcatcaata gcacggtgcg gctctatgag tggacaacag agaaggagct
2941 gcgcactgag tgcaaccact acaacaacat catggccctc tacctgaaga ccaagggcga
3001 cttcatcctg gtgggcgacc ttatgcgctc agtgctgctg cttgcctaca gcccatgga
3061 aggaaacttt gaagagattg ctcgagactt taatcccaac tggatgagtg ctgtggaaat
3121 cttggatgat gacaatttc tgggggctga aaatgccttt aacttgtttg tgtgtcaaaa
```

-continued

```
3181 ggatagcgct gccaccactg acgaggagcg gcagcacctc caggaggttg gtcttttcca
3241 cctgggcgag tttgtcaatg tcttttgcca cggctctctg gtaatgcaga atctgggtga
3301 gacttccacc cccacacaag gctcggtgct cttcggcacg gtcaacggca tgatagggct
3361 ggtgacctca ctgtcagaga gctggtacaa cctcctgctg gacatgcaga atcgactcaa
3421 taaagtcatc aaaagtgtgg ggaagatcga gcactccttc tggagatcct ttcacaccga
3481 gcggaagaca gaaccagcca caggtttcat cgacggtgac ttgattgaga gtttcctgga
3541 tattagccgc cccaagatgc aggaggtggt ggcaaaccta cagtatgacg atggcagcgg
3601 tatgaagcga gaggccactg cagacgacct catcaaggtt gtggaggagc taactcggat
3661 ccattagcca agggcagggg gcccctttgc tgaccctccc caaaggcttt gccctgctgc
3721 cctcccctc ctctccacca tcgtcttctt ggccatggga ggctttccc taagccagct
3781 gccccagag ccacagttcc cctatgtgga agtggggcgg gcttcataga gacttgggaa
3841 tgagctgaag gtgaaacatt ttctccctgg atttttacca gtctcacatg attccagcca
3901 tcaccttaga ccaccaagcc ttgattggtg ttgccagttg tcctccttcc ggggaaggat
3961 tttgcagttc tttggctgaa aggaagctgt gcgtgtgtgt gtgtgtatgt gtgtgtgtgt
4021 atgtgtatct cacactcatg cattgtcctc tttttattta gattggcagt gtagggagtt
4081 gtgggtagtg gggaagaggg ttaggagggt ttcattgtct gtgaagtgag accttccttt
4141 tacttttctt ctattgcctc tgagagcatc aggcctagag gcctgactgc caagccatgg
4201 gtagcctggg tgtaaaacct ggagatggtg gatgatcccc acgccacagc ccttttgtct
4261 ctgcaaactg ccttcttcgg aaagaagaag gtgggaggat gtgaattgtt agtttctgag
4321 ttttaccaaa taaagtagaa tataagaaga aggtaaaaa aaaaaaaaaa aa
```

By "DEPDC5 (DEP domain-containing 5) polypeptide" is meant a polypeptide or fragment thereof having at least 85% amino acid sequence identity to NCBI Accession No. AAI36613.1 and having intracellular signal transduction activity. An exemplary DEPDC5 polypeptide sequence is provided below (SEQ ID NO: 24):

```
  1 mrttkvyklv ihkkgfggsd delvvnpkvf phiklgdive iahpndeysp lllqvkslke
 61 dlqketisvd qtvtqvfrlr pyqdvyvnvv dpkdvtldlv eltfkdqyig rgdmwrlkks
121 lvstcayitq kvefagiraq agelwvknek vmcgyisedt rvvfrstsam vyifiqmsce
181 mwdfdiygdl yfekavngfl adlftkwkek ncshevtvvl fsrtfydaks vdefpeinra
241 sirqdhkgrf yedfykvvvq nerreewtsl lvtikklfiq ypvlvrleqa egfpqgdnst
301 saconyleai nlsfnvfdkh yinrnfdrtg qmsvvitpgv gvfevdrllm iltkqrmidn
361 gigvdlvcmg eqplhavplf klhnrsaprd srlgddynip hwinhsfyts ksqlfcnsft
421 priklagkkp asekakngrd tslgspkese nalpiqvdyd aydaqvfrlp gpsraqcltt
481 crsvreresh srksasscdv ssspslpsrt lpteevrsqa sddsslgksa nilmiphphl
541 hqyevssslg ytstrdvlen mmeppqrdss apgrfhvgsa esmlhvrpgg ytpqralinp
601 fapsrmpmkl tsnrrrwmht fpvgpsgeai qihhqtrqnm aelqgsgqrd pthssaelle
661 layheaagrh snsrqpgdgm sflnfsgtee lsvgllsnsg agmnprtqnk dsledsysts
721 pdpiltlsap pvvpgfcctv gvdwkslttp aclplttdyf pdrqglqndy tegcydllpe
781 adidrrdedg vqmtaqqvfe eficqrlmqg yqiivqpktq kpnpavpppl sssplysrgl
841 vsrnrpeeed qywlsmgrtf hkvtlkdkmi tvtrylpkyp yesaqihyty slcpshsdse
901 fvscwvefsh erleeykwny ldqyicsags edfslieslk fwrtrflllp acvtatkrit
961 egeahcdiyg drpradedew qlldgfvrfv eglnrirrrh rsdrmmrkgt amkglqmtgp
```

-continued

```
1021 isthslesta ppvgkkgtsa lsallemeas qkclgeqqaa vhggkssaqs aesssvamtp 1081 tymdsprkdg affmefvrsp rtassafypq vsvdqtatpm ldgtslgict gqsmdrgnsq 1141 tfgnsqnige qgysstnssd sssqqlvass ltssstltei leamkhpstg vqllseqkgl 1201 spycfisaev vhwlvnhveg iqtqamaidi mqkmleeqli thasgeawrt fiygfyfyki 1261 vtdkepdrva mqqpattwht agvddfasfq rkwfevafva eelvhseipa fllpwlpsrp 1321 asyasrhssf srsfggrsqa aallaatvpe qrtvtldvdv nnrtdrlewc scyyhgnfsl 1381 naafeiklhw mavtaavlfe mvqgwhrkat scgfllvpvl egpfalpsyl ygdplraqlf 1441 ipiniscllk egsehlfdsf epetywdrmh lfqeaiahrf gfvqdkysas afnfpaenkp 1501 qyihvtgtvf lqlpyskrkf sgqqrrrrns tsstnqnmfc eervgynway ntmltktwrs 1561 satgdekfad rllkdftdfc inrdnrlvtf wtsclekmha sap
```

By "DEPDC5 polynucleotide" is meant a nucleic acid molecule encoding a DEPDC5 polypeptide. An exemplary DEPDC5 polynucleotide sequence is provided at NCBI Accession No. NM_014662.4, which is reproduced below (SEQ ID NO: 25):

```
   1 ggaggcaaga tgacttctct gccccaagct tggaacagct aaagggaaaa acagtgcaag 61 atgagaacaa caaaggtcta caaactcgtc atccacaaga agggctttgg gggcagtgat 121 gatgagctag ttgtgaaccc caaagtgttc cctcacatca gcttggaga cattgtagag 181 attgcacacc ccaacgatga atacagcccct ctgcttttgc aggtcaagtc tcttaaggaa 241 gatttacaga aggaaactat cagtgtggac cagactgtga ctcaagtgtt ccggctgaga 301 ccttatcagg atgtctatgt taatgtcgta gaccctaagg atgtgaccct tgacctagtg 361 gaattaactt taaggatca gtatattggc cgtggggata tgtggcgact aaagaaaagt 421 ttggtcagca catgtgccta tatcacccag aaggtggagt ttgctggcat cagagcacag 481 gctggtgaac tgtgggttaa gaatgagaag gtcatgtgtg ctacatcag tgaagatacc 541 agggtggtgt ttcgttctac gtcggctatg gtttacatat ttattcagat gagctgtgaa 601 atgtgggatt ttgatattta tggggatttg tattttgaga aagctgtgaa tggtttcctt 661 gctgatctat ttaccaagtg gaaggagaag aactgtagtc atgaagtgac agtggtcctg 721 ttttctagaa cttttctatga tgcaaaatct gttgatgaat tcctgaaat aaaccgagcc 781 tcaattcgac aggatcacaa ggggagattc tatgaagact tttacaaagt ggtggtgcag 841 aatgagagaa gagaagaatg gacttcactt ctcgtaacca ttaaaaaact cttcatccag 901 tatccagtgt tggtgcgact ggaacaggca gagggctttc ctcaaggaga taattctacc 961 tcagcacaag gaaactacct ggaggccatc aatctgtcat tcaatgtgtt tgataagcac 1021 tacatcaacc gcaactttga ccgaactggg cagatgtcag tggtgatcac gcccggggtg 1081 ggtgtctttg aagtggaccg cctactcatg atcctgacca gcagcggat gatagataat 1141 ggaattggtg tggatttggt gtgcatggga gagcaaccgt tacatgctgt cccattgttc 1201 aagctccata tcggagtgc tcccgtgat tctcgtctgg gcgatgacta taatatccct 1261 cactggataa accacagttt ctacacatcc aaaagccagc tcttttgtaa tagtttcacc 1321 ccacgaataa aactggcagg aaagaagccc gcctctgaga aagcaaaaaa tggccgtgat 1381 acatctctcg ggagtccaaa agaatctgag aacgcccttc ccatccaagt agattatgac 1441 gcctatgacg ctcaagtgtt caggctgccc ggcccatccc gggcccagtg cctcaccacc 1501 tgcagatctg tgcgagagcg agagagtcac agtcgaaaga gtgccagctc ctgtgatgtt
```

-continued

```
1561 tcatccagcc cttccctacc aagccgcaca ctgcccactg aggaagtgag gagccaggct 1621 tctgacgaca gctccctagg caagagtgcc aacatcctga tgatcccaca cccccacctg 1681 caccagtatg aagtcagcag ctccttggga tacaccagca ctcgagatgt cctggagaac 1741 atgatggagc caccacagcg agactccagt gcaccaggga ggtttcacgt tggcagtgca 1801 gaatccatgc tgcatgttcg acctggtgga tacacgcccc agagagcact gattaacccc 1861 ttcgctccct ctcggatgcc catgaagctt acgtccaaca gaaggcgctg gatgcacact 1921 tttcctgtgg ggccatccgg agaagccatc cagatccacc accagacccg acagaatatg 1981 gcggagctac aaggcagcgg gcagagggat ccaactcact cctctgcaga gctgctggag 2041 ttagcatatc atgaagctgc tggaaggcac agcaattccc gccagcctgg tgacggcatg 2101 tccttcttga acttcagtgg aacagaggag ctttctgtcg gcctgcttag caacagtggt 2161 gcaggtatga atcctaggac ccagaataag gattctctag aggacagtgt ttctacctct 2221 ccagacccaa tgccaggctt ctgttgcaca gttggagtgg actggaagtc tctcactact 2281 ccggcgtgcc tccccttac caccgactac ttccctgacc gccagggcct gcagaatgac 2341 tacacagagg gctgttatga tctccttcca gaagcagaca tcgacaggag ggacgaagat 2401 ggtgtgcaga tgacagccca gcaggtattt gaagagttta tttgccaacg tctcatgcag 2461 ggctaccaaa tcatagtgca gcccaagaca cagaaaccca atcctgctgt cccgcccccg 2521 ctgagcagta gcccactcta tagccgaggc cttgtgtccc gaaaccgccc tgaggaggag 2581 gaccagtatt ggctgagtat gggcagaacg ttccacaaag tgacgctgaa ggataagatg 2641 atcacagtga cgcgatacct tcccaagtat ccttatgaat ctgcccagat ccactacacc 2701 tacagcctct gtccttccca ctcagactca gagttcgtct cctgctgggt ggaattctcc 2761 cacgaacggc tggaggagta caagtggaat tacttagatc agtatatctg ttctgccggc 2821 tctgaagact tcagcttaat tgagtccctg aagttctgga ggacccgctt cctgctgctg 2881 ccagcctgtg tcaccgccac caagcgcatc acggaggggg aggcccactg cgacatctat 2941 ggggacaggc cccgtgcaga cgaggacgag tggcaactcc tggatggttt tgtccgcttt 3001 gtggagggct tgaatcgcat tcgcaggcgg catcgctcgg atcgcatgat gcggaagggg 3061 accgccatga aaggcttgca gatgactggg cccatttcca cgcattctct ggagtcaact 3121 gcaccccag tggggaagaa gggaacctca gctctctctg ccctgttgga gatggaggcc 3181 agtcagaagt gcctgggaga acagcaggca gctgtgcatg gtgggaagag ctccgcccag 3241 tcagccgaga gcagcagcgt tgccatgact cccacctaca tggacagccc acgaaaggta 3301 tctgtggacc aaacagccac tcctatgttg gacggcacca gtttgggcat atgcacaggc 3361 caatccatgg acagaggcaa cagccagacc tttgggaact cccagaacat aggagaacag 3421 ggctactcct ccacaaactc cagtgacagc agctctcagc agctggtggc aagctccttg 3481 acctcatcct ctaccctgac agagatcctg aagccatga agcaccctc gacaggagtc 3541 cagctgctct ctgaacagaa gggcctctca ccgtactgct tcatcagcgc ggaggtggta 3601 cactggttgg tgaaccacgt ggaggggatc cagacacagg cgatggccat tgacatcatg 3661 cagaaaatgc tggaagagca gctcatcaca catgcatctg gcgaagcctg gcggaccttc 3721 atctacggct tctatttcta caagatagta acggacaaag agcccgaccg agtggccatg 3781 cagcagcccg ccaccacctg gcacacagca ggagtggacg acttcgccag cttccagcgc 3841 aagtggttg aggtggcctt tgtggcagaa gagctcgtgc actctgagat tcctgccttt 3901 ctcctgccct ggctgcctag ccggccagcc tcctatgcaa gtaggcacag ctcctttagc 3961 cgaagttttg gaggacggag ccaggcggca gcactttag ctgccactgt cccagagcag
```

```
4021 aggactgtga ccctggatgt tgacgtgaac aaccgcacag accggctgga gtggtgcagc
4081 tgttattacc atggcaactt ttctctgaat gcagcctttg agatcaagct gcactggatg
4141 gcggtgaccg cagcagtact cttcgagatg gtccaaggtt ggcatcggaa agccacctcc
4201 tgtggcttct tgttagtccc agttttggag gggccttttg cactgcccag ttacctgtat
4261 ggcgaccccc ttcgtgccca gctcttcatc ccactcaaca tcagctgctt gctcaaggag
4321 ggcagcgagc acctgtttga tagctttgaa cccgaaacgt actgggatcg aatgcacctc
4381 ttccaggaag ccattgcaca caggtttggg tttgtacaag ataaatattc tgcctctgct
4441 tttaacttcc ctgctgagaa caagcctcag tatatccacg ttacaggaac agtgtttctg
4501 cagctgccct actccaagcg caagttctca gggcagcagc ggcggcggcg gaactccacc
4561 agctccacca accagaacat gttctgcgag gagcgggtcg gctacaactg ggcctacaac
4621 accatgctca ccaaaacatg gcgctccagc gccacagggg atgaaaagtt tgctgatcgg
4681 ctgctgaagg acttcacgga cttctgcatc aaccgtgaca accggctggt cacgttctgg
4741 acaagttgcc tggagaagat gcatgccagt gccccgtgag gccaggctgc acctgtgctg
4801 ggggaaggtg ggtgagccac tgccctcaaa cccggggcgg aggattccag gcaggctcta
4861 ggagtcaggt gtccgtttgc tgctatcagt gagtgggggc cattgttttt tgtttgtttg
4921 tttgtttgtt tgtttgtttt tggccccac gacaagtctt ctactctaga agaaagactt
4981 tggaagcagc tgctgctgct gccaccactc ctgtcagcaa gtgctcagag caggtgggag
5041 gcacagattg tccgtgggag ggctccagtg tctgggaaga gggcaggcgg cccccatgaa
5101 tgtcctcgga aggggggtggc tcctggtagc atccttttcc ttcaccatct atgggatatt
5161 aggggcagaa tctgccactt cttgcccagg agtgtgcaca gatgtaagat aattttgtga
5221 aataatgtac catagactct caccaactgt atatacctgt acatatcaga agcaaataaa
5281 gagctccacg tgcatcattt ctttccccac ccagtt
```

By "EDC4 (Enhancer Of MRNA Decapping 4) polypeptide" is meant a polypeptide or fragment thereof having at least 85% amino acid sequence identity to NCBI Accession No. NP_055144.3 and having mRNA decapping and/or mRNA degradation activity. An exemplary EDC4 polypeptide sequence is provided below (SEQ ID NO: 26):

```
  1 mascasidie datqhlrdil kldrpaggps aesprpssay ngdingllvp dplcsgdsts
 61 anktglrtmp pinlqekqvi clsgddsstc igilakevei vassdssiss kargsnkvki
121 qpvakydweq kyyygnliav snsflayair aanngsamvr visystsert llkgftgsva
181 dlafahlnsp qlacldeagn lfvwrlalvn gkiqeeilvh irqpegtpin hfrriiwcpf
241 ipeesedcce essptvallh edraevwdld mlrsshstwp vdvsqikqgf ivvkghstcl
301 segalspdgt vlatashdgy vkfwqiyieg qdeprclhew kphdgrplsc llfcdnhkkq
361 dpdvpfwrfl itgadqnrel kmwctvswtc lqtirfspdi fssysvppsl kvcldlsaey
421 lilsdvqrkv lyvmellqnq eeghacfssi sefllthpvl sfgiqvvsrc rlrhtevlpa
481 eeendslgad gthgagames aagvliklfc vhtkalqdvq irfqpqlnpd vvaplpthta
541 hedftfgesr pelgseglgs aahgsqpdlr rivelpapad flslssetkp klmtpdafmt
601 psaslqqita spsssssgss ssssssssssl taysamssts avdpsltrpp eeltlspklq
661 ldgsltmsss gslqasprgl lpgllpapad kltpkgpgqv ptatsalsle lqeveplglp
721 qaspsrtrsp dvissastal sqdipeiase alsrgfgssa peglepdsma saasalhlls
781 prprpgpelg pqlgldggpg dgdrhntpsl leaaltqeas tpdsqvwpta pditretcst
841 laesprnglq ekhkslafhr ppyhllqqrd sqdasaeqsd hddevaslas asggfgtkvp
```

```
 901 aprlpakdwk tkgsprtspk lkrkskkddg daamgsrlte hqvaeppedw paliwqqqre 961 laelrhsqee llqrlctqle glqstvtghv eraletrheq eqrrlerala egqqrggqlq 1021 eqltqqlsqa lssavagrle rsirdeikkt vppcvsrsle pmagqlsnsv atkltavegs 1081 mkeniskllk sknitdaiar aaadtlqgpm qaayreafqs vvlpafeksc qamfqqinds 1141 frlgtqeylq qleshmksrk areqearepv laqlrglvst lqsateqmaa tvagsvraev 1201 qhqlhvavgs lqesilaqvq rivkgevsva lkeqqaavts simqamrsaa gtpvpsahld 1261 cqaqqahilq llqqghlnqa fqqaltaadl nlvlyvcetv dpaqvfgqpp cplsqpvlls 1321 liqqlasdlg trtdlklsyl eeavmhldhs dpitrdhmgs vmaqvrqklf qflqaephns 1381 lgkaarrlsl mlhglvtpsl p
```

By "EDC4 polynucleotide" is meant a nucleic acid molecule encoding an EDC4 polypeptide. An exemplary EDC4 polynucleotide sequence is provided at NCBI Accession No. NM_014329.4, which is reproduced below (SEQ ID NO: 27):

```
   1 tttcttctcc ggccctggca ggttccggga gcctcggctc gtgggtgccg gaagtggagg 61 cggttggtgg ggttggcggg gctcagcgac gctgcgcggg tggcggtttg cgaactgcgg 121 gtggactgtg tagtgaccgg cgtcccgctg tctcgccccg tggcgggtga gcgagggtgc 181 gtggtgcgcg gcggcggcgg aacgaacgcg gtgcgggcgg ggcgcccgcc gcagggccca 241 tggcctcctg cgcgagcatc gacatcgagg acgccacgca gcacctgcgg gacatcctca 301 agctggaccg gcccgcgggc ggccccagtg cagagagccc acggccatcc agtgcctaca 361 atggggacct caatggactt ctggtcccag acccgctctg ctcaggtgat agtacctcag 421 caaacaagac tggtcttcgg accatgccac ccattaacct gcaagagaag caggtcatct 481 gtctctcagg agatgatagc tccacctgca ttgggatttt ggccaaggag gtggagattg 541 tggctagcag tgactctagc atttcaagca aggcccgggg aagcaacaag gtgaaaattc 601 agcctgtcgc caagtatgac tgggaacaga agtactacta tggcaacctg attgctgtgt 661 ctaactcctt cttggcctat gccattcggg ctgccaacaa tggctctgcc atggtgcggg 721 tgatcagcgt cagcacttcg gagcggacct tgctcaaggg cttcacaggc agtgtggctg 781 atctggcttt cgcgcacctc aactctccac agctggcctg cctggatgag gcaggcaacc 841 tgttcgtgtg gcgcttggct ctggttaatg gcaaaattca agaagagatc ttggtccata 901 ttcggcagcc agagggcacg ccactgaacc actttcgcag gatcatctgg tgccccttca 961 tccctgagga gagcgaagac tgctgtgagg agagcagccc aacagtggcc ctgctgcatg 1021 aagaccgggc tgaggtgtgg gacctggaca tgctccgctc cagccacagt acctggcctg 1081 tggatgttag ccagatcaag cagggcttca ttgtggtaaa aggtcatagc acgtgcctca 1141 gtgaaggagc cctctctcct gatgggactg tgctggctac tgcgagccac gatggctatg 1201 tcaagttctg gcagatctac attgaggggc aagatgagcc aaggtgtctg cacgagtgga 1261 aacctcatga tgggcggccc ctctcctgcc tcctgttctg tgacaaccat aagaaacaag 1321 accctgatgt cccttctctgg aggttcctta ttactggtgc tgaccagaac cgagagttaa 1381 agatgtggta tacagtatcc tggacctgcc tgcagactat tcgcttctcc ccagatatct 1441 tcagctcagt gagtgtgccc cctagcctca aggtttgctt ggacctctca gcagaatacc 1501 tgattctcag cgatgtgcaa cggaaggtcc tctatgtgat ggagctgctg caaaaccagg 1561 aggagggcca cgcctgcttc agctccatct cggagttcct gctcacccac cctgtgctga
```

-continued

```
1621 gctttggtat ccaggttgtg agtcgctgcc ggctacggca cactgaggtg ctgcctgccg
1681 aagaggaaaa tgacagcctg ggtgctgatg gtacccatgg agccggtgcc atggagtctg
1741 cggccggtgt gctcatcaag ctcttttgtg tgcatactaa ggcactgcaa gatgtgcaga
1801 tccgcttcca gccacagctg aaccctgatg tggtggcccc actgcccacc cacactgccc
1861 acgaggactt cacatttgga gagtctcggc ccgaactggg ctctgagggc ctggggtcag
1921 ccgctcacgg ctcccagcct gacctccgac gaatcgtgga gctgcctgca cctgccgact
1981 tcctcagtct gagcagtgag accaagccca agttgatgac acctgacgcc ttcatgacac
2041 ctagcgcctc cttgcagcag atcactgcct ctcccagcag cagcagcagc ggtagcagca
2101 gcagcagcag cagtagcagc agctccctta cagctgtgtc tgccatgagc agcacctcag
2161 ctgtggaccc ctccttgacc aggccacctg aggagctgac cttgagcccc aagctgcagc
2221 tggatggcag cctgacaatg agcagcagtg gcagccttca ggcaagcccg cgtggcctcc
2281 tgcctggcct gctcccagcc ccagctgaca aactgactcc caaggggccg ggccaggtgc
2341 ctactgccac ctctgcactg tccctggagc tgcaggaagt ggagcccctg ggctacccc
2401 aagcctcccc tagccgcact cgttcccctg atgtcatctc ctcagcttcc actgccctgt
2461 cccaggacat ccctgagatt gcatctgagg ccctgtcccg tggttttggc tcctctgcac
2521 cagagggcct tgagccagac agtatggctt cagccgcctc ggcactgcac ctgctgtccc
2581 cacggccccg gccagggccc gagctcggcc cccagctcgg gcttgatgga ggccctgggg
2641 atggagatcg gcataatacc ccctcccctcc tggaggcagc cttgacccag gaggcctcga
2701 ctcctgacag tcaggtttgg cccacagcac ctgacattac tcgtgagacc tgcagcaccc
2761 tggcagaaag ccccaggaat ggccttcagg aaaagcacaa gagcctggcc ttccaccgac
2821 caccatatca cctgctgcag caacgtgaca gccaggatgc cagtgctgag caaagtgacc
2881 atgatgatga ggtggccagc cttgcctctg cttcaggagg cttttggcacc aaagttcctg
2941 ctccacggct gcctgccaag gactggaaga ccaagggatc ccctcgaacc tcacccaagc
3001 tcaagaggaa aagcaagaag gatgatgggg atgcagccat gggatcccgg ctcacagagc
3061 accaggtggc agagccccct gaggactggc agcactaat ttggcaacag cagagagagc
3121 tggcagagct gcggcacagc caggaagagc tgctgcagcg tctgtgtacc caactcgaag
3181 gcctgcagag cacagtcaca ggccacgtag aacgtgccct tgagactcgg cacgagcagg
3241 aacagcggcg gctggagcga gcactggctg aggggcagca gcggggaggg cagctgcagg
3301 agcagctgac acaacagttg tcccaagcac tgtcgtcagc tgtagctggg cggctagagc
3361 gcagcatacg ggatgagatc aagaagacag tccctccatg tgtctcaagg agtctggagc
3421 ctatggcagg ccaactgagc aactcagtgg ctaccaagct cacagctgtg gagggcagca
3481 tgaaagagaa catctccaag ctgctcaagt ccaagaactt gactgatgcc atcgcccgag
3541 cagctgcaga cacattacaa gggccgatgc aggctgccta ccgggaagcc ttccagagtg
3601 tggtgctgcc ggcctttgag aagagctgcc aggccatgtt ccagcaaatc aatgatagct
3661 tccggctggg gacacaggaa tacttgcagc agctagaaag ccacatgaag agccggaagg
3721 cacgggaaca ggaggccagg gagcctgtgc tagcccagct gcggggcctg gtcagcacac
3781 tgcagagtgc cactgagcag atggcagcca ccgtggccgg cagtgttcgt gctgaggtgc
3841 agcaccagct gcatgtggct gtgggcagcc tgcaggagtc catttttagca caggtacagc
3901 gcatcgttaa gggtgaggtg agtgtggcgc tcaaggagca gcaggccgcc gtcacctcca
3961 gcatcatgca ggccatgcgc tcagctgctg gcacacctgt cccctctgcc caccttgact
```

```
4021 gccaggccca gcaagcccat atcctgcagc tgctgcagca gggccacctc aatcaggcct 4081 tccagcaggc gctgacagct gctgacctga acctggtgct gtatgtgtgt gaaactgtgg 4141 acccagccca ggttttgggg cagccaccct gcccgctctc ccagcctgtg ctcctttccc 4201 tcatccagca gctggcatct gaccttggca ctcgaactga cctcaagctc agctacctgg 4261 aagaggccgt gatgcacctg accacagtg acccccatcac tcgggaccac atgggctccg 4321 ttatggccca ggtgcgccaa aagctttttc agttcctgca ggctgagcca cacaactcac 4381 ttggcaaagc agctcggcgt ctcagcctca tgctgcatgg cctcgtgacc cccagcctcc 4441 cttagctgct aagcctgcct tgcccagggg tgggatggca ctgaaggcca gcagacaggc 4501 ctaggctggg gcagggtcac ggctggcctt tacctgctca ggcccccatc tctggggtgt 4561 ttggggtca gggagcaggg agcactggcc gtggtctaca gcgtgtggta gtcagaaggt 4621 ttagctgggc ccagggcagg tattgcgcct gcttgggttc tgccatgcct ggagcatgac 4681 cctgagatcg tgacaccact tgagtggaat tttccatgtt cctttttacc tctaatttgg 4741 atcttttgt ttttgaaaaa cattgagaaa ttcaattaaa tgcttttgga ataaaatgga 4801 gtatgtgtgt g
```

By "EIF4A1 (Eukaryotic Translation Initiation Factor 4A1)) polypeptide" is meant a polypeptide or fragment thereof having at least 85% amino acid sequence identity to NCBI Accession No. NP_001407.1 and having RNA transport and translational control activity, including nucleic acid binding and hydrolase activity. An exemplary EIF4A1 polypeptide sequence is provided below (SEQ ID NO: 28):

```
  1 msasqdsrsr dngpdgmepe gviesnwnei vdsfddmnls esllrgiyay gfekpsaiqq 61 railpcikgy dviaqaqsgt gktatfaisi lqqieldlka tqalvlaptr elaqqiqkvv 121 malgdymgas chaciggtnv raevqklqme aphiivgtpg rvfdmlnrry lspkyikmfv 181 ldeademlsr gfkdqiydif qklnsntqvv llsatmpsdv levtkkfmrd pirilvkkee 241 ltlegirqfy invereewkl dticdlyetl titqavifin trrkvdwlte kmhardftvs 301 amhgdmdqke rdvimrefrs gssrvlittd llargidvqq vslvinydlp tnrenyihri 361 grggrfgrkg vainmvteed krtlrdietf yntsieempl nvadli
```

By "EIF4A1 polynucleotide" is meant a nucleic acid molecule encoding an EIF4A1 polypeptide. An exemplary EIF4A1 polynucleotide sequence is provided at NCBI Accession No. NM_001416.3, which is reproduced below (SEQ ID NO: 29):

```
  1 ggaactaacg tcatgccgag ttgctgagcg ccggcaggcg gggccggggc ggccaaacca 61 atgcgatggc cggggcggag tcgggcgctc tataagttgt cgataggcgg gcactccgcc 121 ctagtttcta aggatcatgt ctgcgagcca ggattcccga tccagagaca atggccccga 181 tgggatggag cccgaaggcg tcatcgagag taactggaat gagattgttg acagctttga 241 tgacatgaac ctctcggagt cccttctccg tggcatctac gcgtatggtt ttgagaagcc 301 ctctgccatc cagcagcgag ccattctacc ttgtatcaag ggttatgatg tgattgctca 361 agcccaatct gggactggga aaacggccac atttgccata tcgattctgc agcagattga 421 attagatcta aaagccaccc aggccttggt cctagcaccc actcgagaat ggctcagca 481 gatacagaag gtggtcatgg cactaggaga ctacatgggc gcctcctgtc acgcctgtat
```

```
 541 cgggggcacc aacgtgcgtg ctgaggtgca gaaactgcag atggaagctc cccacatcat 601 cgtgggtacc cctggccgtg tgtttgatat gcttaaccgg agatacctgt cccccaaata 661 catcaagatg tttgtactgg atgaagctga cgaaatgtta agccgtggat tcaaggacca 721 gatctatgac atattccaaa agctcaacag caacacccag gtagttttgc tgtcagccac 781 aatgccttct gatgtgcttg aggtgaccaa gaagttcatg agggacccca ttcggattct 841 tgtcaagaag gaagagttga ccctggaggg tatccgccag ttctacatca acgtggaacg 901 agaggagtgg aagctggaca cactatgtga cttgtatgaa accctgacca tcacccaggc 961 agtcatcttc atcaacaccc ggaggaaggt ggactggctc accgagaaga tgcatgctcg 1021 agatttcact gtatccgcca tgcatggaga tatggaccaa aaggaacgag acgtgattat 1081 gagggagttt cgttctggct ctagcagagt tttgattacc actgacctgc tggccagagg 1141 cattgatgtg cagcaggttt ctttagtcat caactatgac cttcccacca acagggaaaa 1201 ctatatccac agaatcggtc gaggtggacg gtttggccgt aaaggtgtgg ctattaacat 1261 ggtgacagaa gaagacaaga ggactcttcg agacattgag accttctaca acacctccat 1321 tgaggaaatg cccctcaatg ttgctgacct catctgaggg gctgtcctgc acccagccc 1381 cagccagggc tcaatctctg ggggctgagg agcagcagga ggggggaggg aagggagcca 1441 agggatggac atcttgtcat ttttttttctt tgaataaatg tcactttttg aggcaaaaga 1501 aggaaccgtg aacattttag acacccttt ctttggggta ggctcttgcc ccaggcgccg 1561 gctcttctcc caaaaaaaaa aaaaaacac taatccattt ccctaaccta gtaacctcca 1621 gatcccagag gctctcctca cctcagctga gctcctttga aagtgattca agggactatg 1681 tcactcagcc tcatttgctg gaccaaatct ggagggagaa cccctaaaac ccctaagtga 1741 ggttgcccag ggggttgtcc ccaggtgggg ggaagcaggg gagagaaaat ggtagccatt 1801 tttacattgt tttgtatagt atttattgat tcaggaaaca aacacaaaat tctgaataaa 1861 atgacttgga aactgccaaa aaaaaaaaaa aaa
```

By "GPS1 (G Protein Pathway Suppressor 1) polypeptide" is meant a polypeptide or fragment thereof having at least 85% amino acid sequence identity to NCBI Accession No. AAC50906.2 and having activity including ubiquitin (Ubl) conjugation pathway regulatory activity, suppression of G-protein and mitogen-activated signal transduction in mammalian cells and/or the deneddylation of the cullin subunits of SCF-type E3 ligase complexes. An exemplary GPS1 polypeptide sequence is provided below (SEQ ID NO: 30):

```
  1 mevdgtprrg gckmplpvqv fnlqgavepm qidvdpqedp qnapdvnyvv enpsldleqy 61 aasysglmri erlqfiadhc ptlrvealkm alsfvqrtfn vdmyeeihrk lseatrelqn 121 apdaipesgv eppaldtawv eatrkkallk lekldtdlkn ykgnsikesi rrghddlgdh 181 yldcgdlsna lkcysrardy ctsakhvinm clnvikvsvy lqnwshvlsy vskaestpei 241 aeqrgerdsq tqailtklkc aaglaelaar kykqaakcll lasfdhcdfp ellspsnvai 301 ygglcalatf drgelqrnvi ssssfklfle lepqvrdiif kfyeskyasc lkmldemkdn 361 llldmylaph vrtlytqirn raliqyfspy vsadmhrmaa afnttvaale deltqlileg 421 lisarvdshs kilyardvdq rsttfeksll mgkefqrrak ammlraavlr nqihvksppr 481 egsqgeltpa nsqsrmstnm
```

By "GPS1 polynucleotide" is meant a nucleic acid molecule encoding an GPS1 polypeptide. An exemplary GPS1 polynucleotide sequence is provided at NCBI Accession No., NM_212492.2 which is reproduced below (SEQ ID NO: 31):

```
   1 gcgccccgga agcgacggct tcgctgcccc ggaagtggac ggcacgccgc ggcggggtgg
  61 gtgcaagatg ccgctgccgg ttcaggtgtt taacttgcag gtaacgagcc gaggccgccc
 121 cgggcctccg cgccccgcg ccccccgcca ctggggccgg gctgaggtcg agcaggggcg
 181 cggggcctgc gccaggagtc ggtcgggcac gctccgtgcc gggcctccgc gggcagcgcg
 241 cgtcggggc tgcagggcc agggcgcgtc tccgccgtgg ctgcgcgctg cgatcggggg
 301 ccgccgggcc gcgcccgccc cgcctcccct cccagcagct cacgggagag gttcccggcc
 361 gccccgacgc taacgctctt tctcccttca gcagccagcc agctctgtgt cagggtcggg
 421 gggtgcagaa agtcaggaca gaatgaggga tagctcggcc cccagctcgg cctcctcgtc
 481 agtgacagat ctgtactgca cccctcacag cagtaggtca gacctcgtcc tgcccggcac
 541 ggccgggac ttcagcctga gcgccagcct gtcggcctgt acgctgctct acgaggggc
 601 cgtggagccc atgcagatcg acgtggaccc ccaggaagac ccgcagaatg cacctgacgt
 661 caactacgtg gtggagaacc ccagcctgga tctggaacag tacgcggcca gctacagcgg
 721 cctgatgcgc atcgaacggc tgcagttcat tgctgatcac tgccccacgc tgcgggtgga
 781 ggccctgaag atggccctct ccttcgtgca gagaaccttt aacgtggaca tgtacgagga
 841 gatccaccgc aagctctcag aggccaccag ggagctgcag aacgcacccg acgccatccc
 901 tgagagcggc gtggagcccc cagccctgga cacggcctgg gtggaggcca cgcggaagaa
 961 ggcgctgctg aagctggaga gctggacac agacctgaag aactacaagg gcaactccat
1021 caaagagagc atccggcgcg gccacgacga cctgggcgac cactacctgg actgtgggga
1081 cctcagcaac gccctcaagt gctattcccg ggcccgggac tactgcacca cgccaaaaca
1141 cgtcatcaac atgtgcctca atgtcatcaa ggtcagcgtc tacttgcaga attggtctca
1201 tgtgctcagc tacgtcagca aggctgagtc cacccccagag attgccgagc agcgaggaga
1261 gcgtgacagc cagacccagg ccatcctcac caagctcaag tgtgccgcag gcttggcaga
1321 gctggccgcc aggaagtaca agcaggctgc caagtgcctc ctgctggctt cctttgatca
1381 ctgtgacttc cctgagctgc tgtcccccag caacgtggcc atctacggtg gcctgtgcgc
1441 cttggctacc tttgaccggc aggagctgca gcgcaatgtc atctccagca gctccttcaa
1501 gttgttcttg gagctggagc cacaggtccg agacatcatc ttcaaattct acgagtccaa
1561 gtacgcctca tgtctcaaga tgctggacga gatgaaggac aacctgctcc tggacatgta
1621 tctggccccc catgtcagga ccctgtacac ccagattcgc aaccgtgccc tcatccagta
1681 tttcagcccc tacgtgtcag ccgacatgca taggatggcg gcagccttca ataccacggt
1741 ggccgccctg gaggacgagc tgacgcagct aatcctggag gggctgatca gtgcccgtgt
1801 ggactcacac agcaagatcc tatacgcccg ggacgtggat cagcgcagca ccacctttga
1861 gaagtctctg ttgatgggca aggagttcca gcgccgcgcc aaggccatga tgctgcgggc
1921 agctgtgctc cgcaaccaga tccatgtcaa gtccccgccc agagaaggga gccagggga
1981 gctgactcca gccaacagca gtcccggat gagcaccaac atgtgagggg tgaaccttgg
2041 cctccaggac atctgcaccc cctccccacc tccacggacc tcggacctcc aggcggctca
2101 gtgctgcctg cggcccagct aaggggcctg gccactgggt gccacccagc ctgtgtgccc
2161 tccctggggc tgaggaggca ggcggctgct agttgtggcc cttcctggaa ggagaggcct
```

-continued

```
2221 gcagggctcg accctgtggg tttctgtccc cagggagcag actgtgcggc acccaggccc 2281 agtggcacca tttcccagac ccctcctgtt cccgcctcag tcaggtgcag acaagtgggc 2341 ggtgtccatt aaagagcaga ctcagcgtta aaaaaaaaaa aaaaa
```

By "GLMN (Glomulin, FKBP Associated Protein) polypeptide" is meant a polypeptide or fragment thereof having at least 85% amino acid sequence identity to NCBI Accession No. NP_444504.1 and having ubiquitin protein ligase binding and ubiquitin-protein transferase inhibitor activity. An exemplary GLMN polypeptide sequence is provided below (SEQ ID NO: 32):

```
  1 maveelqsii krcqileeqd fkeedfglfq lagqrcieeg htdqlleiiq neknkviikn 61 mgwnlvgpvv rcllckdked skrkvyflif dllvklcnpk elllglleli eepsgkqisq 121 sillllqplq tviqklhnka ysiglalstl wnqlsllpvp yskeqiqmdd yglcqcckal 181 ieftkpfvee vidnkensle neklkdellk fcfkslkcpl ltaqffeqse eggndpfryf 241 aseiigflsa ighpfpkmif nhgrkkrtwn ylefeeeenk qladsmasla ylvfvqgihi 301 dqlpmvlspl yllqfnmghi evflqrtees viskglelle nsllriedns llyqyleiks 361 fltvpqglvk vmticpietl rkkslamlql yinkldsqgk ytlfrcllnt snhsgveafi 421 igniknqidm slkrtrnnkw ftgpqlisll dlvlflpega etdllqnsdr imaslnllry 481 lvikdnendn qtglwtelgn iennflkplh iglnmskahy eaeiknsgea qkskdlcsit 541 vsgeeipnmp pemqlkvlhs alftfdlies vlarveelie iktkstseen igik
```

By "GLMN polynucleotide" is meant a nucleic acid molecule encoding a GLMN polypeptide. An exemplary GLMN polynucleotide sequence is provided at NCBI Accession No., NM_053274.2 which is reproduced below (SEQ ID NO: 33):

```
  1 acgcgtagcg cggggcgggg ccagaagagc gggctaagac gccggaggag gtggcggcgg 61 ctgggagagg cgagggttct ggccgatttt agcatcgaaa ctaggagaaa taagaatggc 121 tgtagaggaa cttcagtcta taataaagag atgtcaaatc ctagaagagc aagactttaa 181 agaagaggat tttggcctat ttcagttagc tgggcaaaga tgcatagaag aagggcacac 241 agaccagcta ttagaaatta ttcaaaatga aaagaataag gtcatcatca agaatatggg 301 ctggaatctc gttggtcctg ttgttcgatg cctttttgtgt aaagataaag aggatagtaa 361 aagaaaagtt tattttttga tctttgattt attggtaaag ttatgcaatc caaaggaatt 421 attgttgggt ttgcttgaac tgattgaaga gccctctgga aaacagatat cccaaagtat 481 tcttcttttg cttcagccat acaaacagt gattcagaaa cttcataaca aggcatattc 541 aattggatta gcattgtcta ccctttggaa tcagctatct cttcttcctg ttccatactc 601 aaaagaacaa atacaaatgg atgactatgg cctttgtcag tgttgcaagg ccttaataga 661 gttcactaag cctttttgtgg aagaagtcat tgataacaaa gaaaactcac tggaaaatga 721 aaagttaaag gatgaattac tgaaattttg tttcaaaagc ttgaaatgcc ctttgctgac 781 agcacaattc tttgaacagt ctgaagaagg tggaaatgat cctttcaggt attttgcatc 841 agaaataata ggtttttttat cagcaattgg acacccttc cccaaaatga ttttaatca 901 tggaaggaaa aagagaactt ggaattacct tgaatttgaa gaagaagaaa ataaacagtt 961 agcagactca atggcttctc tggcatatct agtatttgta cagggcatcc atattgatca
```

-continued

```
1021  gcttccaatg  gtcttaagcc  cattgtacct  tttgcagttt  aatatggggc  acattgaagt 1081  cttttgcaa   agaacagaag  agtctgttat  ctccaaagga  ttggagctgc  tggagaatag 1141  tttattgaga  atagaagaca  atagtctact  ttaccagtac  ttagaaatca  agagttttct 1201  tactgtacct  cagggcttag  tgaaagtaat  gacactttgc  cccattgaga  cactgaggaa 1261  aaagagttta  gctatgcttc  agctgtatat  taacaagttg  gattcacaag  gcaaatatac 1321  attatttagg  tgcttattga  atacaagtaa  tcactcaggt  gtggaggctt  ttattattca 1381  aaatatcaaa  aatcaaattg  acatgtcatt  aaagagaaca  cgtaacaaca  aatggtttac 1441  aggaccacag  ttgatttccc  ttcttgattt  ggtacttttt  ctcccagagg  gtgcagaaac 1501  agatttactg  caaaactcag  ataggattat  ggcttcatta  aatttattga  ggtatttggt 1561  tatcaaagat  aatgaaaatg  acaatcaaac  tggattatgg  acagaacttg  gaaatattga 1621  gaataatttc  ttaaagccac  ttcatatagg  acttaatatg  tcaaaagcac  attatgaagc 1681  agaaattaaa  aatagccaag  aggcccagaa  atctaaagat  ctttgttcta  taactgtaag 1741  tggagaagag  atccctaata  tgcctcctga  aatgcagctt  aaggtcctgc  attcagctct 1801  tttcacattt  gatttgattg  aaagtgttct  agctcgagtg  gaagaactca  ttgaaataaa 1861  aacaaagtct  acctctgaag  aaaatattgg  gataaagtga  aagttccatt  tcctaaataa 1921  aaactaataa  aatatagtac  tttccattat  gattcattta  atacctttat  aaaaaatttt 1981  tctgtaaaaa  tttactgctt  gaaaataaa  tgtagctttt  ctcatttatc  aaaaaaaaaa 2041  aa
```

By "NCOR1 (Nuclear Receptor Corepressor 1) polypeptide" is meant a polypeptide or fragment thereof having at least 85% amino acid sequence identity to NCBI Accession No. AAI67431.1 and having transcription factor activity, sequence-specific DNA binding and chromatin binding activity. An exemplary NCOR1 polypeptide sequence is provided below (SEQ ID NO: 34):

```
  1  msssgyppnq  gafsteqsry  pphsvqytfp  ntrhqqefav  pdyrsshlev  sqasqllqqq 61  qqqqlrrrps  llsefhpgsd  rpqerrtsye  pfhpgpspvd  hdsleskrpr  leqvsdshfq 121  rvsaavlplv  hplpeglras  adakkdpafg  gkheapsspi  sgqpcgddqn  aspsklskee 181  liqsmdrvdr  eiakveqqil  klkkkqqqle  eeaakppepe  kpvspppveq  khrsivqiiy 241  denrkkaeea  hkifeglgpk  velplynqps  dtkvyhenik  tnqvmrkkli  lffkrrnhar 301  kgreqkicqr  ydqlmeawek  kvdriennpr  rkakesktre  yyekqfpeir  kgreqqerfq 361  rvgqrgagls  atiarsehei  seiidglseq  ennekqmrql  svippmmfda  eqrrvkfinm 421  nglmedpmkv  ykdrqfmnvw  tdhekeifkd  kfiqhpknfg  liasylerks  vpdcvlyyyl 481  tkknenykal  vrrnygkrrg  rnqqiarpsq  eekveekeed  kaektekkee  ekkdeeekde 541  kedskentke  kdkidgtaee  teereqatpr  grktansqgr  rkgritrsmt  neaaaasaaa 601  aaateepppp  lppppepist  epvetsrwte  eemevakkgl  vehgrnwaai  akmvgtksea 661  qcknfyfnyk  rrhnldnllq  qhkqktsrkp  reerdvsqce  svastvsaqe  dediieasnee 721  enpedsegae  nssdtesaps  pspveavkps  edspenatsr  gntepavele  pttetapsts 781  pslavpstkp  aedesvetqv  ndsisaetae  qmdvdqqehs  aeegsvcdpp  patkadsvdv 841  evrvpenhas  kvegdntker  dldrasekve  prdedlvvaq  qinaqrpepq  sdndssatcs 901  adedvdgepe  rqrmfpmdsk  psllnptgsi  lvssplkpnp  ldlpqlqhra  avippmvsct 961  pcnipigtpv  sgyalyqrhi  kamhesalle  eqrqrqeqid  lecrsstspc  gtskspnrew
```

-continued

```
1021  evlqpaphqv  itnlpegvrl  pttrptrppp  plipsskttv  asekpsfimg  gsisqgtpgt
1081  yltshnqasy  tqetpkpsvg  sislglprqq  esaksatlpy  ikqeefsprs  qnsqpegllv
1141  raqhegvvrg  tagaiqegsi  trgtptskis  vesipslrgs  itqgtpalpq  tgiptealvk
1201  gsisrmpied  sspekgreea  askghviyeg  ksghilsydn  iknaregtrs  prtaheislk
1261  rsyesvegni  kqgmsmresp  vsapleglic  ralprgsphs  dlkertvlsg  simqgtprat
1321  tesfedglky  pkqikrespp  irafegaitk  gkpydgitti  kemgrsihei  prqdiltqes
1381  rktpevvqst  rpiiegsisq  gtpikfdnns  gqsaikhnvk  slitgpskls  rgmppleivp
1441  enikvvergk  yedvkagetv  rsrhtsvvss  gpsvirstlh  eapkaqlspg  iyddtsarrt
1501  pvsyqntmsr  gspmmnrtsd  vtissnkstn  herkstltpt  qresipaksp  vpgvdpvvsh
1561  spfdphhrgs  tagevyrshl  pthldpampf  hraldpaaaa  ylfqrqlspt  pgypsqyqly
1621  amentrqtil  ndyitsqqmq  vnlrpdvarg  lspreqpigl  pypatrgiid  ltnmpptilv
1681  phpggtstpp  mdrityipgt  qitfpprpyn  sasmspghpt  hlaaaasaer  erererereker
1741  ereriaaass  dlylrpgseq  pgrpgshgyv  rspspsvrtq  etmlqqrpsv  fqgtngtsvi
1801  tpldptaqlr  implpaggps  isqglpasry  ntaadalaal  vdaaasapqm  dvsktkeiss
1861  hryetpsdai  evispasspa  ppqeklqtyq  pevvkanqae  ndptrqyegp  lhhyrpqqes
1921  pspqqqlpps  sqaegmgqvp  rthrlitlad  hicqiitqdf  arnqvssqtp  qqpptstfqn
1981  spsalvstpv  rtktsnrysp  esqaqsvhhq  rpgsrvspen  lvdksrgsrp  gkspershvs
2041  sepyepispp  qvpvvhekqd  sllllsqrga  epaeqrndar  spgsisylps  ffktklentsp
2101  mvkskkqeif  rklnssgggd  sdmaaaqpgt  eifnlpavtt  sgsyssrghs  fadpasnlgl
2161  ediirkalmg  sfddkvedhg  vvmsqpmgvv  pgtantsvvt  sgetrreegd  psphsggvck
2221  pklisksnsr  kskspipgqg  ylgterpssv  ssvhsegdyh  rqtpgwawed  rpsstgstqf
2281  pynpltmrml  sstpptpiac  apsavnqaap  hqqnriwere  papllsaqye  tlsdsdd
```

By "NCOR1 polynucleotide" is meant a nucleic acid molecule encoding a NCOR1 polypeptide. An exemplary NCOR1 polynucleotide sequence is provided at NCBI Accession No., NM_006311.3 which is reproduced below (SEQ ID NO: 35):

```
  1  gcgggctggg  gggagggaga  ggggttgagt  caagatggcg  gccaaggtgg  cgaagcagca
 61  gccgcggcg   cggcggcggc  tggagtgagc  gtccgactcg  ccgcgccgaa  cgaggtcccg
121  gtgtagggcc  gcgcgccgtg  gccgcgtccc  actcctcagg  ccggggcgca  cgtcggctcc
181  cacgcttagc  cagctcccgg  tggtttccta  gaaacatgat  tgtttattgg  cattgatctc
241  acagtctggt  gaggacttct  ttactgataa  tgtcaagttc  aggttatcct  cccaaccaag
301  gagcattcag  cacagaacaa  agtcgttatc  ctcctcactc  tgtccagtat  acatttccca
361  acacccgcca  ccagcaggag  ttcgcagtcc  ctgattatcg  ttcctctcat  cttgaagtga
421  gtcaggcatc  acagcttttg  cagcaacagc  agcagcaaca  gcttcgaagg  cgaccttcct
481  tgctttcaga  atttcaccca  ggtctgtgaca  ggcctcaaga  aggagaact   agttatgaac
541  cgtttcatcc  aggcccatcc  ccagtggatc  atgattcact  ggaatcgaag  cgaccacgtc
601  tggaacaggt  ttctgattct  cattttcagc  gtgtcagtgc  tgcggttttg  cctttagtgc
661  acccgctgcc  agaagggctg  agggcttctg  cagatgctaa  gaaggatcca  gcattcggag
721  gcaaacatga  agctccatcc  tctccaattt  cggggcaacc  atgtggagat  gatcaaaatg
781  cttcaccttc  aaaactctca  aaggaagagt  taatacagag  tatggatcgt  gtagatcgag
```

-continued

```
 841 aaattgcaaa agtagaacag cagatcctta aactgaaaaa gaaacaacaa cagcttgaag
 901 aagaggcagc taaacctcct gagcctgaga agcccgtgtc ccctcctcct gtggagcaga
 961 aacaccgcag tattgtccaa attatttatg atgagaatcg gaaaaaagca gaagaagctc
1021 ataaaatttt tgaaggtctt ggcccaaaag ttgaactgcc actgtataac cagccatcag
1081 ataccaaggt gtaccatgag aacatcaaga caaaccaggt gatgaggaaa aaactcattt
1141 tattttttaa aagaagaaat catgcaagaa aacaaaggga caaaaaaatc tgccagcgtt
1201 atgatcagct catggaggca tgggagaaaa aagtggacag aatagaaaat aatcctcgga
1261 ggaaagctaa agaaagcaaa acaagggaat actatgaaaa gcagtttcca gaaattcgaa
1321 aacaaagaga acagcaagaa agatttcagc gagttgggca gagggagct ggtctttcag
1381 ccaccattgc taggagtgag catgagattt ctgaaattat tgatgggctc tctgagcagg
1441 agaataatga gaaacaaatg cggcagctct ctgtgattcc acctatgatg tttgatgcag
1501 aacaaagacg agtcaagttc attaacatga atgggcttat ggaggaccct atgaaagtgt
1561 ataaagatag gcagtttatg aatgtttgga ctgaccatga aaaggagatc tttaaggaca
1621 agtttatcca gcatccaaaa aactttggac taattgcatc atacttggag aggaagagtg
1681 ttcctgattg tgttttgtat tactatttaa ccaagaaaaa tgagaattat aaagccctcg
1741 tcagaaggaa ttatgggaaa cgcagaggca gaaaccagca aattgctcga ccctcgcaag
1801 aagaaaaagt agaagaaaaa gaagaggata agcagaaaaa acagaaaaa aaagaagaag
1861 aaaagaaaga tgaagaggaa aaagatgaaa aagaagactc caaagaaaat accaaggaaa
1921 aggacaagat agatggtaca gcagaagaaa ctgaggaaag agagcaagcc acccccggg
1981 ggcgaaagac tgccaacagt cagggccgcc gtaagggccg gatcaccagg tccatgacaa
2041 acgaagctgc agctgccagt gctgcagccg cagcggctac tgaagagccc ccaccacctc
2101 tgccaccgcc accagaaccc atttctacag agcctgtgga gacctctcga tggacagaag
2161 aagaaatgga agttgctaaa aaaggtctag tagaacatgg tcgtaactgg gcagcaattg
2221 ctaaaatggt gggaacgaaa agtgaagctc aatgtaaaaa cttctatttt aactataaaa
2281 ggcgacacaa tcttgacaac ctcttacagc agcataaaca gaaaacttca cgaaaacctc
2341 gtgaagagcg agatgtgtct caatgtgaaa gtgtcgcttc cactgtttct gctcaggagg
2401 atgaagatat tgaagcctcc aatgaagaag aaaatccaga agacagcgaa gttgaagctg
2461 tcaagcccag cgaggacagt cctgaaaatg ctacttctcg aggaaacaca gaacctgcgg
2521 ttgagcttga gcccaccacg gaaactgcac ccagtacatc tccctcctta gcagttccaa
2581 gtacaaaacc agctgaagat gaaagtgtgg agacccaggt gaatgacagc atcagtgctg
2641 agacagcaga gcagatggat gtagatcagc aggagcacag tgctgaagag ggttctgttt
2701 gtgatccccc acccgctacc aaagctgact ctgtggacgt tgaagtgagg gtgccagaaa
2761 accatgcatc taaagttgaa ggtgataata ccaaagaaag agacttggat agagccagtg
2821 agaaggtgga acctagagat gaagatttgg tggtagctca gcaaataaat gcccaaaggc
2881 ccgagcccca gtcagacaat gattccagtg ccacgtgcag cgctgatgag gatgtggatg
2941 gagagccaga gaggcagaga atgtttccta tggactcaaa gccttcactg ttaaacccca
3001 ctggatctat actcgtctca tctccgttaa aaccaaatcc actggatctg ccacagcttc
3061 agcatcgagc tgctgttatc ccaccaatgg tatcctgcac cccatgtaac ataccaattg
3121 gaaccccagt gagcggctat gctctctacc agcgacacat taaagcaatg catgagtcag
3181 cactcctgga ggagcagcgg cagagacaag aacagataga tttggaatgt agaagttcta
```

```
3241 caagtccatg tggcacatcc aagagtccaa acagagagtg ggaagtcctt cagcctgctc 3301 cacatcaagt gataactaat ctccctgaag gcgttcggct tccgacaact cgaccaacca 3361 ggccaccgcc ccctctcatc ccgtcatcca aaaccacagt ggcttcagaa aaaccatctt 3421 ttataatggg aggctccatc tcacagggaa caccaggcac ttatttgact tctcataatc 3481 aggcttccta cactcaagaa acacccaagc cgtcagtggg atctatctct cttggactgc 3541 cacggcaaca ggaatctgcc aaatcagcta ctttgcccta catcaagcag gaagaatttt 3601 ctccccgaag ccaaaactca caacctgagg gtctgttggt cagggcccaa catgaaggtg 3661 tagtcagagg taccgcagga gccatacaag aaggaagtat aactcgggga actccaacca 3721 gcaaaatttc agtggagagc attccatccc tacggggctc tatcactcag ggcaccccgg 3781 ctctgcccca gactggcata ccaacagagg ctttggtgaa ggggtccatt tcgagaatgc 3841 ccattgaaga cagcagtcct gagaaaggca gagaggaagc tgcatccaaa ggccatgtta 3901 tttatgaagg caaaagtgga catatcttgt catatgataa tattaagaat gcccgagaag 3961 ggactaggag tccaagaaca gctcatgaaa tcagtttaaa gagaagctat gaatcagtgg 4021 aaggaaatat aaagcaaggg atgtcaatga gggagtctcc tgtatcagca ccgttagagg 4081 ggctgatatg ccgagcatta cccaggggga gtcctcattc tgacctcaaa gaaaggactg 4141 tattgtctgg ctccataatg caggggacac caagagcaac aactgaaagc tttgaagatg 4201 gccttaaata tcccaaacaa attaaaaggg aaagtcctcc catacgagca tttgaaggtg 4261 ccattaccaa aggaaaacca tatgatggca tcaccaccat caaagaaatg gggcgttcca 4321 ttcatgagat tccaaggcaa gatattttaa ctcaggaaag tcggaaaact ccagaagtgg 4381 tccagagcac acggccgata attgagggtt ccatttccca gggcacacca ataaagtttg 4441 acaacaactc aggtcaatct gccatcaaac acaatgtcaa atccttaatc acgggcccta 4501 gcaaactatc ccgtggaatg cctccgctgg aaattgtgcc agagaacata aaagtggtag 4561 aacggggaaa atatgaggat gtgaaagcag gcgagaccgt gcgttcccgg cacacgtcag 4621 tggtaagctc tggcccctcc gttcttaggt ccacactgca tgaagctccc aaagcacaac 4681 tgagccctgg gatttatgat gacaccagtg cacggaggac ccctgtgagt tatcaaaaca 4741 ccatgtccag aggctcaccc atgatgaaca gaacttctga tgttacaatt tcttctaaca 4801 agtctaccaa tcatgaaagg aaatcgacac tgaccccctac ccagagggaa agtatcccag 4861 cgaagtctcc agtgcctggg gtggaccctg tcgtgagcca cagtccgttt gatccccatc 4921 acagaggcag cactgcaggc gaggtttatc ggagccacct gcccacgcac ttggatccag 4981 ccatgccttt tcacagggct ttggatcctg cagcggctgc ttacctgttt cagagacagc 5041 tttcaccaac tccaggttac ccaagtcagt atcagcttta cgcaatggag aacacaagac 5101 agacaatctt aaatgattac attacctcac aacagatgca agtgaacttg cgtccagatg 5161 tggccagagg actctccccca agagagcagc cactgggtct cccatacccca gcaacgagag 5221 gaatcattga cctgaccaat atgcctccaa caattttagt gcctcatcca gggggaacaa 5281 gcactcctcc catggacaga atcacttata ttcctggtac acagattact ttccctccca 5341 ggccgtacaa ctctgcttcc atgtctccag acacccaac acaccttgca gctgctgcaa 5401 gtgctgagag ggaacgggaa cgggagcggg agaaggagcg ggagcgggaa cggattgctg 5461 cagcttcctc cgacctctac ctgcggccag gctcagaaca gcctggccga cctggcagtc 5521 atggatatgt tcgctcccct tcccccttcag taagaactca ggagaccatg ttgcaacaga 5581 gacccagtgt tttccaagga accaatggaa ccagtgtaat cacacctttg gatccaactg
```

-continued

```
5641 ctcagctacg aatcatgcca ctgcctgctg ggggcccttc aataagccaa ggcctgccag
5701 cctcccgtta caacactgct gcggatgccc tggctgctct tgtggatgct gcagcttctg
5761 cacccccagat ggatgtgtcc aaaacaaaag agagtaagca tgaagctgcc aggttagaag
5821 aaaatttgag aagcaggtca gcagcagtta gtgaacagca gcagctagag cagaaaaccc
5881 tggaggtgga gaagagatct gttcagtgtt tatacacttc ttcagcctttt ccaagtggca
5941 agccccagcc tcattcttca gtagtttatt ctgaggctgg gaaagataaa gggcctcctc
6001 caaaatccag atatgaggaa gagctaagga ccagagggaa gactaccatt actgcagcta
6061 acttcataga cgtgatcatc acccggcaaa ttgcctcgga caaggatgcg agggaacgtg
6121 gctctcaaag ttcagactct tctagtagct tatcttctca caggtatgaa acacctagcg
6181 atgctattga ggtgataagt cctgccagct cacctgcgcc accccaggag aaactgcaga
6241 cctatcagcc agaggttgtt aaggcaaatc aagcggaaaa tgatcctacc agacaatatg
6301 aaggaccatt acatcactat cgaccacagc aggaatcacc atctccccaa caacagctgc
6361 cccettcttc acaggcagag ggaatggggc aagtgcccag gacccatcgg ctgatcacac
6421 ttgctgatca catctgtcaa attatcacac aagattttgc tagaaatcaa gtttcctcgc
6481 agactcccca gcagcctcct acttctacat tccagaactc accttctgct ttggtatcta
6541 cacctgtgag gactaaaaca tcaaaccgtt acagcccaga tcccaggct cagtctgtcc
6601 atcatcaaag accaggttca agggtctctc cagaaaatct tgtggacaaa tccaggggaa
6661 gtaggcctgg aaaatcccca gagaggagtc acgtctcttc ggagccctac gagcccatct
6721 ccccacccca ggttccggtt gtgcatgaga acaggacag cttgctgctc ttgtctcaga
6781 ggggcgcaga gcctgcagag cagaggaatg atgcccgctc accagggagt ataagctact
6841 tgccttcatt cttcaccaag cttgaaaata catcacccat ggttaaatca agaagcagg
6901 agatttttcg taagttgaac tcctctggtg gaggtgactc tgatatggca gctgctcagc
6961 caggaactga gatctttaat ctgccagcag ttactacgtc aggctcagtt agctctagag
7021 gccattcttt tgctgatcct gccagtaatc ttgggctgga agacattatc aggaaggctc
7081 tcatgggaag ctttgatgac aaagttgagg atcatggagt tgtcatgtcc cagcctatgg
7141 gagtagtgcc tggtactgcc aacacctcag ttgtgaccag tggtgagaca cgaagagagg
7201 aagggaccc atcacctcat tcaggaggag tttgcaaacc aaagctgatc agcaagtcaa
7261 acagcaggaa atctaagtct cctatacctg ggcaaggcta cttaggaacg gaacggccct
7321 cttcagtctc ctctgtacat tcagaagggg attaccatag gcagacgcca gggtgggcct
7381 gggaagacag gccctcttca acaggctcaa ctcagtttcc ttataaccct ctgactatgc
7441 ggatgctcag cagtactcca ccaacaccga ttgcatgtgc tccctctgcg gtgaaccaag
7501 cagctcctca ccaacagaac aggatctggg agcgagagcc tgccccactg ctctcagcac
7561 agtacgagac cctgtcggat agtgatgact gaactgcaca aagtgagggg aacagggtgc
7621 aggagaggga tctctagttt ttgtggttta ttttttagta gcaggtcaaa aacctgccct
7681 cctgtgactt attccctgag acttttcagg agagccagcc cacagatgat gaagaaatga
7741 tggaagttca tttggagagt caaatgggaa aaaaacaaac aaaaaactgc ctttgataca
7801 ggcaattcag tggactataa taatagtgga gggttgagat gtagagtttt taaaaagtga
7861 acagttgctg ttcttacatc tgtaaagaaa accataatgt ctttaaatca ctcttctgta
7921 aatagatgac cttttttgcag tgtatatccc cttgctgtag tatctggtgt acttatgttc
7981 aaatcagcgc atcaactttg ggggtgattt ttaaaaatct ttttgtctat ctatctttt
8041 aaccctagcc ttctaaacaa cctcatacag cccagttaca taatgttggc tgtcacgggc
```

```
8101 attgtacttt tatctgatat tgtttcctct aaattcagct ttccagtgat gtttaaaatc
8161 ttgtgaaaat gtttagattt ttaacacaga ccctgtcata aaatctgtac attagggtca
8221 aaaggtaaaa gtaacaaatt ctgccatatt gtaaatttcc agtgcaggct ttaattttt
8281 tttttcatta gtagcactga aaaaatatta ctgcatgggg atgttctagt tcagtttata
8341 aagttttaaa ggcttatttg aggcatacct cactgttacg cacactggta atttaaccat
8401 gccctaagt attccttttc tcctgcattt gatgcagccc aacaaagctt ttgtttgaa
8461 ataaatttga ctaccctgtc catagctaca gtagattatt tgtggtttaa ggctcctggt
8521 gtctcaggtt ccaaaggaaa agcttacata tttttccctt agtttgaata tatgattggt
8581 tgggttaaaa gataatgatc tgtgtagtat ttagataagc tttatgctgc atcctgaaaa
8641 actcatggtg aacacagtcc ttttccccca tcactatgga ccagcattta ctctcacttt
8701 gctcccttgg gacaagagtt tactgttaaa tgttttcatt tcacagagtc tcaaggtgca
8761 aataatttaa aagactgaat tctaaactaa ttatggtact agagggccag ttttatcttt
8821 cattaagaat tgcttgctga attttaaagt ttttttcata caatttatca tagcatttaa
8881 gtatctttct ataacataga tactaacagt tttgggagaa tgccactggt aactggaaag
8941 gggagaaaca gatctctcag gatgataaaa attagcactt tacagacttt caagtagacc
9001 taaacttta aacaaaagta ctcaaggctt ttaaggaagc agctctgtga ttagctactg
9061 accaagaccc tcctatcact ggtgtctaat ccctatgtta cagatgaaga cacaggttta
9121 gtactttgcc catatagtta aattagtgac agagataggc cataagccca catttgtctt
9181 cagtcaaagc tttcactcct gtccctgttc cactcctgta tacctgaggt ccccaacata
9241 aactttgat caggcttagt ggtcagcatt cctagtactt ggaaagttgg tattttttac
9301 aacagatata tgtaaacata taaaaatttc aaaatgaatg aaaaacagtg actaaatgtt
9361 ccacttcaca gttttctgct gaatttttt ttttcaggta ctggtaatat tttagagttt
9421 gttaataatt tatattgcca acctaccata aaagagatta tgatggtatt tttctatgac
9481 cctgagggtc ttaagctatt ctgagtcaga atacagttga cccttgaaca acacgggttt
9541 gaactgtgtg ggtccactta tacatggatt ttcttccacc tctgccaccc aagatagcaa
9601 gaccaacccc ttctcatcct cagcctattc aacatgaaga tgacaaggat gaagaccttc
9661 atgatgatcc acttccactt aatgaaatagt aaatatattt tctcttcctt ataatcttaa
9721 caaacatttt ctcttctcta gcttacttta ttgtaagaat acagtatata atacatatac
9781 aaaatatgtg tcaaaaaaaa aaaaaaaaa
```

By "PLAA (Phospholipase A2 Activating Protein) polypeptide" is meant a polypeptide or fragment thereof having at least 85% amino acid sequence identity to NCBI Accession No. NP_001026859.1 and having phospholipase A2 activator activity. An exemplary PLAA polypeptide sequence is provided below (SEQ ID NO: 36):

```
  1 mtsgatryrl scslrgheld vrglvccayp pgafvsysrd rttrlwapds pnrsftemhc
 61 msghsnfvsc vciipssdiy phgliatggn dhnicifsld spmplyilkg hkntvcslss
121 gkfgtllsgs wdttakvwln dkcmmtlqgh taavwavkil peqglmltgs adktvklwka
181 grcertfsgh edcvrglail seteflscan dasirrwqit geclevyygh tnyiysisvf
241 pncrdfvtta edrslriwkh gecaqtirlp aqsiwcccvl dngdivvgas dgiirvftes
301 edrtasaeei kafekelsha tidsktgdlg dinaeqlpgr ehlnepgtre gqtrlirdge
361 kveayqwsys egrwikigdv vgssganqqt sgkvlyegke fdyvfsidvn eggpsyklpy
421 ntsddpwlta ynflqkndln pmfldqvakf iidntkgqml glgnpsfsdp ftgggryvpg
```

-continued

```
481 ssgssntlpt adpftgagry vpgsasmgtt magvdpftgn sayrsaaskt mniyfpkkea 541 vtfdqanptq ilgklkelng tapeekklte ddlillekil slicnsssek ptvqqlqilw 601 kaincpediv fpaldilrls ikhpsvnenf cnekegaqfs shlinllnpk gkpanqllal 661 rtfcncfvgq agqklmmsqr eslmshaiel ksgsnknihi alatlalnys vcfhkdhnie 721 gkaqclslis tilevvqdle atfrllvalg tlisddsnav qlakslgvds qikkyssyse 781 pakvseccrf ilnll
```

By "PLAA polynucleotide" is meant a nucleic acid molecule encoding a PLAA polypeptide. An exemplary PLAA polynucleotide sequence is provided at NCBI Accession No., NM_001031689.2 which is reproduced below (SEQ ID NO: 37):

```
   1 gatttaccac aaactgttgg gcccggagtc ggaagagacc cgggtttggg aaggacccca 61 gggtcaggcg tcctggtgga agggcgggcc tctttctctc ttgctcagca gggagtccag 121 agccctggag gaaagccagc tcagctccgc atcggcgtcg gcggttggga cgcacacact 181 ctgcgtcatg gagggctgag gccgatgatg aattccggag tgcctgtcag gcttgctgtg 241 tcactcggcc cgctcggcgc gccccttccc agccgccctt ccgtaccggc tctcgggctc 301 ttccggtctc cggccgcccc ttacctgcag gctcttctcc cgccgcggcc cggcgctctc 361 cgagtcgccc ctgcggactg gtctcgcaca gtgcctgggc accgggcgcc agacagacac 421 tggccatgac gagcggcgca accaggtacc ggctgagctg ctcgctccgg ggccacgagc 481 tggacgtacg gggcctggtg tgctgcgcct atccgccggg agcctttgtg tccgtgtccc 541 gagaccgcac cacccgcctc tgggcccag acagtccaaa caggagcttt acagaaatgc 601 actgtatgag tggccattcc aattttgtat cttgtgtatg catcatacc tcaagtgaca 661 tctaccctca tggcctaatt gccaccggtg gaaatgacca caatatatgc attttctcac 721 tggacagtcc aatgccactt tatattctaa aaggccacaa aaatactgtt tgtagtctat 781 catctggaaa atttgggaca ttacttagtg gttcatggga caccactgct aaagtctggc 841 tgaatgacaa gtgcatgatg accttgcagg gtcatacagc tgcagtgtgg gcggtaaaga 901 tcttacctga acagggctta atgttgactg gatcagcaga caagactgtt aaactgtgga 961 aggctggaag atgtgagagg acttttttcag ggcatgaaga ctgtgtaaga ggtttggcaa 1021 ttttgagtga aacagaattt ctttcctgtg caaatgatgc tagtattaga aggtggcaaa 1081 tcactggcga gtgtcttgaa gtatattatg gacatacaaa ttatatttat agcatatccg 1141 ttttttccaaa ttgtagagac tttgtgacaa cagcagagga cagatctctg agaatctgga 1201 aacatgggga atgtgctcaa actatccgac ttccagctca gtctatatgg tgctgctgtg 1261 tgctcgacaa tggtgacatt gtggttggtg cgagtgatgc cattattaga gtgtttacag 1321 aatcagaaga tcgaacagca agtgctgaag aaatcaaggc ttttgaaaaa gaactgtctc 1381 acgcaaccat tgattctaaa actggcgatt taggggacat caatgctgag cagcttcctg 1441 ggagggaaca tcttaatgaa cctggactga gaaggaca gactcgtcta atcagagatg 1501 gggagaaagt cgaagcctat cagtggagtg ttagtgaagg gaggtggata aaaattggtg 1561 atgttgttgg ctcatctggt gctaatcagc aaacatctgg aaaagtttta tatgaaggga 1621 aagaatttga ttatgttttc tcaattgatg tcaatgaagg tggaccatca tataaattgc 1681 catataatac cagtgatgac ccttggttaa ctgcatacaa cttcttacag aagaatgatt 1741 tgaatcctat gtttctggat caagtagcta aatttattat tgataacaca aaaggtcaaa
```

-continued

```
1801  tgttgggact tgggaatccc agcttttcag atccatttac aggtggtggt cggtatgttc
1861  cgggctcttc gggatcttct aacacactac ccacagcaga tccttttaca ggtgctggtc
1921  gttatgtacc aggttctgca agtatgggaa ctaccatggc cggagttgat ccatttacag
1981  ggaatagtgc ctaccgatca gctgcatcta aaacaatgaa tatttatttc cctaaaaaag
2041  aggctgtcac atttgaccaa gcaaacccta cacaaatatt aggtaaactg aaggaactta
2101  atggaactgc acctgaagag aagaagttaa ctgaggatga cttgatactt cttgagaaga
2161  tactgtctct aatatgtaat agttcttcag aaaaacccac agtccagcaa cttcagattt
2221  tgtggaaagc tattaactgt cctgaagata ttgtcttcc tgcacttgac attcttcggt
2281  tgtcaattaa acaccccagt gtgaatgaga acttctgcaa tgaaaaggaa ggggctcagt
2341  tcagcagtca tcttatcaat cttctgaacc ctaaaggaaa gccagcaaac cagctgcttg
2401  ctctcaggac ttttgcaat tgttttgttg gccaggcagg acaaaaactc atgatgtccc
2461  agagggaatc actgatgtcc catgcaatag aactgaaatc agggagcaat aagaacattc
2521  acattgctct ggctacattg gccctgaact attctgtttg ttttcataaa gaccataaca
2581  ttgaagggaa agcccaatgt ttgtcactaa ttagcacaat cttggaagta gtacaagacc
2641  tagaagccac ttttagactt cttgtggctc ttggaacact tatcagtgat gattcaaatg
2701  ctgtacaatt agccaagtct ttaggtgttg attctcaaat aaaaaagtat tcctcagtat
2761  cagaaccagc taaagtaagt gaatgctgta gatttatcct aaatttgctg tagcagtggg
2821  gaagagggac ggatattttt aattgattag tgttttttc ctcacatttg acatgactga
2881  taacagataa ttaaaaaaag agaatacggt ggattaagta aaatttacca tcttgtaaag
2941  tggtggggag gggaaacaga aataaaattt ttgcactgct gaactgtgag attttcctgt
3001  gtaatttggg tagattttca agagtgtgaa cacaaattta aaataagcta taatcagcaa
3061  caacacaatg acaatgacat cttccccta ccttagccac taagaagaca agggctgtta
3121  ctcatataac ttgcttttat tacttaatgt acaccaaact gttgttgtca attatctttt
3181  atttaacttc tccaccttca ttgctagatc cttcgaacag cactgataca tttcaaggtc
3241  ttgttttagg ataactactt taaaatttt taaattatat taaatttata aaataattta
3301  taaattcata tattaaaaca ataaagata attcttgat ttgtcattta taaatcctaa
3361  agtatatttg tttaatggcc tatttttaga tgaagaaaaa gccagttggt aagctgtgtt
3421  agtcatgtat cagttcagac agacgaggtc tcaatttaac tccaggctta gatccagttt
3481  cttttgccct tcactatttg aggtaacttc attttcatt ctagttttga tatttggctg
3541  tttatttttg tcattttcca ttatttcaaa gggaatttgg aacatgttga attttatcag
3601  gtggttacat aagcaagagt acatcaaact gtattatttg aaagtctaga acctgtcatg
3661  tgaaattact attttgagc cctctatgtg gtccaggcag aatagtagac acactgatat
3721  ttaatcctta aaaccctt aaatgagggc cagtattatc tctgctttca gaagtagaca
3781  taataggatg aatcatataa cagaaaaaaa aaagtgaagc caagagggag ttaactactt
3841  aaagtacatg ctatgctata ctttctagag agatcacaga tgtgtgtgaa catcctagca
3901  attaacacaa agaaggaacc atcacattaa ttacacaatt tattgtgtct gaggtaaccc
3961  agtttcttga gagaagcgta actattttca aaagtgggaa agatcttttc ataaagacgt
4021  tgccagaaat agcaacattc tcaatactcg tggtgtaaaa accatgaatc ccctggctta
4081  atgccaaatt atagccttag aagaataatt gttccccaaa tgggcaagaa aggttctaat
4141  tgtcaagagt aacccaagta agaacttttg gaatatcaaa aggaaatgag caaaatgtaa
```

```
-continued
4201 atagagggga tatgtacttt gctgagtatt aaattggaac tacctggtgt gtacctggac 4261 taaatattct gttcactggc tcagttgagt acctatactt ttcgtttttt gattgggttt 4321 aggtggttat gtcaaagtta aatggcaaaa ttaggaattt aacccaggtc tggctggttc 4381 ctttacaata cactgctttc ttaagtacaa ataatttaat tgcaatattt aggaaaagta 4441 ggtacctttg aataatgata agaaacagtc ttggttaaga atatgagttc cctcttcaaa 4501 atgtaagggg tggcaaaatg taaacactgc ttcctattac tgtgcaagtt tttttatgtc 4561 aactttacta tttcatgttt gttgtggaga ttacaaaata tagcttagca aaaggaaaca 4621 atctcacttg aaggatatgt taaataattt aatgatattt taaagatttt ctttttagt 4681 taaactttcc tatgattctc ttaatgtttt ttctgaatac aaaagtaata aatatttatt 4741 gagtaaaaca cacacacccc aaataaaaat tgcctgtaag gccactatct agagaaaact 4801 attcttaaca tcttgtggca tagtgactat gtatgtaaat gtattttatt ttattaaaaa 4861 agcgttgtat catacatact ctttgataac ctgatttta aacttatatt tggtacaaag 4921 agctccacat taataaatac aatattctat cata
```

By "PPP6C (Protein Phosphatase 6 Catalytic Subunit) polypeptide" is meant a polypeptide or fragment thereof having at least 85% amino acid sequence identity to NCBI Accession No. NP_001116827.1 and having hydrolase activity and protein serine/threonine phosphatase activity. An exemplary PPP6 polypeptide sequences is provided below (SEQ ID NO: 38):

```
  1 mapldldkyv eiarlckylp endlkvspic glapsgcgap agrpflspgp ppvfhflrfl 61 kerlcdyvcd llleesnvqp vstpvtvcgd ihgqfydlce lfrtggqvpd tnyifmgdfv 121 drgyysletf tyllalkakw pdritllrgn hesrqitqvy gfydecqtky gnanawryct 181 kvfdmltvaa lideqilcvh gglspdiktl dqirtiernq eiphkgafcd lvwsdpedvd 241 twaisprgag wlfgakvtne fvhinnlkli crahqlvheg ykfmfdeklv tvwsapnycy 301 rcgniasimv fkdvntrepk lfravpdser vipprttpy fl
```

By "PPP6C polynucleotide" is meant a nucleic acid molecule encoding a PPP6 polypeptide. An exemplary PPP6 polynucleotide sequence is provided at NCBI Accession No., NM_001123355.1 which is reproduced below (SEQ ID NO: 39):

```
  1 gaagcgggct ctcttggggc ctgcagtcgg ggttcagcca gaggggggcgc cgggcgtacc 61 gacgtagcgg ggagaaacgg gtcgcgcttt aacggcgctg cgcaggcgcc actcacgggc 121 cggacgtgac gcagggaaag ttccggcttc ggcctccgcc gctgccgccg ccgctgctac 181 agccgccgcc gccgctgttg ccgcggcttg ttattcttaa aatggcgccg ctagacctgg 241 acaagtatgt ggaaatagcg cggctgtgca agtacctgcc agagaacgac ctgaaggtga 301 gccctatttg cgggctcgcc ccttccggct gtggggcgcc cgccggccgg cccttccttt 361 ctccaggacc cccgccggta tttcattttc ttcgttttct aaaggagcgg ctatgtgact 421 acgtttgtga cctcctctta gaagagtcaa atgttcagcc agtatcaaca ccagtaacag 481 tgtgtggaga tatccatgga cagttttatg acctttgtga actgttcaga actggaggtc 541 aggttcctga cacaaactac atatttatgg gtgattttgt agacagaggt tactatagtt 601 tggagacctt cacttacctt cttgcattaa aggctaaatg gcctgatcgt attacacttt
```

```
                              -continued
 661 tgcgaggaaa tcatgagagt agacagataa cacaggtcta tggattttat gatgagtgcc 721 aaaccaaata tggaaatgct aatgcctgga gatactgtac caaagttttt gacatgctca 781 cagtagcagc tttaatagat gagcagattt tgtgtgtcca tggtggttta tctcctgata 841 tcaaaacact ggatcaaatt cgaaccatcg aacggaatca ggaaattcct cataaaggag 901 cattttgtga tctggtttgg tcagatcctg aagatgtgga tacctgggct atcagtcccc 961 gaggagcagg ttggcttttt ggagcaaagg tcacaaatga gtttgttcat atcaacaact 1021 taaaactcat ctgcagagca catcaactag tgcacgaagg ctataaattt atgtttgatg 1081 agaagctggt gacagtatgg tctgctccta attactgcta tcgttgtgga aatattgctt 1141 cgatcatggt cttcaaagat gtaaatacaa gagaaccaaa gttattccgg gcagttccag 1201 attcagaacg tgttattcct cccagaacga caacgccata tttcctttga ggccttcgcc 1261 catcctgctg acccattttt ctgccctctt cttaccccaa ttttcttgta ttaccctcta 1321 caatatactt tttattgagc actttgctgc tgaaatgctg cctcttgcct ttttttttt 1381 aaattttaaa ttatctaaat ttattgtttg ttgtggtgtc tatagcaaag ttttttctatc 1441 aattttcccc catcccatcc ccaccctgga ctcatttgag aagacttgag aaatgtctta 1501 atactcacac tgctgcatgt agctcttgct tatttactgg tctgggaaac aggatgtgtt 1561 tccttttttt aaaagccaat tgacagatta cacctaaata ctcctccttt tgtatcattc 1621 agccttttgt tttagtttgg taagtttaa gaaatttcag cagcaaagtt gttattcagt 1681 gggcacgatg gactccaaat gcctcaagtt atgtatacct gtcccagatg taaacttcat 1741 tgtcctttgt tggatgatat tttaaatgga tataaaataa attggtctaa agggctgccc 1801 tccttgttgt gttttaaat tttagttaaa aactgctaca gcttatgact ttgtacttta 1861 agataattgt attgatcttt tttcagattc cttgtatttt ttaataaagt aatcttaaat 1921 aaaactcaga taggttaagt gttagaaatt ttaaacagct tacattgtta gcgtaaagtt 1981 atcttttctt ttttcctaat cagagttctt gacccttttgg ttattgagtt taaaacttca 2041 attgaaattc aatagtattt attttttgaaa aaaatcacta aactgtgcct aaagaacata 2101 actgccatat taatgttttg gtttatatcc tctatagtaa tagaaaaaca tttaatactt 2161 gtaatgctga tgtgttaatt tgataccagt tgagtagaat gtgatcaatc cagtttacaa 2221 tctatcatga gtattattaa ctaaaatcta tgtgcttttc aataggaatc attcttctct 2281 tgctgtaaca cttgacccta acttttagaa agtgttcatt tttaaactgc aactggaaag 2341 gttgaaaagt taggactctt gtatttgtga actgtaatct gaagcagatt atttaaagtg 2401 tagaaaaaga aacaagttct tctttttttgc aaaggtctgt gataccatat ttcagctttg 2461 tgtaagtaat ttgaatatcc aaagggttgt gatgatcagt tctgaatatg caactgtcca 2521 cttaataagg acaagtattc cagtatctct tatgactgta gtcataaatg atgttggaat 2581 gtacattttg tgaaatagtt ggtatcccctt tactatgatt aattttttgtt attccaggaa 2641 atacttgtga agccagccaa ttaataaagc actttagcat ctgttcaggt agttttgaaa 2701 acccactttt cccccttcagg ataagaactt ccaggttacc taaaaatgca ataaaaatct 2761 ttatagtcta agcttcttgg catataattt ttcatcaggg ttttcttttta ttaattgagc 2821 acaatactgt tttgatttaa tttttttccc tcaaaccacc cagctcctta catagttttt 2881 aattatatag ctatatgaaa gaggtggcta agacatttgc tgcacacact tgaactaatg 2941 ttgggtcagt agcttcgtgt tactgccctg atcccagtgt aattcaggtg gaaaggtatt 3001 tttatctcac agggatatgt agctatgtat tttactaatt gtgaaacact ggaaattaat 3061 gatgcagaca acttggtgtg gtctttgaac agctctctgc agtattttttt tttttcctgt
```

```
3121 taccataaat tgtatttaag tgcttgcttt ccacttaagt tgtactaata gaaccggtaa
3181 ctcccagccc tccctgtttg acactcctta gcttagattg atgtagttgt ttttgttatc
3241 cctataatgt gactttatt tttaagtcat tgtgtactgc atttgtttgt cactagttgg
3301 gcacgtgcca ataatattct ctccattcct tatctgccat ctctgttttg cctgatttct
3361 cttcaactga ataatggctt tttgcatgga aaaatagtt tttactatta gacgtgtaaa
3421 gggaagagag agctaatgta ttggactttg tgagcctaca aggaatattt tggatccctc
3481 caataaataa gggctatgta ctatatgtac tatatagagt tatcatgtgg tggaagatac
3541 ttgcaagtca tagatttatg ggcaggagga tttgttactc cctatatcta ggctgaatgt
3601 aaaatccctt atgttgtatc aatgggggta aaaactattt ttatttgcct atgatatact
3661 tggtttctaa taaagtgccc taggctctag tgagaactgt ctactttgaa ttgccattta
3721 ctcccttttcc tcctttggcc gatatgctct tggctagctt tttataagtt aatgtgtttc
3781 cccaaaaagt ttcactactt tatattcatt tgagtgtgat cctaaaacac ctggatcaac
3841 agtacatctc atatgcaatc tgcatcagct cctattctgt ctggatgtct agaactgttg
3901 gaagattttg acgtcttaag ccctaggttt tgctttggga aataaggttt gaaatattgt
3961 tcattgcatt aagatttgtg tgtgtgtgct ttgtaagccc agaaccaggt tttggaaaat
4021 gcctgtactg tgaaagcaaa ttaggactct ttctgagcct ctttcattgt cagaaataga
4081 atcactttcc atcagcttcc aggaaattgt gtatctggag tcgaagagat ttgacatcaa
4141 gaatccagat ttttaaatgt aattgttttt taaatgctaa tgtttgtaaa gcaccttcag
4201 ttcttcggat gaaaggtgct atattccctc agtgtaaatt aataaaaaga ttacaggaag
4261 tttgtcaaaa aattcaatgc atagtctgta gtatgtcctg acaagaagtt agcattttat
4321 ataagaaatt aaaaaatgct tattcctcca aaaaaaaaaa aaaaaaa
```

By "OTUB1 (Ubiquitin thioesterase OTUB1) polypeptide" is meant a polypeptide or fragment thereof having at least 85% amino acid sequence identity to NCBI Accession No. NP_060140.2 and having ubiquitin thioesterase activity. An exemplary OTUB1 polypeptide sequence is provided below (SEQ ID NO: 40):

```
  1 maaeepqqqk qeplgsdseg vnclaydeai maqqdriqqe iavqnplvse rlelsvlyke
 61 yaeddniyqq kikdlhkkys yirktrpdgn cfyrafgfsh leallddske lqrfkaysak
121 skedlvsqgf teftiedfhn tfmdlieqve kqtsvadlla sfndqstsdy lvvylrllts
181 gylqreskff ehfieggrtv kefcqqevep mckesdhihi ialacialsys iqveymdrge
241 ggttnphifp egsepkvyll yrpghydily k
```

By "OTUB1 polynucleotide" is meant a nucleic acid molecule encoding an OTUB1 polypeptide. An exemplary OTUB1 polynucleotide sequence is provided at NCBI Accession No., NM_017670.2 which is reproduced below (SEQ ID NO: 41):

```
  1 agttaggtca tgaggctttg gccttgacac caagggatgc tgtctccttg ccggaagcag
 61 ctcaccaaag ccggcagaga acccaggttc cgtggggcca cgatgtgggg ctccgcgggc
121 gccccggcgc tggccgactt cctgtctcct gggtcagatg ctgctccgca ctgcagctat
181 ggtcgcatgc agtgcctgcc gaagcccgca gcaggaatgc tgccttcggt gatttttaatt
241 tcacttttct acttctctca ataacaaaat ccgcgtttca aactccaggg aaaagaaaac
```

-continued

```
301 ggaattggct ccaggaggat ctgcaatcac caccgggaac tttgggaggc tgggaagatg 361 gagccaaacc aatgtgtggg gtggaggtgc ggatctgggg cggccggcct ctcctacagg 421 tctcaggtcc gcaggcctgg cgtgccagca cctgccacgg gactggaagc ccattccttg 481 acaacgccta aggggatccc gttgctaggg ctgttgccaa ggcggggcaa cgaggagggg 541 ctcgcttccg ggaggacggc aattggcaac ccggaagcgg tcggtagtgc ggcgctgttt 601 aaagatggcg gcggaggaac ctcagcagca gaagcaggag ccgctgggca gcgactccga 661 aggtgttaac tgtctggcct atgatgaagc catcatggct cagcaggacc gaattcagca 721 agagattgct gtgcagaacc ctctggtgtc agagcggctg gagctctcgg tcctatacaa 781 ggagtatgct gaagatgaca acatctatca acagaagatc aaggacctcc acaaaaagta 841 ctcgtacatc cgcaagacca ggcctgacgg caactgtttc tatcgggctt tcggattctc 901 ccacttggag gcactgctgg atgacagcaa ggagttgcag cggttcaagg ctgtgtctgc 961 caagagcaag gaagacctgg tgtcccaggg cttcactgaa ttcacaattg aggatttcca 1021 caacacgttc atggacctga ttgagcaggt ggagaagcag acctctgtcg ccgacctgct 1081 ggcctccttc aatgaccaga gcacctccga ctaccttgtg gtctacctgc ggctgctcac 1141 ctcgggctac ctgcagcgcg agagcaagtt cttcgagcac ttcatcgagg tggacggac 1201 tgtcaaggag ttctgccagc aggaggtgga gcccatgtgc aaggagagcg accacatcca 1261 catcattgcg ctggcccagg ccctcagcgt gtccatccag gtggagtaca tggaccgcgg 1321 cgagggcggc accaccaatc cgcacatctt ccctgagggc tccgagccca aggtctacct 1381 tctctaccgg cctggacact acgatatcct ctacaaatag gctggctcc agcccgctgc 1441 tgccctgctg ccccccctctg ccaggcgcta gacatgtaca gaggttttc tgtggttgta 1501 aatggtccta tttcacccccc ttcttcctgt cacatgaccc cccccatgt tttattaaag 1561 ggggtgctgg tggtgagccg tgtgtgcgtg tccctgctct gctgcccgcc tggctgctct 1621 gtctgctgcc ccctccccc aggtgggtcc ccctgctttt cacctatcta ctcctgagct 1681 tccccaacag gagcaggttt gagggggccag gcctcttgga ggcccctcct gcttcgttgg 1741 gttctgcttc cttcccttct tagctggctc aggggcttct atgggatcct ggaagttcct 1801 tagggacttg cccagggtcc cagggccacc cacacttcat ctgctccctc ataggcccca 1861 cctccacgtc ccggctgggc cccagacccc agcttcctgc cctccaccgg gagtctgcat 1921 ggttgggagt cctgggtgga ggggcctttg tgaggctgga cccggctcag ggcaggtgga 1981 ggagctgggc ctcccacagg gtgcccgggc agtgccatcc tggtgggga gggcagcctt 2041 caaacgtgtg gggtctacag tcctcaggtc taggcagggc tgccggttct ccacctcccc 2101 atccgcccca ggccccctgc ctgtgcctgc cttgcacccc ctctgcttgg gccacggtgt 2161 ctctgcattg cctgccttt tgccttcacc tcttttcttc cccgccccct gcacattcgg 2221 ggtctcagcc cccaggctgt gagctccttg ggggcaggcc ctcaataaat gtgaactgct 2281 gctgccgcct ctgcaaaaaa aaaaaaaaaa
```

By "RARA (Retinoic Acid Receptor Alpha) polypeptide" is meant a polypeptide or fragment thereof having at least 85% amino acid sequence identity to NCBI Accession No. NP_001138773.1 and having transcription factor activity, sequence-specific DNA binding and protein heterodimerization activity. An exemplary RARA polypeptide sequence is provided below (SEQ ID NO: 42):

```
  1 masnssscpt pggghlngyp vppyafffpp mlgglsppga lttlqhqlpv sgystpspat
 61 ietqssssee ivpsppsppp lpriykpcfv cqdkssgyhy gvsacegckg ffrrsiqknm
121 vytchrdknc iinkvtrnrc qycrlqkcfe vgmskesvrn drnkkkkevp kpecsesytl
181 tpevgeliek vrkahqetfp alcqlgkytt nnsseqrvsl didlwdkfse lstkciiktv
241 efakqlpgft tltiadqitl lkaacldili lrictrytpe qdtmtfsdgl tlnrtqmhna
301 gfgpltdlvf afanqllple mddaetglls aiclicgdrq dleqpdrvdm lqepllealk
361 vyvrkrrpsr phmfpkmlmk itdlrsisak gaervitlkm eipgsmppli qemlensegl
421 dtlsgqpggg grdggglapp pgscspslsp ssnrsspath sp
```

By "RARA polynucleotide" is meant a nucleic acid molecule encoding an RARA polypeptide. An exemplary RARA polynucleotide sequence is provided at NCBI Accession No., NM_000964.3 which is reproduced below (SEQ ID NO: 43):

```
   1 gtgcctcttg cagcagccta acccagaagc aggggggaat cctgaatcga gctgagaggg
  61 cttccccggt tctcctggga accccatcgg cccctgcca gcacacacct gagcagcatc
 121 acaggacatg gcccctcag ccacctagct ggggcccatc taggagtggc atcttttttg
 181 gtgccctgaa ggccagctct ggaccttccc aggaaaagtg ccagctcaca gaactgcttg
 241 accaaaggac cggctcttga gacatccccc aacccacctg gccccagct agggtggggg
 301 ctccaggaga ctgagattag cctgccctct ttggacagca gctccaggac agggcgggtg
 361 ggctgaccac ccaaacccca tctgggccca ggcccatgc cccgaggagg ggtggtctga
 421 agcccaccag agcccctgc cagactgtct gcctcccttc tgactgtggc cgcttggcat
 481 ggccagcaac agcagctcct gcccgacacc tgggggcggg cacctcaatg ggtacccggt
 541 gcctccctac gccttcttct tcccccctat gctgggtgga ctctccccgc caggcgctct
 601 gaccactctc cagcaccagc ttccagttag tggatatagc acaccatccc cagccaccat
 661 tgagacccag agcagcagtt ctgaagagat agtgcccagc cctccctcgc caccccctct
 721 accccgcatc tacaagcctt gctttgtctg tcaggacaag tcctcaggct accactatgg
 781 ggtcagcgcc tgtgagggct gcaagggctt cttccgccgc agcatccaga gaacatggt
 841 gtacacgtgt caccgggaca gaactgcat catcaacaag gtgacccgga accgctgcca
 901 gtactgccga ctgcagaagt gctttgaagt gggcatgtcc aaggagtctg tgagaaacga
 961 ccgaaacaag aagaagaagg aggtgcccaa gcccgagtgc tctgagagct acacgctgac
1021 gccggaggtg ggggagctca ttgagaaggt gcgcaaagcg caccaggaaa ccttccctgc
1081 cctctgccag ctgggcaaat acactacgaa caacagctca gaacaacgtg tctctctgga
1141 cattgacctc tgggacaagt tcagtgaact ctccaccaag tgcatcatta agactgtgga
1201 gttcgccaag cagctgcccg gcttcaccac cctcaccatc gccgaccaga tcaccctcct
1261 caaggctgcc tgcctggaca tcctgatcct gcggatctgc acgcggtaca cgcccgagca
1321 ggacaccatg accttctcgg acgggctgac cctgaaccgg acccagatgc acaacgctgg
1381 cttcggcccc ctcaccgacc tggtctttgc cttcgccaac cagctgctgc ccctggagat
```

```
1441  ggatgatgcg gagacggggc tgctcagcgc catctgcctc atctgcggag accgccagga
1501  cctggagcag ccggaccggg tggacatgct gcaggagccg ctgctggagg cgctaaaggt
1561  ctacgtgcgg aagcggaggc ccagccgccc ccacatgttc cccaagatgc taatgaagat
1621  tactgacctg cgaagcatca gcgccaaggg ggctgagcgg gtgatcacgc tgaagatgga
1681  gatcccgggc tccatgccgc ctctcatcca ggaaatgttg gagaactcag agggcctgga
1741  cactctgagc ggacagccgg ggggtggggg gcgggacggg ggtggcctgg ccccccccgcc
1801  aggcagctgt agccccagcc tcagccccag ctccaacaga agcagcccgg ccacccactc
1861  cccgtgaccg cccacgccac atggacacag ccctcgcccc ccgccccggc ttttctctgc
1921  ctttctaccg accatgtgac cccgcaccag ccctgccccc acctgccctc ccgggcagta
1981  ctggggacct tccctggggg acggggaggg aggaggcagc gactccttgg acagaggcct
2041  gggccctcag tggactgcct gctcccacag cctgggctga cgtcagaggc cgaggccagg
2101  aactgagtga ggcccctggt cctgggtctc aggatgggtc ctgggggcct cgtgttcatc
2161  aagacacccc tctgcccagc tcaccacatc ttcatcacca gcaaacgcca ggacttggct
2221  cccccatcct cagaactcac aagccattgc tccccagctg gggaacctca acctcccccc
2281  tgcctcggtt ggtgacagag ggggtgggac aggggcgggg ggttccccct gtacataccc
2341  tgccatacca accccaggta ttaattctcg ctggttttgt ttttatttta attttttttgt
2401  tttgatttt  ttaataagaa ttttcatttt aagcacattt atactgaagg aatttgtgct
2461  gtgtattggg gggagctgga tccagagctg gaggggtgg gtccggggga gggagtggct
2521  cggaaggggc ccccactctc ctttcatgtc cctgtgcccc ccagttctcc tcctcagcct
2581  tttcctcctc agttttctct ttaaaactgt gaagtactaa cttttccaagg cctgccttcc
2641  cctccctccc actggagaag ccgccagccc ctttctcct  ctgcctgacc actgggtgtg
2701  gacggtgtgg ggcagccctg aaaggacagg ctcctggcct tggcacttgc ctgcacccac
2761  catgaggcat ggagcagggc agagcaaggg cccgggaca gagtttttccc agacctggct
2821  cctcggcaga gctgcctccc gtcagggccc acatcatcta ggctccccag cccccactgt
2881  gaaggggctg gccaggggcc cgagctgccc ccacccccgg cctcagccac cagcacccccc
2941  atagggcccc cagacaccac acacatgcgc gtgcgcacac acaaacac  acacacactg
3001  gacagtagat gggccgacac acacttggcc cgagttcctc catttccctg gcctgccccc
3061  caccccaaac ctgtcccacc cccgtgcccc ctccttaccc cgcaggacgg gcctacaggg
3121  gggtctcccc tcacccctgc accccagct ggggagctg gtctgcccc gacctccttc
3181  accaggggtt ggggcccctt ccctggagc ccgtgggtgc acctgttact gttgggcttt
3241  ccactgagat ctactggata aagaataaag ttctatttat tctaaaaaaa aaaaaaaaaa
3301  a
```

By "SNRNP25 (small nuclear ribonucleoprotein 25 kDa protein) polypeptide" is meant a polypeptide or fragment thereof having at least 85% amino acid sequence identity to NCBI Accession No. NP_078847.1 and having spliceosome activity, for example, catalyzing the splicing of pre-mRNAs. An exemplary SNRNP25 polypeptide sequence is provided below (SEQ ID NO: 44):

```
  1 mdvfqeglam vvqdpllcdl piqvtleevn sqialeygqa mtvrvckmdg evmpvvvvqs
 61 atvldlkkai qryvqlkqer eggiqhisws yvwrtyhlts agekltedrk klrdygirnr
121 devsfikklr qk
```

By "SNRNP25 polynucleotide" is meant a nucleic acid molecule encoding an SNRNP25 polypeptide. An exemplary SNRNP25 polynucleotide sequence is provided at NCBI Accession No., NM_024571.3 which is reproduced below (SEQ ID NO: 45):

```
   1 cagttcctgc gcgtgcgcgc ttggcctccc tagtgcgggc tggcagtgcg ggcagagccc
  61 ggctgagagg ggcggccctg gaggagacgg aggccgcggg tgggcccgag gcgcaagagg
 121 aagatgagga cgaagaagag gcgctgccgc actccgaggc catggacgtg ttccaggagg
 181 gtctggctat ggtggtgcag gacccgctgc tctgcgatct gccgatccag gttactctgg
 241 aagaagtcaa ctcccaaata gccctagaat acggccaggc aatgacggtc cgagtgtgca
 301 agatggatgg agaagtaatg cccgtggttg tagtgcagag tgccacagtc ctggacctga
 361 agaaggccat ccagagatac gtgcagctca agcaggagcg tgaaggggc attcagcaca
 421 tcagctggtc ctacgtgtgg aggacgtacc atctgacctc tgcaggagag aaactcacgg
 481 aagacagaaa gaagctccga gactacggca tccggaatcg agacgaggtt tccttcatca
 541 aaaagctgag gcaaaagtga gcctccagac aggacaaccc tcttcatcac tggtggctga
 601 gcttttcc agcaggaatg ggtcctcgaa tcatcgtgcc tctttcacag aaaggacgtt
 661 gtggtggcct cacccaggc atgcccaaca gtaactgtca gcataaacct gggggccctc
 721 aggactagga cagggtgagc cagtgctccc tcctttcatg tacttggcct gagactgacc
 781 tctccctagg tccaaatgcc ctagtcacat ggcagaccca cggcctggcc cactgtataa
 841 aataaacctg tttgcttctt agtttgaaaa gtagaaagcc acagtaacct gggtagcaaa
 901 gactgagatt gccccatcac agaggtgagt taaggggaga gaattggtac aggcgagtcc
 961 tatagtccaa gatggcgcca caccaccaaa gccttgaggc cacaccactc cccaaaccac
1021 acaactgtgt taccatgatc tccacagcaa ggaggaaata aaagcagagc ggctttaggg
1081 tttgcaaaaa aaaaaaaaaa aaa
```

By "SPOP (speckle type BTB/POZ protein) polypeptide" is meant a polypeptide or fragment thereof having at least 85% amino acid sequence identity to NCBI Accession No. CAA04199.1 and having intracellular signaling activity, for example, modulation of the transcriptional repression activities of death-associated protein 6 (DAXX), and structural interactions with histone deacetylase, core histones, and other histone-associated proteins. An exemplary SPOP polypeptide sequence is provided below (SEQ ID NO: 46):

```
  1 msrvpspppp aemssgpvae swcytqikvv kfsymwtinn fsfcreemge viksstfssg
 61 andklkwclr vnpkgldees kdylslylll vscpksevra kfkfsilnak geetkamesq
121 rayrfvqgkd wgfkkfirrd fllldeangll pddkltlfce vsvvqdsvni sgqntmnmvk
181 vpecrladel gglwensrft dccicvagqe fqahkailaa rspvfsamfe hemeeskknr
241 veindvepev fkemmcfiyt gkapnldkma ddllaaadky alerlkvmce dalcsnlsve
301 naaeililad lhsadqlktq avdfinyhas dvletsgwks mvvshphlva eayrslasaq
361 cpflgpprkr lkqs
```

By "SPOP polynucleotide" is meant a nucleic acid molecule encoding a SPOP polypeptide. An exemplary SPOP polynucleotide sequence is provided at NCBI Accession No., NM_001007226.1 which is reproduced below (SEQ ID NO: 47):

```
  1 ggggaggagg ccgcgcgggg tggggtctgg cggtacgcgc tggctgcgtc gacgtgctga
 61 cgccatgacg ccccggctgg tgtgtgtcgg tgtgtatgtg tgtgtgtgag tgtgcgcgct
```

-continued

```
 121 ccgagtgtgt gtgtatttgt gtatcggcgg tcccgcaggt cccggatgtt gcggacagta
 181 tgaggcaagc gcaggggggac ggggaccagc agctgtcgcc gccgctctca gatcgagtct
 241 tgctctgtca cccaggctgg agtgcagtgg cgcgatctca gctcactgcc acctttgcct
 301 cctgggttca agcgattctt ctgcctcagc ctcccgagta gctgggatta caggctctgg
 361 gaaccaccct tctactttct gtctctagga atttcactac tctagggtga agagggaaca
 421 gaaatctttg cccctgact ttggaaatct cgtttaacct tcaaactggc gatgtcaagg
 481 gttccaagtc ctccacctcc ggcagaaatg tcgagtggcc ccgtagctga gagttggtgc
 541 tacacacaga tcaaggtagt gaaattctcc tacatgtgga ccatcaataa ctttagcttt
 601 tgccgggagg aaatgggtga agtcattaaa agttctacat tttcatcagg agcaaatgat
 661 aaactgaaat ggtgtttgcg agtaaacccc aaagggttag atgaagaaag caaagattac
 721 ctgtcacttt acctgttact ggtcagctgt ccaaagagtg aagttcgggc aaaattcaaa
 781 ttctccatcc tgaatgccaa gggagaagaa accaaagcta tggagagtca acgggcatat
 841 aggtttgtgc aaggcaaaga ctggggattc aagaaattca tccgtagaga ttttcttttg
 901 gatgaggcca acgggcttct ccctgatgac aagcttaccc tcttctgcga ggtgagtgtt
 961 gtgcaagatt ctgtcaacat ttctggccag aataccatga acatggtaaa ggttcctgag
1021 tgccggctgg cagatgagtt aggaggactg tgggagaatt cccggttcac agactgctgc
1081 ttgtgtgttg ccggccagga attccaggct cacaaggcta tcttagcagc tcgttctccg
1141 gttttagtg ccatgtttga acatgaaatg gaggagagca aaaagaatcg agttgaaatc
1201 aatgatgtgg agcctgaagt ttttaaggaa atgatgtgct tcatttacac ggggaaggct
1261 ccaaacctcg acaaaatggc tgatgatttg ctggcagctg ctgacaagta tgccctggag
1321 cgcttaaagg tcatgtgtga ggatgccctc tgcagtaacc tgtccgtgga gaacgctgca
1381 gaaattctca tcctggccga cctccacagt gcagatcagt tgaaaactca ggcagtggat
1441 ttcatcaact atcatgcttc ggatgtcttg gagacctctg ggtggaagtc aatggtggtg
1501 tcacatcccc acttggtggc tgaggcatac cgctctctgg cttcagcaca gtgccctttt
1561 ctgggacccc cacgcaaacg cctgaagcaa tcctaagatc ctgcttgttg taagactccg
1621 tttaatttcc agaagcagca gccactgttg ctgccactga ccaccaggta gacagcgcaa
1681 tctgtggagc ttttactctg ttgtgagggg aagagactgc attgtggccc cagactttta
1741 aaacagcact aaataacttg ggggaaacgg ggggagggaa aatgaaatga aaaccctgtt
1801 gctgcgtcac tgtgttccct ttggcctggc tgagtttgat actgtgggga ttcagtttag
1861 gcgctggccc gaggatatcc cagcggtggt acttcggaga cacctgtctg catctgactg
1921 agcagaacaa atcgtcaggt gcctggagca aaaggaaaa aaaaaaaga aaggacattg
1981 agttttaaca gaagggaaaa ggaagaaga aaagattttt gcagaatttc tcaaaaatca
2041 gtttgtggat tccagtagta tttatattga gagaaacaaa ttttagtcct tctaactgtg
2101 ctaaaacttg gatatttgtg aaaactcctt accaccatac aagcatcaga agagctctct
2161 tgttgttagc acttattgtt tgcaagaaca gaatacatcc ttttatcctt ttatgaaaaa
2221 tgacaagtga aggcaaaagg ggaaggttat ttgatctgga agatgagtgt tctgatgtgg
2281 tggcttttgc aaaaatcttt attggtgttg aaaactgaaa aaataactc atccagaatt
2341 catattgtct tgacaagaac tatggttctc tgttttaga tattgtggaa aatgttttg
2401 ggcattttc tctgatttta tttcttctcc cccaccccttt tttctaaaaa acaaacaaaa
2461 aaaaaacac acaaaacaaa aacagaacaa aagaagagag aaggaaattt tatcaattaa
2521 aaatgctgtg tgataaaatc ccagcccaga ttgctcagct gtttgtacct gacttgccgc
```

-continued

```
2581 ctgcatagga gccagttctg ttccttctga ctagcccctc ttcctccagg ggagaacttc 2641 caaatgttaa ttttttttt tttgaaaata taaataatta ctattttgta ctgtgtggta 2701 tctctggtct tttgtttcac tcacctgcct tgtctcttgg gtctgagtcc cttgcttaag 2761 ggattttgaa gtcctagttt tcagcttgca gagattatgt ctgaaatgcc taatgagtcg 2821 cagggatttg ttgagactcc gtaatctcaa gttctctttg tgagctatca gcatctgcca 2881 gtctcttgtc ctccctgagt atctcacagt ccatatcctg atgagggatc aggcccctac 2941 ctctgccaag gcaagtaatg gtagtgggct tttaaactgc cccccgtatg ttttaagacc 3001 taatccccac ctcccttctt ctaactaaat ataaaaagat ccagggggaca taaatgtgga 3061 gattaaataa agggaaatta ttgtctctaa aaaaaaaaaa aaaaa
```

By "SRP14 (signal recognition particle 14 kDa protein) polypeptide" is meant a polypeptide or fragment thereof having at least 85% amino acid sequence identity to NCBI Accession No. NP_003125.3 and having intracellular signaling activity, for example, recognition and targeting of specific proteins to the endoplasmic reticulum in eukaryotes. An exemplary SRP14 polypeptide sequence is provided below (SEQ ID NO: 48):

```
  1 mvlleseqfl teltrlfqkc rtsgsvyitl kkydgrtkpi pkkgtvegfe padnkcllra 61 tdgkkkistv vsskevnkfq maysnllran mdglkkrdkk nktkktkaaa aaaaaapaaa 121 atapttaatt aataaq
```

By "SRP14 polynucleotide" is meant a nucleic acid molecule encoding a SRP14 polypeptide. An exemplary SRP14 polynucleotide sequence is provided at NCBI Accession No., NM_003134.5 which is reproduced below (SEQ ID NO: 49):

```
  1 agcggaagtc ccgcccagcc taggccgaac ttccggctct cactgctagg ggcttaagcg 61 gagggagtcg agccagcgtc gccgcgatgg tgttgttgga gagcgagcag ttcctgacgg 121 agctgaccag acttttccag aagtgccgga cgtcgggcag cgtctatatc accttgaaga 181 agtatgacgg tcgaaccaaa cccattccaa agaagggtac tgtggagggc tttgagcccg 241 cagacaacaa gtgtctgtta agagctaccg atgggaagaa gaagatcagc actgtggtga 301 gctccaagga agtgaataag tttcagatgg cttattcaaa cctccttaga gctaacatgg 361 atgggctgaa gaagagagac aaaaagaaca aaactaagaa gaccaaagca gcagcagcag 421 cagcagcagc agcacctgcc gcagcagcaa cagcaccaac aacagcagca acaacagcag 481 caacagcagc acagtaaagg gcatacattt cctgctttca ccaattaacc actgaattgc 541 tatttttttcc ttttggccag atagctaggt ttctggttcc cccacagtag gtgttttcac 601 ataagattag ggtccttttg gaaagaatag ttgcagtgtt tataggatag ttgtggtaag 661 aatctagttt attttgcatt tggctaattg gtctgtgctg catggttata tactcctgga 721 ttatagatta aaagtctctg tagacatctc tgtgaagagc aagctatcat taaacatgtc 781 tgtttatcag cactgtctct ttattccttt cccaacccat tttaatagtt ctggcaataa 841 ctactaaatc tagaatgatg tgattaatga ataggcttta gctctataat atcttctagg 901 ttattagaat tgaaacctga cagtttata aaaagtcatg ttatctcatg agctgcttcc 961 cacctggctg tataatttta tcatcatggt tccccagttt cgatgagttc tcacagtcaa
```

-continued
```
1021 atgagagttt gtttaaccac cttaggagaa acatactaca aagtcatcaa gaataaaggt 1081 tccaaagtaa ttatgatttt tggtttcttt atgcccttttg gtttggatat tttcatgtgc
```

By "SYCP2L (Synaptonemal Complex Protein 2 Like) polypeptide" is meant a polypeptide or fragment thereof having at least 85% amino acid sequence identity to NCBI Accession No. NP_001035364.2 and having meiotic activity, for example, facilitation of the synaptonemal complex during meiotic prophase. An exemplary SYCP2L polypeptide sequence is provided below (SEQ ID NO: 50):

```
  1 mqaknkdalq pikedrtgka qddafwlqsl itdafhdkgf qkikeyfqqk eshfpqkynr 61 lllyrldrsi nkeldknefq syslllkciq rflvdglked epllirqgli pklvswfert 121 tgiltsegla sdtslicvie dffdtaliis rsssegkiqm ldsfllslgf lvtektvnhl 181 lqqeglktfn cilhavpree rkkfplsegm chlmkdlart lltvgdydqq vaisealcrl 241 tikksrdelv hkwfddevia eafkeikdre fetdsrrfln hlnnrlgdqr rvysfpciaa 301 fadehemrkp adeklekfwi dfnlgsqsvt fyidnaentl wdsvtlpkea vmnfsitete 361 kikifiiylk kpmiisykev mkieihfdlq fnisqvsiqa lgedkqmlpd qtkisselfs 421 ksdkedresp sglereteqa eestnmvefm saeddrclit lhlndqsepp vigepasdsh 481 lqpvppfgvp dfpqqpkshy rkhlfsesnq dsstselswt snqkkkslks yssrkktrtr 541 snlrilpvfp pssgsghekd qakllspsek eipeqnntts pktseqkfqd sfafltaeds 601 aqktelqdph slselsslkh sedeekpkiv nqesltests lkhklrnled kdipegsfak 661 sqqsrleeev apgspfsite erelpegist sslevvpenl ngsailptfe nftkkrkrky 721 elryrkrpfn senakkapdc likllnqmql frinklerfq nlvlqelssl kqdicialehl 781 ekevlefwgk qsadlqsfcd lqvlrfnstq ts
```

By "SYCP2L polynucleotide" is meant a nucleic acid molecule encoding a SYCP2L polypeptide. An exemplary SYCP2L polynucleotide sequence is provided at NCBI Accession No., NM_001040274.2 which is reproduced below (SEQ ID NO: 51):

```
  1 gagtgctggc tttctcttaa agggtgagtg cgtgcgccca ggtggtttgg cctgtgtgcg 61 ctagttactt gcacgcgctt cttgagtctc aaaacacaga gctctagtaa acttcagggg 121 gcggattcgt caattacagt tgcggaagaa gactcgactc gaagagcggt ccgccaccag 181 ggctctttcg gcagcgcccc cagcgggcgg ggctcttggg cggggaagca ggagagggcc 241 gaccgagcgc aacaaagctg agcggcgcgt cgcttcagga acgaagaagc ctcgttatgc 301 aagcgaaaaa caaagatgct ttgcagccta ttaaggaaga caggactggg aaggcccagg 361 atgatgcttt ctggcttcaa tcacttatta cggatgcatt ccatgataaa ggatttcaga 421 aaataaaaga atactttcaa cagaaagaga gccactttcc tcaaaaatat aatcgtcttc 481 tattataccg tcttgacaga tcaataaata aggaactaga taaaaatgaa tttcagtctg 541 tgtcactgtt gctgaaatgt attcagcgat tcctcgtaga tggcctgaaa gaagatgaac 601 ctctgctaat tcggcaggga ctgatcccaa agctagtttc ctggtttgaa agaacaacag 661 gaattctgac ctcggaaggc ctagcctcag acacgtcgct gatttgtgtt atagaagatt 721 tctttgacac tgcattgatt atttccagga gtagtagtga agggaaaatt cagatgttgg 781 attccttcct acttagctta ggattcctgg tgacagaaaa gactgtaaat catttgcttc
```

-continued

```
 841 aacaggaggg cttgaagact tttaactgca ttttgcacgc tgtccctcga gaagagagaa
 901 aaaaattccc tttgtcagaa ggcatgtgtc atcttatgaa agaccttgca aggacactct
 961 tgactgtggg tgattatgac cagcaggttg ctatttctga agcgctgtgt agactgacga
1021 ttaaaaaatc aagggatgaa cttgtccata aatggtttga tgatgaagtc attgctgaag
1081 ctttcaaaga aattaaggat cgagaatttg agacggacag tagacgtttt ctcaatcacc
1141 taaacaacag acttggtgac caaagaaggg tgtattcatt tccgtgtatt gctgcttttg
1201 ctgatgagca tgagatgaga aaaccagcgg atgaaaaatt agagaaattt tggatcgact
1261 tcaacctagg aagtcagagt gtcactttt atatagacaa tgctgagaat actctatggg
1321 actcagtgac acttccgaag gaagcggtga tgaatttcag cataacagaa acgagaaga
1381 taaagatatt tatcatttac ctgaagaagc ccatgattat cagctacaaa gaagtcatga
1441 aaatagaaat ccattttgat ttgcagttca acatatcaca gtttccatt caagctttag
1501 gagaagacaa acagatgttg cctgaccaga cgaaaatctc ctcagaactt tttagtaagt
1561 ctgataaaga agacagggag agtcccagtg gccttgaaag agaaacagag caggcagaag
1621 aatccactaa catggtggag tttatgagtg ctgaagatga ccgctgccta ataactctcc
1681 acttaaatga ccaatctgag ccacctgtta ttggggaacc tgcctctgat agtcaccttc
1741 agccggtccc tccgttcggg gtccctgact tcccgcaaca acctaagtct cattacagaa
1801 aacatctctt ctctgagagt aatcaagatt caagtaccag tgaactatct tggaccagta
1861 accagaaaaa gaaatcccta aaatcatatt ccagtagaaa gaagacaaga accagaagta
1921 atttgagaat cttgccagtt ttccctccca gtagtggcag tggccatgag aaagaccaag
1981 ctaagcttct atcaccatca gagaaagaaa tacccgagca aaataacacc acatctccaa
2041 agacttctga acaaaaattc caagatagtt ttgcttttt gactgctgaa gattctgccc
2101 agaaaacaga gcttcaagat cctcactcac tgagtgagct ctcttccttg aagcactcag
2161 aagatgaaga aaaacctaag attgtgaacc aagaatcact aacagaaagt actagcttga
2221 aacataagct gagaaacttg aagacaaag acataccaga aggtagtttt gctaagtcac
2281 aacaatcaag attggaagaa gaggttgctc cgggatcccc tttctcaata acagaagaaa
2341 gagagttgcc agaaggaatt tccacttcat ccctagaagt tgtgccagag aacttgaacg
2401 gttctgccat tctcccaacc tttgaaaact tcactaaaaa acggaaaaga aaatatgagc
2461 ttaggtacag aaaagcgtccg tttaattcag aaaatgcaaa gaaagcaccg gattgcctaa
2521 taaaactttt aaaccagatg caactgttca gactcaataa actagagcgc tttcaaaatt
2581 tggttcttca agagttgagc agtcttaagc aggatattca ggccctggaa caccttgaga
2641 aggaggttct ggaattctgg gggaaacagt ctgctgatct gcaatctttc tgtgatctgc
2701 aagtgctgag gttcaattca actcagactt cataagaaag ccaaagcctg gttttatgat 2761 tgcagccctc agcctgggct gcctgaagac gaagagaaag agcaaggtta ttgttggctc
2821 aggccttgtt agccagactt cgtgctctgt acgcattcaa tttcctcccc tccaaacatc
2881 atccctggga actgctgagt tcagatagaa tatatgttgg tagtttgcag ttgggttatt
2941 atccatttgt tcataaaaat taacctttttg tattaaaatt tggtcagata gtattaatag
3001 aaagttcagg atgttaaaca acttggagtg gtgttgcttt ttttttataa aagtaaaatg
3061 gactttttt tgtttgagaa atgtcttcaa gttttgtgtg aataaaacac tttagcagca
3121 tctgtataaa aaaaaaaaa
```

By "TRAF2 (TNF receptor-associated factor 2) polypeptide" is meant a polypeptide or fragment thereof having at least 85% amino acid sequence identity to NCBI Accession No. NP_066961.2 and having intracellular signaling activity associated with the TNF-receptor superfamily, for example direct interaction with TNF receptors, and the formation of complexes with other TRAF proteins, as well as TNF-alpha-mediated activation of MAPK8/JNK and NF-κB. An exemplary TRAF2 polypeptide sequence is provided below (SEQ ID NO: 52):

```
  1 maaasvtppg slellqpgfs ktllgtklea kylcsacrnv lrrpfqaqcg hrycsfclas
 61 ilssgpqnca acvhegiyee gisilessssa fpdnaarrev eslpavcpsd gctwkgtlke
121 yeschegrcp lmltecpack glvrlgeker hlehecpers lscrhcrapc cgadvkahhe
181 vcpkfpltcd gcgkkkipre kfqdhvktcg kcrvperfha igcletvege kqqehevqwl
241 rehlamllss vleakpllgd qshagsellq rceslekkta tfenivcvin revervamta
301 eacsrqhrld qdkiealssk vqqlersigl kdlamadleq kvlemeasty dgvfiwkisd
361 farkrqeava gripaifspa fytsrygykm clriylngdg tgrgthlslf fvvmkgpnda
421 llrwpfnqkv tlmlldqnnr ehvidafrpd vtsssfqrpv ndmniasgcp lfcpvskmea
481 knsyvrddai fikaivdltg l
```

By "TRAF2 polynucleotide" is meant a nucleic acid molecule encoding a TRAF2 polypeptide. An exemplary TRAF2 polynucleotide sequence is provided at NCBI Accession No., NM_021138.3 which is reproduced below (SEQ ID NO: 53):

```
   1 cttagttccg ggcgcgctgc gaccgttggg gctttgttcg cgggggtcac agctctcatg
  61 gctgcagcta gcgtgacccc ccctggctcc ctggagttgc tacagcccgg cttctccaag
 121 accctcctgg ggaccaagct ggaagccaag tacctgtgct ccgcctgcag aaacgtcctc
 181 cgcaggccct tccaggcgca gtgtggccac cggtactgct ccttctgcct ggccagcatc
 241 ctcagctctg ggcctcagaa ctgtgctgcc tgtgttcacg agggcatata tgaagaaggc
 301 atttctattt tagaaagcag ttcggccttc ccagataatg ctgcccgcag ggaggtggag
 361 agcctgccgg ccgtctgtcc cagtgatgga tgcacctgga aggggaccct gaaagaatac
 421 gagagctgcc acgaaggccg ctgcccgctc atgctgaccg aatgtcccgc gtgcaaaggc
 481 ctggtccgcc ttggtgaaaa ggagcgccac ctggagcacg agtgcccgga gagaagcctg
 541 agctgccggc attgccgggc accctgctgc ggagcagacg tgaaggcgca ccacgaggtc
 601 tgccccaagt tccccttaac ttgtgacggc tgcggcaaga gaagatccc cgggagaag
 661 tttcaggacc acgtcaagac ttgtggcaag tgtcgagtcc cttgcagatt ccacgccatc
 721 ggctgcctcg agacggtaga gggtgagaaa cagcaggagc acgaggtgca gtggctgcgg
 781 gagcacctgg ccatgctact gagctcggtg ctggaggcaa agcccctctt gggagaccag
 841 agccacgcgg ggtcagagct cctgcagagg tgcgagagcc tggagaagaa gacggccact
 901 tttgagaaca ttgtctgcgt cctgaaccgg gaggtggaga gggtggccat gactgccgag
 961 gcctgcagcc ggcagcaccg gctggaccaa gacaagattg aagccctgag tagcaaggtg
1021 cagcagctgg agaggagcat tggcctcaag gacctggcga tggctgactt ggagcagaag
1081 gtcttggaga tggaggcatc cacctacgat ggggtcttca tctggaagat ctcagacttc
1141 gccaggaagc gccaggaagc tgtggctggc cgcataccg ccatcttctc cccagccttc
1201 tacaccagca ggtacggcta caagatgtgt ctgcgtatct acctgaacgg cgacggcacc
1261 gggcgaggaa cacacctgtc cctcttcttt gtggtgatga agggcccgaa tgacgccctg
1321 ctgcggtggc ccttcaacca gaaggtgacc ttaatgctgc tcgaccagaa taaccgggag
1381 cacgtgattg acgccttcag gcccgacgtg acttcatcct cttttcagag gccagtcaac
```

-continued

```
1441 gacatgaaca tcgcaagcgg ctgcccctc ttctgcccg tctccaagat ggaggcaaag 1501 aattcctacg tgcgggacga tgccatcttc atcaaggcca ttgtggacct gacagggctc 1561 taactgcccc ctactggtgt ctgggggttg ggggcagcca ggcacagccg gctcacggag 1621 gggccaccac gctgggccag ggtctcactg tacaagtggg caggggccgc gcttgggcgc 1681 ttgggagggt gtcggcctgc agccaagttc actgtcacgg gggaaggagc caccagccag 1741 tcctcagatt tcagagactg cggaggggct tggcagacgg tcttagccaa gggctgtggt 1801 ggcattggcc gagggtcttc gggtgcttcc cagcacaagc tgcccttgct gtcctgtgca 1861 gtgaagggag aggccctggg tgggggacac tcagagtggg agcacatccc agcagtgccc 1921 atgtagcagg agcacagtgg atggccttgt gtccctcggg catgacaggc agaaacgagg 1981 gctgctccag gagaagggcc tcctgctggc cagagcaagg aaggctgagc agcttggttc 2041 tccctctgg ccctggaga gaagggagca ttcctagacc cctgggtgct tgtctgcaca 2101 gagctctggt ctgtgccacc ttggccaggc tggctgtggg agagggtctg gtcccacgcc 2161 gcctctgctc agaccactgt gtgggaggtg cacagcacag cctgcgggta aagtgtgaga 2221 gcttgccatc cagctcacga agacagagtt attaaaccat tcaaatctct gtggtcaaaa 2281 aaaaaaaaaa aaaaaaaa
```

By "UBE2D3 (ubiquitin-conjugating enzyme E2 D3) polypeptide" is meant a polypeptide or fragment thereof having at least 85% amino acid sequence identity to NCBI Accession No. NP_871620.1 and having signaling activity associated with the ubiquitin pathway, for example, ligase activity and ubiquitin protein ligase binding activity. An exemplary UBE2D3 polypeptide sequence is provided below (SEQ ID NO: 54):

```
  1 malkrinkel sdlardppaq csagpvgddm fhwqatimgp ndspyqggvf fltihfptdy 61 pfkppkvaft triyhpnins ngsicldilr sqwspaltis kvilsicsll cdpnpddplv 121 peiariyktd rdkynrisre wtqkyam
```

By "UBE2D3 polynucleotide" is meant a nucleic acid molecule encoding an UBE2D3 polypeptide. An exemplary UBE2D3 polynucleotide sequence is provided at NCBI Accession No., NM_003340.6 which is reproduced below (SEQ ID NO: 55):

```
  1 accaagtgag gaaactgggg gacgctgtgg ggaggggcgt ggggctggat cgcgcagcgg 61 ctgcttcctt taccttcctc ccatggtctc cttccggttc tcgatgcttc tctgagccta 121 agggtttccg ccactcgttc accctcccc cagctcatga tcctcctccc tccccgccc 181 tcctggtcca atctccgatc tgtttagtaa gaaggtgctg ttccgagaag aaggaaaagg 241 gcttgacacg tattcactcg gccccggacg tgggaagcaa gccgtctggc ttcggcctca 301 catcggtctt gtgctcggga cggcggcgtt ggcggactga tccgcggcgg tgaagaggcg 361 cctgtgtctg gcagagctgg tgtgagacga gacaatcctg ccccgccgcc gggataatca 421 agagttttgg ccggaccttt gagcatacac cgagagagtt aggagccaga cgacaagcac 481 acactatggc gctgaaacgg attaataagg aacttagtga tttggcccgt gaccctccag 541 cacaatgttc tgcaggtcca gttggggatg atatgtttca ttggcaagcc acaattatgg 601 gacctaatga cagcccatat caaggcggtg tattctttt gacaattcat tttcctacag
```

-continued

```
 661 actacccctt caaaccacct aaggttgcat ttacaacaag aatttatcat ccaaatatta
 721 acagtaatgg cagcatttgt ctcgatattc taagatcaca gtggtcgcct gctttaacaa
 781 tttctaaagt tctttttatcc atttgttcac tgctatgtga tccaaaccca gatgacccccc
 841 tagtgccaga gattgcacgg atctataaaa cagacagaga taagtacaac agaatatctc
 901 gggaatggac tcagaagtat gccatgtgat gctaccttaa agtcagaata acctgcatta
 961 tagctggaat aaactttaaa ttactgttcc ttttttgatt ttcttatccg gctgctcccc
1021 tatcagacct catcttttt aattttattt tttgtttacc tccctccatt cattcacatg
1081 ctcatctgag aagacttaag ttcttccagc tttggacaat aactgctttt agaaactgta
1141 aagtagttac aagagaacag ttgcccaaga ctcagaattt ttaaaaaaaa aaatggagca
1201 tgtgtattat gtggccaatg tcttcactct aacttggtta tgagactaaa accattcctc
1261 actgctctaa catgctgaag aaatcatctg agggggaggg agatggatgc tcagttgtca
1321 catcaaagga tacagcatta ttctagcagc atccattctt gtttaagcct tccactgtta
1381 gagatttgag gttacatgat atgctttatg ctcataactg atgtggctgg agaattggta
1441 ttgaatttat agcatcagca gaacagaaaa tgtgatgtat tttatgcatg tcaataaagg
1501 aatgacctgt tcttgttcta cagagaatgg aaattggaag tcaaacaccc tttgtattcc
1561 aaaatagggt ctcaaacatt ttgtaatttt catttaaatt gttaggaggc ttggagctat
1621 tagttaatct atcttccaat acactgttta atatagcact gaataaatga tgcaagttgt
1681 caatggatga gtgatcaact aatagctctg ctagtaattg atttatttt cttcaataaa
1741 gttgcataaa ccaatgagtt agctgcctgg attaatcagt atgggaaaca atcttttgta
1801 aatgcaaagc tgttttttgt atatactgtt gggatttgct tcattgtttg acatcaaatg
1861 atgatgtaaa gttcgaaaga gtgaatattt tgccatgttc agttaaagtg cacagtctgt
1921 tacaggttga cacattgctt gacctgattt atgcagaatt aataagctat ttggatagtg
1981 tagctttaat gtgctgcaca tgatactggc agccctagag ttcatagatg gacttttggg
2041 acccagcagt tttgaaatgt gtttatggag tttaagaaat ttattttcca ggtgcagccc
2101 ctgtctaact gaaatttctc ttcaccttgt acacttgaca gctgaaaaaa aacaacatgg
2161 gagtaataat gggtcaaaat ttgcaaaata aagtactgtt ttggtgtggg agttgtcatg
2221 aggctgtgtt gaagtgactt atctatgtgg gatattgagt atccattgaa atggatttgt
2281 tcagccattt acattaatga gcatttaaat gcaacagata tcatttcagg tgacttaaca
2341 tgaatgaata aaagtcaatg ctattggatt gttttttgtt tgacaagtgc tatctgtgcc
2401 actgatttaa cttctgtagt aacaagggca ttaccattct tcacctttcc taattctgat
2461 cccatagttt tacatttttc ctgtttattt tgattttgtt cactgcttta tttcttaaag
2521 ttctagcaca tctgtgactc ctccacttcc acatttttgc actgcttaca cttacgtgca
2581 atcttattcc ttgtctgcac acacatgtgg aaagctagaa ataaatgtta aaacttactt
2641 tttataaaca ttttaatatg tagtttggac atgatttatt gacttaaggt tcttctctaa
2701 actggaagtg aaatgcatgc cttctgaaga tgttctggct tgttaattc tgtaatcatt
2761 tcattgggga aaaaaccagc tacgcagttt ttccaatgag tgaattttt catttgtgt
2821 tttgcttaaa acggctcctt cagggtagat gtcatactgc ataacttttt tggattcaaa
2881 ttatgaatga gaaattagtt aacattctgc tccacaaggt aagaaaaact gctctttggc
2941 tctattttca aaattacttc tgagatgcat atagtctcaa aataacagct ttagtaggca
3001 tatcacttct tgaaagccaa acatgagtgt aagacacttt tatgaaacac ggtggatccc
3061 taactggctt tcaaattgac ctttatagcc ttagacaacc cttaggtatt tacggagatg
```

-continued

```
3121 acttctttga ttgtcataac aattagtgga tgtgtccagt tctctgtatc tttgacttga 3181 tgctttatac atcatttcat ttgttgcttc taagggaata agccatagag gcttctccag 3241 gtttaaaaga acagtaaagt acctggaaaa ccaacatttt tgaatgtatg gacactggac 3301 atgagatatg tacaatgaaa tcttaaaaga atctaagaat ttgccctctt tgccccactc 3361 cacccagtaa tttgacatta ctagtgccat gtataggacc caactgagta ttagaatcag 3421 ttttgactat gtctttgtat ttcctaaatc ttttaatgca taaaccgaat tagggtccag 3481 ttggcctgtt aatggtaaat ttacatttta aatgactcag tttgtttttc ctgggcgagt 3541 ttgcaatgtg ataatcagat tttttaaaac tgattaattt gctttcttgt gtgggtgtac 3601 tcacatttta aagtatgaac cacagttaac tagtggtctc aggggtagtg aaacactcac 3661 tttttttttt gtttgttttt ttttgtttgt tgaaatggct tagttgaagt atacttaagg 3721 tactgatcat gctgtgttag taatttgggc ggggaggggg gtaactcagc catgttttgt 3781 gttggcataa caaaactgtt aatgattgtt gattacactt ttaagtgaat ttgtcttta 3841 tgaggaaccc agtgcaagtc actaaatatt gtctaatagt gacatctgca taagacttgt 3901 aatagctgaa gttaattgag cttaaaggaa ttgttaccat taaagtctgt gtttaaagac 3961 aaaaaaaaaa aaaaaa
```

By "UBE2G1 (ubiquitin-conjugating enzyme E2 G1) polypeptide" is meant a polypeptide or fragment thereof having at least 85% amino acid sequence identity to NCBI Accession No. AAH26288.2 and having signaling activity associated with the ubiquitin pathway, for example, ligase activity and ubiquitin protein ligase binding activity. An exemplary UBE2G1 polypeptide sequence is provided below (SEQ ID NO: 56):

```
  1 paarrrsrrl spaflgsgap vagpgflgtp rssrpqslsp alrkprrqpg psagrmtelq 61 salllrrqla elnknpvegf sagliddndl yrwevliigp pdtlyeggvf kahltfpkdy 121 plrppkmkfi teiwhpnvdk ngdvcisilh epgedkygye kpeerwlpih tvetimisvi 181 smladpngds panvdaakew redrngefkr kvarcvrksq etafe
```

By "UBE2G1 polynucleotide" is meant a nucleic acid molecule encoding an UBE2G1 polypeptide. An exemplary UBE2G1 polynucleotide sequence is provided at NCBI Accession No., NM_003342.4 which is reproduced below (SEQ ID NO: 57):

```
  1 gtctcagcgc gcctgcgccg agcggccctg cgcgcagtga ggcagtggcg ggggaaggca 61 ccggtggggc cgacgggcgg gttgaaggag ggaagcgggc gagcgaagtc ccagtgcgcg 121 ccgcggcagc ccgggcaccc tcccctccg ggcgtgagtc gctgtgaaaa gagctgaagc 181 gagcggactc gcaccggcag cgaggcgccg ctcccgccgc ctcagcccgg ccttcctcgg 241 ctccggcgct ccggtcgcgg ggcccgggtt cctcggcaca ccccgctcca gccgccccca 301 gagcctgtcc ccagcccttc ggaagccccg gcgccagccc gggccctcgg cagggaggat 361 gacggagctg cagtcggcac tgctactgcg aagacagctg gcagaactca acaaaaatcc 421 agtggaaggc ttttctgcag gtttaataga tgacaatgat ctctaccgat gggaagtcct 481 tattattggc cctccagata cactttatga aggtggtgtt tttaaggctc atcttacttt 541 cccaaaagat tatcccctcc gacctcctaa aatgaaattc attacagaaa tctggcaccc
```

-continued

```
 601 aaatgttgat aaaaatggtg atgtgtgcat ttctattctt catgagcctg gggaagataa 661 gtatggttat gaaaagccag aggaacgctg gctccctatc cacactgtgg aaaccatcat 721 gattagtgtc atttctatgc tggcagaccc taatggagac tcacctgcta atgttgatgc 781 tgcgaaagaa tggagggaag atagaaatgg agaatttaaa agaaaagttg cccgctgtgt 841 aagaaaaagc caagagactg cttttgagtg acatttattt agcagctagt aacttcactt 901 atttcagggt ctccaattga gaaacatggc actgtttttc ctgcactcta cccacctatt 961 gctggacttc tgttgtacaa gttggcaaac actggctgga actgggctgc aataaaacat 1021 gccagttatc aatgctgaca agagcctaac aagtgccaac ttacagatga ttacgcattt 1081 tgaattctaa tgaactgttt taaccttcag gaagaattgt aaagacctgt acatagcaca 1141 acatgatccg gataatatat atactgttca tgtacatcca caaatacacc ttgtaccaaa 1201 taatgctttc ttgtagtaga ataagaatcg tgtaaattct aagagatttt agcaggtttt 1261 ctttcctatt cattgtttct tatcagttta aaaggattcc tttaagcatg tcagatgaaa 1321 agcaattagg attaaaagtt tccatttaat ttcccttaaa cccttgaggc ttcattaaac 1381 tcttttcact tactaaactt ttgtatcttc tttgttttga cacactcccc tttgctttta 1441 tctcttacct gccagaatgt tctcaaatga tttagttcaa atactgaaat acttaatgag 1501 caattacttg atttttaatg atgacttcga aggagtcatc actaggtgct ttgtccttt 1561 tgtattctag ttgcacccac ctcttggatt ggatatagca ataacattta ttggccgttg 1621 tgagctcttg atcccagtca ttacccctga gaactaaaaa tagatggttc ttaattcaac 1681 ttactgaaaa ttttccccaaa caatagcaaa tctgactttt ccctcttcag ttgcctggta 1741 ttaaggttgg ataaatgaag catgcacagc tacaggcttt ctacttaact tctgggtttg 1801 ctattacaaa tcctatttac tctcatacccc ttctccttag tccttcatat ttctctgcct 1861 ctattcttct atactgcaga ttttttctcac ctattgtaca aagaaattgc gatgtatatt 1921 ttcatgtaat ttgattttgg aattctgtca ccttatgtag tgagttcttc caaaatataa 1981 ttttttttca ataattgtca agttgttggc ttttattgta ttgaatgaag gctataatac 2041 tgagtgccag agaagtgggt taggaaaatc tcaggttgat tccttatgca aatgaacttt 2101 taatacttga aaatcacatg gccatggcag tatatgtatt tggttctatc tagattcttc 2161 tgtgaatcta aaagcattac aggggtaaat gctttgctat ttgacgtata gatcccgtca 2221 ctaacaatag tacacttgga tgtgattaat gtttgagctt caatatattt catatcatac 2281 agttttctaa aacaacttca gcaaatggta aaatgaacat gtgcagtgtt aaaggcaggc 2341 cttaggctcc ttcatgtttg ttgtgaggtt gtgtgtggga agtagtcttt ggcttataag 2401 ggatagaact tgagacagta gcagatggga catggtgttt gattgtgaga atcagtgaga 2461 attcgtgcat ctctgctctg tggggtttgg agaaatgctt tggcagaaga gtgaaagaac 2521 tcctgccaag agcccagacc tctacaaacg ttgtatgtcc tttttttaagc agaaataaaa 2581 tggttgagga tgtagtcaca gtagagagtg attttttttct aagtccctgt cctctactct 2641 gaagcgttat aaaaacctgt aaacattata caaacccaca aaccttatag aaactcgtaa 2701 gtgtgttgtg actggaaatt gattcattag aacccagttt tcttttaagaa ctttgtgact 2761 tggtttttttt tttccttttc caaagactgt aaaaatagtt gccccaaaat gtcagcactg 2821 cacaccctcc agggacttgg aatacaatcc ttttttactttt tttttttttt tttttaagaa 2881 actgggtctc tctgtcaccc aggctggagt gcagtggcaa cgatcatagc taactgcagc 2941 tttgacctcc tgggctcaag tgatcctcct gcctcagcct cctgagtagc taggactaca 3001 ggtgtatgcc accatgcctg gctaatacaa aaaaattctt ttaagagatg ggatccctcc
```

-continued

```
3061 cttttaaaat cagaacttgt tcacatggtg gttgcttgtg gcaaaacgga gttcaaattt
3121 tgctctccta ttgctataat tctgctagca atctgttgag gtgaaacttg ggatctgact
3181 cttcagcaag cagcaaatga cctagtaact cagggacaac tattttttgaa ctttaagtgc
3241 cactttaatg cagttagttt gataaaacca tgtgggtttt ttttttaggg ctagctctac
3301 gggagtggaa gtgagagcca ggcatgagtg cgtctccaca tgcttttcca cctgccctga
3361 gtgtgttaca tactgaaaca ggcctacata gatgttacaa cttcccttcc tctgtcggag
3421 atgtcatctg tgcctttctc agtgttcatc tgataatgta aatttaaatg cctctacatt
3481 tgatacgaaa cccacattca ggtgacactg aacgaggtgg cttttgtccc accagtgcct
3541 catcagtgtg aggcgattcc tctctgcttt aggaaaatga ttttttcccc taaacttgtg
3601 ccaaccatca acaacatctc catagatctt atggattgta gaactgttgg ctgtttccta
3661 aatttattcc aagttctcgt agaggcatat agatttcagt ctgtgcttgt atgggataga
3721 tgatctgagt ggctttctgg cctcttttt gagtttaaaa tccatatgag gttgacgtgt
3781 catactaagg taacatgttt gtgaggttat tccactagta ctgtgatcac gtgggtgtca
3841 gtatctttaa cggccttcat tcttggttgt gagattttat ttgatatgcc cactcaccct
3901 cgacgaatct gcccgctttg ggctgtggtg cctgtgtatc tttgcccgtc tggtctccag
3961 ttggtggaat tacctttttt gtactgccac ttctcagcat cttttgaaatt tgacataatg
4021 ttgcttcatt tcagttttttt tagttctgta atttgttgat tgtatttaac tatgtgagtt
4081 ctgttgtgat gtttactgta ttgtaaagca cctcattcat gtgatgagtg ctctataaat
4141 caataaatga tgacttagag gctgtatcac gagctatttt ggttttagga tgcaggtctc
4201 aaaagcaa
```

By "UBE2M (ubiquitin-conjugating enzyme E2 M) polypeptide" is meant a polypeptide or fragment thereof having at least 85% amino acid sequence identity to NCBI Accession No. EAW72613.1 and having signaling activity associated with the ubiquitin pathway, for example, ligase activity and ubiquitin protein ligase binding activity. An exemplary UBE2M polypeptide sequence is provided below (SEQ ID NO: 58):

```
  1 miklfslkqq kkeeesaggt kgsskkasaa qlriqkdine lnlpktcdis fsdpddllnf
 61 klvicpdegf yksgkfvfsf kvgqgyphdp pkvkcetmvy hpnidlegnv clnilredwk
121 pvltinsiiy glqylflepn pedpinkeaa evlqnnrrlf eqnvqrsmrg gyigstyfer
181 clk
```

By "UBE2M polynucleotide" is meant a nucleic acid molecule encoding an UBE2M polypeptide. An exemplary UBE2M polynucleotide sequence is provided at NCBI Accession No., NM_003969.3 which is reproduced below (SEQ ID NO: 59):

```
  1 aggcgcacaa cgcaggccgg gcgggaagag ccaaagcggg caggcggcgg aaatatccga
 61 agcggcgggg cgcccgaggc cgttgccgac ctccgcgcta aagccgctgc tgccgcggaa
121 gacgatcctc cagtacccgc ccgccgtcac cgcagctgcc gtgtcctcct cccacccta
181 gccgcacccc ctcgcggagg gatcagctga gcggccaaac ggcacggtcg ggggagcccc
241 gagtccgcag ctgcagcggg gcctgagacc agagttggcg agggcaagga aggagcggcc
301 ccgggcagtg gggcggggc cgggcgggcc cgagaacagc cgaatttggc cgagcgctgc
361 cgagcgagtc cgaggcgctg ggccaggccg gagccggact acgggagccg aggcgggccg
421 cgcggtgggc gcggagagga gcggagcggc gcggcaggcc gggcgggtgg cggcagcagc
```

-continued

```
 481 ggaggaggcc gcagctgcgg gtccgaggag cggaggcgac gcgggcggcg gcggggggcc 541 gggtggccgg ggtcccgggc cccgcggcgg cggcagcggc ggcggcggcg gcaggatgat 601 caagctgttc tcgctgaagc agcagaagaa ggaggaggag tcggcgggcg gcaccaaggg 661 cagcagcaag aaggcgtcgg cggcgcagct gcggatccag aaggacataa acgagctgaa 721 cctgcccaag acgtgtgata tcagcttctc agatccagac gacctcctca acttcaagct 781 ggtcatctgt cctgatgagg gcttctacaa gagtgggaag tttgtgttca gttttaaggt 841 gggccagggt taccgcatg atcccccaa ggtgaagtgt gagacaatgg tctatcaccc 901 caacattgac ctcgagggca acgtctgcct caacatcctc agagaggact ggaagccagt 961 ccttacgata aactccataa tttatggcct gcagtatctc ttcttggagc ccaacccga 1021 ggacccactg aacaaggagg ccgcagaggt cctgcagaac aaccggcggc tgtttgagca 1081 gaacgtgcag cgctccatgc ggggtggcta catcggctcc acctactttg agcgctgcct 1141 gaaataggt tggcgcatac ccaccccgc cacggccaca agccctggca tccctgcaa 1201 atattattg ggggccatgg gtagggttt gggggggcggc cggtggggga atccctgcc 1261 ttggccttgc ctcccttcc tgccacgtgc ccctagttat ttttttttt ttaacaccat 1321 gtgattaagg tcggcgctgc ctccccgac ccactcagcg atgggaaatg aattggcttg 1381 tctagcccc ctgctgggtg cttgttcagc ccccactctg ggctgtggag tgggtgggca 1441 acgggcctgg gtagctgggc ccaggcaacc caccctcca cctctggagg tcccaccagg 1501 ctattaaagg ggaatgttac tgcaaaaaaa aaaaaaaaa
```

By "XRN1 (5'-3' Exoribonuclease 1) polypeptide" is meant a polypeptide or fragment thereof having at least 85% amino acid sequence identity to NCBI Accession No. NP_061874.3 and having nucleic acid binding and exonuclease activity. An exemplary XRN1 polypeptide sequence is provided below (SEQ ID NO: 60):

```
  1 mgvpkfyrwi serypclsev vkehqipefd nlyldmngii hqcshpnddd vhfrisddki 61 ftdifhylev lfriikprkv ffmavdgvap rakmnqqrgr rfrsakeaed kikkaiekge 121 tlptearfds ncitpgtefm arlhehlkyf vnmkistdks wqgvtiyfsg hetpgegehk 181 imefirseka kpdhdpntrh clygldadli mlgltsheah fsllreevrf ggkktqrvca 241 peettfhllh lslmreyidy efsvlkekit fkydieriid dwilmgflvg ndfiphlphl 301 hinhdalpll ygtyvtilpe lggyinesgh lnlprfekyl vklsdfdreh fsevfvdlkw 361 feskvgnkyl neaagvaaee arnykekkkl kgqenslcwt aldknegemi tskdnledet 421 edddlfetef rqykrtyymt kmgvdvvsdd fladqaacyv qaiqwilhyy yhgvqswswy 481 ypyhyapfls dihnistlki hfelgkpfkp feqllavlpa asknllpacy qhlmtnedsp 541 iieyyppdfk tdlngkqqew eavvlipfid ekrlleamet cnhslkkeer krnqhseclm 601 cwydrdtefi ypspwpekfp aiercctryk iisldawrvd inknkitrid qkalyfcgfp 661 tlkhirhkff lkksgvqvfq qssrgenmml eilvdaesde ltvenvassv lgksvfvnwp 721 hleearvvav sdgetkfyle eppgtqklys grtappskvv hlgdkeqsnw akevqgiseh 781 ylrrkgiiin etsavvyaql ltgrkyqinq ngevrlekqw skqvvpfvyq tivkdirafd 841 srfsniktld dlfplrsmvf mlgtpyygct gevqdsgdvi tegrirvifs ipcepnldal 901 iqnqhkysik ynpgyvlasr lgvsgylvsr ftgsifigrg srrnphgdhk anvglnlkfn 961 kkneevpgyt kkvgsewmys saaeqllaey lerapelfsy iaknsqedvf yeddiwpgen
```

-continued

```
1021  engaekvqei itwlkghpvs tlsrsscdlq ildaaiveki eeevekckqr knnkkvrvtv
1081  kphllyrple qqhgvipdrd aefclfdrvv nvrenfsvpv glrgtiigik ganreadvlf
1141  evlfdeefpg gltircspgr gyrlptsalv nlshgsrset gnqkltaivk pqpavhqhss
1201  sssyssghlg alnhspqslf vptqvptkdd defcniwqsl qgsgkmqyfq ptiqekgavl
1261  pqeisqvnqh hksgfndnsv kyqqrkhdph rkfkeecksp kaecwsqkms nkqpnsgien
1321  flaslniske nevqsshhge ppseehlspq sfamgtrmlk eilkidgsnt vdhkneikqi
1381  aneipvssnr rdeyglpsqp kqnkklasym nkphsaneyh nvqsmdnmcw papsqippvs
1441  tpvtelsric slvgmpqpdf sflrmpqtmt vcqvklsngl lvhgpqchse neakekaalf
1501  alqqlgslgm nfplpsqvfa nypsavppgt ippafppptg wdhygsnyal gaanimpsss
1561  hlfgsmpwgp svpvpgkpfh htlysgtmpm aggipggvhn qfiplqvtkk rvankknfen
1621  keaqssqatp vqtsqpdssn ivkvspress saslksspia qpassfqvet asqghsishh
1681  kstpissrr ksrklavnfg vskpse
```

By "XRN1 polynucleotide" is meant a nucleic acid molecule encoding a XRN1 polypeptide. An exemplary XRN1 polynucleotide sequence is provided at NCBI Accession No., NM_019001.4 which is reproduced below (SEQ ID NO: 61):

```
   1  atggtcggcc gggcggtgtg ttgtcatccg cggagcgacg accggaggct gcggcggagc
  61  cccggcgggg cgtttggttt cggtttggcc ctgactggga ttagtgttga cgatcgaaat
 121  gggagtcccc aagttttaca gatggatctc agagcggtat ccctgtctca gcgaagtggt
 181  gaaagagcat cagattcctg aatttgacaa cttgtacctg gatatgaatg gaattataca
 241  tcagtgctcc catcctaatg atgatgatgt tcactttaga atttcagatg ataaaatctt
 301  tactgatatt tttcactacc tggaggtgtt gtttcgcatt attaaaccca ggaaagtgtt
 361  ctttatggct gtagatggtg tggctcctcg agcaaaaatg aaccagcagc gtgggaggcg
 421  ttttaggtca gcaaaggagg cagaagacaa aattaaaaag gcaatagaga agggagaaac
 481  tcttcctaca gaggccagat ttgattccaa ctgtatcaca ccaggaactg aatttatggc
 541  caggttacat gaacatctga agtattttgt aaatatgaaa atttccacag acaagtcatg
 601  gcaaggagtt accatctact tctcaggcca tgagactcct ggagaaggag agcataaaat
 661  catggaattt atcagatccg agaaagcaaa gccagatcat gatccaaaca ccagacactg
 721  tctttatggt ttagatgctg acttgattat gcttggatta acaagtcatg aggcacattt
 781  ttctctctta agagaagaag ttcgatttgg tggcaaaaaa acacaacggg tatgtgctcc
 841  agaagaaact acatttcacc ttctacactt gtcttttaatg agagagtata ttgactatga
 901  gttttcagta ttaaaagaaa agatcacatt taaatatgat attgaaagga atagatgaa
 961  ttggattttg atggggtttc ttgttggtaa tgattttatc cctcatctac ctcatttaca
1021  tattaatcat gatgcactgc ctcttcttta tggaacatat gttaccatcc tgccagaact
1081  tgggggttat attaatgaaa gtgggcacct caacttacct cgatttgaga ataccttgt
1141  gaaactatca gattttgatc gggagcactt cagtgaagtt tttgtggacc taaaatggtt
1201  tgaaagcaaa gttggtaaca agtacctcaa tgaagcagca ggtgtcgcag cagaagaagc
1261  caggaactac aaggaaaaga aaagttaaa gggccaggaa aattctctgt gttggactgc
1321  tttagacaaa atgaaggcg aaatgataac ttctaaggat aatttagaag atgagactga
1381  agatgatgac ctatttgaaa ctgagtttag acaatataaa agaacatatt acatgacgaa
```

-continued

```
1441 gatgggggtt gacgtagtat ctgatgactt tctggctgat caagctgcat gttatgttca
1501 ggcaatacag tggattttgc actattacta tcatggagtt cagtcctgga gctggtatta
1561 tccttatcat tatgcacctt tcctgtctga tatacacaac atcagtacac tcaaaatcca
1621 ttttgaacta ggaaaacctt ttaagccatt tgaacagctt cttgctgtac ttccagcagc
1681 cagcaaaaat ttacttcctg catgctacca gcatttgatg accaatgaag actcaccaat
1741 tatagaatat tacccacctg atttttaaaac tgacctaaat gggaaacaac aggaatggga
1801 agctgtggtg ttaatccctt ttattgatga aagcgattta ttggaagcca tggagacatg
1861 taaccactcc ctcaaaaagg aagagaggaa aagaaaccaa catagtgagt gcctaatgtg
1921 ctggtatgat agagacacag agtttatcta tccttctcca tggccagaaa agttccctgc
1981 catagaacga tgttgtacaa ggtataaaat aatatcctta gatgcttggc gtgtagacat
2041 aaacaaaaac aaaataacca gaattgacca gaaagcatta tatttctgtg gatttcctac
2101 tctgaaacac atcagacaca aatttttttt gaagaaaagt ggtgttcaag tattccagca
2161 aagcagtcgt ggagaaaaca tgatgttgga atcttagtg gatgcagaat cagatgaact
2221 taccgtagaa aatgtagctt catcagtgct tggaaaatct gtctttgtta attggcctca
2281 ccttgaggaa gctagagtcg tggctgtatc agatggagaa actaagtttt acttggaaga
2341 acctccagga acacagaagc tttattcagg aagaactgcc ccaccatcta aagtggttca
2401 tcttggagat aaagaacaat ctaactgggc aaaagaagta caaggaattt cagaacacta
2461 cctgagaaga aaggaataa taataaatga acatctgca gttgtgtatg ctcagttact
2521 cacaggtcgt aaatatcaaa taaatcaaaa tggtgaagtt cgtctagaga acagtggtc
2581 aaaacaagtt gttccttttg tttatcaaac tattgtcaag gacatccgag ctttcgactc
2641 ccgtttctcc aatatcaaaa cattggatga tttgtttcct ctgagaagta tggtctttat
2701 gctgggaact ccctatatg gctgcactgg agaagttcag gattcaggtg atgtgattac
2761 agaaggtagg attcgtgtga ttttcagcat tccatgtgaa cccaatcttg atgctttaat
2821 acagaaccag cataaatatt ctataaagta caacccagga tatgtgttgg ccagtcgcct
2881 tggagtgagt ggataccttg tttcaaggtt tacaggaagt atttttattg gaagaggatc
2941 taggagaaac cctcatggag accataaagc aaatgtgggt ttaaatctca aattcaacaa
3001 gaaaaatgag gaggtacctg gatatactaa gaaagttgga agtgaatgga tgtattcatc
3061 tgcagcagaa caacttctgg cagagtactt agagagagct ccagaactat ttagttatat
3121 agccaaaaat agccaagagg atgtgttcta tgaagatgac atttggcctg agaaaatga
3181 gaatggtgct gaaaaagttc aagaaattat tacttggcta aaaggacatc ctgtcagtac
3241 tttatctcgt tcttcttgtg atttacaaat tctggatgca gctattgttg agaaaattga
3301 ggaagaagtc gaaaagtgca agcaaagaaa gaataataag aaggtgcgag taacagtgaa
3361 accccatttg ctatacagac ctttagaaca gcaacatgga gtcattcctg atcgggatgc
3421 agaattttgt cttttttgacc gtgttgtaaa tgtgagagaa aacttctcag ttccagttgg
3481 ccttcgaggc accatcatag gaataaaagg agctaataga gaagccgatg tactatttga
3541 agtattattt gatgaagaat ttcctggagg gttaacaata agatgctcac ctggtagagg
3601 ttatcgactg ccaacaagtg ccttggtgaa cctttctcat gggagtcgct ctgaaactgg
3661 aaatcagaag ttgacagcca tcgtaaaacc acaaccagct gtacatcaac atagctcaag
3721 ttcatcagtt tcctctgggc atttgggagc cctcaaccat tcccctcaat cacttttttgt
3781 tcctactcaa gtacctacta aagatgatga tgaattctgc aacatttggc agtccttaca
3841 gggatctgga aagatgcaat actttcagcc aactatacaa gagaagggtg cagttctacc
```

```
3901 tcaagaaata agccaagtaa atcaacatca taaatctggc tttaatgaca acagtgttaa
3961 atatcagcaa agaaaacatg accctcacag aaaatttaaa gaagagtgta agagtcctaa
4021 agctgagtgt tggtcccaaa aaatgtccaa taagcagcct aactctggaa ttgagaactt
4081 tttagcatct ttgaatatct ccaaagaaaa tgaagtacag tcatctcatc atggggagcc
4141 tccaagtgaa gagcatttgt caccacagtc atttgccatg gaacacgga tgcttaaaga
4201 aattctaaaa attgatggct ctaacactgt ggaccataag aatgaaatca acagattgc
4261 taatgaaatc cctgtttcct ctaacagaag agatgaatat ggattaccct ctcagcctaa
4321 acaaaataag aaattagcat cttatatgaa caagcctcac agtgctaatg agtaccataa
4381 tgttcagtct atggacaata tgtgttggcc tgcccccagc cagatccctc ctgtatccac
4441 accagtaact gaactttctc gaatttgttc ccttgttgga atgccacaac ctgatttctc
4501 cttcttagg atgccacaga caatgaccgt tgccaagta aaattatcta atggcttact
4561 ggtacatggg ccacagtgcc actctgaaaa tgaagccaaa gagaaagctg cacttttgc
4621 tttacaacag ttgggctcct taggcatgaa tttcccttg ccttcacaag tatttgcaaa
4681 ttatcctca gctgtaccac ctggaaccat tcctccagcc tttcccccac ctactggctg
4741 ggatcactat ggaagcaact atgcattggg ggcagctaat ataatgcctt cgtcgtctca
4801 tctctttggc tcaatgccat ggggaccatc ggtgccagtt cctgggaagc ccttccatca
4861 tactttatat tctgggacca tgcccatggc tgggggaata ccagggggtg tgcacaatca
4921 gtttatacct ctgcaggtta ctaaaaaaag ggttgcaaac aaaaagaact tgagaataa
4981 ggaagcccag agttctcaag ccactccagt tcagactagc cagccagatt cttccaacat
5041 tgtcaaagta agtccacggg agagctcatc agcttctttg aagtcctctc cgattgctca
5101 acctgcatct tcttttcaag ttgaaactgc ctctcaaggc catagtatat ctcaccataa
5161 gtcaacacca atctcttctt caagaagaaa atcaagaaaa ctggctgtta attttggtgt
5221 ttctaaacct tctgagtaaa tttggctctt agaattaagt taatttcttc tctttccatc
5281 tacctttta taaaatacata tctatgtctc ataaaaatta gaatgtacta ttttaaaata
5341 atatgtgtaa attgaaattt ttttcatttt taagttatca ggcacttttc atgctgttta
5401 aaagactgtg tatcaaattg tgcactttaa gtatgtgcag tttgttgtat gtcaattata
5461 cctcaataaa tctgtaataa aaaactaaat taaaccttgc attaaaataa tatcacagta
5521 tcagtggact aaacattaaa atgtaccact ctaatcattg gcctcatgat tgaagcatcc
5581 tgaactatga attagacatc agttagcaat aataagcatt ttttacacta tcattgagga
5641 ataattacat ggagcatgaa atttgggcct ccagtataac ttactgaatg tggatttat
5701 ttctctttt aatgatgtaa gaaaattgtc aggagaatgg ctcttattta tgtgtgtttt
5761 aacttatgct ttgttgcctc tgagggtctt tagacctgct gtgaaaggat cacatttgtt
5821 gtggtgctgc cagttttgct ttattctaaa ttttgtacca aagcaacttt agaataatca
5881 gaatatttca tctaactgct tagaactata aatagcattc taaatttgag taaatacaat
5941 ttttaggtt actcaagaac cagcattagt aatttctagt aaaattgttt caaatctac
6001 agggtacaat gattacaaat taatcttcta acaaaataaa atatgaaata ttagtcatgt
6061 taattaataa actgtattat tttgtatagc ttttatttg cttacctgac atttatgag
6121 agcttcatag ttggtcggta tgtagtgctt cttgggactg aagaaattct aattgttgtt
6181 taagttccaa ggtgtgctac aatataggag gcacagtcat cagtttgtga catacattat
6241 ttactgccta tttcattctg attctatatt tttagcttta tgctgaactg ttcaatgatg
```

```
6301 ctgggattct ctctttgcat gtcatatgtg aatgtgtggt tcaagctgta actgttgaaa
6361 ttattttaga atttatgacg atttctcagc agggcctatg tttatatata tatatatatt
6421 tattctttag ttttttgtgat atgcttatat ttttaaggaa gtaagttata gcatactttt
6481 ttaaaagtag gaaccacaat ctttatatgg agcagcttgt tatatctgat tttcatgtaa
6541 ctcattggaa actctgccat gactcttaaa gtagtcttac ttgttttttta aaatgctggt
6601 attaaactaa atggactcct ttcactaact gctgatttca gagtttaaat gttagcagga
6661 tatttgtgta ttagcagtgc cttcagtata agagagaaat attcattatc tgtcatttat
6721 catagtcgta taagtttcca tgattttatt ttctgttatt ttcataagtt cagatgttta
6781 tcagttccca acattgtttc tttatctgta gtgggatctt gagtaatgag gctcaagtaa
6841 atcctcaatg tgtataatta ttgcctcata aactctctct ttgtttttaa aggaaacatc
6901 tattatggta atacaaagaa aagttaaatt gtgacagtaa tgttatatta acctcttcct
6961 actttaaagt gtgaaatgtt tcacctcagc tgtacaaact ccagcattga gaatttgcct
7021 cactcattac tcctgtgtga cagttatata aatagcatgc agctcacatc tgttttagag
7081 catagaagaa gcggcacctg ccatcttctg aaaactccaa agggaaattt cagtagacat
7141 agtgcactaa acccataagg atacttgacc aatatttgag cacagcaagc tgacagttct
7201 atacagatag gcagtgaaag agtttttattt tccagccagg cgcagtggct caaatcccag
7261 cacttcggga ggctaaggca ggcggatcac ttgaggtccg gagttccaga caagcctggc
7321 caacatgatg aagccctgtc tctactaaaa atacaaaaat tagccgggcg tgatggcaca
7381 tgcctttagt cccagctact cgggaggctg aggcatgaga atcatttgaa cccgcgaggc
7441 agagtctgca gtgagccgag attgcaccac tgcactccag cctggagagc agagcaagac
7501 tctgtctcaa aaaaagaaa aaagttttat tatccttact ttttttttaa cattattatt
7561 ctaaaggtca aaactgagaa gagattaaga taggagagag ctccataatg gctggatagt
7621 ggtcaggcat tctctattct ttttcccctg tagacccatt ctaaatgtgg gcctgaggtc
7681 aatgggagat gtgccctccc tatggaggat gtaagaagca gaggccattt ctgccccatg
7741 ttgaggaaac aatctgttga tagacctgga atttagagta tatctgaaaa gcagttggac
7801 ttcaagaaat ttaaaattct ctctttgaga tggggtggac taagaccacc cccaaagttt
7861 aaaaatatgc tcattcaact tgaatcttct gaggacttt tgtgaaaatg gtggactgtt
7921 tagggcatag gacagattcc ccaaattgct ttatgcttcc acataactag agcacttcaa
7981 tctatttaag cctttgtctc ctaactgaaa cattattctc aaatatttct attcaataag
8041 ttttttcttt tttgagcaac ttaagtgaat tttgaagatt gctccttcca gtctcgttcc
8101 ttttcacatt ttcctgcatt acctaataat tacctcagcg ttagaatttg aatgtattaa
8161 ttgatttaaa catcatgtag actaaagtct taaacatcta agactcagtt gtagttgcag
8221 aaaaaaatta agtcacctc tactgaacct tggtttcaat ttaagatttt tcttgctttt
8281 caaagggta actaataaag attgaagggt ttttttcccg attggtggag gaatgaagaa
8341 ctattgatgc aagtttttt attgtttctt tctatgatca ggtacctgct ttcatttttag
8401 actgctactt ccaaactaag ctagattctt ggttttaatg agaggaggca gagagaggga
8461 ggcagatgga agaagaaaaa cagttaaata agacatacc agtcactgca tttttggact
8521 ataccgtatc tttctagcac aaggaaatag ataaactgta aggtctttt tactcacttt
8581 ttatttatgt gttctatttg tgttagtcat aactgtttat agtggttgtc taattttttac
8641 ttttattata tgagatagag ctgtgcagat cttcactcaa gttagttctg tcacgcttct
8701 tcccattatt tagagcacag tttttttaaag caactgtaca atttctcagc cttatgagct
```

```
-continued
8761 tgctgtattt cttggtatca tgttgcttcc aaatttttgtt tttactgtag aagacaatta 8821 atttattgta gagaagtggc tgtgaaagtc gttctctgtc tttaaaaatc aattgcagaa 8881 gttcatttgt catttttcta gagataaatt atagtactca aactggcagt gctcagtata 8941 tacattttgt aagctttgtc agtgaaacca tcagttttgc aggagcttcc tttcctagtc 9001 aagataaagc ttaaaattcc agaaattaat gtcgttcgga ctgactttat tcatatttcc 9061 atcaaacttc tccaatacag taagagatag tgttgaacca gcatcaagtc tccagaaaca 9121 tggcagagca gacaggccgt taagtttcac agacatcata gatccttttc ttaaagaaga 9181 aaaacatgta taaaatagtt ttagtagtcc aaaatgtcaa ctatctgtag ctgcttttgt 9241 gtgtgtgtca gtgaacaaat aataatgcct tgctcaatca atgcattcag ccatctcaag 9301 tgcaatttgt gaaggagact atggtttcca aaagatacat ttttttacaa agttaaacct 9361 gtaaaaagtc ttttttttttt tccctccagc cgtacaccaa ctgcacttgg ttgtttcagc 9421 agttggtata ctattaaatt gtccaggcca aataggtttc tgtagctgtt ttagtaattt 9481 gaagccaaat tctcatgctg tttctcatta aaaagaatga gaatttggtc catagttagc 9541 tttaagttct ctcttccttt ctttcccta cagttaaggg tttggtgggg gatggggagg 9601 ttgttttcgt tttttggatt tttttgtctt ttggctttaa gtatcatatt ttcttttgcc 9661 tgtatccaac tgcttctttg agtattttca tctagtttaa tgtgagtaat agatgctgtg 9721 ctgtcattga agtgttcaac attttgttca tttaaacaaa agtgtaattc atacatatat 9781 agatacatat cttaattgat ttctcaacta ttttataagt aactggaatt tttcattaga 9841 tcttatacag agaagtattt tattaaaaat tcaaaaggga agacttttat gtgctcattt 9901 tgtaattttt gattttaaat atctttacat tgtctgccaa ttaaagtgtt ttaaacttgc 9961 attggaatgg actccgaatg tattttttgtg gtgttacgtt atccgtagat ttctagcatg 10021 aagttagcct cacgatgctg tgcaaaggat tttaaaatat gagagtcact gaaagagttt 10081 aaacatctgt tcatgttaaa tgctctatgg attttaatta aagacttgag aatgatttta 10141 taa
```

"Detect" refers to identifying the presence, absence or amount of the analyte to be detected. In particular embodiments, the sequence of a polynucleotide of a gene in Table 1 is detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include cancer, such as a B cell neoplasia or malignancies, for example, plasma cell malignancy, multiple myeloma or a myelodysplastic syndrome, erythema nodosum leparum, 5q− myelodysplastic syndrome.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "sensitivity to a modulator of CRBN" is meant that at least one symptom of a disease or condition is ameliorated by treatment with a modulator of CRBN.

By "resistant to a modulator of CRBN" is meant that a cell having a disease has acquired an alteration that allows it to escape an anti-disease effect of at least one modulator of CRBN. For example, a resistant cell may be a neoplastic cell that has acquired an alteration that allows it to escape an anti-neoplastic effect of the modulator of CRBN. Exemplary anti-neoplastic effects include, but are not limited to, any effect that reduces proliferation, reduces survival, and/or increases cell death (e.g., increases apoptosis).

By "lenalidomide sensitivity" is meant that at least one symptom of a disease or condition is ameliorated by treatment with lenalidomide. Likewise, by "lenalidomide analog sensitivity" is meant at least one symptom of a disease or condition is ameliorated by treatment with a lenalidomide analog.

By "lenalidomide resistant" is meant that a cell having a disease has acquired an alteration that allows it to escape an anti-disease effect of lenalidomide. Likewise, by "lenalidomide analog resistant" is meant that a cell having a disease has acquired an alteration that allows it to escape an anti-disease effect of a lenalidomide analog. For example, a lenalidomide resistant cell may be a neoplastic cell that has acquired an alteration that allows it to escape an anti-neoplastic effect of lenalidomide. Exemplary anti-neoplastic effects include, but are not limited to, any effect that reduces proliferation, reduces survival, and/or increases cell death (e.g., increases apoptosis).

By "modulator of CRBN" or "modulator of Cereblon" is meant any agent which binds Cereblon (CRBN) and alters an activity of CRBN. In some embodiments, an activity of CRBN includes binding with and/or mediating degradation of Ikaros (IKZF1), Aiolos (IKZF3), or Casein kinase 1 Alpha (CSNK1a1). Thus, a modulator of CRBN includes agents that alter binding of CRBN with IKZF1, IKZF3, or CSNK1a1 and agents that alter CRBN's mediation of IKZF1, IKZF3, or CSNK1a1 degradation. In particular embodiments, a modulator of CRBN is lenalidomide or an analog thereof (e.g., pomalidomide or thalidomide).

As used herein, "obtaining" as in "obtaining an agent" includes synthesizing, purchasing, or otherwise acquiring the agent.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reduces" is meant a negative alteration of at least 10%, 25%, 50%, 75%, or 100%.

By "reference" is meant a standard or control condition. A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those of ordinary skill in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those of ordinary skill in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those of ordinary skill in the art. Hybridization techniques are well known to those of ordinary skill in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DETAILED DESCRIPTION OF THE INVENTION

The invention features the discovery of genes whose loss confers resistance to at least lenalidomide and to other therapeutic compounds that modulate Cereblon (CRBN). Described herein are details of the results of a genome-wide loss-of-function screen in a multiple myeloma cell line which discovered a number of genes which, when inactivated, mediate resistance to at least lenalidomide. The identification of these genes has potential clinical implications as biomarkers which may be used to determine if multiple myeloma patients are likely to respond to lenalidomide, and to inform choice of secondary therapies post-relapse. Accordingly, the present invention provides methods of characterizing the sensitivity of a subject to therapeutic compounds that modulate CRBN and methods of monitoring the sensitivity of a subject to therapeutic compounds that modulate CRBN.

Figure 1:
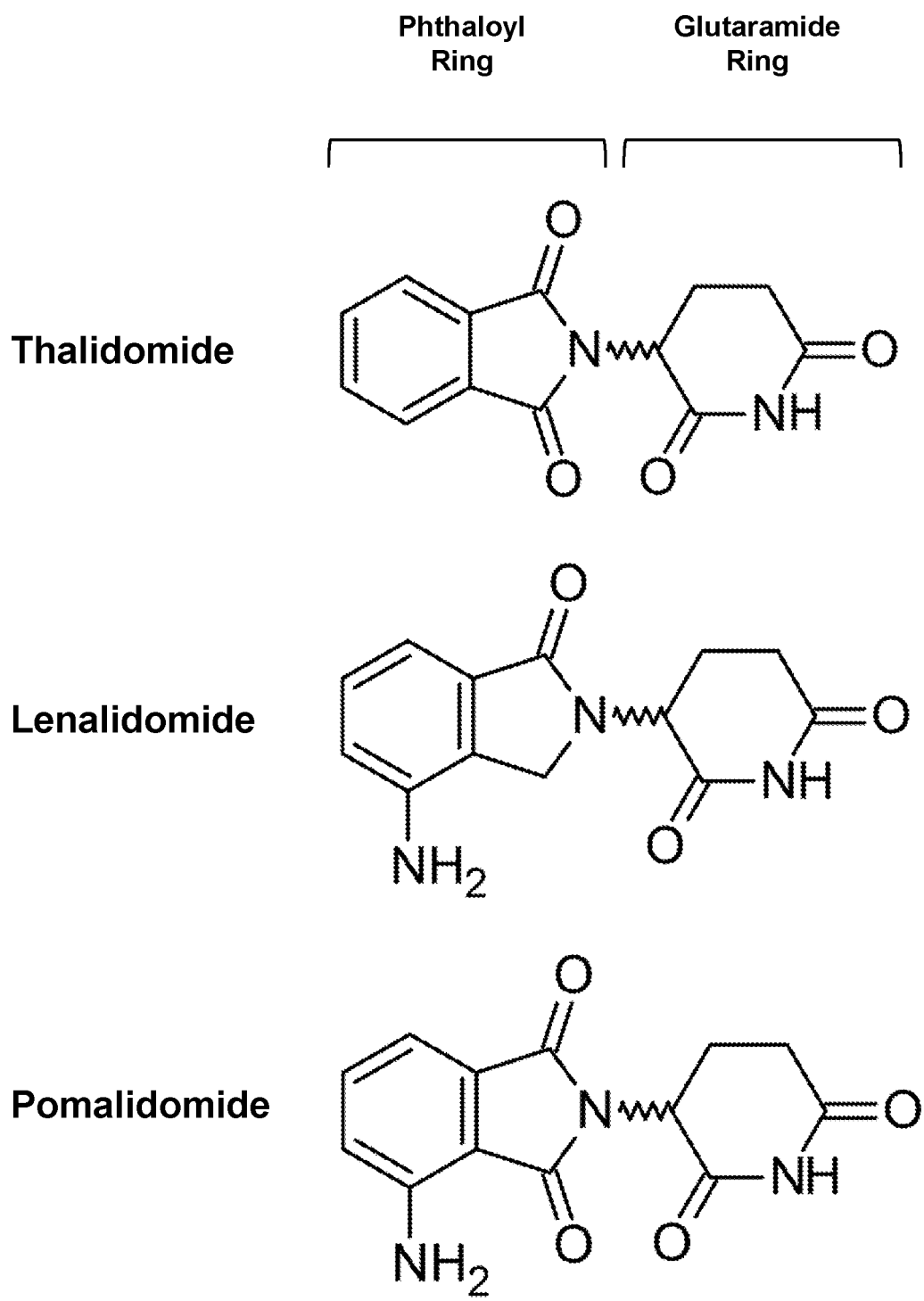
FIG. 1 depicts a schematic representation of the molecular structure of thalidomide and its derivatives.

Lenalidomide- and Lenalidomide Analog Dependent Mediation of Proteasomal Degradation The drug thalidomide became infamous in the early 1960s when its use during the first trimester of pregnancy was linked to profound birth defects, most commonly a malformation of the upper limbs known as phocomelia. The discovery of thalidomide's teratogenic property was a major setback for the compound, however thalidomide was later repurposed and today is an FDA-approved therapy for a number of disorders, including erythema nodosum leparum, 5q– myelodysplastic syndrome (MDS), and several mature B-cell malignancies, most notably the plasma cell malignancy multiple myeloma. Thalidomide's success as a treatment for these disorders motivated the synthesis of lenalidomide and pomalidomide, which are more potent derivatives that have largely replaced thalidomide in the clinic today (FIG. 1).

Figure 2:
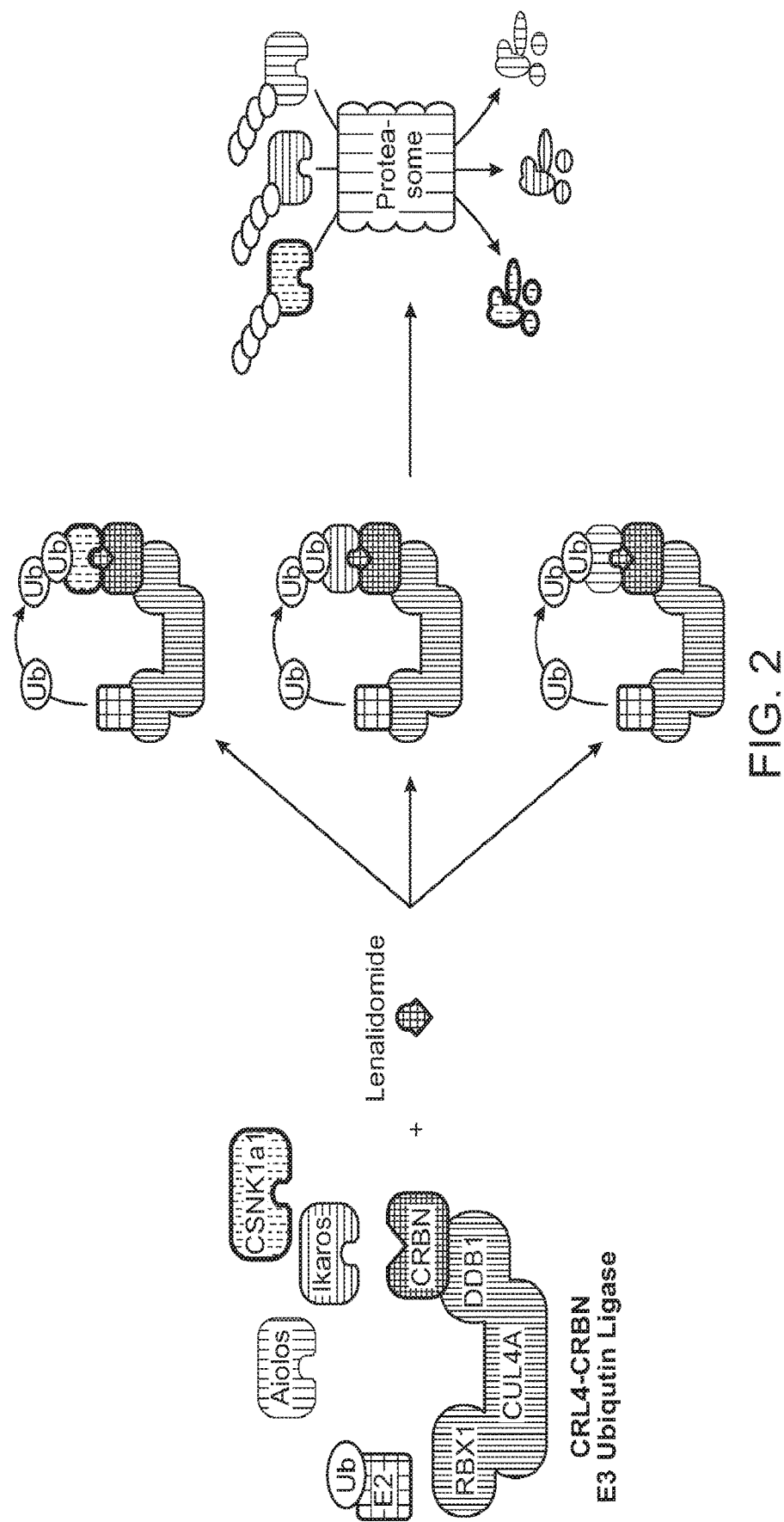
FIG. 2 depicts a schematic representation of the molecular mechanism of lenalidomide-mediated degradation. Lenalidomide binds to cereblon at its putative substrate recognition surface and in doing so, increases the affinity of cereblon for several key substrates; the lymphocyte lineage transcription factors Ikaros (IKZF1) and Aiolos (IKZF3), and Casein Kinase 1 alpha (CSNK1a1). This increase in affinity subsequently results in the efficient CRL4-CRBN-dependent polyubiquitination of these target substrates, causing them to be rapidly degraded by the 26S proteasome. Degradation of Ikaros and Aiolos has been demonstrated to mediate the tumoricidal effects in multiple myeloma as well as the immunomodulatory properties of these compounds. Degradation of casein kinase 1 alpha is responsible for remission of the malignant stem cell clone in 5q– myelodysplastic syndrome.

Despite their clinical success, the mechanism behind the therapeutic benefit of thalidomide and its derivatives remained a mystery for over a decade. It is now understood that these drugs function by mediating efficient proteasomal degradation of several protein targets by the CRL4-CRBN E3 ubiquitin ligase. These targets include the lymphocyte lineage transcription factors Ikaros (IKZF1) and Aiolos (IKZF3), as well as the Wnt pathway regulator Casein Kinase 1 alpha (CSNK1a1). The CRL4-CRBN ubiquitin ligase belongs to the family of cullin-ring ligases and is a multi-subunit complex comprised of Ring Box Protein 1 (RBX1), DNA Damage Binding Protein 1 (DDB1), Cullin 4A (CUL4A), and Cereblon (CRBN). Thalidomide, lenalidomide, and pomalidomide bind specifically to cereblon, the substrate receptor for CRL4-CRBN. In doing so, these drugs increase Cereblon's affinity for Ikaros (IKZF1), Aiolos (IKZF3), and Casein Kinase 1 alpha (CSNK1a1). As a consequence of their increased association with the CRL4-CRBN ubiquitin ligase complex, these factors are efficiently ubiquitinated and degraded by the 26S proteasome (FIG. 2). Without wishing to be bound by theory, the degradation of Ikaros and Aiolos explains not only the tumoricidal effect on myeloma cells, but also the immunomodulatory properties which have until now defined this class of compounds. Similarly, the degradation of Casein Kinase 1 alpha mediates remission of the malignant stem cell clone in 5q– in myelodysplastic syndrome.

Genes which Mediate Resistance to Lenalidomide

Thalidomide, lenalidomide, and pomalidomide are effective therapies for a number of disorders, most notably 5q– myelodysplastic syndrome and the plasma cell malignancy multiple myeloma. However, their effectiveness may be hampered by development of resistance to these drugs. For example, lenalidomide is currently used in combination with dexamethasone as a front-line therapy for standard-risk multiple myeloma. While this combination offers distinct benefits with regard to disease-free and overall survival, the combination of dexamethasone and lenalidomide is not curative; on average disease progression develops 11 months after initiating treatment (Dimopoulos et al., 2007, N. Engl. J. Med., 357, 2123-2132; Weber et al., 2007, N. Engl. J. Med., 357, 2133-2142). The ability to understand the genetic alterations which potentiate acquired resistance to lenalidomide has been hampered by lack of knowledge surrounding the biology of the CRL4-CRBN ubiquitin ligase, specifically the factors which are required for its function.

A study described herein sought to gain insight into mechanisms of acquired resistance by identifying in an unbiased fashion the genes which are required for lenalidomide-induced degradation of Ikaros and Aiolos by the CRL4-CRBN ubiquitin ligase. The study reports the results of a genome-wide loss-of-function screen in a multiple myeloma cell line which discovered a number of genes which, when inactivated, mediate resistance to lenalidomide. The genes are listed in Table 1. The preliminary discovery of genes whose loss confers resistance to lenalidomide has potential clinical ramifications, for the mutation status of these genes may serve as biomarkers capable of stratifying multiple myeloma patients with regard to their potential to respond to lenalidomide, and with regard to the choice of secondary therapies following relapse. Additionally, these genes may be relevant biomarkers in the context of other malignancies treated with lenalidomide. Accordingly, the present invention features methods of characterizing and monitoring the lenalidomide sensitivity of a subject, as described further herein.

Lenalidomide and Lenalidomide Analog Therapies

Lenalidomide and lenalidomide analogs are effective therapies for a number of diseases or disorders, including 5q– myelodysplastic syndrome (MDS), erythema nodosum leparum, and several mature B-cell malignancies, most notably, the plasma cell malignancy multiple myeloma. Lenalidomide analogs approved for clinical use by the Food and Drug Administration (FDA) include thalidomide and pomalidomide. Lenalidomide is approved by the FDA for treatment of 5q– myelodysplastic syndrome (MDS), erythema nodosum leparum, and multiple myeloma. In some embodiments, lenalidomide and lenalidomide analogs are administered to a subject having 5q– myelodysplastic syndrome (MDS) or plasma cell malignancy multiple myeloma.

In some aspects, methods of the invention (which include prophylactic treatment) comprise administration of a therapeutically effective amount of lenalidomide or a lenalidomide analog, such as thalidomide or pomalidomide, to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, family history, and the like). Lenalidomide or lenalidomide analogs may be also used in the treatment of any other disorders in which Ikaros (IKZF1), Aiolos (IKZF3), Casein Kinase 1 alpha (CSNK1a1), or other targets of lenalidomide may be implicated.

Characterizing and Monitoring Effectiveness of Lenalidomide and Lenalidomide Analog Therapies Although lenalidomide and lenalidomide analogs are effective therapies for a number of disorders, a subject may develop resistance to lenalidomide or lenalidomide analogs, thus making these drugs ineffective. It is therefore important to determine whether a subject is resistant to lenalidomide or lenalidomide analogs to allow for selection of alternative therapies. In one aspect, the invention provides a method of characterizing lenalidomide or lenalidomide analog sensitivity of a subject. In another aspect, the invention provides a method of monitoring lenalidomide or lenalidomide analog sensitivity of a subject.

In some embodiments, the method includes the step of detecting a sequence of a polypeptide or polynucleotide of at least one gene in Table 1 (e.g., CRBN, COPS2, COPS7B, CAND1, TRAF2, COPS8, EDC4, PLAA, COPS6, COPS4, UBE2G1, GPS1, UBE2D3, COPS7A, NCOR1, DEPDC5, DDB1, SRP14, XRN1, EIF4A1, SNRNP25, UBE2M, GLMN, OTUB1, RARA, PPP6C, COPS3, SPOP, SYCP2L, COPS5) in a biological sample from a subject suffering from or susceptible to a disorder or symptoms thereof associated with protein targets of lenalidomide, in which the subject has been administered a therapeutic amount of lenalidomide sufficient to treat the disease or symptoms thereof. The detection of a mutation in a polypeptide or polynucleotide of at least one gene in Table 1 is indicative of lenalidomide resistance and failure to detect a mutation is indicative of lenalidomide sensitivity.

The sequence of a polypeptide or polynucleotide of at least one gene in Table 1 detected in the method can be compared to a reference sequence. The reference sequence may be a known sequence of the gene in healthy normal controls. In some embodiments, at least one gene in Table 1 in the subject is determined at a time point later than the initial determination of the sequence, and the sequences are compared to monitor the efficacy of the therapy. In other embodiments, a pre-treatment sequence of a polypeptide or polynucleotide of at least one gene in Table 1 in the subject is determined prior to beginning treatment according to this invention; this pre-treatment sequence of a polypeptide or polynucleotide of at least one gene in Table 1 can then be compared to the sequence of the polypeptide or polynucleotide of at least one gene in Table 1 in the subject after the treatment commences, to determine the efficacy of the treatment.

In some embodiments, thalidomide, lenalidomide, and pomalidomide are administered to a subject having a B cell neoplasia, such as multiple myeloma. Over time, many patients treated with lenalidomide acquire resistance to the therapeutic effects of lenalidomide. For example, lenalidomide is currently used in combination with dexamethasone as a front-line therapy for standard-risk multiple myeloma. While this combination offers distinct benefits with regards to disease-free and overall survival, the combination of dexamethasone and lenalidomide is not curative; on average disease progression develops 11 months after initiating treatment (Dimopoulos et al., 2007, N. Engl. J. Med., 357, 2123-2132; Weber et al., 2007, N. Engl. J. Med., 357, 2133-2142).

The early identification of lenalidomide resistance in a B cell neoplasia patient is important to patient survival because it allows for the selection of alternate therapies. In one embodiment, a lenalidomide resistant cell is identified by detection of a mutation in at least one gene in Table 1.

Subjects identified as having a lenalidomide resistant B cell neoplasia are identified as in need of alternative treatment. Subjects identified as having a lenalidomide resistant myeloma, for example, are treated with Velcade, corticosteroids, or other anti-neoplastic therapy. For subjects identified as having lenalidomide resistant myelodysplastic syndrome are treated, for example, with azacitidine or decitabine.

In other embodiments, lenalidomide sensitivity in a subject is characterized by detecting a mutation in the polynucleotide or polypeptide sequence of at least one gene in Table 1. In some embodiments, the mutation in the polynucleotide or polypeptide sequence of at least one gene in Table 1 confers loss of the gene. Methods for detecting a mutation of the invention include immunoassay, direct sequencing, and probe hybridization to a polynucleotide encoding the mutant polypeptide. Exemplary methods of detecting a mutation of the invention are described in, for example, U.S. Patent Application Publication No. US2014/0127690, which is incorporated by reference herein in its entirety.

Methods of monitoring the sensitivity to lenalidomide or lenalidomide analog of a subject having a disease (e.g., a B cell neoplasia) are useful in managing subject treatment. Provided are methods where alterations in a polynucleotide or polypeptide of at least one gene in Table 1 (e.g, sequence, level, post-transcriptional modification, biological activity) are analysed, such as before and again after subject management or treatment. In these cases, the methods are used to monitor the status of lenalidomide sensitivity (e.g., response to lenalidomide treatment, resistance to lenalidomide, amelioration of the disease, or progression of the disease).

For example, polypeptides or polynucleotides of at least one gene in Table 1 can be used to monitor a subject's response to certain treatments of a disease (e.g., B cell neoplasia). The level, biological activity, sequence, post-transcriptional modification, or sensitivity to lenalidomide-induced degradation of a polypeptide or polynucleotide of at least one gene in Table 1 may be assayed before treatment, during treatment, or following the conclusion of a treatment regimen. In some embodiments, multiple assays (e.g., 2, 3, 4, 5) are made at one or more of those times to assay resistance to lenalidomide.

Alterations in polynucleotides or polypeptides of at least one gene in Table 1 (e.g, sequence, level, post-transcriptional modification, biological activity) are detected in a biological sample obtained from a patient that has or has a propensity to develop a disease, such as a B cell neoplasia. Such biological samples include, but are not limited to, peripheral blood, bone marrow, or lymphoid tissue obtained from the subject relative to the level of such biomarkers in a reference.

Combination Therapies

In some aspects, the present invention provides methods for detecting alterations in a polypeptide or polynucleotide of a gene in Table 1 in a biological sample (e.g., peripheral blood, bone marrow) derived from a subject having a B cell neoplasia to determine whether the B cell neoplasia is sensitive to treatment with lenalidomide or whether it has acquired lenalidomide resistance. Alterations in at least one gene in Table 1 (e.g, CRBN, COPS2, COPS7B, CAND1, TRAF2, COPS8, EDC4, PLAA, COPS6, COPS4, UBE2G1, GPS1, UBE2D3, COPS7A, NCOR1, DEPDC5, DDB1, SRP14, XRN1, EIF4A1, SNRNP25, UBE2M, GLMN, OTUB1, RARA, PPP6C, COPS3, SPOP, SYCP2L, COPS5) are useful individually, or in combination with other markers typically used in characterizing a B cell neoplasia.

B-cell neoplasms typically recapitulate the normal stages of B-cell differentiation, and can be classified according to their putative cell of origin. Accordingly, alterations in at least one gene in Table 1 may be assayed alone or in combination with the neoplasm's cytogenetic profile, genotype, and immunophenotype. B cell markers useful in the methods of the invention include, but are not limited to, characterization of CDS, CD10, CD19, CD20, CD22, CD23, FMC7, CD79a, CD40, CD38, and CD138.

Kits

In one aspect, the invention provides kits for monitoring lenalidomide- or lenalidomide analog sensitivity, including the development of lenalidomide- or lenalidomide analog resistance. For example, the kits can be used to detect an alteration in a polypeptide or polynucleotide (e.g, sequence level, post-transcriptional modification, biological activity) of at least one gene in Table 1 (e.g., CRBN, COPS2, COPS7B, CAND1, TRAF2, COPS8, EDC4, PLAA, COPS6, COPS4, UBE2G1, GPS1, UBE2D3, COPS7A, NCOR1, DEPDC5, DDB1, SRP14, XRN1, EIF4A1, SNRNP25, UBE2M, GLMN, OTUB1, RARA, PPP6C, COPS3, SPOP, SYCP2L, and COPS5). If desired a kit includes any one or more of the following: capture molecules that bind a polynucleotide or polypeptide of at least one gene in Table 1. The capture molecules may be sequencing primers or hybridization probes for detecting the sequence of a polynucleotide of a gene in Table 1. The kits have many applications. For example, the kits can be used to determine if a subject has a lenalidomide sensitive disorder (e.g., a lenalidomide sensitive multiple myeloma) or if the subject has developed resistance to lenalidomide.

The kits may include instructions for the assay, reagents, testing equipment (test tubes, reaction vessels, needles, syringes, etc.), standards for calibrating the assay, and/or equipment provided or used to conduct the assay. The instructions provided in a kit according to the invention may be directed to suitable operational parameters in the form of a label or a separate insert.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology;" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Results of Screen for Genes that Mediate Resistance to Lenalidomide in Multiple Myeloma In an effort to discover genes whose loss confers resistance to lenalidomide, a pooled, genome-wide CRISPR-Cas9 screen in the lenalidomide-sensitive myeloma cell line, MM1S, was performed. Loss of cereblon has been noted to promote resistance to lenalidomide in cell line models (Zhu et al., 2011, Blood 118, 4771-4779; Lopez-Girona et al., 2012, Leukemia 26, 2326-2335). Therefore, parameters for the screen, including dose and endpoints, were optimized using cereblon gRNAs as a positive control.

Figure 3:
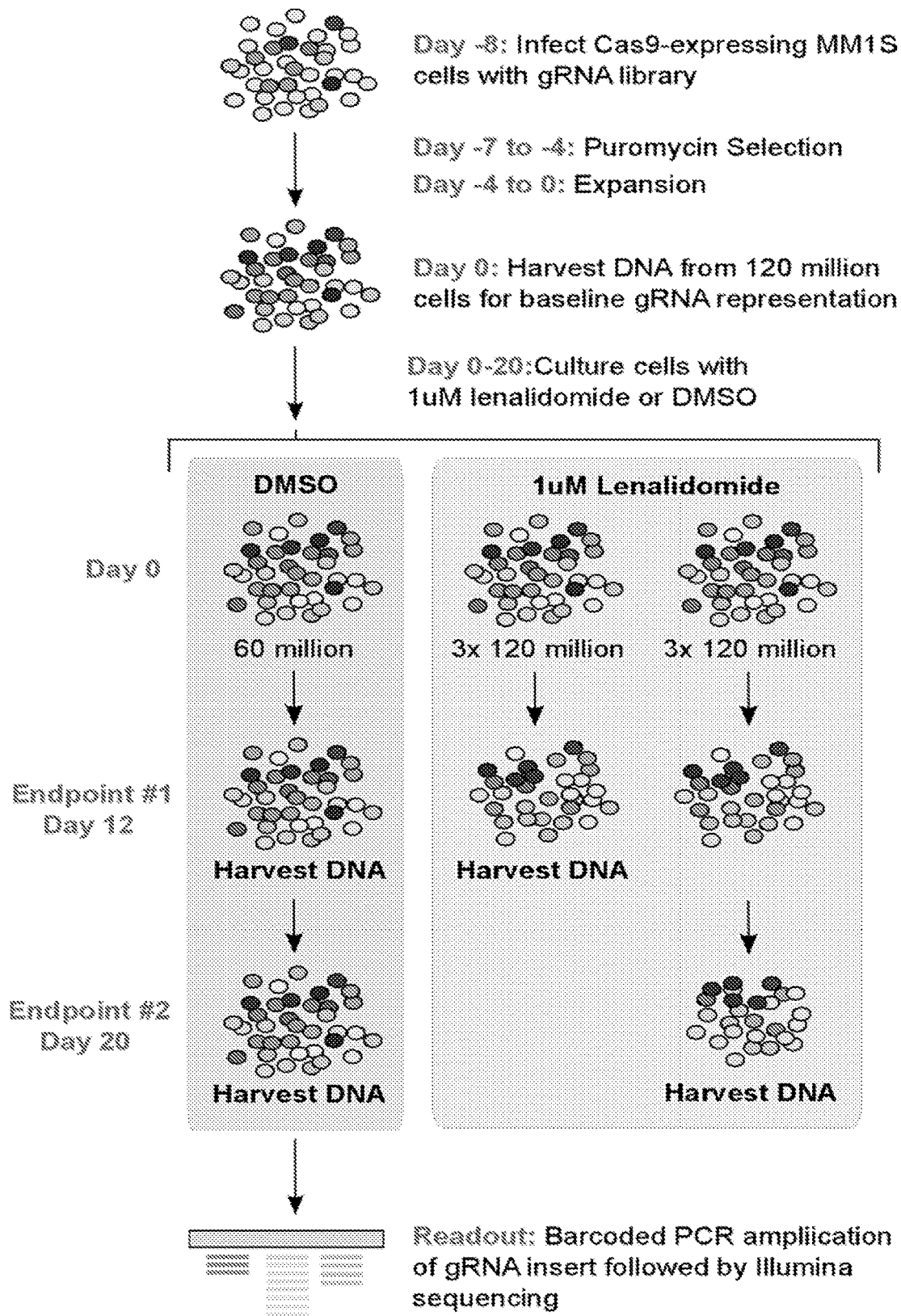
FIG. 3 depicts a schematic diagram depicting the workflow of the genome-wide CRISPR-Cas9 screen described herein.

In this study, a set of genes whose loss conferred resistance to lenalidomide was identified from a genome-wide screen performed in a lenalidomide-sensitive myeloma cell line. The screen was carried out as follows: on day 8, Cas9-expressing MM1S cells were infected at an efficiency of 46% with the second-generation "GEKO" gRNA library designed by the Zhang lab and Genetic Perturbations Platform at the Broad Institute; this library contains approximately 120,000 gRNAs targeting 18,000 genes (~6 gRNA/gene) (Sanjana et al., 2014, Nature Methods 11, 783-784). On day 0, a baseline control sample of 120 million cells was taken and the remaining infected cells began treatment with either DMSO (1x 60 million cells) or 1 µM lenalidomide (2 sets of 3×120 million cells). The number of cells per replicate in the DMSO and 1 µM lenalidomide treatment groups ensured an estimated representation of each gRNA in 500 and 1000 cells, respectively. Endpoint samples were collected on day 12 (D12) and day 20 (D20) (FIG. 3). Genomic DNA was isolated from each of the collected samples and relative gRNA abundance was determined via barcoded PCR amplification of the genomic gRNA insert and pooled sequencing of the resultant amplicons across four lanes of the Illumina HiSeq. Read counts were normalized and log 2 transformed, and the D12 and D20 replicates were averaged. The fold-change in gRNA abundance upon selection with lenalidomide was calculated by comparing the relative abundance of a given gRNA in the lenalidomide-treated experimental condition to its relative abundance in the corresponding DMSO control.

Figure 4:
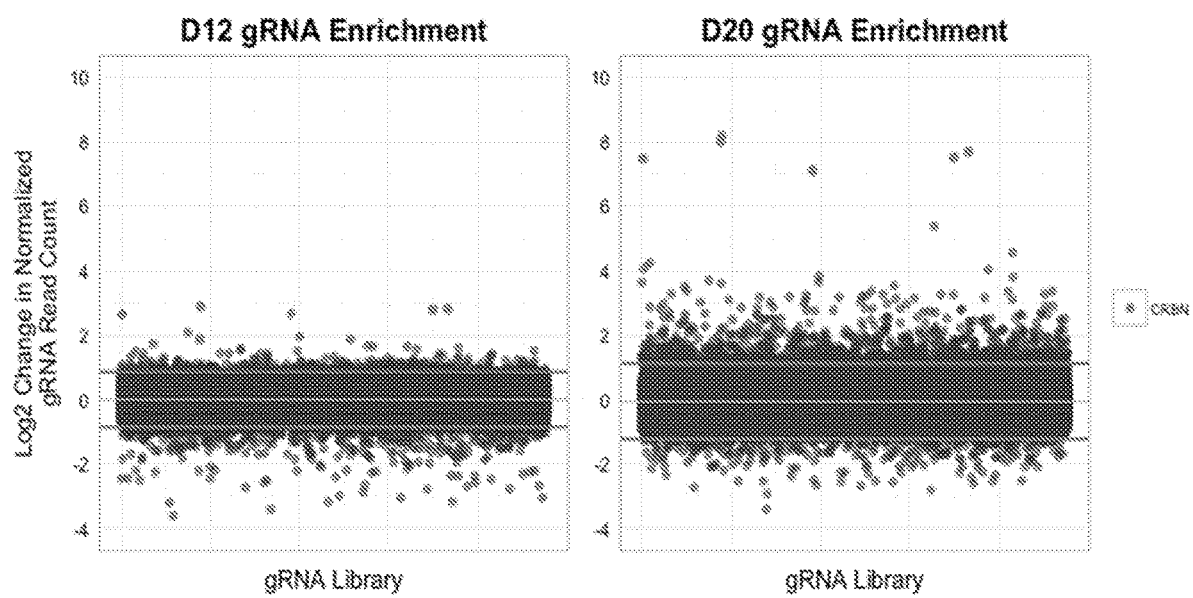
FIG. 4 provides a set of plots showing that CRBN gRNAs enrich upon selection with lenalidomide. All six of the gRNAs targeting cereblon rank amongst the top 7 and top 6 gRNAs at the Day 12 (D12) and Day (D20) time points respectively, confirming the optimization parameters for the screen. Also notable was the relative increase in gRNAs falling above the three standard deviations line in the D20 timepoint as compared to D12. (Middle horizontal line indicates mean; horizontal lines above and below the middle horizontal line indicate 3 standard deviations above and below the mean).

An examination of the gRNA rankings at D20 revealed that all six of the gRNAs targeting cereblon (CRBN) to be amongst the top 7 and top 6 gRNAs, respectively, confirming the screen optimization procedures (FIG. 4). To discover additional genes whose loss confers resistance to lenalidomide, the STARS algorithm (Genetic Perturbations Platform) was used to collapse gRNA rankings by gene and assign p, FDR (false discovery rate), and q values, as well as a composite STARS score (Table 1). In comparison to D12, the D20 data yielded hits with much higher confidence, with the top 30 genes possessing FDR values below 0.05. In keeping with the mechanism of lenalidomide, cereblon was ranked first, and of the top 30 genes, 18 are regulators of cullin-ring ligases and/or participants in the ubiquitin-proteasome pathway. Most notably, all 9 members of the COPS signalosome complex in scored with FDRs less than 0.05 (GPS1 [12], COPS2 [2], COPS3 [27], COPS4 [10], COPS5 [30], COPS6 [9], COPS7A [14], COPS7B [3], COPS8 [6]). Additional genetic modules that emerged as themes in the D20 STARS ranking of genes are CRL4-CRBN complex members (CRBN [1], DDB1 [17], CUL4B [52]), NFKB pathway (TRAF2 [5], NFKBIA [32]), members of the 5' mRNA decapping complex (EDC4 [7], XRN1 [19], DCP2 [36]), nuclear hormone receptor signaling (NCOR1 [15], RARA [25]), and tumor suppressors which have recently been noted to be relevant in melanoma (PPP6C [26], SPOP [28]).

A focused, pooled viral gRNA library was made containing an orthogonal set of gRNAs targeting the top 30 hits from the screen as well as NFKBIA [32], DCP2 [36], CUL4B [52], and the CRL4-CRBN complex members which did not score in the screen, CUL4A and RBX1. The focused library was designed using an on-target prediction algorithm and specifically contains three gRNAs per gene, each targeting a different exon in the first 50% of the protein (Doench et al., 2014, Nat. Biotechnol. doi:10.1038/nbt.3026). In the same manner as the original screen, this library will be used to validate the hits in Cas9-expressing MM1S cells as well as three other lenalidomide-sensitive myeloma cell lines: OPM2, U266, and NCIH929.

To determine which of the hits prevent degradation of the Aiolos transcription factor the same focused viral library was screened in an MM1S, NCIH929, and 293 T reporter cell lines expressing Aiolos tagged to GFP; flow cytometry-based sorting of GFP high and low cells following a 20 hour incubation with lenalidomide was used to isolate cells carrying gRNAs that did or did not impair Aiolos degradation. Subsequently, gDNA isolation, PCR amplification of the gRNA insert, and Illumina-based sequencing were used as a readout.

OTHER EMBODIMENTS

From the foregoing description, it will be apparent that variations and modifications may be made to the invention

TABLE 1

Day 20 (D20) STARS algorithm ranking of genes whose loss conferred resistance to lenalidomide in the screen described herein. Genes known to regulate the ubiquitin-proteasome system are designated in bold font and underlined in the table.

| Rank | Gene | gRNAs | gRNA Rankings | Number of scoring gRNAs | STARS Score | p-value | FDR | q-value |
|---|---|---|---|---|---|---|---|---|
| 1 | CRBN | 6 | 1; 2; 3; 4; 5; 6 | 6 | 25.794 | 0 | 0 | 0 |
| 2 | COPS2 | 6 | 32; 46; 67; 74; 124; 6348 | 5 | 14.141 | 0 | 0 | 0 |
| 3 | COPS7B | 6 | 8; 13; 36; 58; 152; 53703 | 5 | 13.699 | 0 | 0 | 0 |
| 4 | CAND1 | 6 | 11; 24; 29; 38; 31109; 111756 | 4 | 12.814 | 0 | 0 | 0 |
| 5 | TRAF2 | 6 | 17; 186; 187; 563; 671; 913 | 6 | 12.701 | 0 | 0 | 0 |
| 6 | COPS8 | 6 | 27; 42; 52; 64; 1002; 4357 | 4 | 11.909 | 0 | 0 | 0 |
| 7 | EDC4 | 6 | 128; 136; 318; 784; 1184; 1497 | 6 | 11.412 | 0 | 0 | 0 |
| 8 | PLAA | 6 | 191; 267; 379; 568; 664; 1702 | 6 | 11.078 | 0 | 0 | 0 |
| 9 | COPS6 | 6 | 18; 19; 113; 475; 900; 73096 | 5 | 9.840 | 0 | 0 | 0 |
| 10 | COPS4 | 6 | 76; 94; 158; 281; 1965; 3045 | 4 | 9.340 | 0 | 0 | 0 |
| 11 | UBE2G1 | 6 | 22; 98; 140; 326; 7406; 99037 | 4 | 9.082 | 3.07E−05 | 0.000485533 | 0.000356058 |
| 12 | GPS1 | 6 | 73; 104; 146; 372; 23755; 110214 | 4 | 8.853 | 3.07E−05 | 0.000445072 | 0.000356058 |
| 13 | UBE2D3 | 6 | 167; 185; 918; 959; 1564; 4207 | 5 | 8.643 | 3.07E−05 | 0.000410836 | 0.000356058 |
| 14 | COPS7A | 6 | 286; 400; 1145; 1429; 2025; 4852 | 5 | 8.083 | 3.07E−05 | 0.00038149 | 0.000356058 |
| 15 | NCOR1 | 6 | 44; 224; 416; 674; 2152; 3339 | 5 | 7.952 | 3.07E−05 | 0.000356058 | 0.000356058 |
| 16 | DEPDC5 | 6 | 451; 482; 720; 894; 2390; 6435 | 4 | 7.334 | 6.14E−05 | 0.000667608 | 0.000667608 |
| 17 | DDB1 | 6 | 99; 195; 1021; 1314; 113192; 113536 | 4 | 6.668 | 0.000184168 | 0.001885011 | 0.001885011 |
| 18 | SRP14 | 6 | 455; 605; 818; 1492; 46015; 84784 | 4 | 6.449 | 0.000276252 | 0.002670432 | 0.002670432 |
| 19 | XRN1 | 6 | 149; 356; 370; 4404; 8029; 54053 | 3 | 6.230 | 0.000429725 | 0.003935373 | 0.003738605 |
| 20 | EIF4A1 | 6 | 912; 1294; 1463; 1711; 7857; 22928 | 4 | 6.212 | 0.000429725 | 0.003738605 | 0.003738605 |
| 21 | SNRNP25 | 6 | 653; 1201; 1296; 1827; 18237; 100552 | 4 | 6.099 | 0.000583198 | 0.00483221 | 0.004612564 |
| 22 | UBE2M | 6 | 569; 872; 947; 1873; 2559; 29126 | 4 | 6.056 | 0.000583198 | 0.004612564 | 0.004612564 |
| 23 | GLMN | 6 | 123; 138; 817; 2032; 21286; 33356 | 4 | 5.916 | 0.000767365 | 0.005805287 | 0.0055634 |
| 24 | OTUB1 | 6 | 45; 70; 493; 4267; 4935; 24307 | 3 | 5.587 | 0.000767365 | 0.0055634 | 0.0055634 |
| 25 | RARA | 6 | 612; 851; 2118; 2305; 83094; 95108 | 4 | 5.699 | 0.001074312 | 0.007477209 | 0.007477209 |
| 26 | PPP6C | 6 | 91; 467; 708; 7219; 10474; 34526 | 3 | 5.388 | 0.001841677 | 0.01232507 | 0.01232507 |
| 27 | COPS3 | 6 | 43; 266; 719; 4078; 30794; 103889 | 3 | 5.368 | 0.00199515 | 0.012857635 | 0.012857635 |
| 28 | SPOP | 6 | 162; 260; 831; 2579; 97646; 110954 | 3 | 5.181 | 0.002823905 | 0.017548552 | 0.017548552 |
| 29 | SYCP2L | 6 | 48; 103; 34844; 70874; 72747; 111974 | 2 | 4.954 | 0.004113079 | 0.02467874 | 0.024678474 |
| 30 | COPS5 | 6 | 97; 127; 1628; 8546; 9715; 16865 | 2 | 4.773 | 0.005924062 | 0.034359557 | 0.034359557 | described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method comprising:
   (a) detecting loss of function of cereblon (CRBN) and ubiquitin conjugating enzyme E2 (UBE2G1) in B cells or cells derived from B cells in a sample obtained from a human subject having a disease or disorder selected from a plasma cell malignancy, a mature B-cell malignancy, a B-cell neoplasia, multiple myeloma, erythema nodosum leparum, or a myelodysplastic syndrome, by immunoassay, sequencing, or probe hybridization;
   (b) stratifying the human subject having loss of function of CRBN and UBE2G1 in the subject's B cells or cells derived from B cells into a patient population that is resistant to lenalidomide or an analog thereof based on detecting the loss of function of CRBN and UBE2G1 in said cells of the subject's sample; and
   (c) administering to the human subject a drug that is not lenalidomide or an analog thereof for treating the plasma cell malignancy, mature B-cell malignancy, B-cell neoplasia, multiple myeloma, erythema nodosum leparum, or myelodysplastic syndrome.

2. The method of claim 1, wherein the subject has a plasma cell malignancy, multiple myeloma, or a myelodysplastic syndrome.

3. The method of claim 1, further comprising detecting loss of function of COPS2 in the subject's B cells or cells derived from B cells.

4. The method of claim 1, wherein the analog of lenalidomide is thalidomide or pomalidomide.

5. The method of claim 1, further comprising detecting loss of function of ubiquitin conjugating enzyme UBE2D3 in the subject's B cells or cells derived from B cells.

6. The method of claim 1, further comprising detecting loss of function of ubiquitin conjugating enzyme UBE2M in the subject's B cells or cells derived from B cells.

7. A method comprising:
   (a) detecting loss of function of cereblon (CRBN) and ubiquitin conjugating enzyme E2 (UBE2G1) in B cells or cells derived from B cells in a biological sample obtained from a human subject having, at risk of having, or susceptible to having a disease or disorder selected from a plasma cell malignancy, a mature B-cell malignancy, a B-cell neoplasia, multiple myeloma, erythema nodosum leparum, or a myelodysplastic syndrome by immunoassay, sequencing, or probe hybridization;
   (b) identifying the subject having loss of function of CRBN and UBE2G1 in the subject's B cells or cells derived from B cells as being resistant to lenalidomide or an analog thereof based on said detecting step (a); and
   (c) administering to the identified subject a drug that is not lenalidomide or an analog thereof for treating or preventing the disease or disorder selected from plasma cell malignancy, mature B-cell malignancy, B-cell neoplasia, multiple myeloma, erythema nodosum leparum, or myelodysplastic syndrome.

8. The method of claim 7, wherein the subject has, is at risk of having, or is susceptible to having a plasma cell malignancy, multiple myeloma, or a myelodysplastic syndrome.

9. The method of claim 7, wherein the analog of lenalidomide is thalidomide or pomalidomide.

10. The method of claim 7, further comprising detecting loss of function of COPS2 in the subject's B cells or cells derived from B cells.

11. The method of claim 7, further comprising detecting loss of function of ubiquitin conjugating enzyme UBE2D3 in the subject's B cells or cells derived from B cells.

12. The method of claim 7, further comprising detecting loss of function of ubiquitin conjugating enzyme UBE2M in the subject's B cells or cells derived from B cells.

13. A method comprising:
(a) detecting loss of function of cereblon (CRBN) and ubiquitin conjugating enzyme E2 (UBE2G1) in B cells or cells derived from B cells in a sample obtained from a human subject having a disease or disorder selected from a plasma cell malignancy, a mature B-cell malignancy, a B-cell neoplasia, multiple myeloma, erythema nodosum leparum, or a myelodysplastic syndrome, by immunoassay, sequencing, or probe hybridization; and
(b) administering to the human subject a drug that is not lenalidomide or an analog thereof for treating the plasma cell malignancy, mature B-cell malignancy, B-cell neoplasia, multiple myeloma, erythema nodosum leparum, or myelodysplastic syndrome in the human subject.

14. The method of claim 13, wherein the analog of lenalidomide is thalidomide or pomalidomide.

15. The method of claim 13, further comprising detecting loss of function of COPS2, UBE2D3, or UBE2M in the subject's B cells or cells derived from B cells.

\* \* \* \* \*

SEQUENCE LISTING

```
<160> NUMBER OF SEQ ID NOS: 61

<210> SEQ ID NO 1
<211> LENGTH: 441
<212> TYPE: PRT
<213> ORGANISM: Homo sapiens

<400> SEQUENCE: 1

Met Ala Gly Glu Gly Asp Gln Gln Asp Ala Ala His Asn Met Gly Asn
1               5                   10                  15

His Leu Pro Leu Leu Pro Glu Ser Glu Glu Asp Glu Met Glu Val
            20                  25                  30

Glu Asp Gln Asp Ser Lys Glu Ala Lys Lys Pro Asn Ile Ile Asn Phe
        35                  40                  45

Asp Thr Ser Leu Pro Thr Ser His Thr Tyr Leu Gly Ala Asp Met Glu
    50                  55                  60

Glu Phe His Gly Arg Thr Leu His Asp Asp Ser Cys Gln Val Ile
65                  70                  75                  80

Pro Val Leu Pro Gln Val Met Met Ile Leu Ile Pro Gly Gln Thr Leu
                85                  90                  95

Pro Leu Gln Leu Phe His Pro Gln Glu Val Ser Met Val Arg Asn Leu
            100                 105                 110

Ile Gln Lys Asp Arg Thr Phe Ala Val Leu Ala Tyr Ser Asn Val Gln
        115                 120                 125

Glu Arg Glu Ala Gln Phe Gly Thr Thr Ala Glu Ile Tyr Ala Tyr Arg
    130                 135                 140

Glu Glu Gln Asp Phe Gly Ile Glu Ile Val Lys Val Lys Ala Ile Gly
145                 150                 155                 160

Arg Gln Arg Phe Lys Val Leu Glu Leu Arg Thr Gln Ser Asp Gly Ile
                165                 170                 175

Gln Gln Ala Lys Val Gln Ile Leu Pro Glu Cys Val Leu Pro Ser Thr
            180                 185                 190

Met Ser Ala Val Gln Leu Glu Ser Leu Asn Lys Cys Gln Ile Phe Pro
        195                 200                 205

Ser Lys Pro Val Ser Arg Glu Asp Gln Cys Ser Tyr Lys Trp Trp Gln
    210                 215                 220

Lys Tyr Gln Arg Arg Lys Phe His Cys Ala Asn Leu Thr Ser Trp Pro
225                 230                 235                 240

Arg Trp Leu Tyr Ser Leu Tyr Asp Ala Glu Thr Leu Met Asp Arg Ile
                245                 250                 255

Lys Lys Gln Leu Arg Glu Trp Asp Glu Asn Leu Lys Asp Asp Ser Leu
            260                 265                 270

Pro Ser Asn Pro Ile Asp Phe Ser Tyr Arg Val Ala Ala Cys Leu Pro
        275                 280                 285

Ile Asp Asp Val Leu Arg Ile Gln Leu Leu Lys Ile Gly Ser Ala Ile
    290                 295                 300

Gln Arg Leu Arg Cys Glu Leu Asp Ile Met Asn Lys Cys Thr Ser Leu
305                 310                 315                 320
```

```
Cys Cys Lys Gln Cys Gln Glu Thr Glu Ile Thr Thr Lys Asn Glu Ile
            325                 330                 335

Phe Ser Leu Ser Leu Cys Gly Pro Met Ala Ala Tyr Val Asn Pro His
            340                 345                 350

Gly Tyr Val His Glu Thr Leu Thr Val Tyr Lys Ala Cys Asn Leu Asn
            355                 360                 365

Leu Ile Gly Arg Pro Ser Thr Glu His Ser Trp Phe Pro Gly Tyr Ala
            370                 375                 380

Trp Thr Val Ala Gln Cys Lys Ile Cys Ala Ser His Ile Gly Trp Lys
385                 390                 395                 400

Phe Thr Ala Thr Lys Lys Asp Met Ser Pro Gln Lys Phe Trp Gly Leu
            405                 410                 415

Thr Arg Ser Ala Leu Leu Pro Thr Ile Pro Asp Thr Glu Asp Glu Ile
            420                 425                 430

Ser Pro Asp Lys Val Ile Leu Cys Leu
            435                 440

<210> SEQ ID NO 2
<211> LENGTH: 441
<212> TYPE: PRT
<213> ORGANISM: Homo sapiens

<400> SEQUENCE: 2

Met Ala Gly Glu Gly Asp Gln Gln Asp Ala Ala His Asn Met Gly Asn
1               5                   10                  15

His Leu Pro Leu Leu Pro Glu Ser Glu Glu Asp Glu Met Glu Val
            20                  25                  30

Glu Asp Gln Asp Ser Lys Glu Ala Lys Lys Pro Asn Ile Ile Asn Phe
            35                  40                  45

Asp Thr Ser Leu Pro Thr Ser His Thr Tyr Leu Gly Ala Asp Met Glu
        50                  55                  60

Glu Phe His Gly Arg Thr Leu His Asp Asp Ser Cys Gln Val Ile
65                  70                  75                  80

Pro Val Leu Pro Gln Val Met Met Ile Leu Ile Pro Gly Gln Thr Leu
                85                  90                  95

Pro Leu Gln Leu Phe His Pro Gln Glu Val Ser Met Val Arg Asn Leu
            100                 105                 110

Ile Gln Lys Asp Arg Thr Phe Ala Val Leu Ala Tyr Ser Asn Val Gln
            115                 120                 125

Glu Arg Glu Ala Gln Phe Gly Thr Thr Ala Glu Ile Tyr Ala Tyr Arg
        130                 135                 140

Glu Glu Gln Asp Phe Gly Ile Glu Ile Val Lys Val Lys Ala Ile Gly
145                 150                 155                 160

Arg Gln Arg Phe Lys Val Leu Glu Leu Arg Thr Gln Ser Asp Gly Ile
                165                 170                 175

Gln Gln Ala Lys Val Gln Ile Leu Pro Glu Cys Val Leu Pro Ser Thr
            180                 185                 190

Met Ser Ala Val Gln Leu Glu Ser Leu Asn Lys Cys Gln Ile Phe Pro
        195                 200                 205

Ser Lys Pro Val Ser Arg Glu Asp Gln Cys Ser Tyr Lys Trp Trp Gln
        210                 215                 220

Lys Tyr Gln Lys Arg Lys Phe His Cys Ala Asn Leu Thr Ser Trp Pro
225                 230                 235                 240

Arg Trp Leu Tyr Ser Leu Tyr Asp Ala Glu Thr Leu Met Asp Arg Ile
```

```
            245                 250                 255
Lys Lys Gln Leu Arg Glu Trp Asp Glu Asn Leu Lys Asp Asp Ser Leu
        260                 265                 270

Pro Ser Asn Pro Ile Asp Phe Ser Tyr Arg Val Ala Ala Cys Leu Pro
        275                 280                 285

Ile Asp Asp Val Leu Arg Ile Gln Leu Leu Lys Ile Gly Ser Ala Ile
        290                 295                 300

Gln Arg Leu Arg Cys Glu Leu Asp Ile Met Asn Lys Cys Thr Ser Leu
305                 310                 315                 320

Cys Cys Lys Gln Cys Gln Glu Thr Glu Ile Thr Thr Lys Asn Glu Ile
                325                 330                 335

Phe Ser Leu Ser Leu Cys Gly Pro Met Ala Ala Tyr Val Asn Pro His
        340                 345                 350

Gly Tyr Val His Glu Thr Leu Thr Val Tyr Lys Ala Cys Asn Leu Asn
        355                 360                 365

Leu Ile Gly Arg Pro Ser Thr Glu His Ser Trp Phe Pro Gly Tyr Ala
        370                 375                 380

Trp Thr Val Ala Gln Cys Lys Ile Cys Ala Ser His Ile Gly Trp Lys
385                 390                 395                 400

Phe Thr Ala Thr Lys Lys Asp Met Ser Pro Gln Lys Phe Trp Gly Leu
                405                 410                 415

Thr Arg Ser Ala Leu Leu Pro Thr Ile Pro Asp Thr Glu Asp Glu Ile
                420                 425                 430

Ser Pro Asp Lys Val Ile Leu Cys Leu
                435                 440

<210> SEQ ID NO 3
<211> LENGTH: 2213
<212> TYPE: DNA
<213> ORGANISM: Homo sapiens

<400> SEQUENCE: 3
gcgtgtaaac agacatggcc ggcgaaggag atcagcagga cgctgcgcac aacatgggca      60
accacctgcc gctcctgcct gagagtgagg aagaagatga atggaagtt gaagaccagg      120 atagtaaaga agccaaaaaa ccaaacatca taaattttga caccagtctg ccgacatcac     180 atacataccct aggtgctgat atggaagaat tcatggcag gactttgcac gatgacgaca     240
gctgtcaggt gattccagtt cttccacaag tgatgatgat cctgattccc ggacagacat     300
tacctcttca gctttttcac cctcaagaag tcagtatggt gcggaattta attcagaaag     360
atagaacctt tgctgttctt gcatacagca atgtacagga aagggaagca cagtttggaa     420
caacagcaga gatatatgcc tatcgagaag aacaggattt tggaattgag atagtgaaag     480
tgaaagcaat tggaagacaa aggttcaaag tccttgagct aagaacacag tcagatggaa     540
tccagcaagc taaagtgcaa attcttcccg aatgtgtgtt gccttcaacc atgtctgcag     600
ttcaattaga atccctcaat aagtgccaga tatttccttc aaaacctgtc tcaagagaag     660
accaatgttc atataaatgg tggcagaaat accagaggag aaagtttcat tgtgcaaatc     720
taacttcatg gcctcgctgg ctgtattcct tatgatgc tgagacctta atggacagaa      780
tcaagaaaca gctacgtgaa tgggatgaaa atctaaaaga tgattctctt ccttcaaatc     840
caatagattt ttcttacaga gtagctgctt gtcttcctat tgatgatgta ttgagaattc     900
agctccttaa aattggcagt gctatccagc gacttcgctg tgaattagac attatgaata     960
aatgtacttc cctttgctgt aaacaatgtc aagaaacaga aataacaacc aaaaatgaaa    1020
```

```
tattcagttt atccttatgt gggccgatgg cagcttatgt gaatcctcat ggatatgtgc    1080
atgagacact tactgtgtat aaggcttgca acttgaatct gataggccgg ccttctacag    1140
aacacagctg gtttcctggg tatgcctgga ctgttgccca gtgtaagatc tgtgcaagcc    1200
atattggatg gaagtttacg gccaccaaaa aagacatgtc acctcaaaaa ttttggggct    1260
taacgcgatc tgctctgttg cccacgatcc cagacactga agatgaaata agtccagaca    1320
aagtaatact ttgcttgtaa acagatgtga tagagataaa gttagttatc taacaaattg    1380
gttatattct aagatctgct ttggaaatta ttgcctctga tacataccta agtaaacata    1440
acattaatac ctaagtaaac ataacattac ttggagggtt gcagtttcta agtgaaactg    1500
tatttgaaac ttttaagtat actttaggaa acaagcatga acggcagtct agaataccag    1560
aaacatctac ttgggtagct tggtgccatt atcctgtgga atctgatatg tctggtagcg    1620
tgtcattgat gggacatgaa gacatctttg gaaatgatga gattatttcc tgtgttaaaa    1680
aaaaaaaaaa aatcttaaat tcctacaatg tgaaactgaa actaataatt tgatcctgat    1740
gtatgggaca gcgtatctgt accagtgctc taaataacaa aagctagggt gacaagtaca    1800
tgttcctttt ggaaagaagc aaggcaatgt atattaatta ttctaaaagg gctttgttcc    1860
tttccatttt ctttaacttc tctgagatac tgatttgtaa attttgaaaa ttagttaaaa    1920
tatgcagttt tttgagccca cgaatagttg tcatttcctt tatgtgcctg ttagtaaaaa    1980
gtagtattgt gtatttgctc agtatctgaa ctataagccc atttatactg ttccatacaa    2040
aagctatttt tcaaaaatta atttgaacca aaactactac tatagggaaa agatgccaaa    2100
acatgtcccc tcacccaggc taaacttgat actgtattat tttgttcaat gtaaattgaa    2160
gaaaatctgt aagtaagtaa accttaagtg tgaaactaaa aaaaaaaaaa aaa          2213
```

<210> SEQ ID NO 4
<211> LENGTH: 443
<212> TYPE: PRT
<213> ORGANISM: Homo sapiens

<400> SEQUENCE: 4

```
Met Ser Asp Met Glu Asp Asp Phe Met Cys Asp Asp Glu Glu Asp Tyr
1               5                  10                  15

Asp Leu Glu Tyr Ser Glu Asp Ser Asn Ser Glu Pro Asn Val Asp Leu
            20                  25                  30

Glu Asn Gln Tyr Tyr Asn Ser Lys Ala Leu Lys Glu Asp Asp Pro Lys
        35                  40                  45

Ala Ala Leu Ser Ser Phe Gln Lys Val Leu Glu Leu Glu Gly Glu Lys
    50                  55                  60

Gly Glu Trp Gly Phe Lys Ala Leu Lys Gln Met Ile Lys Ile Asn Phe
65                  70                  75                  80

Lys Leu Thr Asn Phe Pro Glu Met Met Asn Arg Tyr Lys Gln Leu Leu
                85                  90                  95

Thr Tyr Ile Arg Ser Ala Val Thr Arg Asn Tyr Ser Glu Lys Ser Ile
            100                 105                 110

Asn Ser Ile Leu Asp Tyr Ile Ser Thr Ser Lys Gln Met Asp Leu Leu
        115                 120                 125

Gln Glu Phe Tyr Glu Thr Thr Leu Glu Ala Leu Lys Asp Ala Lys Asn
    130                 135                 140

Asp Arg Leu Trp Phe Lys Thr Asn Thr Lys Leu Gly Lys Leu Tyr Leu
145                 150                 155                 160
```

Glu Arg Glu Glu Tyr Gly Lys Leu Gln Lys Ile Leu Arg Gln Leu His
            165                 170                 175
Gln Ser Cys Gln Thr Asp Asp Gly Glu Asp Leu Lys Lys Gly Thr
        180                 185                 190
Gln Leu Leu Glu Ile Tyr Ala Leu Glu Ile Gln Met Tyr Thr Ala Gln
            195                 200                 205
Lys Asn Asn Lys Lys Leu Lys Ala Leu Tyr Glu Gln Ser Leu His Ile
    210                 215                 220
Lys Ser Ala Ile Pro His Pro Leu Ile Met Gly Val Ile Arg Glu Cys
225                 230                 235                 240
Gly Gly Lys Met His Leu Arg Glu Gly Glu Phe Glu Lys Ala His Thr
            245                 250                 255
Asp Phe Phe Glu Ala Phe Lys Asn Tyr Asp Glu Ser Gly Ser Pro Arg
        260                 265                 270
Arg Thr Thr Cys Leu Lys Tyr Leu Val Leu Ala Asn Met Leu Met Lys
    275                 280                 285
Ser Gly Ile Asn Pro Phe Asp Ser Gln Glu Ala Lys Pro Tyr Lys Asn
    290                 295                 300
Asp Pro Glu Ile Leu Ala Met Thr Asn Leu Val Ser Ala Tyr Gln Asn
305                 310                 315                 320
Asn Asp Ile Thr Glu Phe Glu Lys Ile Leu Lys Thr Asn His Ser Asn
            325                 330                 335
Ile Met Asp Asp Pro Phe Ile Arg Glu His Ile Glu Glu Leu Leu Arg
            340                 345                 350
Asn Ile Arg Thr Gln Val Leu Ile Lys Leu Ile Lys Pro Tyr Thr Arg
            355                 360                 365
Ile His Ile Pro Phe Ile Ser Lys Glu Leu Asn Ile Asp Val Ala Asp
        370                 375                 380
Val Glu Ser Leu Leu Val Gln Cys Ile Leu Asp Asn Thr Ile His Gly
385                 390                 395                 400
Arg Ile Asp Gln Val Asn Gln Leu Leu Glu Leu Asp His Gln Lys Arg
            405                 410                 415
Gly Gly Ala Arg Tyr Thr Ala Leu Asp Lys Trp Thr Asn Gln Leu Asn
            420                 425                 430
Ser Leu Asn Gln Ala Val Val Ser Lys Leu Ala
        435                 440

<210> SEQ ID NO 5
<211> LENGTH: 4103
<212> TYPE: DNA
<213> ORGANISM: Homo sapiens

<400> SEQUENCE: 5
agctgagagt gacgcctctg agccgcggag gattgtggga ggaggttgtc tccaatttct      60 cctcccctc ccggccaaga tgtctgacat ggaggatgat ttcatgtgcg atgatgagga     120
ggactacgac ctggaatact ctgaagatag taactccgag ccaaatgtgg atttggaaaa     180
tcagtactat aattccaaag cattaaaaga agatgaccca aaagcggcat taagcagttt     240
ccaaaaggtt ttggaacttg aaggtgaaaa aggagaatgg ggatttaaag cactgaaaca     300
aatgattaag attaacttca gttgacaaa cttttccagaa atgatgaata gatataagca     360
gctattgacc tatattcgga gtgcagtcac aagaaattat tctgaaaaat ccattaattc     420
tattcttgat tatatctcta cttctaaaca gatggattta ctgcaggaat tctatgaaac     480
aacactggaa gctttgaaag atgctaagaa tgatagactg tggtttaaga caaacacaaa     540

```
gcttggaaaa ttatatttag aacgagagga atatggaaag cttcaaaaaa ttttacgcca      600
gttacatcag tcgtgccaga ctgatgatgg agaagatgat ctgaaaaaag gtacacagtt      660
attagaaata tatgctttgg aaattcaaat gtacacagca cagaaaaata acaaaaaact      720
taaagcactc tatgaacagt cacttcacat caagtctgcc atccctcatc cactgattat      780
gggagttatc agagaatgtg gtggtaaaat gcacttgagg aaggtgaat ttgaaaaggc       840 acacactgat ttttttgaag ccttcaagaa ttatgatgaa tctggaagtc caagacgaac      900
cacttgctta aaatatttgg tcttagcaaa tatgcttatg aaatcgggaa taaatccatt      960
tgactcacag gaggccaagc cgtacaaaaa tgatccagaa attttagcaa tgacgaattt     1020
agtaagtgcc tatcagaata atgacatcac tgaatttgaa aagattctaa aaacaaatca     1080
cagcaacatc atggatgatc ctttcataag agaaacacatt gaagagcttt tgcgaaacat    1140
cagaacacaa gtgcttataa aattaattaa gccttacaca agaatacata ttccttttat     1200
ttctaaggag ttaaacatag atgtagctga tgtggagagc ttgctggtgc agtgcatatt     1260
ggataacact attcatggcc gaattgatca agtcaaccaa ctccttgaac tggatcatca     1320
gaagaggggg ggtgcacgat atactgcact agataaatgg accaaccaac taaattctct     1380
caaccaggct gtagtcagta aactggctta acagagaaca agcttttaca gacgtcctta     1440
aggcaacagt gcagagatgt aatccttaaa agaactggga atggcaaaac tactgtcggt     1500
tgatgtgtcc tgaaaattat tggagttatg gcagaagtgc ttttttgatc aactggtttg     1560
tgttttgctg ctgcatttat cccaagaaaa acagctttaa tctccagaag aaaaccaaaa     1620
taccatggga tttatgctgt attgacatct tgccctaaac gtacaacatc atagtaattt     1680
gtcatgggca acatgaccag agagaagatt tttgtcatga ttttaaatac actgacacgc     1740
tactgttggt taaatttaaa catgttttac ctgcagaaat tctctcacaa ataacctgca     1800
ataacttgaa atgcataccc ttttgaacac ttccttttct catgtataaa ttaaaatgtt     1860
tgctgcattt tgcaaaatgt caattctcta aaaatgtgtc cgtatatttc tgtacctgca     1920
gtgtagtaaa ggtttagacg aaacccata attatagtgg catactgtca cttaggtttc       1980
aagcagcaaa ataaacagtg cagctcagaa attgtagttt ggttcttgat gtgttttat      2040 tacatttgga gttgttttgt tttttagtac cttcgaaatt tcaaattatt ttatcttcag     2100
ttaatgattt taaaaagcct gggggcaaat aagttggtta tttgctttca agttttttaaa    2160 agtagtcttt attgatagag taaggagaac tactttctaa caaaacacgt gcatagttat     2220
gacagtgatg ctttaaagga ataaaattct ttttttttaa agagtgatat tccttttcaa     2280
aagaatacta actctcagaa tgttcacttt aaacgaatat gccagaacat agacagctaa     2340
atgaatgtta ctctgcatag tgatcatgct ggaaggttat ttcctaatgc cagcaatcta     2400
ccattgccca aaacctgctg agtttactct tttagaattg cattcaaagt taatttgtca     2460
cacacactaa actttatgat tatacattgt tttaaaaaat atagtattag gaagcttgat     2520 tattttttagt taccattact tggcaccaaa tgaaagtttc caaaacttcc acctaacttt    2580
gaggtaatgc agaaagtata taactggctt tgaaggcaat cccaaaagag ttttaaaggt     2640 ttttttgagca gtggcagtat acttaggaga atgaactgtg gccttccaag gtaactacct    2700
taaaggaact cagctcattt gaatgtattg agttttggat gtatttgttt catttttttaa    2760 aaagttcaca ttattttata gtgtcgaaag gaagaactag gattaacata atttctttgg     2820 ttttctatt gcttgttatt attatgtaaa aactgggtgg cagttcagaa ggaagattgt      2880
```

```
ggttacagaa gagtgacaac caagaatttt ttgatcatta aatcagattt tataaacagt    2940
ggaaggagca tggacttaaa acaaggcatg cttattcggt tttgtcaaaa ttttacgaaa    3000
atatgtgata tatatttata ctaaaaatat ataatcctta gatttagaaa agcaatcagt    3060
taatgtcttt agcagactaa agcagtatta acacaggta caagttggaa attgtagaaa     3120
acggaaagaa aacaaaagac aaaatgtcta tggtagggaa taaaagttta agatattata    3180
aaattatgtg tattttctct tttacataaa tcatttgtga aaagtgtgct aaactttttt    3240
tacaagagtg atattaatta ggatttattt ttcaatataa tttggagacc ctttgttatc    3300
caaataaaaa tgatgagttt ttgtgcctgt attcaaatat gtatgcatgt gataacccctt   3360 gaaagctaaa gcccttctta acttttgagt tgatggaatt agaattcaaa gatttgaatg    3420
aaatgattta acctttatcc tccaattctt acagtgccca gttctcctgt gctatctttg    3480
ctttgtacaa tagtgcatct tccactttct agagagaaag catgcacttg ttatttggaa    3540
aactgggcta atatataac agtatccaaa gttataccat aataatttat tgtaattgtg     3600
tattacatag ctttgtttac ccagatatag gtgcgttctt ttttttctgt tagtcatctg    3660
tgacttttgt tctggaatac aggttttaa atatatctta acagtctgac taacttaaaa    3720
taatttattc ttcccttaaa acattttct gtgttttgt gcatcaaata ttgtagagtt      3780
gaaatcttag agattgctta tcgaaatata aatttagggg aagttaaaaa tcgattggca    3840
aatttgtagc atttattcac tgattaaatc ttttccactt ttgtgaaaac cataccagtg    3900
gtttacatca tattgtaatg tgttcatctc attcttcttt ttatccctaa acctagctaa    3960
aagttactgc aaagaaatct ttggctgcca caagtagatg ctctctacta caagagctgg    4020
atttccatta ctcactcttg ctcttacatt aaagttgttg attaaatact ttttctctac    4080
atcttaaaaa aaaaaaaaaa aaa                                            4103
```

<210> SEQ ID NO 6
<211> LENGTH: 423
<212> TYPE: PRT
<213> ORGANISM: Homo sapiens

<400> SEQUENCE: 6

```
Met Ala Ser Ala Leu Glu Gln Phe Val Asn Ser Val Arg Gln Leu Ser
1               5                   10                  15

Ala Gln Gly Gln Met Thr Gln Leu Cys Glu Leu Ile Asn Lys Ser Gly
            20                  25                  30

Glu Leu Leu Ala Lys Asn Leu Ser His Leu Asp Thr Val Leu Gly Ala
        35                  40                  45

Leu Asp Val Gln Glu His Ser Leu Gly Val Leu Ala Val Leu Phe Val
    50                  55                  60

Lys Phe Ser Met Pro Ser Val Pro Asp Phe Glu Thr Leu Phe Ser Gln
65                  70                  75                  80

Val Gln Leu Phe Ile Ser Thr Cys Asn Gly Glu His Ile Arg Tyr Ala
                85                  90                  95

Thr Asp Thr Phe Ala Gly Leu Cys His Gln Leu Thr Asn Ala Leu Val
            100                 105                 110

Glu Arg Lys Gln Pro Leu Arg Gly Ile Gly Ile Leu Lys Gln Ala Ile
        115                 120                 125

Asp Lys Met Gln Met Asn Thr Asn Gln Leu Thr Ser Ile His Ala Asp
    130                 135                 140

Leu Cys Gln Leu Cys Leu Leu Ala Lys Cys Phe Lys Pro Ala Leu Pro
145                 150                 155                 160
```

Tyr Leu Asp Val Asp Met Met Asp Ile Cys Lys Glu Asn Gly Ala Tyr
            165                 170                 175

Asp Ala Lys His Phe Leu Cys Tyr Tyr Tyr Gly Met Ile Tyr
            180                 185                 190

Thr Gly Leu Lys Asn Phe Glu Arg Ala Leu Tyr Phe Glu Gln Ala
            195                 200                 205

Ile Thr Thr Pro Ala Met Ala Val Ser His Ile Met Leu Glu Ser Tyr
210                 215                 220

Lys Lys Tyr Ile Leu Val Ser Leu Ile Leu Leu Gly Lys Val Gln Gln
225                 230                 235                 240

Leu Pro Lys Tyr Thr Ser Gln Ile Val Gly Arg Phe Ile Lys Pro Leu
            245                 250                 255

Ser Asn Ala Tyr His Glu Leu Ala Gln Val Tyr Ser Thr Asn Asn Pro
            260                 265                 270

Ser Glu Leu Arg Asn Leu Val Asn Lys His Ser Glu Thr Phe Thr Arg
            275                 280                 285

Asp Asn Asn Met Gly Leu Val Lys Gln Cys Leu Ser Ser Leu Tyr Lys
290                 295                 300

Lys Asn Ile Gln Arg Leu Thr Lys Thr Phe Leu Thr Leu Ser Leu Gln
305                 310                 315                 320

Asp Met Ala Ser Arg Val Gln Leu Ser Gly Pro Gln Glu Ala Glu Lys
            325                 330                 335

Tyr Val Leu His Met Ile Glu Asp Gly Glu Ile Phe Ala Ser Ile Asn
            340                 345                 350

Gln Lys Asp Gly Met Val Ser Phe His Asp Asn Pro Glu Lys Tyr Asn
            355                 360                 365

Asn Pro Ala Met Leu His Asn Ile Asp Gln Glu Met Leu Lys Cys Ile
            370                 375                 380

Glu Leu Asp Glu Arg Leu Lys Ala Met Asp Gln Glu Ile Thr Val Asn
385                 390                 395                 400

Pro Gln Phe Val Gln Lys Ser Met Gly Ser Gln Glu Asp Asp Ser Gly
            405                 410                 415

Asn Lys Pro Ser Ser Tyr Ser
            420

<210> SEQ ID NO 7
<211> LENGTH: 1865
<212> TYPE: DNA
<213> ORGANISM: Homo sapiens

<400> SEQUENCE: 7

```
ggaagtgacg tcgccgctcg cgaggacctc aggtggatcg ccgcggcccc tcctcccaga     60
gcggcagcct tttccgcgc gtgctgcctt cgccgctcgg gccgcccggg ggaaaacatg    120
gcgtctgccc tggagcagtt cgtgaacagt gtccgacagc tctcagctca agggcaaatg    180
acacagcttt gtgaactgat caacaagagt ggggaactcc ttgcgaagaa cttatcccat    240
ctggacactg tgctcggggc tctggatgta caagaacact ccttgggcgt ccttgctgtt    300
ttgtttgtga agttttctat gcccagtgtt cctgacttcg aaacgctatt ctcacaggtt    360
cagctcttca tcagcacttg taatggggag cacattcgat atgcaacaga cactttttgct   420 gggctttgcc atcagctaac aaatgcactt gtggaaagaa acagcccct gcgaggaatt    480 ggcatcctta gcaagccat agacaagatg cagatgaata caaaccagct gacctcaata    540
catgctgatc tctgccagct ttgtttgcta gcaaaatgct ttaagcctgc ccttccatat    600
```

-continued

```
cttgacgtgg atatgatgga tatctgtaaa gagaatggag cctatgatgc aaaacacttt    660
ttatgttact attattatgg agggatgatc tatactgggc tgaagaactt tgaaagagct    720
ctctactttt atgaacaggc tataactact cctgccatgg cggtcagtca tcatgttg     780 gaatcatata aaaagtatat tttagtgtct ttgatattac ttggcaaagt acaacagcta    840
ccaaaatata catctcaaat tgtgggtaga ttcattaagc ctcttagcaa tgcataccac    900
gagttagcac aagtgtattc aaccaacaac ccctcagaac tccgaaacct ggtgaataag    960
cacagtgaaa ccttcactcg cgataacaac atggggctgg tgaagcaatg cttgtcatct   1020
ctttataaga agaatattca gaggctaaca aagaccttt taactctatc attacaagat    1080
atggcaagtc gtgtgcagtt gtctggacct caggaggcag agaaatacgt tctgcacatg   1140
atagaagatg tgagattttt tgcaagtatt aaccagaagg acggtatggt cagtttccat   1200
gataaccctg aaaaatataa taacccagcc atgcttcata acattgatca ggagatgctg   1260
aagtgcattg agctggatga gcggctgaaa gccatggacc aggagatcac agtgaaccct   1320
cagtttgtac aaaagagtat gggctcacaa gaagatgatt caggaaacaa accatccagt   1380
tattcttgaa actaacatcc atcctgagct aaacaagaga actaccatc ttggccagtg    1440 acaagtgttc ggagggcagc agagaggacc aagcctgtgt cacctggaga ctaagaaatt   1500 aagtttgtt ttgacatctt cagtcctgtg tgctttcaga aaaccatttt ctctgcaaag    1560
aaaggaaaca gatttgcaaa cttttaaagtc tgtcgtggat ttatttatcc tcagattatt   1620
gttactgcat aaatctacc ttttttgtttt aagttgcttg aacattaatg tgtcttctgt    1680 atcactttt tctcctctga agttttttaat aagcacattc attgtgaaca gaaatagctg   1740
gattttagga atttttggaa gatttggatc tgaaaggttt ttattttattg acaaatttgt   1800 atctacaaaa aaatctaaaa gttgtaatca ttgtcttcag aaaataaaag aaagaaagg    1860 ccaaa                                                               1865
```

<210> SEQ ID NO 8
<211> LENGTH: 406
<212> TYPE: PRT
<213> ORGANISM: Homo sapiens

<400> SEQUENCE: 8

Met Ala Ala Val Arg Gln Asp Leu Ala Gln Leu Met Asn Ser Ser
1               5                   10                  15

Gly Ser His Lys Asp Leu Ala Gly Lys Tyr Arg Gln Ile Leu Glu Lys
                20                  25                  30

Ala Ile Gln Leu Ser Gly Ala Glu Gln Leu Glu Ala Leu Lys Ala Phe
            35                  40                  45

Val Glu Ala Met Val Asn Glu Asn Val Ser Leu Val Ile Ser Arg Gln
        50                  55                  60

Leu Leu Thr Asp Phe Cys Thr His Leu Pro Asn Leu Pro Asp Ser Thr
65                  70                  75                  80

Ala Lys Glu Ile Tyr His Phe Thr Leu Glu Lys Ile Gln Pro Arg Val
                85                  90                  95

Ile Ser Phe Glu Glu Gln Val Ala Ser Ile Arg Gln His Leu Ala Ser
            100                 105                 110

Ile Tyr Glu Lys Glu Glu Asp Trp Arg Asn Ala Ala Gln Val Leu Val
        115                 120                 125

Gly Ile Pro Leu Glu Thr Gly Gln Lys Gln Tyr Asn Val Asp Tyr Lys
    130                 135                 140

```
Leu Glu Thr Tyr Leu Lys Ile Ala Arg Leu Tyr Leu Glu Asp Asp Asp
145                 150                 155                 160

Pro Val Gln Ala Glu Ala Tyr Ile Asn Arg Ala Ser Leu Leu Gln Asn
                165                 170                 175

Glu Ser Thr Asn Glu Gln Leu Gln Ile His Tyr Lys Val Cys Tyr Ala
            180                 185                 190

Arg Val Leu Asp Tyr Arg Arg Lys Phe Ile Glu Ala Ala Gln Arg Tyr
        195                 200                 205

Asn Glu Leu Ser Tyr Lys Thr Ile Val His Glu Ser Glu Arg Leu Glu
210                 215                 220

Ala Leu Lys His Ala Leu His Cys Thr Ile Leu Ala Ser Ala Gly Gln
225                 230                 235                 240

Gln Arg Ser Arg Met Leu Ala Thr Leu Phe Lys Asp Glu Arg Cys Gln
                245                 250                 255

Gln Leu Ala Ala Tyr Gly Ile Leu Glu Lys Met Tyr Leu Asp Arg Ile
            260                 265                 270

Ile Arg Gly Asn Gln Leu Gln Glu Phe Ala Ala Met Leu Met Pro His
        275                 280                 285

Gln Lys Ala Thr Thr Ala Asp Gly Ser Ser Ile Leu Asp Arg Ala Val
290                 295                 300

Ile Glu His Asn Leu Leu Ser Ala Ser Lys Leu Tyr Asn Asn Ile Thr
305                 310                 315                 320

Phe Glu Glu Leu Gly Ala Leu Leu Glu Ile Pro Ala Ala Lys Ala Glu
                325                 330                 335

Lys Ile Ala Ser Gln Met Ile Thr Glu Gly Arg Met Asn Gly Phe Ile
            340                 345                 350

Asp Gln Ile Asp Gly Ile Val His Phe Glu Thr Arg Glu Ala Leu Pro
        355                 360                 365

Thr Trp Asp Lys Gln Ile Gln Ser Leu Cys Phe Gln Val Asn Asn Leu
370                 375                 380

Leu Glu Lys Ile Ser Gln Thr Ala Pro Glu Trp Thr Ala Gln Ala Met
385                 390                 395                 400

Glu Ala Gln Met Ala Gln
                405

<210> SEQ ID NO 9
<211> LENGTH: 1763
<212> TYPE: DNA
<213> ORGANISM: Homo sapiens

<400> SEQUENCE: 9
tcccacaccc gacgctctgg cccacacaga cgctactctg tagcatctca ggttccctct      60
ggctgcactc tggaggacca cactcgtttt cttttggct gccagaggcc cccgcatcca     120
ccgctgagct gggagaaaga tggcggcagc cgtgcgacag gatttggccc agctcatgaa    180
ttcgagcggc tctcataaag atctggctgg caagtatcgt cagatcctgg aaaaagccat    240
tcagttatct ggagcagaac aactagaagc tttgaaagct tttgtggaag caatggtaaa    300
tgagaatgtc agtctcgtga tctcgcggca gttgctgact gattttttgca cacatcttcc    360 taacttgcct gatagcacag ccaaagaaat ctatcacttc accttggaaa agatccagcc    420
tagagtcatt tcatttgagg agcaggttgc ttccataaga cagcatcctg catctatata    480
tgagaaagaa gaagattgga gaaatgcagc ccaagtgttg gtgggaattc ctttggaaac    540
aggacaaaaa cagtacaatg tagattataa actggagact tacttgaaga ttgctaggct    600
```

```
atatctggag gatgatgatc cagtccaggc agaggcttac ataaatcgag catcgttgct     660
tcagaatgaa tcaaccaatg aacaattaca gatacattat aaggtatgct atgcacgtgt     720
tcttgattat agaagaaaat tcattgaagc tgcacaaagg tacaatgagc tctcttacaa     780
gacaatagtc cacgaaagtg aaagactaga ggccttaaaa catgctttgc actgtacgat     840
cttagcatca gcagggcagc agcgttctcg gatgctagct actctttta aggatgaaag     900 gtgccagcaa cttgctgcct atgggatcct agagaaaatg tatctagata ggatcatcag     960
aggaaatcaa cttcaagaat tgctgccat gctgatgcct caccaaaaag caactacagc    1020
tgatggttcc agcatcttgg acagagctgt tattgaacac aatttgttgt ctgcaagcaa    1080
attatataat aatattacct tcgaagaact tggagctctt ttagagatcc ctgcagctaa    1140
ggcggaaaag atagcatctc aaatgataac cgaaggacgt atgaatggat ttattgacca    1200
gattgatgga atagttcatt ttgaaacacg agaagccctg ccaacgtggg ataagcagat    1260
ccaatcactt tgtttccaag tgataaccct tttggagaaa attagtcaaa cagcaccaga    1320
atggacagca caagccatgg aagcccagat ggctcagtga atccttgcag aacttctgtg    1380
cacatgacat cttttccat gttgtgcaga tcagtttcac tatctccaaa gcatttgcat    1440
catgacctta tacatttcaa tccctttat gctggattcc gtttaaagaa gacattatta    1500
gagcaggaag tacaagcatt taaaatatgt agttcccata tatttcaggg tctctgtgta    1560
ttaagctaac tcagatgttt tgaaagcttt ttctttaaac agaggtgaaa tatctgtggc    1620
taaaaagttt gagatttgtg ataactttgt agtcatgtaa aacttaagtg cttcatgcct    1680
ctccaaatgt ggttattcta ataaatggag aaatgagcca aataaaagta gtactttgtt    1740
tttagttaaa aaaaaaaaaa aaa                                            1763

<210> SEQ ID NO 10
<211> LENGTH: 334
<212> TYPE: PRT
<213> ORGANISM: Homo sapiens

<400> SEQUENCE: 10

Met Ala Ala Ser Gly Ser Gly Met Ala Gln Lys Thr Trp Glu Leu Ala
1               5                   10                  15

Asn Asn Met Gln Glu Ala Gln Ser Ile Asp Glu Ile Tyr Lys Tyr Asp
                20                  25                  30

Lys Lys Gln Gln Gln Glu Ile Leu Ala Ala Lys Pro Trp Thr Lys Asp
            35                  40                  45

His His Tyr Phe Lys Tyr Cys Lys Ile Ser Ala Leu Ala Leu Leu Lys
        50                  55                  60

Met Val Met His Ala Arg Ser Gly Gly Asn Leu Glu Val Met Gly Leu
65                  70                  75                  80

Met Leu Gly Lys Val Asp Gly Glu Thr Met Ile Ile Met Asp Ser Phe
                85                  90                  95

Ala Leu Pro Val Glu Gly Thr Glu Thr Arg Val Asn Ala Gln Ala Ala
            100                 105                 110

Ala Tyr Glu Tyr Met Ala Ala Tyr Ile Glu Asn Ala Lys Gln Val Gly
        115                 120                 125

Arg Leu Glu Asn Ala Ile Gly Trp Tyr His Ser His Pro Gly Tyr Gly
    130                 135                 140

Cys Trp Leu Ser Gly Ile Asp Val Ser Thr Gln Met Leu Asn Gln Gln
145                 150                 155                 160
```

```
Phe Gln Glu Pro Phe Val Ala Val Val Ile Asp Pro Thr Arg Thr Ile
                165                 170                 175

Ser Ala Gly Lys Val Asn Leu Gly Ala Phe Arg Thr Tyr Pro Lys Gly
            180                 185                 190

Tyr Lys Pro Pro Asp Glu Gly Pro Ser Glu Tyr Gln Thr Ile Pro Leu
        195                 200                 205

Asn Lys Ile Glu Asp Phe Gly Val His Cys Lys Gln Tyr Tyr Ala Leu
    210                 215                 220

Glu Val Ser Tyr Phe Lys Ser Ser Leu Asp Arg Lys Leu Leu Glu Leu
225                 230                 235                 240

Leu Trp Asn Lys Tyr Trp Val Asn Thr Leu Ser Ser Ser Leu Leu
                245                 250                 255

Thr Asn Ala Asp Tyr Thr Thr Gly Gln Val Phe Asp Leu Ser Glu Lys
            260                 265                 270

Leu Glu Gln Ser Glu Ala Gln Leu Gly Arg Gly Ser Phe Met Leu Gly
        275                 280                 285

Leu Glu Thr His Asp Arg Lys Ser Glu Asp Lys Leu Ala Lys Ala Thr
    290                 295                 300

Arg Asp Ser Cys Lys Thr Thr Ile Glu Ala Ile His Gly Leu Met Ser
305                 310                 315                 320

Gln Val Ile Lys Asp Lys Leu Phe Asn Gln Ile Asn Ile Ser
                325                 330

<210> SEQ ID NO 11
<211> LENGTH: 1510
<212> TYPE: DNA
<213> ORGANISM: Homo sapiens

<400> SEQUENCE: 11
gactatacca ctcccatacc ctataacttt gtttgttcta tttcacacat ataattttcc      60
gagacaagat gttctcattt aagcaacaag aagattcgtc tctcgctatt actgtaactg     120
ctgtttatat cgtcatgtcc cggaaaggtc cctgtcttcc ctgaatggtc tctaccaact     180
tcacctccgg ttctaggtgt catggctgcc caagagtct aggtaagagt ttgttcccgt      240
ggtgcggagg gtcaaggccc acacccggaa acctagcgag gtaaagttgc gtcttggttg     300
tagagacgac aacttctccg cttcctcggc gatggcggcg tccggagcg gtatggccca      360 gaaaacctgg gaactggcca acaacatgca ggaagctcag agtatcgatg aaatctacaa     420
atacgacaag aaacagcagc aagaaatcct ggcggcgaag ccctggacta aggatcacca     480
ttactttaag tactgcaaaa tctcagcatt ggctctgctg aagatggtga tgcatgccag     540
atcgggaggc aacttggaag tgatgggtct gatgctagga aaggtggatg gtgaaaccat     600
gatcattatg gacagtttg ctttgcctgt ggagggcact gaaacccgag taaatgctca      660
ggctgctgca tatgaataca tggctgcata catagaaaat gcaaaacagg ttggccgcct     720
tgaaaatgca atcgggtggt atcatagcca ccctggctat ggctgctggc tttctgggat     780
tgatgttagt actcagatgc tcaatcagca gttccaggaa ccatttgtag cagtggtgat     840
tgatccaaca agaacaatat ccgcagggaa agtgaatctt ggcgccttta ggacatacccc    900 aaagggctac aaacctcctg atgaaggacc ttctgagtac cagactattc cacttaataa     960
aatagaagat tttggtgtac actgcaaaca atattatgcc ttagaagtct catatttcaa    1020
atcctctttg gatcgcaaat tgcttgagct gttgtggaat aaatactggg tgaatacgtt    1080
gagttcttct agcttgctta ctaatgcaga ctataccact ggtcaggtct ttgatttgtc    1140
```

```
tgaaaagtta gagcagtcag aagcccagct gggacgaggg agtttcatgt tgggtttaga    1200
aacgcatgac cgaaaatcag aagacaaact tgccaaagct acaagagaca gctgtaaaac    1260
taccatagaa gctatccatg gattgatgtc tcaggttatt aaggataaac tgtttaatca    1320
aattaacatc tcttaaacag tctctgagaa gtactttacc tgaaagacag tatgagaaaa    1380
atattcaagt aacactttaa aaccagttac ccaaaatctg attagaagta taaggtgctc    1440
tgaagtgtcc taaatattaa tatcctgtaa taaagctctt taaaatgaaa aaaaaaaaa     1500 aaaaaaaaaa                                                          1510
```

<210> SEQ ID NO 12
<211> LENGTH: 327
<212> TYPE: PRT
<213> ORGANISM: Homo sapiens

<400> SEQUENCE: 12

```
Met Ala Ala Ala Ala Ala Ala Ala Thr Asn Gly Thr Gly Gly
1               5                   10                  15

Ser Ser Gly Met Glu Val Asp Ala Ala Val Val Pro Ser Val Met Ala
                20                  25                  30

Cys Gly Val Thr Gly Ser Val Ser Val Ala Leu His Pro Leu Val Ile
            35                  40                  45

Leu Asn Ile Ser Asp His Trp Ile Arg Met Arg Ser Gln Glu Gly Arg
        50                  55                  60

Pro Val Gln Val Ile Gly Ala Leu Ile Gly Lys Gln Glu Gly Arg Asn
65                  70                  75                  80

Ile Glu Val Met Asn Ser Phe Glu Leu Leu Ser His Thr Val Glu Glu
                85                  90                  95

Lys Ile Ile Ile Asp Lys Glu Tyr Tyr Tyr Thr Lys Glu Glu Gln Phe
            100                 105                 110

Lys Gln Val Phe Lys Glu Leu Glu Phe Leu Gly Trp Tyr Thr Thr Gly
        115                 120                 125

Gly Pro Pro Asp Pro Ser Asp Ile His Val His Lys Gln Val Cys Glu
130                 135                 140

Ile Ile Glu Ser Pro Leu Phe Leu Lys Leu Asn Pro Met Thr Lys His
145                 150                 155                 160

Thr Asp Leu Pro Val Ser Val Phe Glu Ser Val Ile Asp Ile Ile Asn
                165                 170                 175

Gly Glu Ala Thr Met Leu Phe Ala Glu Leu Thr Tyr Thr Leu Ala Thr
            180                 185                 190

Glu Glu Ala Glu Arg Ile Gly Val Asp His Val Ala Arg Met Thr Ala
        195                 200                 205

Thr Gly Ser Gly Glu Asn Ser Thr Val Ala Glu His Leu Ile Ala Gln
    210                 215                 220

His Ser Ala Ile Lys Met Leu His Ser Arg Val Lys Leu Ile Leu Glu
225                 230                 235                 240

Tyr Val Lys Ala Ser Glu Ala Gly Glu Val Pro Phe Asn His Glu Ile
                245                 250                 255

Leu Arg Glu Ala Tyr Ala Leu Cys His Cys Leu Pro Val Leu Ser Thr
            260                 265                 270

Asp Lys Phe Lys Thr Asp Phe Tyr Asp Gln Cys Asn Asp Val Gly Leu
        275                 280                 285

Met Ala Tyr Leu Gly Thr Ile Thr Lys Thr Cys Asn Thr Met Asn Gln
    290                 295                 300
```

```
Phe Val Asn Lys Phe Asn Val Leu Tyr Asp Arg Gln Gly Ile Gly Arg
305                 310                 315                 320

Arg Met Arg Gly Leu Phe Phe
                325

<210> SEQ ID NO 13
<211> LENGTH: 1441
<212> TYPE: DNA
<213> ORGANISM: Homo sapiens

<400> SEQUENCE: 13
ggcggggccg aggctggcgg gcgcggggaa aatggcggcg gcggcggcgg cggctgcagc      60
tacgaacggg accggaggaa gcagcgggat ggaggtggat gcagcagtag tccccagcgt     120
gatggcctgc ggagtgactg ggagtgtttc cgtcgctctc catcccttg tcattctcaa      180 catctcagac cactggatcc gcatgcgctc ccaggagggg cggcctgtgc aggtgattgg     240
ggctctgatt ggcaagcagg agggccgaaa tatcgaggtg atgaactcct ttgagctgct     300
gtcccacacc gtggaagaga agattatcat tgacaaggaa tattattaca ccaaggagga     360
gcagtttaaa caggtgttca aggagctgga gtttctgggt tggtatacca caggggggcc     420
acctgacccc tcggacatcc acgtccataa gcaggtgtgt gagatcatcg agagccccct     480
ctttctgaag ttgaacccta tgaccaagca cacagatctt cctgtcagcg ttttgagtc      540 tgtcattgat ataatcaatg agagggccac aatgctgttt gctgagctga cctacactct     600
ggccacagag gaagcggaac gcattggtgt agaccacgta gcccgaatga cagcaacagg     660
cagtggagag aactccactg tggctgaaca cctgatagca cagcacagcg ccatcaagat     720
gctgcacagc cgcgtcaagc tcatcttgga gtacgtcaag gcctctgaag cgggagaggt     780
cccctttaat catgagatcc tgcgggaggc ctatgctctg tgtcactgtc tcccggtgct     840
cagcacagac aagttcaaga cagatttta tgatcaatgc aacgacgtgg ggctcatggc      900
ctacctcggc accatcacca aaacgtgcaa caccatgaac cagtttgtga acaagttcaa     960
tgtcctctac gaccgacaag gcatcggcag gagaatgcgc gggctcttt tctgatgagg     1020 gtacttgaag ggctgatgga cagggggtcag gcaactatcc caaaggggag ggcactacac    1080
ttccttgaga gaaaccgctg tcattaataa aaggggagca gcccctgagc acccctgctg     1140
gtggctctgt cctctgttag gcaccacact ggttggtcaa cttggatgtt catcgaggct     1200
cattctggcc ttgctcagaa gcccttctga tgctcttcag tgagggaggc actaccattt     1260
gaagtgaccc catgtcagtc acatggactg gtctttagca aagtccaagg ctgcctgctt     1320
ccacctaagt ggtctctgtt ctacactta atgtcaccct ctacatcatc ttacctagcc      1380
cacccaacct tataaacatg ataattgact actttcctga gctaaaaaaa aaaaaaaaaa     1440
a                                                                    1441

<210> SEQ ID NO 14
<211> LENGTH: 275
<212> TYPE: PRT
<213> ORGANISM: Homo sapiens

<400> SEQUENCE: 14

Met Ser Ala Glu Val Lys Val Thr Gly Gln Asn Gln Glu Gln Phe Leu
1               5                   10                  15

Leu Leu Ala Lys Ser Ala Lys Gly Ala Ala Leu Ala Thr Leu Ile His
                20                  25                  30

Gln Val Leu Glu Ala Pro Gly Val Tyr Val Phe Gly Glu Leu Leu Asp
```

```
                35                  40                  45
Met Pro Asn Val Arg Glu Leu Ala Glu Ser Asp Phe Ala Ser Thr Phe
 50                  55                  60

Arg Leu Leu Thr Val Phe Ala Tyr Gly Thr Tyr Ala Asp Tyr Leu Ala
 65                  70                  75                  80

Glu Ala Arg Asn Leu Pro Pro Leu Thr Glu Ala Gln Lys Asn Lys Leu
                 85                  90                  95

Arg His Leu Ser Val Val Thr Leu Ala Ala Lys Val Lys Cys Ile Pro
                100                 105                 110

Tyr Ala Val Leu Leu Glu Ala Leu Ala Leu Arg Asn Val Arg Gln Leu
                115                 120                 125

Glu Asp Leu Val Ile Glu Ala Val Tyr Ala Asp Val Leu Arg Gly Ser
            130                 135                 140

Leu Asp Gln Arg Asn Gln Arg Leu Glu Val Asp Tyr Ser Ile Gly Arg
145                 150                 155                 160

Asp Ile Gln Arg Gln Asp Leu Ser Ala Ile Ala Arg Thr Leu Gln Glu
                165                 170                 175

Trp Cys Val Gly Cys Glu Val Val Leu Ser Gly Ile Glu Glu Gln Val
            180                 185                 190

Ser Arg Ala Asn Gln His Lys Glu Gln Gln Leu Gly Leu Lys Gln Gln
        195                 200                 205

Ile Glu Ser Glu Val Ala Asn Leu Lys Lys Thr Ile Lys Val Thr Thr
210                 215                 220

Ala Ala Ala Ala Ala Thr Ser Gln Asp Pro Glu Gln His Leu Thr
225                 230                 235                 240

Glu Leu Arg Glu Pro Ala Pro Gly Thr Asn Gln Arg Gln Pro Ser Lys
                245                 250                 255

Lys Ala Ser Lys Gly Lys Gly Leu Arg Gly Ser Ala Lys Ile Trp Ser
            260                 265                 270

Lys Ser Asn
        275

<210> SEQ ID NO 15
<211> LENGTH: 2053
<212> TYPE: DNA
<213> ORGANISM: Homo sapiens

<400> SEQUENCE: 15
gtgggcgcgt gcggggcagc aatggagagc tgagggagcg tcgtcagggt ggacaccatg      60 cgacaccat ttctcctttg catcctgtgt cttggggttc aatggggtgc acgtgatggg     120
gcttggggtt aggcccaggg gaggggtgg tgtggcagc cttgcgaagt ggctgacttt      180
aggattccta gatcagaatt ttagaccgct ccatgtctga ttcctcaccg cagaaccgac     240
ttagtgcctt tacaatccag tccctcagcc ttgtgcttcc catccgacca gccatcgggg     300
acctctagct tcacatcctc tttccttgca gctctggaca tcctgagccc aagtccccca     360
cactcagtgc agtgatgagt gcggaagtga aggtgacagg gcagaaccag gagcaatttc     420
tgctcctagc caagtcggcc aaggggcag cgctggccac actcatccat caggtgctgg     480
aggcccctgg tgtctacgtg tttggagaac tgctggacat gcccaatgtt agagagctgg     540
ctgagagtga ctttgcctct accttccggc tgctcacagt gtttgcttat gggacatacg     600
ctgactactt agctgaagcc cggaatcttc ctccactaac agaggctcag aagaataagc     660
ttcgacacct ctcagttgtc accctggctg ctaaagtaaa gtgtatccca tatgcagtgt     720
```

```
tgctggaggc tcttgccctg cgtaatgtgc ggcagctgga agaccttgtg attgaggctg      780
tgtatgctga cgtgcttcgt ggctccctgg accagcgcaa ccagcggctc gaggttgact      840
acagcatcgg gcgggacatc cagcgccagg acctcagtgc cattgcccga accctgcagg      900
aatggtgtgt gggctgtgag gtcgtgctgt caggcattga ggagcaggtg agccgtgcca      960
accaacacaa ggagcagcag ctgggcctga agcagcagat tgagagtgag gttgccaacc     1020
ttaaaaaaac cattaaagtt acgacggcag cagcagccgc agccacatct caggaccctg     1080
agcaacacct gactgagctg agggaaccag ctcctggcac caaccagcgc cagcccagca     1140
agaaagcctc aaagggcaag gggctccgag ggagcgccaa gatttggtcc aagtcgaatt     1200
gaaaggactg tcgtttcctc cctggggatg tggggtccca gctgcctgcc tgcctcttag     1260
gagtcctcag agagccttct gtgccctggc cagctgata atcctaggtt catgaccctt     1320
cacctcccct aaccccaaac atagatcaca ccttctctag ggaggaggca aatgtaggtc     1380 atgttttgt tggtactttc tgttttttgt gacttcatgt gttccattgc tccccgctgc     1440
catgctctct cccttgtttc cttaagagct cagcatctgt ccctgttcat tacatgtcat     1500
tgagtaggtg ggtagccctg atggggtcg ctctgtctgg agcataaccc acaggcgttt     1560
tttctgccac cccatccctg catgcctgat ccccagttcc tataccctac ccctgaccta     1620
ttgagcagcc tctgaagagc cagggccc ccacctttac tcacaccctg agaattctgg     1680
gagccagtct gccatgccag gagtcactgg acatgttcat cctagaatcc tgtcacacta     1740
cagtcatttc ttttcctctc tctggcccctt gggtcctggg aatgctgctg cttcaacccc     1800
agagcctaag aatggcagcc gtttcttaac atgttgagag atgattcttt cttggccctg     1860
gccatctcgg gaagcttgat ggcaatcctg aagggttta atctccttt gtgagtttgg     1920 tggggaaggg aagggtatat agattgtatt aaaaaaaaaa aggtatatat gcatatatct     1980
atatataata tgacgcagaa ataaatctat gagaaatcta tctacaaact accctgaaaa     2040
aaaaaaaaaa aaa                                                       2053
```

<210> SEQ ID NO 16
<211> LENGTH: 273
<212> TYPE: PRT
<213> ORGANISM: Homo sapiens

<400> SEQUENCE: 16

```
Met Ala Gly Glu Gln Lys Pro Ser Ser Asn Leu Leu Glu Gln Phe Ile
1               5                   10                  15

Leu Leu Ala Lys Gly Thr Ser Gly Ser Ala Leu Thr Ala Leu Ile Ser
            20                  25                  30

Gln Val Leu Glu Ala Pro Gly Val Tyr Val Phe Gly Glu Leu Leu Glu
        35                  40                  45

Leu Ala Asn Val Gln Glu Leu Ala Glu Gly Ala Asn Ala Ala Tyr Leu
    50                  55                  60

Gln Leu Leu Asn Leu Phe Ala Tyr Gly Thr Tyr Pro Asp Tyr Ile Ala
65                  70                  75                  80

Asn Lys Glu Ser Leu Pro Glu Leu Ser Thr Ala Gln Gln Asn Lys Leu
                85                  90                  95

Lys His Leu Thr Ile Val Ser Leu Ala Ser Arg Met Lys Cys Ile Pro
            100                 105                 110

Tyr Ser Val Leu Leu Lys Asp Leu Glu Met Arg Asn Leu Arg Glu Leu
        115                 120                 125

Glu Asp Leu Ile Ile Glu Ala Val Tyr Thr Asp Ile Ile Gln Gly Lys
```

```
                130                 135                 140
Leu Asp Gln Arg Asn Gln Leu Leu Glu Val Asp Phe Cys Ile Gly Arg
145                 150                 155                 160

Asp Ile Arg Lys Lys Asp Ile Asn Asn Ile Val Lys Thr Leu His Glu
                165                 170                 175

Trp Cys Asp Gly Cys Glu Ala Val Leu Leu Gly Ile Glu Gln Gln Val
            180                 185                 190

Leu Arg Ala Asn Gln Tyr Lys Glu Asn His Asn Arg Thr Gln Gln Gln
            195                 200                 205

Val Glu Ala Glu Arg Glu Lys Arg Asp Val Pro Leu Leu Asn Leu Ile
        210                 215                 220

Thr Thr Ala Phe Phe Trp Leu Pro Thr Ser Arg His Ser Lys Pro
225                 230                 235                 240

Pro His Pro Pro Arg Leu Arg Arg Trp Ser Ser Ser Trp Leu Asn Gly
                245                 250                 255

Ser Val Pro Leu Thr Leu Ser Arg Gly Ser Pro Pro Arg Arg Cys Pro
            260                 265                 270

Lys

<210> SEQ ID NO 17
<211> LENGTH: 2635
<212> TYPE: DNA
<213> ORGANISM: Homo sapiens

<400> SEQUENCE: 17
agcggtggga ggcttccggg ggagctgcac gggcgacggg tcggcggaga cagaaaagcg      60
ccggacgccg gggtgatcat ggacgcttga caacctgcgg gcaggcgccg ggaggccgag     120
ccagcgacta agaggaccga gaggtggcgt ggacagattt caaggccaga gaatggcagg     180
ggaacagaaa ccctcaagta atctcctgga gcagtttatt ttactagcca aaggtaccag     240
tggctcagcc ctcactgctc tcataagcca ggtcttagag gctcccggag tgtatgtctt     300
tggagaactt ctggagctgg ccaacgtgca ggagcttgcg gaaggagcta atgctgctta     360
tttgcagttg ttgaacctgt ttgcctatgg gacataccca gattacatag ccaacaagga     420
gagcctgcca gaactgagca cagctcagca gaacaagctg aagcatctta ccatcgtgag     480
cttggcatca agaatgaagt gtatccccta ctccgtgttg ctgaaagacc tggagatgcg     540
gaatctccgg gaactagaag acctttatcat tgaggctgtc tacactgaca tcatccaggg     600
caagctggac cagcgaaacc agctgctgga agtggatttc tgcattggcc gtgacatccg     660
aaagaaggat atcaataata ttgtcaagac cctgcatgaa tggtgtgatg gctgtgaagc     720
agttctactg ggcatcgagc agcaagttct gagagccaac cagtacaaag agaaccacaa     780
ccgaactcag cagcaggtag aagcagagag ggaaaaacgt gatgtccccc tcctgaatct     840
tataacaaca gctttcttct ggttaccaac atcaagaaga cactcaaagc caccgcatcc     900
tcctcggctc aggagatgga gcagcagctg gctgaacggg agtgtccccc tcacgctgag     960
cagaggcagc ccaccaagaa gatgtccaaa gtgaaggtc tggtctccag ccgccactag    1020
ggccggctgg ggcagctggc actcaccagg cctgggtcag gtggggaggg gacaccaagg    1080
gcccatttcc tcccctctct acctgcagtg agttccagac ctgcccgtcc cctcaccagc    1140
gcctccccac cctgttggta ctgttccaga aaaactgtta ctcccccctca cccactccct    1200 ccttcccag ttgttccctt cagactcagg ggctccacca atgccatccc aaaacagggt    1260
cagacactgc ccagcttccc tccaggaggt tcttgtctct gtgtaagggc ttgtctccct    1320
```

```
cccagttttt cttttgctcc acgtcatttt gtcaggctgg ttataagccg gaggcagctt    1380
taaccagccc ccagggatga ttgtgaagga ggcccctccc cttgtgagga gggggcactc    1440
ctctccagcc cctggtacca cagtcctcac gatggtgcag tgatttctag ccaggcgtca    1500
agatgcgctg ctttccctct cctgcctcat cccttgttgg cagctccagt tcaggccgtg    1560
gagggacgtg atgctgggct gtgtttacta aacccacggg ttttcagcct cttaagccca    1620
gctccgatct ccaattagtt gagagcgctg ggttgactaa cctctggtat ctgagcacag    1680
acagagggtg ctgtgggtct gctgggtggc agaaatggtt ccttccggct ggcgttctc     1740 tcctggccac tcttcctgct gcctctgact actcagcctt gttttcggtg tgtaggcccc    1800
agctgcccac tggaactgcc ggctaatgct tgctctccca agatctttaa ctcctcctgg    1860
ctgcacctgg gtagggatgg tggcatcgat gcccctctgt ctgctgaagg acctgttgct    1920
gcttctgtct tttcacccct ccttggctga tgacccagag ccctctgatg atggcattct    1980
cctggcaaga gaaaagact taactagact tctgaacttg aacagtttca ggttatattt     2040
taattttttt tttttgtac aggttctgat tctaatacat ttcaacatgc ttttgtcccc     2100
cctcgtgtca atatttgtta tagactaatc gccggggatt tttcacctgg ttggaggggtg   2160 ggggtggggt ggggtgtgtg tgtgtgtgtg tgtgtgtgtg tgtgtgtgtg tgtgtgtttg    2220
taggtcctgg actgattaaa gttcattgag gaaaaagcac attttacaac aaaaaaataa    2280
aagtgtagat ttaatgtatg tgactggggt ttggggttgc atacctggtg gatcttgagg    2340
ggctgggatt agggtggttc aggaaaatgt gatgctgttt ccccatgttt agccatggtc    2400
aaaaaatgga tttctccttt ttctaaaatg tccagcaact gcctactgtt gatcaaatgt    2460
tgaagtattc ttgtttccct tttaagccaa tccatgtgcc cacataacat tatgcccaag    2520
tggagagttc actttaattt ccaaagtatg tttcatgcag cccctgtca gctgctctgt     2580 ggaaaagggg ttctgttatg aaataaatgt tgcactccct gcatcccaaa aaaaa         2635
```

<210> SEQ ID NO 18
<211> LENGTH: 209
<212> TYPE: PRT
<213> ORGANISM: Homo sapiens

<400> SEQUENCE: 18

```
Met Pro Val Ala Val Met Ala Glu Ser Ala Phe Ser Phe Lys Lys Leu
1               5                   10                  15

Leu Asp Gln Cys Glu Asn Gln Glu Leu Glu Ala Pro Gly Gly Ile Ala
            20                  25                  30

Thr Pro Pro Val Tyr Gly Gln Leu Leu Ala Leu Tyr Leu Leu His Asn
        35                  40                  45

Asp Met Asn Asn Ala Arg Tyr Leu Trp Lys Arg Ile Pro Pro Ala Ile
    50                  55                  60

Lys Ser Ala Asn Ser Glu Leu Gly Gly Ile Trp Ser Val Gly Gln Arg
65                  70                  75                  80

Ile Trp Gln Arg Asp Phe Pro Gly Ile Tyr Thr Thr Ile Asn Ala His
                85                  90                  95

Gln Trp Ser Glu Thr Val Gln Pro Ile Met Glu Ala Leu Arg Asp Ala
            100                 105                 110

Thr Arg Arg Ala Phe Ala Leu Val Ser Gln Ala Tyr Thr Ser Ile
        115                 120                 125

Ile Ala Asp Asp Phe Ala Ala Phe Val Gly Leu Pro Val Glu Glu Ala
    130                 135                 140
```

```
Val Lys Gly Ile Leu Glu Gln Gly Trp Gln Ala Asp Ser Thr Thr Arg
145                 150                 155                 160

Met Val Leu Pro Arg Lys Pro Val Ala Gly Ala Leu Asp Val Ser Phe
                165                 170                 175

Asn Lys Phe Ile Pro Leu Ser Glu Pro Ala Pro Val Pro Pro Ile Pro
            180                 185                 190

Asn Glu Gln Gln Leu Ala Arg Leu Thr Asp Tyr Val Ala Phe Leu Glu
        195                 200                 205

Asn

<210> SEQ ID NO 19
<211> LENGTH: 2273
<212> TYPE: DNA
<213> ORGANISM: Homo sapiens

<400> SEQUENCE: 19
```

| | | | | | |
|---|---|---|---|---|---|
| ggagactcac | accttagatt | ctgagttttt | aagcttgttt | cctcagagca | gggaactcac | 60 |
| gaacgtttcg | tgagcaccta | cggtatgcag | ggtacggtgc | ggagccctag | cgtcactgac | 120 |
| gaccgggaca | gccgagcagc | tgcaggatcc | gtcgtgttcc | ccagcaattt | taatatttaa | 180 |
| aaattcgtta | ctgttgctgt | tacttgtttt | ctatgtattg | gatgtcttcg | tgaagaaccc | 240 |
| tcaaaagtgc | aacgaactcc | tccctgccag | agggcggccg | cgcgctctga | gtacagcttc | 300 |
| ccgcggagcc | ggccaggtcc | tccagggcac | cgagaaagcc | ggccagaacg | gcggcgccct | 360 |
| atcccggccg | cagcgatgtc | tgacggcgcc | ccggaactga | cggtctggta | cgcaggggcg | 420 |
| ctcggcggca | acggcggctt | taacgtcat | cgcgggcgcg | acgcctgagg | acagtctgg | 480 |
| ggtttggctg | tccggacggt | gcagcggcga | ggccggccgc | gaagatgcca | gtggcggtga | 540 |
| tggcggaaag | cgcctttagt | ttcaaaaagt | tgctggatca | gtgcgagaac | caggagctcg | 600 |
| aggcccctgg | aggaattgct | acaccccag | tgtatggtca | gcttctagct | ttatatttgc | 660 |
| tccataatga | catgaataat | gcaagatatc | tttggaaaag | aataccacct | gctataaaat | 720 |
| ctgcaaattc | tgaacttggg | ggaatttggt | cagtaggaca | aagaatctgg | cagagagatt | 780 |
| tccctgggat | ctatacaacc | atcaacgctc | accagtggtc | tgagacggtc | cagccaatta | 840 |
| tggaagcact | tagagatgca | acaaggagac | gcgcctttgc | cctggtctct | caagcgtata | 900 |
| cttcaatcat | cgccgatgat | tttgcagcct | tgttggact | tcctgtagaa | gaggctgtga | 960 |
| aaggcatatt | gaacaagga | tggcaagctg | attccaccac | aagaatggtt | ctgcccagaa | 1020 |
| agccagttgc | aggggccctg | gatgtttcct | ttaacaagtt | tattcccctta | tcagagcctg | 1080 |
| ctccagttcc | cccaataccc | aatgaacagc | agttagccag | actgacggat | tatgtggctt | 1140 |
| tccttgaaaa | ctgatttatc | actctgagtt | caagattcat | cttcagaatc | ctgtatactg | 1200 |
| acaaacgtag | aaatgtaaag | tttgtatttt | caatttattg | gatggcttaa | gcacctcagc | 1260 |
| attccttact | atgtgataaa | atacatatag | aatataagat | atactatata | cattttgtcc | 1320 |
| ataaacgtta | tgctgaatag | ttgttgaaac | agttctcatt | ttgtagtatt | taataatctg | 1380 |
| gatggagcct | gtcagtatta | cagttagttt | tctagtgact | cataaaataa | gatttcctgt | 1440 |
| ttcatgtaga | atagtgtttg | tcaactgtct | tttctctgtc | ccagcacatg | ccgtactctt | 1500 |
| atatgtacca | ttggttgata | attataatga | ttcatttgga | cttgaagaaa | gattgtcccc | 1560 |
| aggcacagta | tctgaatcac | tgggattat | gattcaccct | ctttggagaa | catgctctct | 1620 |
| tttcaccccc | cacctcctga | gagccactaa | tgtaagatac | agaaacatag | ctgaggaaca | 1680 |

-continued

```
aatagaccat tccatacta aaccagtttg ttaactttag attttttcca atagtgtgag   1740
tatatccatt gctggcagtg gagggcttgc catgaaaatg caacttattt aagacattta   1800
tgagacatat taacttgtgc tgtcgccttt tagaaggaga aacttaagtg tggaatgcat   1860
tatatgggca aagaagctat gaagatacat gatacacttt gtacaactat cctgcagccc   1920
attggttgct tatatttatc gcttggctca agttctgccc tttggagaaa tactgagcaa   1980
gtctttcatt ctctgtgtga cagccctctg aatatttgaa gttgtttgtt gtaacttaag   2040
gttataacag cccttagttc atttactctg catttgttca ataaatattt aactgaattc   2100
ttcaattatt tcatctaaga tagtttctgg aaatttcact ctcgatcttt ctgtggacac   2160
aatctatttt gtcattgtgt ctatatgaat ctcttaagta gaaatgagtt gtatggtgaa   2220
tctgtgtagt gataattata taatttattt attttgaaaa aaaaaaaaaa aaa          2273
```

<210> SEQ ID NO 20
<211> LENGTH: 1159
<212> TYPE: PRT
<213> ORGANISM: Homo sapiens

<400> SEQUENCE: 20

```
Leu Gly Pro Leu Val Ser Lys Val Lys Glu Tyr Gln Val Glu Thr Ile
1               5                   10                  15

Val Asp Thr Leu Cys Thr Asn Met Leu Ser Asp Lys Glu Gln Leu Arg
            20                  25                  30

Asp Ile Ser Ser Ile Gly Leu Lys Thr Val Ile Gly Glu Leu Pro Pro
        35                  40                  45

Ala Ser Ser Gly Ser Ala Leu Ala Ala Asn Val Cys Lys Lys Ile Thr
    50                  55                  60

Gly Arg Leu Thr Ser Ala Ile Ala Lys Gln Glu Asp Val Ser Val Gln
65                  70                  75                  80

Leu Glu Ala Leu Asp Ile Met Ala Asp Met Leu Ser Arg Gln Gly Gly
                85                  90                  95

Leu Leu Val Asn Phe His Pro Ser Ile Leu Thr Cys Leu Leu Pro Gln
            100                 105                 110

Leu Thr Ser Pro Arg Leu Ala Val Arg Lys Arg Thr Ile Ile Ala Leu
        115                 120                 125

Gly His Leu Val Met Ser Cys Gly Asn Ile Val Phe Val Asp Leu Ile
    130                 135                 140

Glu His Leu Leu Ser Glu Leu Ser Lys Asn Asp Ser Met Ser Thr Thr
145                 150                 155                 160

Arg Thr Tyr Ile Gln Cys Ile Ala Ala Ile Ser Arg Gln Ala Gly His
                165                 170                 175

Arg Ile Gly Glu Tyr Leu Glu Lys Ile Ile Pro Leu Val Val Lys Phe
            180                 185                 190

Cys Asn Val Asp Asp Asp Glu Leu Arg Glu Tyr Cys Ile Gln Ala Phe
        195                 200                 205

Glu Ser Phe Val Arg Arg Cys Pro Lys Glu Val Tyr Pro His Val Ser
    210                 215                 220

Thr Ile Ile Asn Ile Cys Leu Lys Tyr Leu Thr Tyr Asp Pro Asn Tyr
225                 230                 235                 240

Asn Tyr Asp Asp Glu Asp Glu Asp Glu Asn Ala Met Asp Ala Asp Gly
                245                 250                 255

Gly Asp Asp Asp Asp Gln Gly Ser Asp Asp Glu Tyr Ser Asp Asp Asp
            260                 265                 270
```

```
Asp Met Ser Trp Lys Val Arg Arg Ala Ala Lys Cys Leu Asp Ala
            275                 280                 285

Val Val Ser Thr Arg His Glu Met Leu Pro Glu Phe Tyr Lys Thr Val
    290                 295                 300

Ser Pro Ala Leu Ile Ser Arg Phe Lys Glu Arg Glu Asn Val Lys
305                 310                 315                 320

Ala Asp Val Phe His Ala Tyr Leu Ser Leu Leu Lys Gln Thr Arg Pro
                325                 330                 335

Val Gln Ser Trp Leu Cys Asp Pro Asp Ala Met Glu Gln Gly Glu Thr
            340                 345                 350

Pro Leu Thr Met Leu Gln Ser Gln Val Pro Asn Ile Val Lys Ala Leu
            355                 360                 365

His Lys Gln Met Lys Glu Lys Ser Val Lys Thr Arg Gln Cys Cys Phe
    370                 375                 380

Asn Met Leu Thr Glu Leu Val Asn Val Leu Pro Gly Ala Leu Thr Gln
385                 390                 395                 400

His Ile Pro Val Leu Val Pro Gly Ile Ile Phe Ser Leu Asn Asp Lys
                405                 410                 415

Ser Ser Ser Ser Asn Leu Lys Ile Asp Ala Leu Ser Cys Leu Tyr Val
            420                 425                 430

Ile Leu Cys Asn His Ser Pro Gln Val Phe His Pro His Val Gln Ala
    435                 440                 445

Leu Val Pro Pro Val Val Ala Cys Val Gly Asp Pro Phe Tyr Lys Ile
    450                 455                 460

Thr Ser Glu Ala Leu Leu Val Thr Gln Gln Leu Val Lys Val Ile Arg
465                 470                 475                 480

Pro Leu Asp Gln Pro Ser Ser Phe Asp Ala Thr Pro Tyr Ile Lys Asp
                485                 490                 495

Leu Phe Thr Cys Thr Ile Lys Arg Leu Lys Ala Ala Asp Ile Asp Gln
            500                 505                 510

Glu Val Lys Glu Arg Ala Ile Ser Cys Met Gly Gln Ile Ile Cys Asn
            515                 520                 525

Leu Gly Asp Asn Leu Gly Ser Asp Leu Pro Asn Thr Leu Gln Ile Phe
            530                 535                 540

Leu Glu Arg Leu Lys Asn Glu Ile Thr Arg Leu Thr Thr Val Lys Ala
545                 550                 555                 560

Leu Thr Leu Ile Ala Gly Ser Pro Leu Lys Ile Asp Leu Arg Pro Val
                565                 570                 575

Leu Gly Glu Gly Val Pro Ile Leu Ala Ser Phe Leu Arg Lys Asn Gln
            580                 585                 590

Arg Ala Leu Lys Leu Gly Thr Leu Ser Ala Leu Asp Ile Leu Ile Lys
            595                 600                 605

Asn Tyr Ser Asp Ser Leu Thr Ala Ala Met Ile Asp Ala Val Leu Asp
            610                 615                 620

Glu Leu Pro Pro Leu Ile Ser Glu Ser Asp Met His Val Ser Gln Met
625                 630                 635                 640

Ala Ile Ser Phe Leu Thr Thr Leu Ala Lys Val Tyr Pro Ser Ser Leu
                645                 650                 655

Ser Lys Ile Ser Gly Ser Ile Leu Asn Glu Leu Ile Gly Leu Val Arg
            660                 665                 670

Ser Pro Leu Leu Gln Gly Gly Ala Leu Ser Ala Met Leu Asp Phe Phe
            675                 680                 685

Gln Ala Leu Val Val Thr Gly Thr Asn Asn Leu Gly Tyr Met Asp Leu
```

-continued

```
                690                 695                 700
Leu Arg Met Leu Thr Gly Pro Val Tyr Ser Gln Ser Thr Ala Leu Thr
705                 710                 715                 720

His Lys Gln Ser Tyr Tyr Ser Ile Ala Lys Cys Val Ala Ala Leu Thr
                725                 730                 735

Arg Ala Cys Pro Lys Glu Gly Pro Ala Val Val Gly Gln Phe Ile Gln
                740                 745                 750

Asp Val Lys Asn Ser Arg Ser Thr Asp Ser Ile Arg Leu Leu Ala Leu
                755                 760                 765

Leu Ser Leu Gly Glu Val Gly His His Ile Asp Leu Ser Gly Gln Leu
                770                 775                 780

Glu Leu Lys Ser Val Ile Leu Glu Ala Phe Ser Ser Pro Ser Glu Glu
785                 790                 795                 800

Val Lys Ser Ala Ala Ser Tyr Ala Leu Gly Ser Ile Ser Val Gly Asn
                805                 810                 815

Leu Pro Glu Tyr Leu Pro Phe Val Leu Gln Glu Ile Thr Ser Gln Pro
                820                 825                 830

Lys Arg Gln Tyr Leu Leu Leu His Ser Leu Lys Glu Ile Ile Ser Ser
                835                 840                 845

Ala Ser Val Val Gly Leu Lys Pro Tyr Val Glu Asn Ile Trp Ala Leu
850                 855                 860

Leu Leu Lys His Cys Glu Cys Ala Glu Glu Gly Thr Arg Asn Val Val
865                 870                 875                 880

Ala Glu Cys Leu Gly Lys Leu Thr Leu Ile Asp Pro Glu Thr Leu Leu
                885                 890                 895

Pro Arg Leu Lys Gly Tyr Leu Ile Ser Gly Ser Ser Tyr Ala Arg Ser
                900                 905                 910

Ser Val Val Thr Ala Val Lys Phe Thr Ile Ser Asp His Pro Gln Pro
                915                 920                 925

Ile Asp Pro Leu Leu Lys Asn Cys Ile Gly Asp Phe Leu Lys Thr Leu
                930                 935                 940

Glu Asp Pro Asp Leu Asn Val Arg Arg Val Ala Leu Val Thr Phe Asn
945                 950                 955                 960

Ser Ala Ala His Asn Lys Pro Ser Leu Ile Arg Asp Leu Leu Asp Thr
                965                 970                 975

Val Leu Pro His Leu Tyr Asn Glu Thr Lys Val Arg Lys Glu Leu Ile
                980                 985                 990

Arg Glu Val Glu Met Gly Pro Phe Lys His Thr Val Asp Asp Gly Leu
                995                 1000                1005

Asp Ile Arg Lys Ala Ala Phe Glu Cys Met Tyr Thr Leu Leu Asp
                1010                1015                1020

Ser Cys Leu Asp Arg Leu Asp Ile Phe Glu Phe Leu Asn His Val
                1025                1030                1035

Glu Asp Gly Leu Lys Asp His Tyr Asp Ile Lys Met Leu Thr Phe
                1040                1045                1050

Leu Met Leu Val Arg Leu Ser Thr Leu Cys Pro Ser Ala Val Leu
                1055                1060                1065

Gln Arg Leu Asp Arg Leu Val Glu Pro Leu Arg Ala Thr Cys Thr
                1070                1075                1080

Thr Lys Val Lys Ala Asn Ser Val Lys Gln Glu Phe Glu Lys Gln
                1085                1090                1095

Asp Glu Leu Lys Arg Ser Ala Met Arg Ala Val Ala Ala Leu Leu
                1100                1105                1110
```

```
Thr Ile Pro Glu Ala Glu Lys Ser Pro Leu Met Ser Glu Phe Gln
1115                1120                1125

Ser Gln Ile Ser Ser Asn Pro Glu Leu Ala Ala Ile Phe Glu Ser
1130                1135                1140

Ile Gln Lys Asp Ser Ser Ser Thr Asn Leu Glu Ser Met Asp Thr
1145                1150                1155

Ser
```

<210> SEQ ID NO 21
<211> LENGTH: 6010
<212> TYPE: DNA
<213> ORGANISM: Homo sapiens

<400> SEQUENCE: 21

```
gtgaactctg accttagctt tccgtagcgc ccgcgtctgc cgccccgcc      60
cccggagcga
aggaggcggg ctttggcctt ttgccctagg gagcgagtgc ggagcgagtg    120
ggagcgagac
ggccctgagt ggaagtgtct ggctccccgt agaggcccct ctgtacgccc    180
cgccgcccat
gagctcgttc tcacgcgaac agcgccgtcg ttaggctggc tctgtagcct    240
cggcttaccc
cgggacaggc ccacgcctcg ccagggaggg ggcagcccgt cgaggcgcct    300
ccctagtcag
cgtcggcgtc gcgctgcgac cctggaagcg ggagccgccg cgagcgagag    360
gaggagctcc
agtggcggcg gcggcggcgg cagcggcagc gggcagcagc tccagcagcg    420
ccagcaggcg
ggatcgaggc cgtcaacatg gcgagcgcct cgtaccacat ttccaatttg    480
ctggaaaaaa
tgacatccag cgacaaggac tttaggttta tggctacaaa tgatttgatg    540
acggaactgc
agaaagattc catcaagttg gatgatgata gtgaaaggaa agtagtgaaa    600
atgattttga
agttattgga agataaaaat ggagaggtac agaatttagc tgtcaaatgt    660
cttggtcctt
tagtgagtaa agtgaaagaa taccaagtag agacaattgt agataccctc    720
tgcactaaca
tgctttctga taaagaacaa cttcgagaca tttcaagtat tggtcttaaa    780
acagtaattg
gagaacttcc tccagcttcc agtggctctg cattagctgc taatgtatgt    840
aaaaagatta
ctggacgtct tacaagtgca atagcaaaac aggaagatgt ctctgttcag    900
ctagaagcct
tggatattat ggctgatatg ttgagcaggc aaggaggact tcttgttaat    960
ttccatcctt
caattctgac ctgtctactt ccccagttga ccagccctag acttgcagtg   1020
aggaaaagaa
ccattatcgc tcttggccat ctggttatga gctgtggaaa tatagttttt   1080
gtagatctta
ttgaacatct gttgtcagag ttgtccaaaa atgattctat gtcaacaaca   1140
agaacctaca
tacaatgtat tgctgctatt agtaggcaag ctggtcatag aataggtgaa   1200
taccttgaga
agataattcc tttggtggta aaattttgca atgtagatga tgatgaatta   1260
agagagtact
gtattcaagc ctttgaatca tttgtaagaa gatgtcctaa ggaagtatat   1320
cctcatgttt
ctaccattat aaatatttgt cttaaatatc ttacctatga tccaaattat   1380
aattacgatg
atgaagatga agatgaaaat gcaatggatg ctgatggtgg tgatgatgat   1440
gatcaaggga
gtgatgatga atacagtgat gatgatgaca tgagttggaa agtgagacgt   1500
gcagctgcga
agtgcttgga tgctgtagtt agcacaaggc atgaaatgct tccagaattc   1560
tacaagaccg
tctctcctgc actaatatcc agatttaaag agcgtgaaga gaatgtaaag   1620
gcagatgttt
ttcacgcata ccttttctct tttgaagcaa ctcgtcctgt acaaagttgg   1680
ctatgtgacc
ctgatgcaat ggagcaggga gaaacacctt taacaatgct tcagagtcag   1740
gttcccaaca
ttgttaaagc tcttcacaaa cagatgaaag aaaaaagtgt gaagacccga   1800
cagtgttgtt
```

```
ttaacatgtt aactgagctg gtaaatgtat tacctggggc cctaactcaa cacattcctg    1860
tacttgtacc aggaatcatt ttctcactga atgataaatc aagctcatcg aatttgaaga    1920
tcgatgcttt gtcatgtcta tacgtaatcc tctgtaacca ttctcctcaa gtcttccatc    1980
ctcacgttca ggctttggtt cctccagtgg tggcttgtgt tggagaccca ttttacaaaa    2040
ttacatctga agcacttctt gttactcaac agcttgtcaa agtaattcgt cctttagatc    2100
agccttcctc gtttgatgca actccttata tcaaagatct atttacctgt accattaaga    2160
gattaaaagc agctgacatt gatcaggaag tcaaggaaag ggctatttcc tgtatgggac    2220 aaaattatttg caaccttgga gacaatttgg gttctgactt gcctaataca cttcagattt    2280
tcttggagag actaaagaat gaaattacca ggttaactac agtaaaggca ttgacactga    2340
ttgctgggtc accttttgaag atagatttga ggcctgttct gggagaaggg gttcctatcc    2400
ttgcttcatt tcttagaaaa aaccagagag ctttgaaact gggtactctt tctgcccttg    2460
atattctaat aaaaaactat agtgacagct tgacagctgc catgattgat gcagttctag    2520
atgagctccc acctcttatc agcgaaagtg atatgcatgt ttcacaaatg gccatcagtt    2580
ttcttaccac tttggcaaaa gtatatccct cctccctttc aaagataagt ggatccattc    2640
tcaatgaact tattggactt gtgagatcac ccttattgca ggggggagct cttagtgcca    2700
tgctagactt tttccaagct ctggttgtca ctggaacaaa taatttagga tacatggatt    2760
tgttgcgcat gctgactggt ccagtttact ctcagagcac agctcttact cataagcagt    2820
cttattattc cattgccaaa tgtgtagctg cccttactcg agcatgccct aaagagggac    2880
cagctgtagt aggtcagttt attcaagatg tcaagaactc aaggtctaca gattccattc    2940
gtctcttagc tctactttct cttggagaag ttgggcatca tattgactta agtggacagt    3000
tggaactaaa atctgtaata ctagaagctt tctcatctcc tagtgaagaa gtcaaatcag    3060
ctgcatccta tgcattaggc agcattagtg tgggcaacct tcctgaatat ctgccgtttg    3120
tcctgcaaga aataactagt caacccaaaa ggcagtatct tttacttcat tccttgaagg    3180
aaattattag ctctgcatca gtggtgggcc ttaaaccata tgttgaaaac atctgggcct    3240
tattactaaa gcactgtgag tgtgcagagg aaggaaccag aaatgttgtt gctgaatgtc    3300
taggaaaact cactctaatt gatccagaaa ctctccttcc acggcttaag gggtacttga    3360
tatcaggctc atcatatgcc cgaagctcag tggttacggc tgtgaaattt acaatttctg    3420
accatccaca acctattgat ccactgttaa agaactgcat aggtgatttc ctaaaaactt    3480
tggaagaccc agatttgaat gtgagaagag tagccttggt cacatttaat tcagcagcac    3540
ataacaagcc atcattaata agggatctat tggatactgt tcttccacat ctttacaatg    3600
aaacaaaagt tagaaaggag cttataagag aggtagaaat gggtccattt aaacatacgg    3660
ttgatgatgg tctggatatt agaaaggcag catttgagtg tatgtacaca cttctagaca    3720
gttgtcttga tagacttgat atctttgaat ttctaaatca tgttgaagat ggtttgaagg    3780
accattatga tattaagatg ctgacatttt taatgttggt gagactgtct accctttgtc    3840
caagtgcagt actgcagagg ttggaccgac ttgttgagcc attacgtgca acatgtacaa    3900
ctaaggtaaa ggcaaactca gtaaagcagg agtttgaaaa acaagatgaa ttaaagcgat    3960
ctgccatgag agcagtagca gcactgctaa ccattccaga agcagagaag agtccactga    4020
tgagtgaatt ccagtcacag atcagttcta accctgagct ggcggctatc tttgaaagta    4080
tccagaaaga ttcatcatct actaacttgg aatcaatgga cactagttag atgtttgttc    4140
```

-continued

```
accatgggga ccattacata tgaccataca atgcactgaa ttgacaggtt aatcataaga    4200
catggaaaga gaagtgtcta aaagcttcaa aatgttccac ttttttttcc ttcatggaga    4260
ctgtttgttt ggctttcttc cattgttgtt tttgtagcat ttatttcaga aatgtgtatt    4320
tccataatcc agaggttgta aaaccactag tgttttagtg gttacagcaa catttgaaat    4380
ggaaactaaa agttaggatt ttatggagta tggagatagg gtccagtatc tatttaccct    4440
gtaatgttta ggattaaaat gttaaaattt tgtgaccatg aatttctttc ttttataaat    4500
tttctcattt aaaaatcaaa aatcttgcaa aacaaaaacc atgtttcttt ttcttgtata    4560
acttttttgtt ttcagcaaca taaattgatt tttagctggc agacaagaat atccatataa   4620
gatttgttaa ccatttcaga gagtttggca attttttaaaa gataataagg tatcatttttt  4680
aagtatgaaa attaacaata tccctgttgc gcacactaat tttgcatgag taagtttaca    4740
aatatgtatc gtctgtaaag cagcatgtgc agattattca taatatagaa gttaaaataa    4800
gtattagtgc aattttcaga tatttatttt tgcacagaaa acacattatc tggagagaaa    4860
gaaaggagaa ttttttgagac ttgggttttc ttaatgccag tgtgaatttg cagatgttt    4920
cagaaaatca agtcacagta acaatttgcc acttttttct attataaatc ttcttactta    4980
aattttgaat atttagtttt tctcagttac ccatttgtgt gtgtgtgatt ccacttagaa    5040
attcttaaaa ccagattttt ctttcattcc gtttggatgt ctacattcct tatcaaagga    5100
tataaatact gtgtatgctt ttgaatttta tttttaggaa aattctgaag ccagctatca    5160
caggtttgtt agctaataat agtattttct tttagttgag ttaggttttt ccccatctcc    5220
tgtagagcga atttacatat tgtattgggt aagtgttcac tacttttcct gattaaggga    5280
tctgtgctgg ggaacaaagc ttttgcagta ccttatattg tagttaaaat tttatttaac    5340
atatccttca gtgagctcat ttcacactgt agcctcttcc ttaaaatttg tggtgctcct    5400
gtaacagtaa gaactaattc tgaaataaaa gacatctcct aatgctgtgc aaacatagtt    5460
tacatgtatt gaaggaggca gttgttaaat tgagtgacca atttaagcaa tcagatattt    5520
gaaaactgca ccctttagtt ttgaaactgt gaattagaaa cacttttcct gctgtattac    5580
tacctgcttt aacatccaaa tatacagtga ttttaaatga taacatactg tggttattag    5640
attaacagct tgattttgaa tgttcagatg ataatgcaga agacatcact tctagtaagg    5700
attttgacta gtgcattgat gttgaagttg gtgccatttc aaaatgtggc aggtgataat    5760
cttttaccat aatttgcata aaactgtaat agaagtttat tttgagatgt tagtatatta    5820
tgtactatgc atttctgtgg tatagatgtt gtggatatat ttaagtattt ggttacatgg    5880
ttttacaata aattacaata ctgcaggctc taggactgaa caggagactg acatgcatat    5940
gttgtgtgaa tgtcttagtt gggtaaagtt aaatccaaat acttcaactg gcaaaaaaaa    6000
aaaaaaaaa                                                            6010
```

<210> SEQ ID NO 22
<211> LENGTH: 1140
<212> TYPE: PRT
<213> ORGANISM: Homo sapiens

<400> SEQUENCE: 22

Met Ser Tyr Asn Tyr Val Val Thr Ala Gln Lys Pro Thr Ala Val Asn
1               5                   10                  15

Gly Cys Val Thr Gly His Phe Thr Ser Ala Glu Asp Leu Asn Leu Leu
            20                  25                  30

Ile Ala Lys Asn Thr Arg Leu Glu Ile Tyr Val Val Thr Ala Glu Gly

```
                35                  40                  45
Leu Arg Pro Val Lys Glu Val Gly Met Tyr Gly Lys Ile Ala Val Met
             50                  55                  60
Glu Leu Phe Arg Pro Lys Gly Glu Ser Lys Asp Leu Leu Phe Ile Leu
 65                  70                  75                  80
Thr Ala Lys Tyr Asn Ala Cys Ile Leu Glu Tyr Lys Gln Ser Gly Glu
                 85                  90                  95
Ser Ile Asp Ile Ile Thr Arg Ala His Gly Asn Val Gln Asp Arg Ile
                100                 105                 110
Gly Arg Pro Ser Glu Thr Gly Ile Ile Gly Ile Ile Asp Pro Glu Cys
            115                 120                 125
Arg Met Ile Gly Leu Arg Leu Tyr Asp Gly Leu Phe Lys Val Ile Pro
        130                 135                 140
Leu Asp Arg Asp Asn Lys Glu Leu Lys Ala Phe Asn Ile Arg Leu Glu
145                 150                 155                 160
Glu Leu His Val Ile Asp Val Lys Phe Leu Tyr Gly Cys Gln Ala Pro
                165                 170                 175
Thr Ile Cys Phe Val Tyr Gln Asp Pro Gln Gly Arg His Val Lys Thr
            180                 185                 190
Tyr Glu Val Ser Leu Arg Glu Lys Glu Phe Asn Lys Gly Pro Trp Lys
        195                 200                 205
Gln Glu Asn Val Glu Ala Glu Ser Met Val Ile Ala Val Pro Glu
210                 215                 220
Pro Phe Gly Gly Ala Ile Ile Gly Gln Glu Ser Ile Thr Tyr His
225                 230                 235                 240
Asn Gly Asp Lys Tyr Leu Ala Ile Ala Pro Pro Ile Ile Lys Gln Ser
                245                 250                 255
Thr Ile Val Cys His Asn Arg Val Asp Pro Asn Gly Ser Arg Tyr Leu
            260                 265                 270
Leu Gly Asp Met Glu Gly Arg Leu Phe Met Leu Leu Leu Glu Lys Glu
        275                 280                 285
Glu Gln Met Asp Gly Thr Val Thr Leu Lys Asp Leu Arg Val Glu Leu
    290                 295                 300
Leu Gly Glu Thr Ser Ile Ala Glu Cys Leu Thr Tyr Leu Asp Asn Gly
305                 310                 315                 320
Val Val Phe Val Gly Ser Arg Leu Gly Asp Ser Gln Leu Val Lys Leu
                325                 330                 335
Asn Val Asp Ser Asn Glu Gln Gly Ser Tyr Val Val Ala Met Glu Thr
            340                 345                 350
Phe Thr Asn Leu Gly Pro Ile Val Asp Met Cys Val Val Asp Leu Glu
        355                 360                 365
Arg Gln Gly Gln Gly Gln Leu Val Thr Cys Ser Gly Ala Phe Lys Glu
    370                 375                 380
Gly Ser Leu Arg Ile Ile Arg Asn Gly Ile Gly Ile His Glu His Ala
385                 390                 395                 400
Ser Ile Asp Leu Pro Gly Ile Lys Gly Leu Trp Pro Leu Arg Ser Asp
                405                 410                 415
Pro Asn Arg Glu Thr Asp Asp Thr Leu Val Leu Ser Phe Val Gly Gln
            420                 425                 430
Thr Arg Val Leu Met Leu Asn Gly Glu Glu Val Glu Glu Thr Glu Leu
        435                 440                 445
Met Gly Phe Val Asp Asp Gln Gln Thr Phe Phe Cys Gly Asn Val Ala
    450                 455                 460
```

```
His Gln Gln Leu Ile Gln Ile Thr Ser Ala Ser Val Arg Leu Val Ser
465                 470                 475                 480

Gln Glu Pro Lys Ala Leu Val Ser Glu Trp Lys Glu Pro Gln Ala Lys
                485                 490                 495

Asn Ile Ser Val Ala Ser Cys Asn Ser Ser Gln Val Val Ala Val
                500                 505                 510

Gly Arg Ala Leu Tyr Tyr Leu Gln Ile His Pro Gln Glu Leu Arg Gln
                515                 520                 525

Ile Ser His Thr Glu Met Glu His Glu Val Ala Cys Leu Asp Ile Thr
            530                 535                 540

Pro Leu Gly Asp Ser Asn Gly Leu Ser Pro Leu Cys Ala Ile Gly Leu
545                 550                 555                 560

Trp Thr Asp Ile Ser Ala Arg Ile Leu Lys Leu Pro Ser Phe Glu Leu
                565                 570                 575

Leu His Lys Glu Met Leu Gly Gly Glu Ile Ile Pro Arg Ser Ile Leu
                580                 585                 590

Met Thr Thr Phe Glu Ser Ser His Tyr Leu Leu Cys Ala Leu Gly Asp
                595                 600                 605

Gly Ala Leu Phe Tyr Phe Gly Leu Asn Ile Glu Thr Gly Leu Leu Ser
610                 615                 620

Asp Arg Lys Lys Val Thr Leu Gly Thr Gln Pro Thr Val Leu Arg Thr
625                 630                 635                 640

Phe Arg Ser Leu Ser Thr Thr Asn Val Phe Ala Cys Ser Asp Arg Pro
                645                 650                 655

Thr Val Ile Tyr Ser Ser Asn His Lys Leu Val Phe Ser Asn Val Asn
                660                 665                 670

Leu Lys Glu Val Asn Tyr Met Cys Pro Leu Asn Ser Asp Gly Tyr Pro
                675                 680                 685

Asp Ser Leu Ala Leu Ala Asn Asn Ser Thr Leu Thr Ile Gly Thr Ile
690                 695                 700

Asp Glu Ile Gln Lys Leu His Ile Arg Thr Val Pro Leu Tyr Glu Ser
705                 710                 715                 720

Pro Arg Lys Ile Cys Tyr Gln Glu Val Ser Gln Cys Phe Gly Val Leu
                725                 730                 735

Ser Ser Arg Ile Glu Val Gln Asp Thr Ser Gly Gly Thr Thr Ala Leu
                740                 745                 750

Arg Pro Ser Ala Ser Thr Gln Ala Leu Ser Ser Val Ser Ser Ser
                755                 760                 765

Lys Leu Phe Ser Ser Ser Thr Ala Pro His Glu Thr Ser Phe Gly Glu
                770                 775                 780

Glu Val Glu Val His Asn Leu Leu Ile Ile Asp Gln His Thr Phe Glu
785                 790                 795                 800

Val Leu His Ala His Gln Phe Leu Gln Asn Glu Tyr Ala Leu Ser Leu
                805                 810                 815

Val Ser Cys Lys Leu Gly Lys Asp Pro Asn Thr Tyr Phe Ile Val Gly
                820                 825                 830

Thr Ala Met Val Tyr Pro Glu Glu Ala Glu Pro Lys Gln Gly Arg Ile
                835                 840                 845

Val Val Phe Gln Tyr Ser Asp Gly Lys Leu Gln Thr Val Ala Glu Lys
                850                 855                 860

Glu Val Lys Gly Ala Val Tyr Ser Met Val Glu Phe Asn Gly Lys Leu
865                 870                 875                 880
```

-continued

```
Leu Ala Ser Ile Asn Ser Thr Val Arg Leu Tyr Glu Trp Thr Thr Glu
            885                 890                 895

Lys Glu Leu Arg Thr Glu Cys Asn His Tyr Asn Asn Ile Met Ala Leu
    900                 905                 910

Tyr Leu Lys Thr Lys Gly Asp Phe Ile Leu Val Gly Asp Leu Met Arg
        915                 920                 925

Ser Val Leu Leu Ala Tyr Lys Pro Met Glu Gly Asn Phe Glu Glu
    930                 935                 940

Ile Ala Arg Asp Phe Asn Pro Asn Trp Met Ser Ala Val Glu Ile Leu
945                 950                 955                 960

Asp Asp Asp Asn Phe Leu Gly Ala Glu Asn Ala Phe Asn Leu Phe Val
                965                 970                 975

Cys Gln Lys Asp Ser Ala Ala Thr Thr Asp Glu Glu Arg Gln His Leu
            980                 985                 990

Gln Glu Val Gly Leu Phe His Leu Gly Glu Phe Val Asn Val Phe Cys
        995                1000                1005

His Gly Ser Leu Val Met Gln Asn Leu Gly Glu Thr Ser Thr Pro
    1010                1015                1020

Thr Gln Gly Ser Val Leu Phe Gly Thr Val Asn Gly Met Ile Gly
    1025                1030                1035

Leu Val Thr Ser Leu Ser Glu Ser Trp Tyr Asn Leu Leu Leu Asp
    1040                1045                1050

Met Gln Asn Arg Leu Asn Lys Val Ile Lys Ser Val Gly Lys Ile
    1055                1060                1065

Glu His Ser Phe Trp Arg Ser Phe His Thr Glu Arg Lys Thr Glu
    1070                1075                1080

Pro Ala Thr Gly Phe Ile Asp Gly Asp Leu Ile Glu Ser Phe Leu
    1085                1090                1095

Asp Ile Ser Arg Pro Lys Met Gln Glu Val Val Ala Asn Leu Gln
    1100                1105                1110

Tyr Asp Asp Gly Ser Gly Met Lys Arg Glu Ala Thr Ala Asp Asp
    1115                1120                1125

Leu Ile Lys Val Val Glu Glu Leu Thr Arg Ile His
    1130                1135                1140
```

<210> SEQ ID NO 23
<211> LENGTH: 4372
<212> TYPE: DNA
<213> ORGANISM: Homo sapiens

<400> SEQUENCE: 23

```
ggtgcctccg gggcggggc ctccttcggt tggcggcctc gggcttcggg agtcctccaa      60
gaggccaggt gaggccgtcc cgtgatgccc cgcgccccgg ccgctctggc ctgcaacgtg     120
tctctggggc ggaggcagcg gcagtggagt tcgctgcgcg ctgttggggg ccacctgtct     180
tttcgcttgt gtccctcttt ctagtgtcgc gctcgagtcc cgacgggccg ctccaagcct     240
cgacatgtcg tacaactacg tggtaacggc ccagaagccc accgccgtga acggctgcgt     300
gaccggacac tttacttcgg ccgaagactt aaacctgttg attgccaaaa acacgagatt     360
agagatctat gtggtcaccg ccgaggggct tcggcccgtc aaagaggtgg gcatgtatgg     420
gaagattgcg gtcatggagc ttttcaggcc aaggggggag agcaaggacc tgctgtttat     480
cttgacagcg aagtacaatg cctgcatcct ggagtataaa cagagtggcg agagcattga     540
catcattacg cgagcccatg gcaatgtcca ggaccgcatt ggccgcccct cagagaccgg     600
```

```
cattattggc atcattgacc ctgagtgccg gatgattggc ctgcgtctct atgatggcct    660
tttcaaggtt attccactag atcgcgataa taaagaactc aaggccttca acatccgcct    720
ggaggagctg catgtcattg atgtcaagtt cctatatggt tgccaagcac ctactatttg    780
ctttgtctac caggaccctc aggggcggca cgtaaaaacc tatgaggtgt ctctccgaga    840
aaaggaattc aataagggcc cttggaaaca ggaaaatgtc gaagctgaag cttccatggt    900
gatcgcagtc ccagagccct tgggggggc catcatcatt ggacaggagt caatcaccta    960
tcacaatggt gacaaatacc tggctattgc ccctcctatc atcaagcaaa gcacgattgt   1020
gtgccacaat cgagtggacc ctaatggctc aagatacctg ctgggagaca tggaaggccg   1080
gctcttcatg ctgcttttgg agaaggagga acagatggat ggcaccgtca ctctcaagga   1140
tctccgtgta gaactccttg gagagacctc tattgctgag tgcttgacat accttgataa   1200
tggtgttgtg tttgtcgggt ctcgcctggg tgactcccag cttgtgaagc tcaacgttga   1260
cagtaatgaa caaggctcct atgtagtggc catggaaacc tttaccaact taggacccat   1320
tgtcgatatg tgcgtggtgg acctggagag gcaggggcag gggcagctgg tcacttgctc   1380
tggggctttc aaggaaggtt ctttgcggat catccggaat ggaattggaa tccacgagca   1440
tgccagcatt gacttaccag gcatcaaagg attatggcca ctgcggtctg accctaatcg   1500
tgagactgat gacactttgg tgctctcttt tgtgggccag acaagagttc tcatgttaaa   1560
tggagaggag gtagaagaaa ccgaactgat gggtttcgtg gatgatcagc agactttctt   1620
ctgtggcaac gtggctcatc agcagcttat ccagatcact tcagcatcgg tgaggttggt   1680
ctctcaagaa cccaaagctc tggtcagtga atggaaggag cctcaggcca agaacatcag   1740
tgtggcctcc tgcaatagca gccaggtggt ggtggctgta ggcagggccc tctactatct   1800
gcagatccat cctcaggagc tccggcagat cagccacaca gagatggaac atgaagtggc   1860
ttgcttggac atcaccccat taggagacag caatggactg tccctctttt gtgccattgg   1920
cctctggacg gacatctcgg ctcgtatctt gaagttgccc tcttttgaac tactgcacaa   1980
ggagatgctg ggtggagaga tcattcctcg ctccatcctg atgaccacct tgagagtag   2040
ccattacctc ctttgtgcct tgggagatgg agcgcttttc tactttgggc tcaacattga   2100
gacaggtctg ttgagcgacc gtaagaaggt gactttgggc acccagccca ccgtattgag   2160
gacttttcgt tctctttcta ccaccaacgt cttttgcttgt tctgaccgcc ccactgtcat   2220
ctatagcagc aaccacaaat tggtcttctc aaatgtcaac ctcaaggaag tgaactacat   2280
gtgtcccctc aattcagatg gctatcctga cagcctggcg ctggccaaca atagcaccct   2340
caccattggc accatcgatg agatccagaa gctgcacatt cgcacagttc ccctctatga   2400
gtctccaagg aagatctgct accaggaagt gtcccagtgt ttcggggtcc tctccagccg   2460
cattgaagtc caagacacga gtgggggcac gacagccttg aggcccagcg ctagcaccca   2520
ggctctgtcc agcagtgtaa gctccagcaa gctgttctcc agcagcactg ctcctcatga   2580
gacctccttt ggagaagagg tggaggtgca caacctactt atcattgacc aacacacctt   2640
tgaagtgctt catgcccacc agtttctgca gaatgaatat gccctcagtc tggtttcctg   2700
caagctgggc aaagacccca acacttactt cattgtgggc acagcaatgg tgtatcctga   2760
agaggcagag cccaagcagg gtcgcattgt ggtctttcag tattcggatg gaaaactaca   2820
gactgtggct gaaaaggaag tgaaggggc cgtgtactct atggtggaat taacgggaa    2880
gctgttagcc agcatcaata gcacggtgcg gctctatgaa tggacaacag agaaggagct   2940
gcgcactgag tgcaaccact acaacaacat catggccctc tacctgaaga ccaagggcga   3000
```

```
cttcatcctg gtgggcgacc ttatgcgctc agtgctgctg cttgcctaca agcccatgga    3060
aggaaacttt gaagagattg ctcgagactt taatcccaac tggatgagtg ctgtggaaat    3120
cttggatgat gacaattttc tggggctga aaatgccttt aacttgtttg tgtgtcaaaa    3180
ggatagcgct gccaccactg acgaggagcg gcagcacctc caggaggttg gtcttttcca    3240
cctgggcgag tttgtcaatg tcttttgcca cggctctctg gtaatgcaga atctgggtga    3300
gacttccacc cccacacaag gctcggtgct cttcggcacg tcaacggca tgatagggct     3360
ggtgacctca ctgtcagaga gctggtacaa cctcctgctg gacatgcaga atcgactcaa    3420
taaagtcatc aaaagtgtgg ggaagatcga gcactccttc tggagatcct ttcacaccga    3480
gcggaagaca gaaccagcca caggtttcat cgacggtgac ttgattgaga gtttcctgga    3540
tattagccgc cccaagatgc aggaggtggt ggcaaaccta cagtatgacg atggcagcgg    3600
tatgaagcga gaggccactg cagacgacct catcaaggtt gtggaggagc taactcggat    3660
ccattagcca agggcagggg gcccctttgc tgaccctccc caaaggcttt gccctgctgc    3720
cctcccccctc ctctccacca tcgtcttctt ggccatggga ggccttttcc taagccagct    3780
gcccccagag ccacagttcc cctatgtgga agtggggcgg gcttcataga gacttgggaa    3840
tgagctgaag gtgaaacatt ttctccctgg attttaccaa gtctcacatg attccagcca    3900
tcaccttaga ccaccaagcc ttgattggtg ttgccagttg tcctccttcc ggggaaggat    3960
tttgcagttc tttggctgaa aggaagctgt gcgtgtgtgt gtgtgtatgt gtgtgtgtgt    4020
atgtgtatct cacactcatg cattgtcctc ttttttattta gattggcagt gtagggagtt    4080
gtgggtagtg gggaagaggg ttaggagggt ttcattgtct gtgaagtgag accttccttt    4140
tactttttctt ctattgcctc tgagagcatc aggcctagag gcctgactgc caagccatgg    4200
gtagcctggg tgtaaaacct ggagatggtg gatgatcccc acgccacagc ccttttgtct    4260
ctgcaaactg ccttcttcgg aaagaagaag gtgggaggat gtgaattgtt agtttctgag    4320
ttttaccaaa taaagtagaa tataagaaga aggtaaaaa aaaaaaaaa aa              4372
```

<210> SEQ ID NO 24
<211> LENGTH: 1603
<212> TYPE: PRT
<213> ORGANISM: Homo sapiens

<400> SEQUENCE: 24

Met Arg Thr Thr Lys Val Tyr Lys Leu Val Ile His Lys Lys Gly Phe
1               5                   10                  15

Gly Gly Ser Asp Asp Glu Leu Val Val Asn Pro Lys Val Phe Pro His
                20                  25                  30

Ile Lys Leu Gly Asp Ile Val Glu Ile Ala His Pro Asn Asp Glu Tyr
            35                  40                  45

Ser Pro Leu Leu Leu Gln Val Lys Ser Leu Lys Glu Asp Leu Gln Lys
        50                  55                  60

Glu Thr Ile Ser Val Asp Gln Thr Val Thr Gln Val Phe Arg Leu Arg
65                  70                  75                  80

Pro Tyr Gln Asp Val Tyr Val Asn Val Asp Pro Lys Asp Val Thr
                85                  90                  95

Leu Asp Leu Val Glu Leu Thr Phe Lys Asp Gln Tyr Ile Gly Arg Gly
            100                 105                 110

Asp Met Trp Arg Leu Lys Lys Ser Leu Val Ser Thr Cys Ala Tyr Ile
            115                 120                 125

```
Thr Gln Lys Val Glu Phe Ala Gly Ile Arg Ala Gln Ala Gly Glu Leu
130                 135                 140

Trp Val Lys Asn Glu Lys Val Met Cys Gly Tyr Ile Ser Glu Asp Thr
145                 150                 155                 160

Arg Val Val Phe Arg Ser Thr Ser Ala Met Val Tyr Ile Phe Ile Gln
                165                 170                 175

Met Ser Cys Glu Met Trp Asp Phe Asp Ile Tyr Gly Asp Leu Tyr Phe
            180                 185                 190

Glu Lys Ala Val Asn Gly Phe Leu Ala Asp Leu Phe Thr Lys Trp Lys
        195                 200                 205

Glu Lys Asn Cys Ser His Glu Val Thr Val Val Leu Phe Ser Arg Thr
    210                 215                 220

Phe Tyr Asp Ala Lys Ser Val Asp Glu Phe Pro Glu Ile Asn Arg Ala
225                 230                 235                 240

Ser Ile Arg Gln Asp His Lys Gly Arg Phe Tyr Glu Asp Phe Tyr Lys
                245                 250                 255

Val Val Val Gln Asn Glu Arg Arg Glu Glu Trp Thr Ser Leu Leu Val
            260                 265                 270

Thr Ile Lys Lys Leu Phe Ile Gln Tyr Pro Val Leu Val Arg Leu Glu
        275                 280                 285

Gln Ala Glu Gly Phe Pro Gln Gly Asp Asn Ser Thr Ser Ala Gln Gly
    290                 295                 300

Asn Tyr Leu Glu Ala Ile Asn Leu Ser Phe Asn Val Phe Asp Lys His
305                 310                 315                 320

Tyr Ile Asn Arg Asn Phe Asp Arg Thr Gly Gln Met Ser Val Val Ile
                325                 330                 335

Thr Pro Gly Val Gly Val Phe Glu Val Asp Arg Leu Leu Met Ile Leu
            340                 345                 350

Thr Lys Gln Arg Met Ile Asp Asn Gly Ile Gly Val Asp Leu Val Cys
        355                 360                 365

Met Gly Glu Gln Pro Leu His Ala Val Pro Leu Phe Lys Leu His Asn
    370                 375                 380

Arg Ser Ala Pro Arg Asp Ser Arg Leu Gly Asp Asp Tyr Asn Ile Pro
385                 390                 395                 400

His Trp Ile Asn His Ser Phe Tyr Thr Ser Lys Ser Gln Leu Phe Cys
                405                 410                 415

Asn Ser Phe Thr Pro Arg Ile Lys Leu Ala Gly Lys Lys Pro Ala Ser
            420                 425                 430

Glu Lys Ala Lys Asn Gly Arg Asp Thr Ser Leu Gly Ser Pro Lys Glu
        435                 440                 445

Ser Glu Asn Ala Leu Pro Ile Gln Val Asp Tyr Asp Ala Tyr Asp Ala
    450                 455                 460

Gln Val Phe Arg Leu Pro Gly Pro Ser Arg Ala Gln Cys Leu Thr Thr
465                 470                 475                 480

Cys Arg Ser Val Arg Glu Arg Glu Ser His Ser Arg Lys Ser Ala Ser
                485                 490                 495

Ser Cys Asp Val Ser Ser Pro Ser Leu Pro Ser Arg Thr Leu Pro
            500                 505                 510

Thr Glu Glu Val Arg Ser Gln Ala Ser Asp Asp Ser Ser Leu Gly Lys
        515                 520                 525

Ser Ala Asn Ile Leu Met Ile Pro His Pro His Leu His Gln Tyr Glu
    530                 535                 540

Val Ser Ser Ser Leu Gly Tyr Thr Ser Thr Arg Asp Val Leu Glu Asn
```

```
             545                 550                 555                 560
        Met Met Glu Pro Pro Gln Arg Asp Ser Ser Ala Pro Gly Arg Phe His
                        565                 570                 575

Val Gly Ser Ala Glu Ser Met Leu His Val Arg Pro Gly Gly Tyr Thr
                        580                 585                 590

Pro Gln Arg Ala Leu Ile Asn Pro Phe Ala Pro Ser Arg Met Pro Met
                        595                 600                 605

Lys Leu Thr Ser Asn Arg Arg Trp Met His Thr Phe Pro Val Gly
                        610                 615                 620

Pro Ser Gly Glu Ala Ile Gln Ile His His Gln Thr Arg Gln Asn Met
        625                 630                 635                 640

Ala Glu Leu Gln Gly Ser Gly Gln Arg Asp Pro Thr His Ser Ser Ala
                        645                 650                 655

Glu Leu Leu Glu Leu Ala Tyr His Glu Ala Ala Gly Arg His Ser Asn
                        660                 665                 670

Ser Arg Gln Pro Gly Asp Gly Met Ser Phe Leu Asn Phe Ser Gly Thr
                        675                 680                 685

Glu Glu Leu Ser Val Gly Leu Leu Ser Asn Ser Gly Ala Gly Met Asn
                        690                 695                 700

Pro Arg Thr Gln Asn Lys Asp Ser Leu Glu Asp Ser Val Ser Thr Ser
        705                 710                 715                 720

Pro Asp Pro Ile Leu Thr Leu Ser Ala Pro Pro Val Val Pro Gly Phe
                        725                 730                 735

Cys Cys Thr Val Gly Val Asp Trp Lys Ser Leu Thr Thr Pro Ala Cys
                        740                 745                 750

Leu Pro Leu Thr Thr Asp Tyr Phe Pro Asp Arg Gln Gly Leu Gln Asn
                        755                 760                 765

Asp Tyr Thr Glu Gly Cys Tyr Asp Leu Leu Pro Glu Ala Asp Ile Asp
                        770                 775                 780

Arg Arg Asp Glu Asp Gly Val Gln Met Thr Ala Gln Gln Val Phe Glu
        785                 790                 795                 800

Glu Phe Ile Cys Gln Arg Leu Met Gln Gly Tyr Gln Ile Ile Val Gln
                        805                 810                 815

Pro Lys Thr Gln Lys Pro Asn Pro Ala Val Pro Pro Leu Ser Ser
                        820                 825                 830

Ser Pro Leu Tyr Ser Arg Gly Leu Val Ser Arg Asn Arg Pro Glu Glu
                        835                 840                 845

Glu Asp Gln Tyr Trp Leu Ser Met Gly Arg Thr Phe His Lys Val Thr
        850                 855                 860

Leu Lys Asp Lys Met Ile Thr Val Thr Arg Tyr Leu Pro Lys Tyr Pro
        865                 870                 875                 880

Tyr Glu Ser Ala Gln Ile His Tyr Thr Tyr Ser Leu Cys Pro Ser His
                        885                 890                 895

Ser Asp Ser Glu Phe Val Ser Cys Trp Val Glu Phe Ser His Glu Arg
                        900                 905                 910

Leu Glu Glu Tyr Lys Trp Asn Tyr Leu Asp Gln Tyr Ile Cys Ser Ala
                        915                 920                 925

Gly Ser Glu Asp Phe Ser Leu Ile Glu Ser Leu Lys Phe Trp Arg Thr
                        930                 935                 940

Arg Phe Leu Leu Leu Pro Ala Cys Val Thr Ala Thr Lys Arg Ile Thr
        945                 950                 955                 960

Glu Gly Glu Ala His Cys Asp Ile Tyr Gly Asp Arg Pro Arg Ala Asp
                        965                 970                 975
```

```
Glu Asp Glu Trp Gln Leu Leu Asp Gly Phe Val Arg Phe Val Glu Gly
            980                 985                 990

Leu Asn Arg Ile Arg Arg Arg His Arg Ser Asp Arg Met Met Arg Lys
        995                 1000                1005

Gly Thr Ala Met Lys Gly Leu Gln Met Thr Gly Pro Ile Ser Thr
    1010                1015                1020

His Ser Leu Glu Ser Thr Ala Pro Pro Val Gly Lys Lys Gly Thr
    1025                1030                1035

Ser Ala Leu Ser Ala Leu Leu Glu Met Glu Ala Ser Gln Lys Cys
    1040                1045                1050

Leu Gly Glu Gln Gln Ala Ala Val His Gly Gly Lys Ser Ser Ala
    1055                1060                1065

Gln Ser Ala Glu Ser Ser Ser Val Ala Met Thr Pro Thr Tyr Met
    1070                1075                1080

Asp Ser Pro Arg Lys Asp Gly Ala Phe Phe Met Glu Phe Val Arg
    1085                1090                1095

Ser Pro Arg Thr Ala Ser Ser Ala Phe Tyr Pro Gln Val Ser Val
    1100                1105                1110

Asp Gln Thr Ala Thr Pro Met Leu Asp Gly Thr Ser Leu Gly Ile
    1115                1120                1125

Cys Thr Gly Gln Ser Met Asp Arg Gly Asn Ser Gln Thr Phe Gly
    1130                1135                1140

Asn Ser Gln Asn Ile Gly Glu Gln Gly Tyr Ser Ser Thr Asn Ser
    1145                1150                1155

Ser Asp Ser Ser Ser Gln Gln Leu Val Ala Ser Ser Leu Thr Ser
    1160                1165                1170

Ser Ser Thr Leu Thr Glu Ile Leu Glu Ala Met Lys His Pro Ser
    1175                1180                1185

Thr Gly Val Gln Leu Leu Ser Glu Gln Lys Gly Leu Ser Pro Tyr
    1190                1195                1200

Cys Phe Ile Ser Ala Glu Val Val His Trp Leu Val Asn His Val
    1205                1210                1215

Glu Gly Ile Gln Thr Gln Ala Met Ala Ile Asp Ile Met Gln Lys
    1220                1225                1230

Met Leu Glu Glu Gln Leu Ile Thr His Ala Ser Gly Glu Ala Trp
    1235                1240                1245

Arg Thr Phe Ile Tyr Gly Phe Tyr Phe Tyr Lys Ile Val Thr Asp
    1250                1255                1260

Lys Glu Pro Asp Arg Val Ala Met Gln Gln Pro Ala Thr Thr Trp
    1265                1270                1275

His Thr Ala Gly Val Asp Asp Phe Ala Ser Phe Gln Arg Lys Trp
    1280                1285                1290

Phe Glu Val Ala Phe Val Ala Glu Glu Leu Val His Ser Glu Ile
    1295                1300                1305

Pro Ala Phe Leu Leu Pro Trp Leu Pro Ser Arg Pro Ala Ser Tyr
    1310                1315                1320

Ala Ser Arg His Ser Ser Phe Ser Arg Ser Phe Gly Gly Arg Ser
    1325                1330                1335

Gln Ala Ala Ala Leu Leu Ala Ala Thr Val Pro Glu Gln Arg Thr
    1340                1345                1350

Val Thr Leu Asp Val Asp Val Asn Asn Arg Thr Asp Arg Leu Glu
    1355                1360                1365
```

```
Trp Cys Ser Cys Tyr Tyr His Gly Asn Phe Ser Leu Asn Ala Ala
    1370            1375            1380

Phe Glu Ile Lys Leu His Trp Met Ala Val Thr Ala Ala Val Leu
1385            1390            1395

Phe Glu Met Val Gln Gly Trp His Arg Lys Ala Thr Ser Cys Gly
1400            1405            1410

Phe Leu Leu Val Pro Val Leu Glu Gly Pro Phe Ala Leu Pro Ser
1415            1420            1425

Tyr Leu Tyr Gly Asp Pro Leu Arg Ala Gln Leu Phe Ile Pro Leu
    1430            1435            1440

Asn Ile Ser Cys Leu Leu Lys Glu Gly Ser Glu His Leu Phe Asp
1445            1450            1455

Ser Phe Glu Pro Glu Thr Tyr Trp Asp Arg Met His Leu Phe Gln
1460            1465            1470

Glu Ala Ile Ala His Arg Phe Gly Phe Val Gln Asp Lys Tyr Ser
    1475            1480            1485

Ala Ser Ala Phe Asn Phe Pro Ala Glu Asn Lys Pro Gln Tyr Ile
    1490            1495            1500

His Val Thr Gly Thr Val Phe Leu Gln Leu Pro Tyr Ser Lys Arg
    1505            1510            1515

Lys Phe Ser Gly Gln Gln Arg Arg Arg Arg Asn Ser Thr Ser Ser
    1520            1525            1530

Thr Asn Gln Asn Met Phe Cys Glu Glu Arg Val Gly Tyr Asn Trp
1535            1540            1545

Ala Tyr Asn Thr Met Leu Thr Lys Thr Trp Arg Ser Ser Ala Thr
    1550            1555            1560

Gly Asp Glu Lys Phe Ala Asp Arg Leu Leu Lys Asp Phe Thr Asp
    1565            1570            1575

Phe Cys Ile Asn Arg Asp Asn Arg Leu Val Thr Phe Trp Thr Ser
1580            1585            1590

Cys Leu Glu Lys Met His Ala Ser Ala Pro
1595            1600

<210> SEQ ID NO 25
<211> LENGTH: 5316
<212> TYPE: DNA
<213> ORGANISM: Homo sapiens

<400> SEQUENCE: 25
ggaggcaaga tgacttctct gccccaagct tggaacagct aaagggaaaa acagtgcaag      60
atgagaacaa caaaggtcta caaactcgtc atccacaaga agggctttgg gggcagtgat     120
gatgagctag ttgtgaaccc caaagtgttc cctcacatca gcttggagac attgtagag      180
attgcacacc ccaacgatga atacagccct ctgcttttgc aggtcaagtc tcttaaggaa     240
gatttacaga aggaaactat cagtgtggac cagactgtga ctcaagtgtt ccggctgaga     300
ccttatcagg atgtctatgt taatgtcgta gaccctaagg atgtgaccct tgacctagtg     360
gaattaactt ttaaggatca gtatattggc cgtggggata tgtggcgact aaagaaaagt     420
ttggtcagca catgtgccta tatcacccag aaggtggagt tgctggcat cagagcacag     480
gctggtgaac tgtgggttaa gaatgagaag gtcatgtgtg ctacatcag tgaagatacc     540
agggtggtgt tcgttctac gtcggctatg gtttacatat ttattcagat gagctgtgaa     600
atgtgggatt tgatatttta tggggatttg tattttgaga aagctgtgaa tggtttcctt     660
gctgatctat ttaccaagtg gaaggagaag aactgtagtc atgaagtgac agtggtcctg     720
```

```
ttttctagaa ctttctatga tgcaaaatct gttgatgaat ttcctgaaat aaaccgagcc    780
tcaattcgac aggatcacaa ggggagattc tatgaagact tttacaaagt ggtggtgcag    840
aatgagagaa gagaagaatg gacttcactt ctcgtaacca ttaaaaaact cttcatccag    900
tatccagtgt tggtgcgact ggaacaggca gagggctttc ctcaaggaga taattctacc    960
tcagcacaag gaaactacct ggaggccatc aatctgtcat tcaatgtgtt tgataagcac   1020
tacatcaacc gcaactttga ccgaactggg cagatgtcag tggtgatcac gcccggggtg   1080
ggtgtctttg aagtggaccg cctactcatg atcctgacca agcagcggat gatagataat   1140
ggaattggtg tggatttggt gtgcatggga gagcaaccgt tacatgctgt cccattgttc   1200
aagctccata atcggagtgc tccccgtgat tctcgtctgg gcgatgacta atatatccct   1260
cactggataa accacagttt ctacacatcc aaaagccagc tcttttgtaa tagtttcacc   1320
ccacgaataa aactggcagg aaagaagccc gcctctgaga aagcaaaaaa tggccgtgat   1380
acatctctcg ggagtccaaa agaatctgag aacgcccttc ccatccaagt agattatgac   1440
gcctatgacg ctcaagtgtt caggctgccc ggcccatccc gggcccagtg cctcaccacc   1500
tgcagatctg tgcgagagcg agagagtcac agtcgaaaga gtgccagctc ctgtgatgtt   1560
tcatccagcc cttccctacc aagccgcaca ctgcccactg aggaagtgag gagccaggct   1620
tctgacgaca gctccctagg caagagtgcc aacatcctga tgatcccaca cccccacctg   1680
caccagtatg aagtcagcag ctccttggga tacaccagca ctcgagatgt cctggagaac   1740
atgatggagc caccacagcg agactccagt gcaccaggga ggtttcacgt tggcagtgca   1800
gaatccatgc tgcatgttcg acctggtgga tacacgcccc agagagcact gattaacccc   1860
ttcgctccct ctcggatgcc catgaagctt acgtccaaca gaaggcgctg gatgcacact   1920
tttcctgtgg ggccatccgg agaagccatc cagatccacc accagacccg acagaatatg   1980
gcggagctac aaggcagcgg gcagagggat ccaactcact cctctgcaga gctgctggag   2040
ttagcatatc atgaagctgc tggaaggcac agcaattccc gccagcctgg tgacggcatg   2100
tccttcttga acttcagtgg aacagaggag cttctctgtcg gcctgcttag caacagtggt   2160
gcaggtatga atcctaggac ccagaataag gattctctag aggacagtgt ttctacctct   2220
ccagacccaa tgccaggctt ctgttgcaca gttggagtgg actggaagtc tctcactact   2280
ccggcgtgcc tcccccttac caccgactac ttccctgacc gccagggcct gcagaatgac   2340
tacacagagg gctgttatga tctccttcca gaagcagaca tcgacaggag ggacgaagat   2400
ggtgtgcaga tgacagccca gcaggtattt gaagagttta tttgccaacg tctcatgcag   2460
ggctaccaaa tcatagtgca gcccaagaca cagaaaccca atcctgctgt cccgcccccg   2520
ctgagcagta gcccactcta tagccgaggc ttgtgtccc gaaaccgccc tgaggaggag   2580
gaccagtatt ggctgagtat gggcagaacg ttccacaaag tgacgctgaa ggataagatg   2640
atcacagtga cgcgataccct tcccaagtat ccttatgaat ctgcccagat ccactacacc   2700
tacagcctct gtcctttccca ctcagactca gagttcgtct cctgctgggt ggaattctcc   2760
cacgaacggc tggaggagta caagtggaat tacttagatc agtatatctg ttctgccggc   2820
tctgaagact tcagcttaat tgagtccctg aagttctgga ggaccgcctt cctgctgctg   2880
ccagcctgtg tcaccgccac caagcgcatc acggaggggg aggcccactg cgacatctat   2940
ggggacaggc cccgtgcaga cgaggacgag tggcaactcc tggatggttt tgtccgcttt   3000
gtggagggct tgaatcgcat tcgcaggcgg catcgctcgg atcgcatgat gcggaaaggg   3060
```

-continued

```
accgccatga aaggcttgca gatgactggg cccatttcca cgcattctct ggagtcaact     3120
gcaccccag tggggaagaa gggaacctca gctctctctg ccctgttgga gatggaggcc     3180
agtcagaagt gcctgggaga acagcaggca gctgtgcatg gtgggaagag ctccgcccag    3240
tcagccgaga gcagcagcgt tgccatgact cccacctaca tggacagccc acgaaaggta    3300
tctgtggacc aaacagccac tcctatgttg gacggcacca gtttgggcat atgcacaggc    3360
caatccatgg acagaggcaa cagccagacc tttgggaact cccagaacat aggagaacag    3420
ggctactcct ccacaaactc cagtgacagc agctctcagc agctggtggc aagctccttg    3480
acctcatcct ctaccctgac agagatcctg gaagccatga agcacccctc gacaggagtc    3540
cagctgctct ctgaacagaa gggcctctca ccgtactgct tcatcagcgc ggaggtggta    3600
cactggttgg tgaaccacgt ggaggggatc cagacacagg cgatggccat tgacatcatg    3660
cagaaaatgc tggaagagca gctcatcaca catgcatctg gcgaagcctg gcggaccttc    3720
atctacggct tctatttcta caagatagta acggacaaag agcccgaccg agtggccatg    3780
cagcagcccg ccaccacctg gcacacagca ggagtggacg acttcgccag cttccagcgc    3840
aagtggtttg aggtggcctt tgtggcagaa gagctcgtgc actctgagat tcctgccttt    3900
ctcctgccct ggctgcctag ccggccagcc tcctatgcaa gtaggcacag ctcctttagc    3960
cgaagttttg gaggacggag ccaggcggca gcacttttag ctgccactgt cccagagcag    4020
aggactgtga ccctggatgt tgacgtgaac aaccgcacag accggctgga gtggtgcagc    4080
tgttattacc atggcaactt ttctctgaat gcagcctttg agatcaagct gcactggatg    4140
gcggtgaccg cagcagtact cttcgagatg gtccaaggtt ggcatcggaa agccacctcc    4200
tgtggcttct tgttagtccc agttttggag gggccttttg cactgcccag ttacctgtat    4260
ggcgaccccc ttcgtgccca gctcttcatc ccactcaaca tcagctgctt gctcaaggag    4320
ggcagcgagc acctgtttga tagctttgaa cccgaaacgt actgggatcg aatgcacctc    4380
ttccaggaag ccattgcaca caggtttggg tttgtacaag ataaatattc tgcctctgct    4440
tttaacttcc ctgctgagaa caagcctcag tatatccacg ttacaggaac agtgtttctg    4500
cagctgccct actccaagcg caagttctca gggcagcagc ggcggcggcg gaactccacc    4560
agctccacca accagaacat gttctgcgag gagcgggtcg gctacaactg ggcctacaac    4620
accatgctca ccaaaacatg ggcgctccagc gccacagggg atgaaaagtt tgctgatcgg    4680
ctgctgaagg acttcacgga cttctgcatc aaccgtgaca accggctggt cacgttctgg    4740
acaagttgcc tggagaagat gcatgccagt gccccgtgag gccaggctgc acctgtgctg    4800
ggggaaggtg ggtgagccac tgccctcaaa cccggggcgg aggattccag gcaggctcta    4860
ggagtcaggt gtccgtttgc tgctatcagt gagtgggggc cattgttttt tgtttgtttg    4920
tttgtttgtt tgtttgtttt tggcccccac gacaagtctt ctactctaga agaaagactt    4980
tggaagcagc tgctgctgct gccaccactc ctgtcagcaa gtgctcagag caggtgggag    5040
gcacagattg tccgtgggag ggctccagtg tctgggaaga gggcaggcgg cccccatgaa    5100
tgtcctcgga aggggggtggc tcctggtagc atccttttcc ttcaccatct atgggatatt    5160
agggggcagaa tctgccactt cttgcccagg agtgtgcaca gatgtaagat aattttgtga    5220
aataatgtac catagactct caccaactgt atatacctgt acatatcaga agcaaataaa    5280
gagctccacg tgcatcattt ctttccccac ccagtt                               5316
```

<210> SEQ ID NO 26
<211> LENGTH: 1401

```
<212> TYPE: PRT
<213> ORGANISM: Homo sapiens

<400> SEQUENCE: 26

Met Ala Ser Cys Ala Ser Ile Asp Ile Glu Asp Ala Thr Gln His Leu
1               5                   10                  15

Arg Asp Ile Leu Lys Leu Asp Arg Pro Ala Gly Gly Pro Ser Ala Glu
            20                  25                  30

Ser Pro Arg Pro Ser Ser Ala Tyr Asn Gly Asp Leu Asn Gly Leu Leu
        35                  40                  45

Val Pro Asp Pro Leu Cys Ser Gly Asp Ser Thr Ser Ala Asn Lys Thr
    50                  55                  60

Gly Leu Arg Thr Met Pro Pro Ile Asn Leu Gln Glu Lys Gln Val Ile
65                  70                  75                  80

Cys Leu Ser Gly Asp Asp Ser Ser Thr Cys Ile Gly Ile Leu Ala Lys
                85                  90                  95

Glu Val Glu Ile Val Ala Ser Ser Asp Ser Ser Ile Ser Ser Lys Ala
            100                 105                 110

Arg Gly Ser Asn Lys Val Lys Ile Gln Pro Val Ala Lys Tyr Asp Trp
        115                 120                 125

Glu Gln Lys Tyr Tyr Tyr Gly Asn Leu Ile Ala Val Ser Asn Ser Phe
    130                 135                 140

Leu Ala Tyr Ala Ile Arg Ala Ala Asn Asn Gly Ser Ala Met Val Arg
145                 150                 155                 160

Val Ile Ser Val Ser Thr Ser Glu Arg Thr Leu Leu Lys Gly Phe Thr
                165                 170                 175

Gly Ser Val Ala Asp Leu Ala Phe Ala His Leu Asn Ser Pro Gln Leu
            180                 185                 190

Ala Cys Leu Asp Glu Ala Gly Asn Leu Phe Val Trp Arg Leu Ala Leu
        195                 200                 205

Val Asn Gly Lys Ile Gln Glu Glu Ile Leu Val His Ile Arg Gln Pro
    210                 215                 220

Glu Gly Thr Pro Leu Asn His Phe Arg Arg Ile Ile Trp Cys Pro Phe
225                 230                 235                 240

Ile Pro Glu Glu Ser Glu Asp Cys Cys Glu Ser Ser Pro Thr Val
                245                 250                 255

Ala Leu Leu His Glu Asp Arg Ala Glu Val Trp Asp Leu Asp Met Leu
            260                 265                 270

Arg Ser Ser His Ser Thr Trp Pro Val Asp Val Ser Gln Ile Lys Gln
        275                 280                 285

Gly Phe Ile Val Val Lys Gly His Ser Thr Cys Leu Ser Glu Gly Ala
    290                 295                 300

Leu Ser Pro Asp Gly Thr Val Leu Ala Thr Ala Ser His Asp Gly Tyr
305                 310                 315                 320

Val Lys Phe Trp Gln Ile Tyr Ile Glu Gly Gln Asp Glu Pro Arg Cys
                325                 330                 335

Leu His Glu Trp Lys Pro His Asp Gly Arg Pro Leu Ser Cys Leu Leu
            340                 345                 350

Phe Cys Asp Asn His Lys Lys Gln Asp Pro Asp Val Pro Phe Trp Arg
        355                 360                 365

Phe Leu Ile Thr Gly Ala Asp Gln Asn Arg Glu Leu Lys Met Trp Cys
    370                 375                 380

Thr Val Ser Trp Thr Cys Leu Gln Thr Ile Arg Phe Ser Pro Asp Ile
385                 390                 395                 400
```

```
Phe Ser Ser Val Ser Val Pro Pro Ser Leu Lys Val Cys Leu Asp Leu
                405                 410                 415

Ser Ala Glu Tyr Leu Ile Leu Ser Asp Val Gln Arg Lys Val Leu Tyr
            420                 425                 430

Val Met Glu Leu Leu Gln Asn Gln Glu Glu Gly His Ala Cys Phe Ser
        435                 440                 445

Ser Ile Ser Glu Phe Leu Leu Thr His Pro Val Leu Ser Phe Gly Ile
    450                 455                 460

Gln Val Val Ser Arg Cys Arg Leu Arg His Thr Glu Val Leu Pro Ala
465                 470                 475                 480

Glu Glu Glu Asn Asp Ser Leu Gly Ala Asp Gly Thr His Gly Ala Gly
                485                 490                 495

Ala Met Glu Ser Ala Ala Gly Val Leu Ile Lys Leu Phe Cys Val His
            500                 505                 510

Thr Lys Ala Leu Gln Asp Val Gln Ile Arg Phe Gln Pro Gln Leu Asn
        515                 520                 525

Pro Asp Val Val Ala Pro Leu Pro Thr His Thr Ala His Glu Asp Phe
    530                 535                 540

Thr Phe Gly Glu Ser Arg Pro Glu Leu Gly Ser Glu Gly Leu Gly Ser
545                 550                 555                 560

Ala Ala His Gly Ser Gln Pro Asp Leu Arg Arg Ile Val Glu Leu Pro
                565                 570                 575

Ala Pro Ala Asp Phe Leu Ser Leu Ser Ser Glu Thr Lys Pro Lys Leu
            580                 585                 590

Met Thr Pro Asp Ala Phe Met Thr Pro Ser Ala Ser Leu Gln Gln Ile
        595                 600                 605

Thr Ala Ser Pro Ser Ser Ser Ser Gly Ser Ser Ser Ser Ser
    610                 615                 620

Ser Ser Ser Ser Ser Leu Thr Ala Val Ser Ala Met Ser Ser Thr Ser
625                 630                 635                 640

Ala Val Asp Pro Ser Leu Thr Arg Pro Pro Glu Glu Leu Thr Leu Ser
                645                 650                 655

Pro Lys Leu Gln Leu Asp Gly Ser Leu Thr Met Ser Ser Ser Gly Ser
            660                 665                 670

Leu Gln Ala Ser Pro Arg Gly Leu Leu Pro Gly Leu Leu Pro Ala Pro
        675                 680                 685

Ala Asp Lys Leu Thr Pro Lys Gly Pro Gly Gln Val Pro Thr Ala Thr
    690                 695                 700

Ser Ala Leu Ser Leu Glu Leu Gln Glu Val Glu Pro Leu Gly Leu Pro
705                 710                 715                 720

Gln Ala Ser Pro Ser Arg Thr Arg Ser Pro Asp Val Ile Ser Ser Ala
                725                 730                 735

Ser Thr Ala Leu Ser Gln Asp Ile Pro Glu Ile Ala Ser Glu Ala Leu
            740                 745                 750

Ser Arg Gly Phe Gly Ser Ser Ala Pro Glu Gly Leu Glu Pro Asp Ser
        755                 760                 765

Met Ala Ser Ala Ala Ser Ala Leu His Leu Leu Ser Pro Arg Pro Arg
    770                 775                 780

Pro Gly Pro Glu Leu Gly Pro Gln Leu Gly Leu Asp Gly Gly Pro Gly
785                 790                 795                 800

Asp Gly Asp Arg His Asn Thr Pro Ser Leu Leu Glu Ala Ala Leu Thr
                805                 810                 815
```

```
Gln Glu Ala Ser Thr Pro Asp Ser Gln Val Trp Pro Thr Ala Pro Asp
                820                 825                 830

Ile Thr Arg Glu Thr Cys Ser Thr Leu Ala Glu Ser Pro Arg Asn Gly
            835                 840                 845

Leu Gln Glu Lys His Lys Ser Leu Ala Phe His Arg Pro Pro Tyr His
        850                 855                 860

Leu Leu Gln Gln Arg Asp Ser Gln Asp Ala Ser Ala Glu Gln Ser Asp
865                 870                 875                 880

His Asp Asp Glu Val Ala Ser Leu Ala Ser Ala Ser Gly Gly Phe Gly
                885                 890                 895

Thr Lys Val Pro Ala Pro Arg Leu Pro Ala Lys Asp Trp Lys Thr Lys
            900                 905                 910

Gly Ser Pro Arg Thr Ser Pro Lys Leu Lys Arg Lys Ser Lys Lys Asp
        915                 920                 925

Asp Gly Asp Ala Ala Met Gly Ser Arg Leu Thr Glu His Gln Val Ala
    930                 935                 940

Glu Pro Pro Glu Asp Trp Pro Ala Leu Ile Trp Gln Gln Arg Glu
945                 950                 955                 960

Leu Ala Glu Leu Arg His Ser Gln Glu Glu Leu Leu Gln Arg Leu Cys
                965                 970                 975

Thr Gln Leu Glu Gly Leu Gln Ser Thr Val Thr Gly His Val Glu Arg
            980                 985                 990

Ala Leu Glu Thr Arg His Glu Gln  Glu Gln Arg Arg Leu  Glu Arg Ala
        995                 1000                1005

Leu Ala Glu Gly Gln Gln Arg  Gly Gly Gln Leu Gln  Glu Gln Leu
    1010                1015                1020

Thr Gln  Gln Leu Ser Gln Ala  Leu Ser Ser Ala Val  Ala Gly Arg
    1025                1030                1035

Leu Glu  Arg Ser Ile Arg Asp  Glu Ile Lys Lys Thr  Val Pro Pro
    1040                1045                1050

Cys Val  Ser Arg Ser Leu Glu  Pro Met Ala Gly Gln  Leu Ser Asn
    1055                1060                1065

Ser Val  Ala Thr Lys Leu Thr  Ala Val Glu Gly Ser  Met Lys Glu
    1070                1075                1080

Asn Ile  Ser Lys Leu Leu Lys  Ser Lys Asn Leu Thr  Asp Ala Ile
    1085                1090                1095

Ala Arg  Ala Ala Ala Asp Thr  Leu Gln Gly Pro Met  Gln Ala Ala
    1100                1105                1110

Tyr Arg  Glu Ala Phe Gln Ser  Val Val Leu Pro Ala  Phe Glu Lys
    1115                1120                1125

Ser Cys  Gln Ala Met Phe Gln  Gln Ile Asn Asp Ser  Phe Arg Leu
    1130                1135                1140

Gly Thr  Gln Glu Tyr Leu Gln  Gln Leu Glu Ser His  Met Lys Ser
    1145                1150                1155

Arg Lys  Ala Arg Glu Gln Glu  Ala Arg Glu Pro Val  Leu Ala Gln
    1160                1165                1170

Leu Arg  Gly Leu Val Ser Thr  Leu Gln Ser Ala Thr  Glu Gln Met
    1175                1180                1185

Ala Ala  Thr Val Ala Gly Ser  Val Arg Ala Glu Val  Gln His Gln
    1190                1195                1200

Leu His  Val Ala Val Gly Ser  Leu Gln Glu Ser Ile  Leu Ala Gln
    1205                1210                1215

Val Gln  Arg Ile Val Lys Gly  Glu Val Ser Val Ala  Leu Lys Glu
```

```
                      1220                1225                1230
Gln Gln Ala Ala Val Thr Ser Ser Ile Met Gln Ala Met Arg Ser
    1235                1240                1245
Ala Ala Gly Thr Pro Val Pro Ser Ala His Leu Asp Cys Gln Ala
    1250                1255                1260
Gln Gln Ala His Ile Leu Gln Leu Leu Gln Gln Gly His Leu Asn
    1265                1270                1275
Gln Ala Phe Gln Gln Ala Leu Thr Ala Ala Asp Leu Asn Leu Val
    1280                1285                1290
Leu Tyr Val Cys Glu Thr Val Asp Pro Ala Gln Val Phe Gly Gln
    1295                1300                1305
Pro Pro Cys Pro Leu Ser Gln Pro Val Leu Leu Ser Leu Ile Gln
    1310                1315                1320
Gln Leu Ala Ser Asp Leu Gly Thr Arg Thr Asp Leu Lys Leu Ser
    1325                1330                1335
Tyr Leu Glu Glu Ala Val Met His Leu Asp His Ser Asp Pro Ile
    1340                1345                1350
Thr Arg Asp His Met Gly Ser Val Met Ala Gln Val Arg Gln Lys
    1355                1360                1365
Leu Phe Gln Phe Leu Gln Ala Glu Pro His Asn Ser Leu Gly Lys
    1370                1375                1380
Ala Ala Arg Arg Leu Ser Leu Met Leu His Gly Leu Val Thr Pro
    1385                1390                1395
Ser Leu Pro
    1400

<210> SEQ ID NO 27
<211> LENGTH: 4811
<212> TYPE: DNA
<213> ORGANISM: Homo sapiens

<400> SEQUENCE: 27
tttcttctcc ggccctggca ggttccggga gcctcggctc gtgggtgccg gaagtggagg      60
cggttggtgg ggttggcggg gctcagcgac gctgcgcggg tggcggtttg cgaactgcgg     120
gtggactgtg tagtgaccgg cgtcccgctg tctcgccccg tggcgggtga gcgagggtgc     180
gtggtgcgcg gcggcggcgg aacgaacgcg gtgcgggcgg ggcgcccgcc gcagggccca     240
tggcctcctg cgcgagcatc gacatcgagg acgccacgca gcacctgcgg gacatcctca     300
agctggaccg gccgcgggc ggccccagtg cagagagccc acggccatcc agtgcctaca     360
atggggacct caatggactt ctggtcccag accgctctg ctcaggtgat agtacctcag     420
caaacaagac tggtcttcgg accatgccac ccattaacct gcaagagaag caggtcatct     480
gtctctcagg agatgatagc tccacctgca ttgggatttt ggccaaggag gtggagattg     540
tggctagcag tgactctagc atttcaagca aggcccgggg aagcaacaag gtgaaaattc     600
agcctgtcgc caagtatgac tgggaacaga gtactacta tggcaacctg attgctgtgt     660
ctaactcctt cttggcctat gccattcggg ctgccaacaa tggctctgcc atggtgcggg     720
tgatcagcgt cagcacttcg gagcggacct tgctcaaggg cttcacaggc agtgtggctg     780
atctggcttt cgcgcacctc aactctccac agctggcctg cctggatgag caggcaacc      840 tgttcgtgtg cgcgcttggct ctggttaatg gcaaaattca agaagagatc ttggtccata     900
ttcggcagcc agagggcacg ccactgaacc actttcgcag gatcatctgg tgcccttca      960 tccctgagga gagcgaagac tgctgtgagg agagcagccc aacagtggcc ctgctgcatg    1020
```

```
aagaccgggc tgaggtgtgg gacctggaca tgctccgctc cagccacagt acctggcctg    1080
tggatgttag ccagatcaag cagggcttca ttgtggtaaa aggtcatagc acgtgcctca    1140
gtgaaggagc cctctctcct gatgggactg tgctggctac tgcgagccac gatggctatg    1200
tcaagttctg gcagatctac attgaggggc aagatgagcc aaggtgtctg cacgagtgga    1260
aacctcatga tgggcggccc ctctcctgcc tcctgttctg tgacaaccat aagaaacaag    1320
accctgatgt ccctttctgg aggttcctta ttactggtgc tgaccagaac cgagagttaa    1380
agatgtggtg tacagtatcc tggacctgcc tgcagactat tcgcttctcc ccagatatct    1440
tcagctcagt gagtgtgccc cctagcctca aggtttgctt ggacctctca gcagaatacc    1500
tgattctcag cgatgtgcaa cggaaggtcc tctatgtgat ggagctgctg caaaaccagg    1560
aggagggcca cgcctgcttc agctccatct cggagttcct gctcacccac cctgtgctga    1620
gctttggtat ccaggttgtg agtcgctgcc ggctacggca cactgaggtg ctgcctgccg    1680
aagaggaaaa tgacagcctg ggtgctgatg gtacccatgg agccggtgcc atggagtctg    1740
cggccggtgt gctcatcaag ctcttttgtg tgcatactaa ggcactgcaa gatgtgcaga    1800
tccgcttcca gccacagctg aaccctgatg tggtggcccc actgcccacc cacactgccc    1860
acgaggactt cacatttgga gagtctcggc ccgaactggg ctctgagggc tggggtcag    1920 ccgctcacgg ctcccagcct gacctccgac gaatcgtgga gctgcctgca cctgccgact    1980
tcctcagtct gagcagtgag accaagccca agttgatgac acctgacgcc ttcatgacac    2040
ctagcgcctc cttgcagcag atcactgcct ctcccagcag cagcagcagc ggtagcagca    2100
gcagcagcag cagtagcagc agctccctta cagctgtgtc tgccatgagc agcacctcag    2160
ctgtggaccc ctccttgacc aggccacctg aggagctgac cttgagcccc aagctgcagc    2220
tggatggcag cctgacaatg agcagcagtg gcagccttca ggcaagcccg cgtggcctcc    2280
tgcctggcct gctcccagcc ccagctgaca aactgactcc caaggggccg ggccaggtgc    2340
ctactgccac ctctgcactg tccctggagc tgcaggaagt ggagcccctg ggctacccc    2400 aagcctcccc tagccgcact cgttcccctg atgtcatctc ctcagcttcc actgccctgt    2460
cccaggacat ccctgagatt gcatctgagg ccctgtcccg tggttttggc tcctctgcac    2520
cagagggcct tgagccagac agtatggctt cagccgcctc ggcactgcac ctgctgtccc    2580
cacggccccg gccagggccc gagctcggcc cccagctcgg gcttgatgga ggccctgggg    2640
atggagatcg gcataatacc ccctccctcc tggaggcagc cttgacccag gaggcctcga    2700
ctcctgacag tcaggtttgg cccacagcac ctgacattac tcgtgagacc tgcagcaccc    2760
tggcagaaag ccccaggaat ggccttcagg aaaagcacaa gagcctggcc ttccaccgac    2820
caccatatca cctgctgcag caacgtgaca gccaggatgc cagtgctgag caaagtgacc    2880
atgatgatga ggtggccagc cttgcctctg cttcaggagg ctttggcacc aaagttcctg    2940
ctccacggct gcctgccaag gactggaaga ccaaggatc ccctcgaacc tcacccaagc    3000
tcaagaggaa aagcaagaag gatgatgggg atgcagccat gggatcccgg ctcacagagc    3060
accaggtggc agagccccct gaggactggc cagcactaat ttggcaacag cagagagagc    3120
tggcagagct gcggcacagc caggaagagc tgctgcagcg tctgtgtacc caactcgaag    3180
gcctgcagag cacagtcaca ggccacgtag aacgtgccct tgagactcgg cacgagcagg    3240
aacagcggcg gctggagcga gcactggctg aggggcagca gcgggagggg cagctgcagg    3300
agcagctgac acaacagttg tcccaagcac tgtcgtcagc tgtagctggg cggctagagc    3360
```

```
gcagcatacg ggatgagatc aagaagacag tccctccatg tgtctcaagg agtctggagc    3420
ctatggcagg ccaactgagc aactcagtgg ctaccaagct cacagctgtg gagggcagca    3480
tgaaagagaa catctccaag ctgctcaagt ccaagaactt gactgatgcc atcgcccgag    3540
cagctgcaga cacattacaa gggccgatgc aggctgccta ccgggaagcc ttccagagtg    3600
tggtgctgcc ggcctttgag aagagctgcc aggccatgtt ccagcaaatc aatgatagct    3660
tccggctggg gacacaggaa tacttgcagc agctagaaag ccacatgaag agccggaagg    3720
cacgggaaca ggaggccagg gagcctgtgc tagcccagct gcggggcctg gtcagcacac    3780
tgcagagtgc cactgagcag atggcagcca ccgtggccgg cagtgttcgt gctgaggtgc    3840
agcaccagct gcatgtggct gtgggcagcc tgcaggagtc cattttagca caggtacagc    3900
gcatcgttaa gggtgaggtg agtgtggcgc tcaaggagca gcaggccgcc gtcacctcca    3960
gcatcatgca ggccatgcgc tcagctgctg gcacacctgt ccctctgcc caccttgact    4020 gccaggccca gcaagcccat atcctgcagc tgctgcagca gggccacctc aatcaggcct    4080
tccagcaggc gctgacagct gctgacctga acctggtgct gtatgtgtgt gaaactgtgg    4140
acccagccca ggttttggg cagccaccct gcccgctctc ccagcctgtg ctcctttccc    4200
tcatccagca gctggcatct gaccttggca ctcgaactga cctcaagctc agctacctgg    4260
aagaggccgt gatgcacctg gaccacagtg accccatcac tcgggaccac atgggctccg    4320
ttatggccca ggtgcgccaa aagcttttc agttcctgca ggctgagcca cacaactcac    4380
ttggcaaagc agctcggcgt ctcagcctca tgctgcatgg cctcgtgacc cccagcctcc    4440
cttagctgct aagcctgcct tgcccagggg tgggatggca ctgaaggcca gcagacaggc    4500
ctaggctggg gcagggtcac ggctggcctt tacctgctca ggcccccatc tctgggtgt    4560 ttgggggtca gggagcaggg agcactggcc gtggtctaca gcgtgtggta gtcagaaggt    4620
ttagctgggc ccagggcagg tattgcgcct gcttgggttc tgccatgcct ggagcatgac    4680
cctgagatcg tgacaccact tgagtggaat tttccatgtt cctttttacc tctaatttgg    4740 atcttttgt ttttgaaaaa cattgagaaa ttcaattaaa tgcttttgga ataaaatgga    4800
gtatgtgtgt g                                                         4811
```

<210> SEQ ID NO 28
<211> LENGTH: 406
<212> TYPE: PRT
<213> ORGANISM: Homo sapiens

<400> SEQUENCE: 28

```
Met Ser Ala Ser Gln Asp Ser Arg Ser Arg Asp Asn Gly Pro Asp Gly
1               5                   10                  15

Met Glu Pro Glu Gly Val Ile Glu Ser Asn Trp Asn Glu Ile Val Asp
                20                  25                  30

Ser Phe Asp Asp Met Asn Leu Ser Glu Ser Leu Leu Arg Gly Ile Tyr
            35                  40                  45

Ala Tyr Gly Phe Glu Lys Pro Ser Ala Ile Gln Gln Arg Ala Ile Leu
        50                  55                  60

Pro Cys Ile Lys Gly Tyr Asp Val Ile Ala Gln Ala Gln Ser Gly Thr
65                  70                  75                  80

Gly Lys Thr Ala Thr Phe Ala Ile Ser Ile Leu Gln Gln Ile Glu Leu
                85                  90                  95

Asp Leu Lys Ala Thr Gln Ala Leu Val Leu Ala Pro Thr Arg Glu Leu
            100                 105                 110
```

```
Ala Gln Gln Ile Gln Lys Val Val Met Ala Leu Gly Asp Tyr Met Gly
            115                 120                 125

Ala Ser Cys His Ala Cys Ile Gly Gly Thr Asn Val Arg Ala Glu Val
        130                 135                 140

Gln Lys Leu Gln Met Glu Ala Pro His Ile Ile Val Gly Thr Pro Gly
145                 150                 155                 160

Arg Val Phe Asp Met Leu Asn Arg Arg Tyr Leu Ser Pro Lys Tyr Ile
                165                 170                 175

Lys Met Phe Val Leu Asp Glu Ala Asp Glu Met Leu Ser Arg Gly Phe
            180                 185                 190

Lys Asp Gln Ile Tyr Asp Ile Phe Gln Lys Leu Asn Ser Asn Thr Gln
        195                 200                 205

Val Val Leu Leu Ser Ala Thr Met Pro Ser Asp Val Leu Glu Val Thr
210                 215                 220

Lys Lys Phe Met Arg Asp Pro Ile Arg Ile Leu Val Lys Lys Glu Glu
225                 230                 235                 240

Leu Thr Leu Glu Gly Ile Arg Gln Phe Tyr Ile Asn Val Glu Arg Glu
                245                 250                 255

Glu Trp Lys Leu Asp Thr Leu Cys Asp Leu Tyr Glu Thr Leu Thr Ile
            260                 265                 270

Thr Gln Ala Val Ile Phe Ile Asn Thr Arg Arg Lys Val Asp Trp Leu
        275                 280                 285

Thr Glu Lys Met His Ala Arg Asp Phe Thr Val Ser Ala Met His Gly
    290                 295                 300

Asp Met Asp Gln Lys Glu Arg Asp Val Ile Met Arg Glu Phe Arg Ser
305                 310                 315                 320

Gly Ser Ser Arg Val Leu Ile Thr Thr Asp Leu Leu Ala Arg Gly Ile
                325                 330                 335

Asp Val Gln Gln Val Ser Leu Val Ile Asn Tyr Asp Leu Pro Thr Asn
            340                 345                 350

Arg Glu Asn Tyr Ile His Arg Ile Gly Arg Gly Gly Arg Phe Gly Arg
        355                 360                 365

Lys Gly Val Ala Ile Asn Met Val Thr Glu Glu Asp Lys Arg Thr Leu
370                 375                 380

Arg Asp Ile Glu Thr Phe Tyr Asn Thr Ser Ile Glu Glu Met Pro Leu
385                 390                 395                 400

Asn Val Ala Asp Leu Ile
                405

<210> SEQ ID NO 29
<211> LENGTH: 1893
<212> TYPE: DNA
<213> ORGANISM: Homo sapiens

<400> SEQUENCE: 29
ggaactaacg tcatgccgag ttgctgagcg ccggcaggcg gggccggggc ggccaaacca    60
atgcgatggc cggggcggag tcgggcgctc tataagttgt cgataggcgg gcactccgcc   120
ctagtttcta aggatcatgt ctgcgagcca ggattcccga tccagagaca atggccccga   180
tgggatggag cccgaaggcg tcatcgagag taactggaat gagattgttg acagctttga   240
tgacatgaac ctctcggagt cccttctccg tggcatctac gcgtatggtt ttgagaagcc   300
ctctgccatc cagcagcgag ccattctacc ttgtatcaag ggttatgatg tgattgctca   360
agcccaatct gggactggga aaacggccac atttgccata tcgattctgc agcagattga   420
```

```
attagatcta aaagccaccc aggccttggt cctagcaccc actcgagaat tggctcagca    480
gatacagaag gtggtcatgg cactaggaga ctacatgggc gcctcctgtc acgcctgtat    540
cgggggcacc aacgtgcgtg ctgaggtgca gaaactgcag atggaagctc cccacatcat    600
cgtgggtacc cctggccgtg tgtttgatat gcttaaccgg agatacctgt cccccaaata    660
catcaagatg tttgtactgg atgaagctga cgaaatgtta agccgtggat tcaaggacca    720
gatctatgac atattccaaa agctcaacag caacacccag gtagttttgc tgtcagccac    780
aatgccttct gatgtgcttg aggtgaccaa gaagttcatg agggacccca ttcggattct    840
tgtcaagaag gaagagttga ccctggaggg tatccgccag ttctacatca acgtggaacg    900
agaggagtgg aagctggaca cactatgtga cttgtatgaa accctgacca tcacccaggc    960
agtcatcttc atcaacaccc ggaggaaggt ggactggctc accgagaaga tgcatgctcg   1020
agatttcact gtatccgcca tgcatggaga tatggaccaa aaggaacgag acgtgattat   1080
gagggagttt cgttctggct ctagcagagt tttgattacc actgacctgc tggccagagg   1140
cattgatgtg cagcaggttt ctttagtcat caactatgac cttcccacca acagggaaaa   1200
ctatatccac agaatcggtc gaggtggacg gtttggccgt aaaggtgtgg ctattaacat   1260
ggtgacagaa gaagacaaga ggactcttcg agacattgag accttctaca cacctccat    1320
tgaggaaatg cccctcaatg ttgctgacct catctgaggg gctgtcctgc acccagccc    1380
cagccagggc tcaatctctg ggggctgagg agcagcagga ggggggaggg aagggagcca   1440
agggatggac atcttgtcat ttttttttctt tgaataaatg tcacttttttg aggcaaaaga   1500
aggaaccgtg aacattttag acacccttttt ctttgggggta ggctcttgcc ccaggcgccg   1560
gctcttctcc caaaaaaaaa aaaaaaacac taatccatttt ccctaaccta gtaacctcca   1620
gatcccagag gctctcctca cctcagctga gctcctttga aagtgattca agggactatg   1680
tcactcagcc tcatttgctg gaccaaatct ggagggagaa cccctaaaac ccctaagtga   1740
ggttgcccag ggggttgtcc ccaggtgggg ggaagcaggg gagagaaaat ggtagccatt   1800
tttacattgt tttgtatagt atttattgat tcaggaaaca aacacaaaat tctgaataaa   1860
atgacttgga aactgccaaa aaaaaaaaaa aaa                                 1893
```

<210> SEQ ID NO 30
<211> LENGTH: 500
<212> TYPE: PRT
<213> ORGANISM: Homo sapiens

<400> SEQUENCE: 30

```
Met Glu Val Asp Gly Thr Pro Arg Arg Gly Gly Cys Lys Met Pro Leu
1               5                   10                  15

Pro Val Gln Val Phe Asn Leu Gln Gly Ala Val Glu Pro Met Gln Ile
                20                  25                  30

Asp Val Asp Pro Gln Glu Asp Pro Gln Asn Ala Pro Asp Val Asn Tyr
            35                  40                  45

Val Val Glu Asn Pro Ser Leu Asp Leu Glu Gln Tyr Ala Ala Ser Tyr
        50                  55                  60

Ser Gly Leu Met Arg Ile Glu Arg Leu Gln Phe Ile Ala Asp His Cys
65                  70                  75                  80

Pro Thr Leu Arg Val Glu Ala Leu Lys Met Ala Leu Ser Phe Val Gln
                85                  90                  95

Arg Thr Phe Asn Val Asp Met Tyr Glu Glu Ile His Arg Lys Leu Ser
                100                 105                 110
```

Glu Ala Thr Arg Glu Leu Gln Asn Ala Pro Asp Ala Ile Pro Glu Ser
            115                 120                 125

Gly Val Glu Pro Pro Ala Leu Asp Thr Ala Trp Val Glu Ala Thr Arg
130                 135                 140

Lys Lys Ala Leu Leu Lys Leu Glu Lys Leu Asp Thr Asp Leu Lys Asn
145                 150                 155                 160

Tyr Lys Gly Asn Ser Ile Lys Glu Ser Ile Arg Arg Gly His Asp Asp
                165                 170                 175

Leu Gly Asp His Tyr Leu Asp Cys Gly Asp Leu Ser Asn Ala Leu Lys
            180                 185                 190

Cys Tyr Ser Arg Ala Arg Asp Tyr Cys Thr Ser Ala Lys His Val Ile
        195                 200                 205

Asn Met Cys Leu Asn Val Ile Lys Val Ser Val Tyr Leu Gln Asn Trp
    210                 215                 220

Ser His Val Leu Ser Tyr Val Ser Lys Ala Glu Ser Thr Pro Glu Ile
225                 230                 235                 240

Ala Glu Gln Arg Gly Glu Arg Asp Ser Gln Thr Gln Ala Ile Leu Thr
                245                 250                 255

Lys Leu Lys Cys Ala Ala Gly Leu Ala Glu Leu Ala Ala Arg Lys Tyr
            260                 265                 270

Lys Gln Ala Ala Lys Cys Leu Leu Leu Ala Ser Phe Asp His Cys Asp
        275                 280                 285

Phe Pro Glu Leu Leu Ser Pro Ser Asn Val Ala Ile Tyr Gly Gly Leu
    290                 295                 300

Cys Ala Leu Ala Thr Phe Asp Arg Gln Glu Leu Gln Arg Asn Val Ile
305                 310                 315                 320

Ser Ser Ser Ser Phe Lys Leu Phe Leu Glu Leu Glu Pro Gln Val Arg
                325                 330                 335

Asp Ile Ile Phe Lys Phe Tyr Glu Ser Lys Tyr Ala Ser Cys Leu Lys
            340                 345                 350

Met Leu Asp Glu Met Lys Asp Asn Leu Leu Asp Met Tyr Leu Ala
        355                 360                 365

Pro His Val Arg Thr Leu Tyr Thr Gln Ile Arg Asn Arg Ala Leu Ile
    370                 375                 380

Gln Tyr Phe Ser Pro Tyr Val Ser Ala Asp Met His Arg Met Ala Ala
385                 390                 395                 400

Ala Phe Asn Thr Thr Val Ala Ala Leu Glu Asp Leu Thr Gln Leu
                405                 410                 415

Ile Leu Glu Gly Leu Ile Ser Ala Arg Val Asp Ser His Ser Lys Ile
            420                 425                 430

Leu Tyr Ala Arg Asp Val Asp Gln Arg Ser Thr Thr Phe Glu Lys Ser
        435                 440                 445

Leu Leu Met Gly Lys Glu Phe Gln Arg Arg Ala Lys Ala Met Met Leu
    450                 455                 460

Arg Ala Ala Val Leu Arg Asn Gln Ile His Val Lys Ser Pro Pro Arg
465                 470                 475                 480

Glu Gly Ser Gln Gly Glu Leu Thr Pro Ala Asn Ser Gln Ser Arg Met
                485                 490                 495

Ser Thr Asn Met
            500

<210> SEQ ID NO 31
<211> LENGTH: 2385
<212> TYPE: DNA

<213> ORGANISM: Homo sapiens

<400> SEQUENCE: 31

```
gcgccccgga agcgacggct tcgctgcccc ggaagtggac ggcacgccgc ggcggggtgg    60
gtgcaagatg ccgctgccgg ttcaggtgtt taacttgcag gtaacgagcc gaggccgccc   120
cgggcctccg cgccccgcg cccccgcca ctggggccgg gctgaggtcg agcaggggcg    180
cggggcctgc gccaggagtc ggtcgggcac gctccgtgcc gggcctccgc gggcagcgcg   240
cgtcggggc tgcagggccg agggcgcgtc tccgccgtgg ctgcgcgctg cgatcggggg    300
ccgccgggcc gcgcccgccc cgcctcccct cccagcagct cacgggagag gttcccggcc   360
gccccgacgc taacgctctt tctcccttca gcagccagcc agctctgtgt cagggtcggg   420
gggtgcagaa agtcaggaca gaatgaggga tagctcggcc cccagctcgg cctcctcgtc   480
agtgacagat ctgtactgca ccctcacag cagtaggtca gacctcgtcc tgcccggcac    540
ggccggggac ttcagcctga cgccagcct gtcggcctgt acgctgctct acgaggggc    600
cgtggagccc atgcagatcg acgtggaccc ccaggaagac ccgcagaatg cacctgacgt    660
caactacgtg gtggagaacc ccagcctgga tctggaacag tacgcggcca gctacagcgg   720
cctgatgcgc atcgaacggc tgcagttcat tgctgatcac tgcccacgc tgcgggtgga    780
ggccctgaag atggccctct ccttcgtgca gagaaccttt aacgtggaca tgtacgagga   840
gatccaccgc aagctctcag aggccaccag ggagctgcag aacgcacccg acgccatccc    900
tgagagcggc gtggagcccc agccctggac acggcctgg gtggaggcca cgcggaagaa    960
ggcgctgctg aagctggaga agctggacac agacctgaag aactacaagg caactccat   1020
caaagagagc atccggcgcg ccacgacga cctgggcgac cactacctgg actgtgggga   1080
cctcagcaac gccctcaagt gctattccg ggccgggac tactgcacca cgccaaaca   1140
cgtcatcaac atgtgcctca atgtcatcaa ggtcagcgtc tacttgcaga attggtctca   1200
tgtgctcagc tacgtcagca aggctgagtc cacccagag attgccgagc agcgaggaga   1260
gcgtgacagc cagacccagg ccatcctcac caagctcaag tgtccgcag cttggcaga   1320
gctgccgcc aggaagtaca agcaggctgc caagtgcctc ctgctggctt cctttgatca   1380
ctgtgacttc cctgagctgc tgtccccag caacgtggcc atctacggtg gcctgtgcgc   1440
cttggctacc tttgaccggc aggagctgca gcgcaatgtc atctccagca gctccttcaa   1500
gttgttcttg gagctggagc acaggtccg agacatcatc ttcaaattct acgagtccaa   1560
gtacgcctca tgtctcaaga tgctggacga gatgaaggac aacctgctcc tggacatgta   1620
tctggccccc catgtcagga ccctgtacac ccagattcgc aaccgtgccc tcatccagta   1680
tttcagcccc tacgtgtcag ccgacatgca taggatggcg gcagccttca ataccacggt   1740
ggccgccctg gaggacgagc tgacgcagct aatcctggag gggctgatca gtgcccgtgt   1800
ggactcacac agcaagatcc tatacgcccg ggacgtggat cagcgcagca ccaccttttga   1860
gaagtctctg ttgatgggca aggagttcca gcgccgcgcc aaggccatga tgctgcgggc   1920
agctgtgctc cgcaaccaga tccatgtcaa gtccccgccc agagaaggga gccaggggga   1980
gctgactcca gccaacagcc agtcccggat gagcaccaac atgtgagggg tgaaccttgg   2040
cctccaggac atctgcaccc cctccccacc tccacggacc tcggacctcc aggcggctca   2100
gtgctgcctc cggcccagct aaggggcctg gccactgggt gccacccagc ctgtgtgccc   2160
tccctggggc tgaggaggca ggcggctgct agttgtggcc cttcctggaa ggagaggcct   2220
gcagggctcg accctgtggg tttctgtccc cagggagcag actgtgcggc acccaggccc   2280
```

```
agtggcacca tttcccagac ccctcctgtt cccgcctcag tcaggtgcag acaagtgggc    2340
ggtgtccatt aaagagcaga ctcagcgtta aaaaaaaaaa aaaaa                    2385
```

<210> SEQ ID NO 32
<211> LENGTH: 594
<212> TYPE: PRT
<213> ORGANISM: Homo sapiens

<400> SEQUENCE: 32

```
Met Ala Val Glu Glu Leu Gln Ser Ile Ile Lys Arg Cys Gln Ile Leu
1               5                   10                  15

Glu Glu Gln Asp Phe Lys Glu Asp Phe Gly Leu Phe Gln Leu Ala
                20                  25                  30

Gly Gln Arg Cys Ile Glu Glu Gly His Thr Asp Gln Leu Leu Glu Ile
            35                  40                  45

Ile Gln Asn Glu Lys Asn Lys Val Ile Ile Lys Asn Met Gly Trp Asn
        50                  55                  60

Leu Val Gly Pro Val Val Arg Cys Leu Leu Cys Lys Asp Lys Glu Asp
65                  70                  75                  80

Ser Lys Arg Lys Val Tyr Phe Leu Ile Phe Asp Leu Leu Val Lys Leu
                85                  90                  95

Cys Asn Pro Lys Glu Leu Leu Leu Gly Leu Leu Glu Leu Ile Glu Glu
            100                 105                 110

Pro Ser Gly Lys Gln Ile Ser Gln Ser Ile Leu Leu Leu Gln Pro
        115                 120                 125

Leu Gln Thr Val Ile Gln Lys Leu His Asn Lys Ala Tyr Ser Ile Gly
130                 135                 140

Leu Ala Leu Ser Thr Leu Trp Asn Gln Leu Ser Leu Leu Pro Val Pro
145                 150                 155                 160

Tyr Ser Lys Glu Gln Ile Gln Met Asp Asp Tyr Gly Leu Cys Gln Cys
                165                 170                 175

Cys Lys Ala Leu Ile Glu Phe Thr Lys Pro Phe Val Glu Glu Val Ile
            180                 185                 190

Asp Asn Lys Glu Asn Ser Leu Glu Asn Glu Lys Leu Lys Asp Glu Leu
        195                 200                 205

Leu Lys Phe Cys Phe Lys Ser Leu Lys Cys Pro Leu Leu Thr Ala Gln
    210                 215                 220

Phe Phe Glu Gln Ser Glu Glu Gly Gly Asn Asp Pro Phe Arg Tyr Phe
225                 230                 235                 240

Ala Ser Glu Ile Ile Gly Phe Leu Ser Ala Ile Gly His Pro Phe Pro
                245                 250                 255

Lys Met Ile Phe Asn His Gly Arg Lys Lys Arg Thr Trp Asn Tyr Leu
            260                 265                 270

Glu Phe Glu Glu Glu Glu Asn Lys Gln Leu Ala Asp Ser Met Ala Ser
        275                 280                 285

Leu Ala Tyr Leu Val Phe Val Gln Gly Ile His Ile Asp Gln Leu Pro
    290                 295                 300

Met Val Leu Ser Pro Leu Tyr Leu Leu Gln Phe Asn Met Gly His Ile
305                 310                 315                 320

Glu Val Phe Leu Gln Arg Thr Glu Glu Ser Val Ile Ser Lys Gly Leu
                325                 330                 335

Glu Leu Leu Glu Asn Ser Leu Leu Arg Ile Glu Asp Asn Ser Leu Leu
            340                 345                 350
```

Tyr Gln Tyr Leu Glu Ile Lys Ser Phe Leu Thr Val Pro Gln Gly Leu
         355                 360                 365

Val Lys Val Met Thr Leu Cys Pro Ile Glu Thr Leu Arg Lys Lys Ser
370                 375                 380

Leu Ala Met Leu Gln Leu Tyr Ile Asn Lys Leu Asp Ser Gln Gly Lys
385                 390                 395                 400

Tyr Thr Leu Phe Arg Cys Leu Leu Asn Thr Ser Asn His Ser Gly Val
             405                 410                 415

Glu Ala Phe Ile Ile Gln Asn Ile Lys Asn Gln Ile Asp Met Ser Leu
             420                 425                 430

Lys Arg Thr Arg Asn Asn Lys Trp Phe Thr Gly Pro Gln Leu Ile Ser
         435                 440                 445

Leu Leu Asp Leu Val Leu Phe Leu Pro Glu Gly Ala Glu Thr Asp Leu
         450                 455                 460

Leu Gln Asn Ser Asp Arg Ile Met Ala Ser Leu Asn Leu Leu Arg Tyr
465                 470                 475                 480

Leu Val Ile Lys Asp Asn Glu Asn Asp Asn Gln Thr Gly Leu Trp Thr
             485                 490                 495

Glu Leu Gly Asn Ile Glu Asn Asn Phe Leu Lys Pro Leu His Ile Gly
             500                 505                 510

Leu Asn Met Ser Lys Ala His Tyr Glu Ala Glu Ile Lys Asn Ser Gln
         515                 520                 525

Glu Ala Gln Lys Ser Lys Asp Leu Cys Ser Ile Thr Val Ser Gly Glu
         530                 535                 540

Glu Ile Pro Asn Met Pro Pro Glu Met Gln Leu Lys Val Leu His Ser
545                 550                 555                 560

Ala Leu Phe Thr Phe Asp Leu Ile Glu Ser Val Leu Ala Arg Val Glu
             565                 570                 575

Glu Leu Ile Glu Ile Lys Thr Lys Ser Thr Ser Glu Glu Asn Ile Gly
             580                 585                 590

Ile Lys

<210> SEQ ID NO 33
<211> LENGTH: 2042
<212> TYPE: DNA
<213> ORGANISM: Homo sapiens

<400> SEQUENCE: 33

```
acgcgtagcg cggggcgggg ccagaagagc gggctaagac gccggaggag gtggcggcgg      60
ctgggagagg cgagggttct ggccgatttt agcatcgaaa ctaggagaaa taagaatggc     120
tgtagaggaa cttcagtcta aataaagag atgtcaaatc ctagaagagc aagactttaa     180
agaagaggat tttggcctat ttcagttagc tgggcaaaga tgcatagaag aagggcacac     240
agaccagcta ttagaaatta ttcaaaatga aagaataag gtcatcatca agaatatggg     300
ctggaatctc gttggtcctg ttgttcgatg ccttttgtgt aaagataaag aggatagtaa     360
aagaaaagtt tattttttga tctttgattt attggtaaag ttatgcaatc caaaggaatt     420
attgttgggt ttgcttgaac tgattgaaga gccctctgga aaacagatat cccaaagtat     480
tcttcttttg cttcagccat acaaacagt gattcagaaa cttcataaca aggcatattc     540
aattggatta gcattgtcta ccctttggaa tcagctatct cttcttcctg ttccatactc     600
aaaagaacaa atacaaatgg atgcactatg cctttgtcag tgttgcaagg ccttaataga     660
gttcactaag ccttttgtgg aagaagtcat tgataacaaa gaaaactcac tggaaaatga     720
```

```
aaagttaaag gatgaattac tgaaattttg tttcaaaagc ttgaaatgcc ctttgctgac      780
agcacaattc tttgaacagt ctgaagaagg tggaaatgat cctttcaggt attttgcatc      840
agaaataata ggttttttat cagcaattgg acacccttc cccaaaatga ttttaatca       900 tggaaggaaa aagagaactt ggaattacct tgaatttgaa gaagaagaaa ataaacagtt      960
agcagactca atggcttctc tggcatatct agtatttgta cagggcatcc atattgatca    1020
gcttccaatg gtcttaagcc cattgtacct tttgcagttt aatatggggc acattgaagt    1080 cttttttgcaa agaacagaag agtctgttat ctccaaagga ttggagctgc tggagaatag   1140
tttattgaga atagaagaca atagtctact ttaccagtac ttagaaatca agagttttct    1200
tactgtacct cagggcttag tgaaagtaat gacactttgc cccattgaga cactgaggaa    1260
aaagagttta gctatgcttc agctgtatat taacaagttg gattcacaag caaatatac     1320 attatttagg tgcttattga atacaagtaa tcactcaggt gtggaggctt ttattattca    1380
aaatatcaaa atcaaattg acatgtcatt aaagagaaca cgtaacaaca aatggtttac     1440
aggaccacag ttgatttccc ttcttgattt ggtactttt ctcccagagg gtgcagaaac     1500
agatttactg caaaactcag ataggattat ggcttcatta aatttattga ggtatttggt    1560
tatcaaagat aatgaaaatg acaatcaaac tggattatgg acagaacttg gaaatattga   1620
gaataatttc ttaaagccac ttcatatagg acttaatatg tcaaaagcac attatgaagc    1680
agaaattaaa aatagccaag aggcccagaa atctaaagat ctttgttcta taactgtaag    1740
tggagaagag atccctaata tgcctcctga aatgcagctt aaggtcctgc attcagctct    1800
tttcacattt gatttgattg aaagtgttct agctcgagtg gaagaactca ttgaaataaa   1860
aacaaagtct acctctgaag aaaatattgg gataaagtga agttccatt tcctaaataa     1920 aaactaataa aatatagtac tttccattat gattcatta ataccttat aaaaaatttt    1980 tctgtaaaaa tttactgctt gaaaaataaa tgtagctttt ctcatttatc aaaaaaaaaa    2040
aa                                                                   2042
```

<210> SEQ ID NO 34
<211> LENGTH: 2337
<212> TYPE: PRT
<213> ORGANISM: Homo sapiens

<400> SEQUENCE: 34

Met Ser Ser Ser Gly Tyr Pro Pro Asn Gln Gly Ala Phe Ser Thr Glu
1               5                   10                  15

Gln Ser Arg Tyr Pro Pro His Ser Val Gln Tyr Thr Phe Pro Asn Thr
            20                  25                  30

Arg His Gln Gln Glu Phe Ala Val Pro Asp Tyr Arg Ser Ser His Leu
        35                  40                  45

Glu Val Ser Gln Ala Ser Gln Leu Leu Gln Gln Gln Gln Gln Gln Gln
    50                  55                  60

Leu Arg Arg Arg Pro Ser Leu Leu Ser Glu Phe His Pro Gly Ser Asp
65                  70                  75                  80

Arg Pro Gln Glu Arg Arg Thr Ser Tyr Glu Pro Phe His Pro Gly Pro
                85                  90                  95

Ser Pro Val Asp His Asp Ser Leu Glu Ser Lys Arg Pro Arg Leu Glu
            100                 105                 110

Gln Val Ser Asp Ser His Phe Gln Arg Val Ser Ala Ala Val Leu Pro
        115                 120                 125

Leu Val His Pro Leu Pro Glu Gly Leu Arg Ala Ser Ala Asp Ala Lys

```
                130             135             140
Lys Asp Pro Ala Phe Gly Gly Lys His Glu Ala Pro Ser Ser Pro Ile
145                 150                 155                 160

Ser Gly Gln Pro Cys Gly Asp Asp Gln Asn Ala Ser Pro Ser Lys Leu
                165                 170                 175

Ser Lys Glu Glu Leu Ile Gln Ser Met Asp Arg Val Asp Arg Glu Ile
            180                 185                 190

Ala Lys Val Glu Gln Gln Ile Leu Lys Leu Lys Lys Lys Gln Gln Gln
        195                 200                 205

Leu Glu Glu Glu Ala Ala Lys Pro Pro Glu Pro Glu Lys Pro Val Ser
    210                 215                 220

Pro Pro Pro Val Glu Gln Lys His Arg Ser Ile Val Gln Ile Ile Tyr
225                 230                 235                 240

Asp Glu Asn Arg Lys Lys Ala Glu Glu Ala His Lys Ile Phe Glu Gly
                245                 250                 255

Leu Gly Pro Lys Val Glu Leu Pro Leu Tyr Asn Gln Pro Ser Asp Thr
            260                 265                 270

Lys Val Tyr His Glu Asn Ile Lys Thr Asn Gln Val Met Arg Lys Lys
        275                 280                 285

Leu Ile Leu Phe Phe Lys Arg Arg Asn His Ala Arg Lys Gln Arg Glu
    290                 295                 300

Gln Lys Ile Cys Gln Arg Tyr Asp Gln Leu Met Glu Ala Trp Glu Lys
305                 310                 315                 320

Lys Val Asp Arg Ile Glu Asn Asn Pro Arg Arg Lys Ala Lys Glu Ser
                325                 330                 335

Lys Thr Arg Glu Tyr Tyr Glu Lys Gln Phe Pro Glu Ile Arg Lys Gln
            340                 345                 350

Arg Glu Gln Gln Glu Arg Phe Gln Arg Val Gly Gln Arg Gly Ala Gly
        355                 360                 365

Leu Ser Ala Thr Ile Ala Arg Ser Glu His Glu Ile Ser Glu Ile Ile
    370                 375                 380

Asp Gly Leu Ser Glu Gln Glu Asn Asn Glu Lys Gln Met Arg Gln Leu
385                 390                 395                 400

Ser Val Ile Pro Pro Met Met Phe Asp Ala Glu Gln Arg Arg Val Lys
                405                 410                 415

Phe Ile Asn Met Asn Gly Leu Met Glu Asp Pro Met Lys Val Tyr Lys
            420                 425                 430

Asp Arg Gln Phe Met Asn Val Trp Thr Asp His Glu Lys Glu Ile Phe
        435                 440                 445

Lys Asp Lys Phe Ile Gln His Pro Lys Asn Phe Gly Leu Ile Ala Ser
    450                 455                 460

Tyr Leu Glu Arg Lys Ser Val Pro Asp Cys Val Leu Tyr Tyr Tyr Leu
465                 470                 475                 480

Thr Lys Lys Asn Glu Asn Tyr Lys Ala Leu Val Arg Arg Asn Tyr Gly
                485                 490                 495

Lys Arg Arg Gly Arg Asn Gln Gln Ile Ala Arg Pro Ser Gln Glu Glu
            500                 505                 510

Lys Val Glu Glu Lys Glu Asp Lys Ala Glu Lys Thr Glu Lys Lys
        515                 520                 525

Glu Glu Glu Lys Lys Asp Glu Glu Lys Asp Glu Lys Asp Ser
    530                 535                 540

Lys Glu Asn Thr Lys Glu Lys Asp Lys Ile Asp Gly Thr Ala Glu Glu
545                 550                 555                 560
```

```
Thr Glu Glu Arg Glu Gln Ala Thr Pro Arg Gly Arg Lys Thr Ala Asn
            565                 570                 575
Ser Gln Gly Arg Arg Lys Gly Arg Ile Thr Arg Ser Met Thr Asn Glu
            580                 585                 590
Ala Ala Ala Ala Ser Ala Ala Ala Ala Ala Thr Glu Glu Pro Pro
            595                 600                 605
Pro Pro Leu Pro Pro Pro Pro Glu Pro Ile Ser Thr Glu Pro Val Glu
            610                 615                 620
Thr Ser Arg Trp Thr Glu Glu Met Glu Val Ala Lys Lys Gly Leu
625                 630                 635                 640
Val Glu His Gly Arg Asn Trp Ala Ala Ile Ala Lys Met Val Gly Thr
            645                 650                 655
Lys Ser Glu Ala Gln Cys Lys Asn Phe Tyr Phe Asn Tyr Lys Arg Arg
            660                 665                 670
His Asn Leu Asp Asn Leu Leu Gln Gln His Lys Gln Lys Thr Ser Arg
            675                 680                 685
Lys Pro Arg Glu Glu Arg Asp Val Ser Gln Cys Glu Ser Val Ala Ser
            690                 695                 700
Thr Val Ser Ala Gln Glu Asp Glu Asp Ile Glu Ala Ser Asn Glu Glu
705                 710                 715                 720
Glu Asn Pro Glu Asp Ser Glu Gly Ala Glu Asn Ser Ser Asp Thr Glu
            725                 730                 735
Ser Ala Pro Ser Pro Ser Pro Val Glu Ala Val Lys Pro Ser Glu Asp
            740                 745                 750
Ser Pro Glu Asn Ala Thr Ser Arg Gly Asn Thr Glu Pro Ala Val Glu
            755                 760                 765
Leu Glu Pro Thr Thr Glu Thr Ala Pro Ser Thr Ser Pro Ser Leu Ala
            770                 775                 780
Val Pro Ser Thr Lys Pro Ala Glu Asp Glu Ser Val Glu Thr Gln Val
785                 790                 795                 800
Asn Asp Ser Ile Ser Ala Glu Thr Ala Glu Gln Met Asp Val Asp Gln
            805                 810                 815
Gln Glu His Ser Ala Glu Glu Gly Ser Val Cys Asp Pro Pro Pro Ala
            820                 825                 830
Thr Lys Ala Asp Ser Val Asp Val Glu Val Arg Val Pro Glu Asn His
            835                 840                 845
Ala Ser Lys Val Glu Gly Asp Asn Thr Lys Glu Arg Asp Leu Asp Arg
850                 855                 860
Ala Ser Glu Lys Val Glu Pro Arg Asp Glu Asp Leu Val Val Ala Gln
865                 870                 875                 880
Gln Ile Asn Ala Gln Arg Pro Glu Pro Gln Ser Asp Asn Asp Ser Ser
            885                 890                 895
Ala Thr Cys Ser Ala Asp Glu Asp Val Asp Gly Glu Pro Glu Arg Gln
            900                 905                 910
Arg Met Phe Pro Met Asp Ser Lys Pro Ser Leu Leu Asn Pro Thr Gly
            915                 920                 925
Ser Ile Leu Val Ser Ser Pro Leu Lys Pro Asn Pro Leu Asp Leu Pro
            930                 935                 940
Gln Leu Gln His Arg Ala Ala Val Ile Pro Pro Met Val Ser Cys Thr
945                 950                 955                 960
Pro Cys Asn Ile Pro Ile Gly Thr Pro Val Ser Gly Tyr Ala Leu Tyr
            965                 970                 975
```

```
Gln Arg His Ile Lys Ala Met His Glu Ser Ala Leu Leu Glu Gln
                980                 985                 990

Arg Gln Arg Gln Glu Gln Ile Asp Leu Glu Cys Arg Ser Ser Thr Ser
            995                1000                1005

Pro Cys Gly Thr Ser Lys Ser Pro Asn Arg Glu Trp Glu Val Leu
        1010                1015                1020

Gln Pro Ala Pro His Gln Val Ile Thr Asn Leu Pro Glu Gly Val
        1025                1030                1035

Arg Leu Pro Thr Thr Arg Pro Thr Arg Pro Pro Pro Leu Ile
        1040                1045                1050

Pro Ser Ser Lys Thr Thr Val Ala Ser Glu Lys Pro Ser Phe Ile
        1055                1060                1065

Met Gly Gly Ser Ile Ser Gln Gly Thr Pro Gly Thr Tyr Leu Thr
        1070                1075                1080

Ser His Asn Gln Ala Ser Tyr Thr Gln Glu Thr Pro Lys Pro Ser
        1085                1090                1095

Val Gly Ser Ile Ser Leu Gly Leu Pro Arg Gln Gln Glu Ser Ala
        1100                1105                1110

Lys Ser Ala Thr Leu Pro Tyr Ile Lys Gln Glu Glu Phe Ser Pro
        1115                1120                1125

Arg Ser Gln Asn Ser Gln Pro Glu Gly Leu Leu Val Arg Ala Gln
        1130                1135                1140

His Glu Gly Val Val Arg Gly Thr Ala Gly Ala Ile Gln Glu Gly
        1145                1150                1155

Ser Ile Thr Arg Gly Thr Pro Thr Ser Lys Ile Ser Val Glu Ser
        1160                1165                1170

Ile Pro Ser Leu Arg Gly Ser Ile Thr Gln Gly Thr Pro Ala Leu
        1175                1180                1185

Pro Gln Thr Gly Ile Pro Thr Glu Ala Leu Val Lys Gly Ser Ile
        1190                1195                1200

Ser Arg Met Pro Ile Glu Asp Ser Ser Pro Glu Lys Gly Arg Glu
        1205                1210                1215

Glu Ala Ala Ser Lys Gly His Val Ile Tyr Glu Gly Lys Ser Gly
        1220                1225                1230

His Ile Leu Ser Tyr Asp Asn Ile Lys Asn Ala Arg Glu Gly Thr
        1235                1240                1245

Arg Ser Pro Arg Thr Ala His Glu Ile Ser Leu Lys Arg Ser Tyr
        1250                1255                1260

Glu Ser Val Glu Gly Asn Ile Lys Gln Gly Met Ser Met Arg Glu
        1265                1270                1275

Ser Pro Val Ser Ala Pro Leu Glu Gly Leu Ile Cys Arg Ala Leu
        1280                1285                1290

Pro Arg Gly Ser Pro His Ser Asp Leu Lys Glu Arg Thr Val Leu
        1295                1300                1305

Ser Gly Ser Ile Met Gln Gly Thr Pro Arg Ala Thr Thr Glu Ser
        1310                1315                1320

Phe Glu Asp Gly Leu Lys Tyr Pro Lys Gln Ile Lys Arg Glu Ser
        1325                1330                1335

Pro Pro Ile Arg Ala Phe Glu Gly Ala Ile Thr Lys Gly Lys Pro
        1340                1345                1350

Tyr Asp Gly Ile Thr Thr Ile Lys Glu Met Gly Arg Ser Ile His
        1355                1360                1365

Glu Ile Pro Arg Gln Asp Ile Leu Thr Gln Glu Ser Arg Lys Thr
```

-continued

```
                 1370              1375              1380
Pro  Glu  Val  Val  Gln  Ser  Thr  Arg  Pro  Ile  Ile  Glu  Gly  Ser  Ile
              1385              1390              1395
Ser  Gln  Gly  Thr  Pro  Ile  Lys  Phe  Asp  Asn  Asn  Ser  Gly  Gln  Ser
              1400              1405              1410
Ala  Ile  Lys  His  Asn  Val  Lys  Ser  Leu  Ile  Thr  Gly  Pro  Ser  Lys
              1415              1420              1425
Leu  Ser  Arg  Gly  Met  Pro  Pro  Leu  Glu  Ile  Val  Pro  Glu  Asn  Ile
              1430              1435              1440
Lys  Val  Val  Glu  Arg  Gly  Lys  Tyr  Glu  Asp  Val  Lys  Ala  Gly  Glu
              1445              1450              1455
Thr  Val  Arg  Ser  Arg  His  Thr  Ser  Val  Val  Ser  Ser  Gly  Pro  Ser
              1460              1465              1470
Val  Leu  Arg  Ser  Thr  Leu  His  Glu  Ala  Pro  Lys  Ala  Gln  Leu  Ser
              1475              1480              1485
Pro  Gly  Ile  Tyr  Asp  Asp  Thr  Ser  Ala  Arg  Arg  Thr  Pro  Val  Ser
              1490              1495              1500
Tyr  Gln  Asn  Thr  Met  Ser  Arg  Gly  Ser  Pro  Met  Met  Asn  Arg  Thr
              1505              1510              1515
Ser  Asp  Val  Thr  Ile  Ser  Ser  Asn  Lys  Ser  Thr  Asn  His  Glu  Arg
              1520              1525              1530
Lys  Ser  Thr  Leu  Thr  Pro  Thr  Gln  Arg  Glu  Ser  Ile  Pro  Ala  Lys
              1535              1540              1545
Ser  Pro  Val  Pro  Gly  Val  Asp  Pro  Val  Val  Ser  His  Ser  Pro  Phe
              1550              1555              1560
Asp  Pro  His  His  Arg  Gly  Ser  Thr  Ala  Gly  Glu  Val  Tyr  Arg  Ser
              1565              1570              1575
His  Leu  Pro  Thr  His  Leu  Asp  Pro  Ala  Met  Pro  Phe  His  Arg  Ala
              1580              1585              1590
Leu  Asp  Pro  Ala  Ala  Ala  Tyr  Leu  Phe  Gln  Arg  Gln  Leu  Ser
              1595              1600              1605
Pro  Thr  Pro  Gly  Tyr  Pro  Ser  Gln  Tyr  Gln  Leu  Tyr  Ala  Met  Glu
              1610              1615              1620
Asn  Thr  Arg  Gln  Thr  Ile  Leu  Asn  Asp  Tyr  Ile  Thr  Ser  Gln  Gln
              1625              1630              1635
Met  Gln  Val  Asn  Leu  Arg  Pro  Asp  Val  Ala  Arg  Gly  Leu  Ser  Pro
              1640              1645              1650
Arg  Glu  Gln  Pro  Leu  Gly  Leu  Pro  Tyr  Pro  Ala  Thr  Arg  Gly  Ile
              1655              1660              1665
Ile  Asp  Leu  Thr  Asn  Met  Pro  Pro  Thr  Ile  Leu  Val  Pro  His  Pro
              1670              1675              1680
Gly  Gly  Thr  Ser  Thr  Pro  Pro  Met  Asp  Arg  Ile  Thr  Tyr  Ile  Pro
              1685              1690              1695
Gly  Thr  Gln  Ile  Thr  Phe  Pro  Pro  Arg  Pro  Tyr  Asn  Ser  Ala  Ser
              1700              1705              1710
Met  Ser  Pro  Gly  His  Pro  Thr  His  Leu  Ala  Ala  Ala  Ala  Ser  Ala
              1715              1720              1725
Glu  Arg  Glu  Arg  Glu  Arg  Glu  Arg  Glu  Lys  Glu  Arg  Glu  Arg  Glu
              1730              1735              1740
Arg  Ile  Ala  Ala  Ala  Ser  Ser  Asp  Leu  Tyr  Leu  Arg  Pro  Gly  Ser
              1745              1750              1755
Glu  Gln  Pro  Gly  Arg  Pro  Gly  Ser  His  Gly  Tyr  Val  Arg  Ser  Pro
              1760              1765              1770
```

```
Ser Pro Ser Val Arg Thr Gln Glu Thr Met Leu Gln Gln Arg Pro
1775                1780                1785

Ser Val Phe Gln Gly Thr Asn Gly Thr Ser Val Ile Thr Pro Leu
1790                1795                1800

Asp Pro Thr Ala Gln Leu Arg Ile Met Pro Leu Pro Ala Gly Gly
1805                1810                1815

Pro Ser Ile Ser Gln Gly Leu Pro Ala Ser Arg Tyr Asn Thr Ala
1820                1825                1830

Ala Asp Ala Leu Ala Ala Leu Val Asp Ala Ala Ser Ala Pro
1835                1840                1845

Gln Met Asp Val Ser Lys Thr Lys Glu Ile Ser Ser His Arg Tyr
1850                1855                1860

Glu Thr Pro Ser Asp Ala Ile Glu Val Ile Ser Pro Ala Ser Ser
1865                1870                1875

Pro Ala Pro Pro Gln Glu Lys Leu Gln Thr Tyr Gln Pro Glu Val
1880                1885                1890

Val Lys Ala Asn Gln Ala Glu Asn Asp Pro Thr Arg Gln Tyr Glu
1895                1900                1905

Gly Pro Leu His His Tyr Arg Pro Gln Gln Glu Ser Pro Ser Pro
1910                1915                1920

Gln Gln Gln Leu Pro Pro Ser Ser Gln Ala Glu Gly Met Gly Gln
1925                1930                1935

Val Pro Arg Thr His Arg Leu Ile Thr Leu Ala Asp His Ile Cys
1940                1945                1950

Gln Ile Ile Thr Gln Asp Phe Ala Arg Asn Gln Val Ser Ser Gln
1955                1960                1965

Thr Pro Gln Gln Pro Pro Thr Ser Thr Phe Gln Asn Ser Pro Ser
1970                1975                1980

Ala Leu Val Ser Thr Pro Val Arg Thr Lys Thr Ser Asn Arg Tyr
1985                1990                1995

Ser Pro Glu Ser Gln Ala Gln Ser Val His His Gln Arg Pro Gly
2000                2005                2010

Ser Arg Val Ser Pro Glu Asn Leu Val Asp Lys Ser Arg Gly Ser
2015                2020                2025

Arg Pro Gly Lys Ser Pro Glu Arg Ser His Val Ser Ser Glu Pro
2030                2035                2040

Tyr Glu Pro Ile Ser Pro Pro Gln Val Pro Val Val His Glu Lys
2045                2050                2055

Gln Asp Ser Leu Leu Leu Leu Ser Gln Arg Gly Ala Glu Pro Ala
2060                2065                2070

Glu Gln Arg Asn Asp Ala Arg Ser Pro Gly Ser Ile Ser Tyr Leu
2075                2080                2085

Pro Ser Phe Phe Thr Lys Leu Glu Asn Thr Ser Pro Met Val Lys
2090                2095                2100

Ser Lys Lys Gln Glu Ile Phe Arg Lys Leu Asn Ser Ser Gly Gly
2105                2110                2115

Gly Asp Ser Asp Met Ala Ala Ala Gln Pro Gly Thr Glu Ile Phe
2120                2125                2130

Asn Leu Pro Ala Val Thr Thr Ser Gly Ser Val Ser Ser Arg Gly
2135                2140                2145

His Ser Phe Ala Asp Pro Ala Ser Asn Leu Gly Leu Glu Asp Ile
2150                2155                2160
```

| | | | | | | | | | | | |
|---|---|---|---|---|---|---|---|---|---|---|---|
|Ile|Arg|Lys|Ala|Leu|Met|Gly|Ser|Phe|Asp|Asp|Lys|Val|Glu|Asp|
| |2165| | | | |2170| | | |2175| | | | |

Ile Arg Lys Ala Leu Met Gly Ser Phe Asp Asp Lys Val Glu Asp
    2165                               2170                    2175

His Gly Val Val Met Ser Gln Pro Met Gly Val Val Pro Gly Thr
    2180                               2185                    2190

Ala Asn Thr Ser Val Val Thr Ser Gly Glu Thr Arg Arg Glu Glu
    2195                              2200                    2205

Gly Asp Pro Ser Pro His Ser Gly Gly Val Cys Lys Pro Lys Leu
    2210                               2215                    2220

Ile Ser Lys Ser Asn Ser Arg Lys Ser Lys Ser Pro Ile Pro Gly
    2225                              2230                    2235

Gln Gly Tyr Leu Gly Thr Glu Arg Pro Ser Ser Val Ser Ser Val
    2240                             2245                    2250

His Ser Glu Gly Asp Tyr His Arg Gln Thr Pro Gly Trp Ala Trp
    2255                              2260                    2265

Glu Asp Arg Pro Ser Ser Thr Gly Ser Thr Gln Phe Pro Tyr Asn
    2270                              2275                    2280

Pro Leu Thr Met Arg Met Leu Ser Ser Thr Pro Pro Thr Pro Ile
    2285                              2290                    2295

Ala Cys Ala Pro Ser Ala Val Asn Gln Ala Ala Pro His Gln Gln
    2300                              2305                    2310

Asn Arg Ile Trp Glu Arg Glu Pro Ala Pro Leu Leu Ser Ala Gln
    2315                              2320                    2325

Tyr Glu Thr Leu Ser Asp Ser Asp Asp
    2330                              2335

```
<210> SEQ ID NO 35
<211> LENGTH: 9810
<212> TYPE: DNA
<213> ORGANISM: Homo sapiens

<400> SEQUENCE: 35
gcgggctggg gggagggaga ggggttgagt caagatggcg gccaaggtgg cgaagcagca      60
gccgcggcgg cggcggcggc tggagtgagc gtccgactcg ccgcgccgaa cgaggtcccg     120
gtgtagggcc gcgcgccgtg gccgcgtccc actcctcagg ccggggcgca cgtcggctcc     180
cacgcttagc cagctcccgg tggtttccta gaaacatgat tgtttattgg cattgatctc     240
acagtctggt gaggacttct ttactgataa tgtcaagttc aggttatcct cccaaccaag     300
gagcattcag cacagaacaa agtcgttatc ctcctcactc tgtccagtat acatttccca     360
acacccgcca ccagcaggag ttcgcagtcc ctgattatcg ttcctctcat cttgaagtga     420
gtcaggcatc acagcttttg cagcaacagc agcagcaaca gcttcgaagg cgaccttcct     480
tgctttcaga atttcaccca ggttctgaca ggcctcaaga aggagaact  agttatgaac     540 cgtttcatcc aggcccatcc ccagtggatc atgattcact ggaatcgaag cgaccacgtc     600
tggaacaggt ttctgattct cattttcagc gtgtcagtgc tgcggttttg cctttagtgc     660
acccgctgcc agaagggctg agggcttctg cagatgctaa gaaggatcca gcattcggag     720
gcaaacatga agctccatcc tctccaattt cggggcaacc atgtggagat gatcaaaatg     780
cttcaccttc aaaactctca aaggaagagt taatacagag tatggatcgt gtagatcgag     840
aaattgcaaa agtagaacag cagatcctta aactgaaaaa gaacaacaa cagcttgaag     900 aagaggcagc taaacctcct gagcctgaga agccgtgtc ccctcctcct gtggagcaga     960
aacaccgcag tattgtccaa attatttatg atgagaatcg gaaaaagca gaagaagctc    1020 ataaaatttt tgaaggtctt ggcccaaaag ttgaactgcc actgtataac cagccatcag    1080
```

-continued

```
ataccaaggt gtaccatgag aacatcaaga caaaccaggt gatgaggaaa aaactcattt    1140
tattttttaa aagaagaaat catgcaagaa aacaaaggga acaaaaaatc tgccagcgtt    1200
atgatcagct catggaggca tgggagaaaa aagtggacag aatagaaaat aatcctcgga    1260
ggaaagctaa agaaagcaaa acaagggaat actatgaaaa gcagtttcca gaaattcgaa    1320
aacaaagaga acagcaagaa agatttcagc gagttgggca gaggggagct ggtctttcag    1380
ccaccattgc taggagtgag catgagattt ctgaaattat tgatgggctc tctgagcagg    1440
agaataatga gaaacaaatg cggcagctct ctgtgattcc acctatgatg tttgatgcag    1500
aacaaagacg agtcaagttc attaacatga atgggcttat ggaggaccct atgaaagtgt    1560
ataaagatag gcagtttatg aatgtttgga ctgaccatga aaaggagatc tttaaggaca    1620
agtttatcca gcatccaaaa aactttggac taattgcatc atacttggag aggaagagtg    1680
ttcctgattg tgttttgtat tactatttaa ccaagaaaaa tgagaattat aaagccctcg    1740
tcagaaggaa ttatgggaaa cgcagaggca gaaaccagca aattgctcga ccctcgcaag    1800
aagaaaaagt agaagaaaaa gaagaggata agcagaaaaa acagaaaaaa aagaagaag     1860 aaaagaaaga tgaagaggaa aaagatgaaa aagaagactc caagaaaaat accaaggaaa    1920
aggacaagat agatggtaca gcagaagaaa ctgaggaaag agagcaagcc acacccgggg    1980
ggcgaaagac tgccaacagt cagggccgcc gtaaggccg gatcaccagg tccatgacaa     2040
acgaagctgc agctgccagt gctgcagccg cagcggctac tgaagagccc ccaccacctc    2100
tgccaccgcc accagaaccc atttctacag agcctgtgga gacctctcga tggacagaag    2160
aagaaatgga agttgctaaa aaaggtctag tagaacatgg tcgtaactgg gcagcaattg    2220
ctaaaatggt gggaacgaaa agtgaagctc aatgtaaaaa cttctatttt aactataaaa    2280
ggcgacacaa tcttgacaac ctcttacagc agcataaaca gaaaacttca cgaaaacctc    2340
gtgaagagcg agatgtgtct caatgtgaaa gtgtcgcttc cactgttttct gctcaggagg    2400 atgaagatat tgaagcctcc aatgaagaag aaaatccaga agacagcgaa gttgaagctg    2460
tcaagcccag cgaggacagt cctgaaaatg ctacttctcg aggaaacaca gaacctgcgg    2520
ttgagcttga gcccaccacg gaaactgcac ccagtacatc tccctcctta gcagttccaa    2580
gtacaaaacc agctgaagat gaaagtgtgg agacccaggt gaatgacagc atcagtgctg    2640
agacagcaga gcagatggat gtagatcagc aggagcacag tgctgaagag ggttctgttt    2700
gtgatccccc acccgctacc aaagctgact ctgtggacgt tgaagtgagg gtgccagaaa    2760
accatgcatc taaagttgaa ggtgataata ccaaagaaag agacttggat agagccagtg    2820
agaaggtgga acctagagat gaagatttgg tggtagctca gcaaataaat gcccaaaggc    2880
ccgagcccca gtcagacaat gattccagtg ccacgtgcag cgctgatgag gatgtggatg    2940
gagagccaga gaggcagaga atgtttccta tggactcaaa gccttcactg ttaaacccca    3000
ctggatctat actcgtctca tctccgttaa accaaatcc actggatctg ccacagcttc     3060
agcatcgagc tgctgttatc ccaccaatgg tatcctgcac cccatgtaac ataccaattg    3120
gaaccccagt gagcggctat gctctctacc agcgacacat taaagcaatg catgagtcag    3180
cactcctgga ggagcagcgg cagagacaag aacagataga tttggaatgt agaagttcta    3240
caagtccatg tggcacatcc aagagtccaa acagagagtg ggaagtcctt cagcctgctc    3300
cacatcaagt gataactaat ctccctgaag gcgttcggct tccgacaact cgaccaacca    3360
ggccaccgcc ccctctcatc ccgtcatcca aaaccacagt ggcttcagaa aaaccatctt    3420
```

```
ttataatggg aggctccatc tcacagggaa caccaggcac ttatttgact tctcataatc    3480
aggcttccta cactcaagaa acacccaagc cgtcagtggg atctatctct cttggactgc    3540
cacggcaaca ggaatctgcc aaatcagcta ctttgcccta catcaagcag gaagaatttt    3600
ctccccgaag ccaaaactca caacctgagg gtctgttggt cagggcccaa catgaaggtg    3660
tagtcagagg taccgcagga gccatacaag aaggaagtat aactcgggga actccaacca    3720
gcaaaatttc agtggagagc attccatccc tacgggctc tatcactcag ggcaccccgg    3780
ctctgcccca gactggcata ccaacagagg ctttggtgaa ggggtccatt tcgagaatgc    3840
ccattgaaga cagcagtcct gagaaaggca gagaggaagc tgcatccaaa ggccatgtta    3900
tttatgaagg caaaagtgga catatcttgt catatgataa tattaagaat gcccgagaag    3960
ggactaggag tccaagaaca gctcatgaaa tcagtttaaa gagaagctat gaatcagtgg    4020
aaggaaatat aaagcaaggg atgtcaatga gggagtctcc tgtatcagca ccgttagagg    4080
ggctgatatg ccgagcatta cccaggggga gtcctcattc tgacctcaaa gaaaggactg    4140
tattgtctgg ctccataatg caggggacac caagagcaac aactgaaagc tttgaagatg    4200
gccttaaata tcccaaacaa attaaaaggg aaagtcctcc catacgagca tttgaaggtg    4260
ccattaccaa aggaaaacca tatgatggca tcaccaccat caagaaatg gggcgttcca    4320
ttcatgagat tccaaggcaa gatattttaa ctcaggaaag tcggaaaact ccagaagtgg    4380
tccagagcac acggccgata attgagggtt ccatttccca gggcacacca ataaagtttg    4440
acaacaactc aggtcaatct gccatcaaac acaatgtcaa atccttaatc acggggccta    4500
gcaaactatc ccgtggaatg cctccgctgg aaattgtgcc agagaacata aaagtggtag    4560
aacgggaaa atatgaggat gtgaaagcag gcgagaccgt gcgttccgg cacacgtcag    4620
tggtaagctc tggccctcc gttcttaggt ccacactgca tgaagctccc aaagcacaac    4680
tgagccctgg gatttatgat gacaccagtg cacggaggac ccctgtgagt tatcaaaaca    4740
ccatgtccag aggctcaccc atgatgaaca gaacttctga tgttacaatt tcttctaaca    4800
agtctaccaa tcatgaaagg aaatcgacac tgaccccctac ccagagggaa agtatcccag    4860
cgaagtctcc agtgcctggg gtggaccctg tcgtgagcca cagtccgttt gatccccatc    4920
acagaggcag cactgcaggc gaggtttatc ggagccacct gcccacgcac ttggatccag    4980
ccatgccttt tcacagggct ttggatcctg cagcggctgc ttacctgttt cagagacagc    5040
tttcaccaac tccaggttac ccaagtcagt atcagcttta cgcaatggag aacacaagac    5100
agacaatctt aaatgattac attacctcac aacagatgca agtgaacttg cgtcagatg    5160
tggccagagg actctcccca agagagcagc cactgggtct cccatacccca gcaacgagag    5220
gaatcattga cctgaccaat atgcctccaa caattttagt gcctcatcca gggggaacaa    5280
gcactcctcc catggacaga atcacttata ttcctggtac acagattact ttccctccca    5340
ggccgtacaa ctctgcttcc atgtctccag gacacccaac acaccttgca gctgctgcaa    5400
gtgctgagag ggaacgggaa cgggagcggg agaaggagcg ggagcgggaa cggattgctg    5460
cagcttcctc cgacctctac ctgcggccag gctcagaaca gcctggccga cctggcagtc    5520
atggatatgt tcgctcccct tccccttcag taagaactca ggagaccatg ttgcaacaga    5580
gacccagtgt tttccaagga accaatggaa ccagtgtaat cacacctttg gatccaactg    5640
ctcagctacg aatcatgcca ctgcctgctg ggggcccttc aataagccaa ggcctgccag    5700
cctcccgtta caacactgct gcggatgccc tggctgctct tgtggatgct gcagcttctg    5760
cacccccagat ggatgtgtcc aaaacaaaag agagtaagca tgaagctgcc aggttagaag    5820
```

```
aaaatttgag aagcaggtca gcagcagtta gtgaacagca gcagctagag cagaaaaccc    5880
tggaggtgga gaagagatct gttcagtgtt tatacacttc ttcagccttt ccaagtggca    5940
agccccagcc tcattcttca gtagtttatt ctgaggctgg gaaagataaa gggcctcctc    6000
caaaatccag atatgaggaa gagctaagga ccagagggaa gactaccatt actgcagcta    6060
acttcataga cgtgatcatc acccggcaaa ttgcctcgga caaggatgcg agggaacgtg    6120
gctctcaaag ttcagactct tctagtagct tatcttctca caggtatgaa acacctagcg    6180
atgctattga ggtgataagt cctgccagct cacctgcgcc accccaggag aaactgcaga    6240
cctatcagcc agaggttgtt aaggcaaatc aagcggaaaa tgatcctacc agacaatatg    6300
aaggaccatt acatcactat cgaccacagc aggaatcacc atctccccaa caacagctgc    6360 cccctttcttc acaggcagag ggaatggggc aagtgcccag gacccatcgg ctgatcacac    6420
ttgctgatca catctgtcaa attatcacac aagattttgc tagaaatcaa gtttcctcgc    6480
agactcccca gcagcctcct acttctacat tccagaactc accttctgct ttggtatcta    6540
cacctgtgag gactaaaaca tcaaaccgtt acagcccaga atcccaggct cagtctgtcc    6600
atcatcaaag accaggttca agggtctctc cagaaaatct tgtggacaaa tccaggggaa    6660
gtaggcctgg aaaatcccca gagaggagtc acgtctcttc ggagccctac gagcccatct    6720
ccccacccca ggttccggtt gtgcatgaga acaggacag cttgctgctc ttgtctcaga    6780
ggggcgcaga gcctgcagag cagaggaatg atgcccgctc accagggagt ataagctact    6840
tgccttcatt cttcaccaag cttgaaaata catcacccat ggttaaatca agaagcagg    6900 agattttcg taagttgaac tcctctggtg gaggtgactc tgatatggca gctgctcagc    6960
caggaactga gatctttaat ctgccagcag ttactacgtc aggctcagtt agctctagag    7020
gccattcttt tgctgatcct gccagtaatc ttgggctgga agacattatc aggaaggctc    7080
tcatgggaag ctttgatgac aaagttgagg atcatggagt tgtcatgtcc agcctatgg    7140 gagtagtgcc tggtactgcc aacacctcag ttgtgaccag tggtgagaca cgaagagagg    7200
aaggggaccc atcacctcat tcaggaggag tttgcaaacc aaagctgatc agcaagtcaa    7260
acagcaggaa atctaagtct cctataccctg ggcaaggcta cttaggaacg gaacggccct    7320
cttcagtctc ctctgtacat tcagaagggg attaccatag gcagacgcca gggtgggcct    7380
gggaagacag gccctcttca acaggctcaa ctcagtttcc ttataaccct ctgactatgc    7440
ggatgctcag cagtactcca ccaacaccga ttgcatgtgc tccctctgcg gtgaaccaag    7500
cagctcctca ccaacagaac aggatctggg agcgagagc tgccccactg ctctcagcac    7560
agtacgagac cctgtcggat agtgatgact gaactgcaca aagtgagggg aacagggtgc    7620
aggagaggga tctctagttt ttgtggttta atttttagta gcaggtcaaa aacctgccct    7680
cctgtgactt attccctgag actttcagg agagccagcc cacagatgat gaagaaatga    7740
tggaagttca tttggagagt caaatgggaa aaaacaaac aaaaaactgc ctttgataca    7800
ggcaattcag tggactataa taatagtgga gggttgagat gtagagtttt taaaaagtga    7860
acagttgctg ttcttacatc tgtaaagaaa accataatgt cttaaatca ctcttctgta    7920 aatagatgac cttttgcag tgtatatccc cttgctgtag tatctggtgt acttatgttc    7980
aaatcagcgc atcaactttg ggggtgattt ttaaaaatct ttttgtctat ctatcttttt    8040
aaccctagcc ttctaaacaa cctcatacag cccagttaca taatgttggc tgtcacgggc    8100
attgtacttt tatctgatat tgtttcctct aaattcagct ttccagtgat gtttaaaatc    8160
```

```
ttgtgaaaat gtttagattt ttaacacaga ccctgtcata aaatctgtac attagggtca    8220
aaaggtaaaa gtaacaaatt ctgccatatt gtaaatttcc agtgcaggct ttaattttt     8280 tttttcatta gtagcactga aaaaatatta ctgcatgggt atgttctagt tcagtttata    8340
aagttttaaa ggcttatttg aggcatacct cactgttacg cacactggta atttaaccat    8400 gccctaagt attccttttc tcctgcattt gatgcagccc aacaaagctt ttgttttgaa     8460
ataaatttga ctaccctgtc catagctaca gtagattatt tgtggtttaa ggctcctggt    8520
gtctcaggtt ccaaaggaaa agcttacata ttttttccctt agtttgaata tatgattggt   8580
tgggttaaaa gataatgatc tgtgtagtat ttagataagc tttatgctgc atcctgaaaa    8640
actcatggtg aacacagtcc ttttttcccca tcactatgga ccagcattta ctctcacttt   8700
gctcccttgg gacaagagtt tactgttaaa tgttttcatt tcacagagtc tcaaggtgca    8760
aataatttaa aagactgaat tctaaactaa ttatggtact agagggccag ttttatcttt    8820
cattaagaat tgcttgctga attttaaagt ttttttcata caattatca tagcatttaa     8880 gtatctttct ataacataga tactaacagt tttgggagaa tgccactggt aactggaaag    8940
gggagaaaca gatctctcag gatgataaaa attagcactt tacagacttt caagtagacc    9000 taaacttta aacaaaagta ctcaaggctt taaggaagc agctctgtga ttagctactg       9060
accaagaccc tcctatcact ggtgtctaat ccctatgtta cagatgaaga cacaggttta    9120
gtactttgcc catatagtta aattagtgac agagataggc cataagccca catttgtctt    9180
cagtcaaagc tttcactcct gtccctgttc cactcctgta tacctgaggt ccccaacata    9240
aactttagat caggcttagt ggtcagcatt cctagtactt ggaaagttgg tatttttac     9300 aacagatata tgtaaacata taaaaattc aaaatgaatg aaaaacagtg actaaatgtt     9360
ccacttcaca gttttctgct gaatttttt ttttcaggta ctggtaatat tttagagttt     9420
gttaataatt tatattgcca acctaccata aaagagatta tgatggtatt tttctatgac    9480
cctgagggtc ttaagctatt ctgagtcaga atacagttga cccttgaaca acacgggttt    9540
gaactgtgtg ggtccactta tacatggatt ttcttccacc tctgccaccc aagatagcaa    9600
gaccaacccc ttctcatcct cagcctattc aacatgaaga tgacaaggat gaagaccttc    9660
atgatgatcc acttccactt aatgaatagt aaatatattt tctcttcctt ataatcttaa    9720
caaacatttt ctcttctcta gcttacttta ttgtaagaat acagtatata atacatatac    9780
aaaatatgtg tcaaaaaaaa aaaaaaaaa                                       9810

<210> SEQ ID NO 36
<211> LENGTH: 795
<212> TYPE: PRT
<213> ORGANISM: Homo sapiens

<400> SEQUENCE: 36

Met Thr Ser Gly Ala Thr Arg Tyr Arg Leu Ser Cys Ser Leu Arg Gly
1               5                   10                  15

His Glu Leu Asp Val Arg Gly Leu Val Cys Cys Ala Tyr Pro Pro Gly
            20                  25                  30

Ala Phe Val Ser Val Ser Arg Asp Arg Thr Thr Arg Leu Trp Ala Pro
        35                  40                  45

Asp Ser Pro Asn Arg Ser Phe Thr Glu Met His Cys Met Ser Gly His
    50                  55                  60

Ser Asn Phe Val Ser Cys Val Cys Ile Ile Pro Ser Ser Asp Ile Tyr
65                  70                  75                  80
```

-continued

```
Pro His Gly Leu Ile Ala Thr Gly Gly Asn Asp His Asn Ile Cys Ile
                 85                  90                  95
Phe Ser Leu Asp Ser Pro Met Pro Leu Tyr Ile Leu Lys Gly His Lys
            100                 105                 110
Asn Thr Val Cys Ser Leu Ser Ser Gly Lys Phe Gly Thr Leu Leu Ser
        115                 120                 125
Gly Ser Trp Asp Thr Thr Ala Lys Val Trp Leu Asn Asp Lys Cys Met
    130                 135                 140
Met Thr Leu Gln Gly His Thr Ala Ala Val Trp Ala Val Lys Ile Leu
145                 150                 155                 160
Pro Glu Gln Gly Leu Met Leu Thr Gly Ser Ala Asp Lys Thr Val Lys
                165                 170                 175
Leu Trp Lys Ala Gly Arg Cys Glu Arg Thr Phe Ser Gly His Glu Asp
            180                 185                 190
Cys Val Arg Gly Leu Ala Ile Leu Ser Glu Thr Glu Phe Leu Ser Cys
        195                 200                 205
Ala Asn Asp Ala Ser Ile Arg Arg Trp Gln Ile Thr Gly Glu Cys Leu
    210                 215                 220
Glu Val Tyr Tyr Gly His Thr Asn Tyr Ile Tyr Ser Ile Ser Val Phe
225                 230                 235                 240
Pro Asn Cys Arg Asp Phe Val Thr Thr Ala Glu Asp Arg Ser Leu Arg
                245                 250                 255
Ile Trp Lys His Gly Glu Cys Ala Gln Thr Ile Arg Leu Pro Ala Gln
            260                 265                 270
Ser Ile Trp Cys Cys Cys Val Leu Asp Asn Gly Asp Ile Val Val Gly
        275                 280                 285
Ala Ser Asp Gly Ile Ile Arg Val Phe Thr Glu Ser Glu Asp Arg Thr
    290                 295                 300
Ala Ser Ala Glu Glu Ile Lys Ala Phe Glu Lys Glu Leu Ser His Ala
305                 310                 315                 320
Thr Ile Asp Ser Lys Thr Gly Asp Leu Gly Asp Ile Asn Ala Glu Gln
                325                 330                 335
Leu Pro Gly Arg Glu His Leu Asn Glu Pro Gly Thr Arg Glu Gly Gln
            340                 345                 350
Thr Arg Leu Ile Arg Asp Gly Glu Lys Val Glu Ala Tyr Gln Trp Ser
        355                 360                 365
Val Ser Glu Gly Arg Trp Ile Lys Ile Gly Asp Val Val Gly Ser Ser
    370                 375                 380
Gly Ala Asn Gln Gln Thr Ser Gly Lys Val Leu Tyr Glu Gly Lys Glu
385                 390                 395                 400
Phe Asp Tyr Val Phe Ser Ile Asp Val Asn Glu Gly Gly Pro Ser Tyr
                405                 410                 415
Lys Leu Pro Tyr Asn Thr Ser Asp Asp Pro Trp Leu Thr Ala Tyr Asn
            420                 425                 430
Phe Leu Gln Lys Asn Asp Leu Asn Pro Met Phe Leu Asp Gln Val Ala
        435                 440                 445
Lys Phe Ile Ile Asp Asn Thr Lys Gly Gln Met Leu Gly Leu Gly Asn
    450                 455                 460
Pro Ser Phe Ser Asp Pro Phe Thr Gly Gly Arg Tyr Val Pro Gly
465                 470                 475                 480
Ser Ser Gly Ser Ser Asn Thr Leu Pro Thr Ala Asp Pro Phe Thr Gly
                485                 490                 495
Ala Gly Arg Tyr Val Pro Gly Ser Ala Ser Met Gly Thr Thr Met Ala
```

```
                500             505             510
Gly Val Asp Pro Phe Thr Gly Asn Ser Ala Tyr Arg Ser Ala Ala Ser
            515                 520             525

Lys Thr Met Asn Ile Tyr Phe Pro Lys Lys Glu Ala Val Thr Phe Asp
        530                 535             540

Gln Ala Asn Pro Thr Gln Ile Leu Gly Lys Leu Lys Glu Leu Asn Gly
545                 550             555                 560

Thr Ala Pro Glu Glu Lys Lys Leu Thr Glu Asp Asp Leu Ile Leu Leu
                565             570             575

Glu Lys Ile Leu Ser Leu Ile Cys Asn Ser Ser Glu Lys Pro Thr
            580             585                 590

Val Gln Gln Leu Gln Ile Leu Trp Lys Ala Ile Asn Cys Pro Glu Asp
            595             600             605

Ile Val Phe Pro Ala Leu Asp Ile Leu Arg Leu Ser Ile Lys His Pro
        610             615             620

Ser Val Asn Glu Asn Phe Cys Asn Glu Lys Glu Gly Ala Gln Phe Ser
625             630             635             640

Ser His Leu Ile Asn Leu Leu Asn Pro Lys Gly Lys Pro Ala Asn Gln
            645             650             655

Leu Leu Ala Leu Arg Thr Phe Cys Asn Cys Phe Val Gly Gln Ala Gly
            660             665             670

Gln Lys Leu Met Met Ser Gln Arg Glu Ser Leu Met Ser His Ala Ile
            675             680             685

Glu Leu Lys Ser Gly Ser Asn Lys Asn Ile His Ile Ala Leu Ala Thr
        690             695             700

Leu Ala Leu Asn Tyr Ser Val Cys Phe His Lys Asp His Asn Ile Glu
705             710             715             720

Gly Lys Ala Gln Cys Leu Ser Leu Ile Ser Thr Ile Leu Glu Val Val
            725             730             735

Gln Asp Leu Glu Ala Thr Phe Arg Leu Leu Val Ala Leu Gly Thr Leu
            740             745             750

Ile Ser Asp Asp Ser Asn Ala Val Gln Leu Ala Lys Ser Leu Gly Val
        755             760             765

Asp Ser Gln Ile Lys Lys Tyr Ser Ser Val Ser Glu Pro Ala Lys Val
            770             775             780

Ser Glu Cys Cys Arg Phe Ile Leu Asn Leu Leu
785             790             795

<210> SEQ ID NO 37
<211> LENGTH: 4954
<212> TYPE: DNA
<213> ORGANISM: Homo sapiens

<400> SEQUENCE: 37
gatttaccac aaactgttgg gcccggagtc ggaagagacc cgggtttggg aaggacccca      60
gggtcaggcg tcctggtgga agggcgggcc tctttctctc ttgctcagca gggagtccag     120
agccctggag gaaagccagc tcagctccgc atcggcgtcg gcggttggga cgcacacact     180
ctgcgtcatg gagggctgag gccgatgatg aattccggag tgcctgtcag gcttgctgtg     240
tcactcggcc cgctcggcgc gccccttccc agccgccctt ccgtaccggc tctcgggctc     300
ttccggtctc cggccgcccc ttacctgcag gctcttctcc cgccgcgcc cggcgctctc      360 cgagtcgccc ctgcggactg gtctcgcaca gtgcctgggc accgggcgcc agacagacac     420
tggccatgac gagcggcgca accaggtacc ggctgagctg ctcgctccgg ggccacgagc     480
```

```
tggacgtacg gggcctggtg tgctgcgcct atccgccggg agcctttgtg tccgtgtccc    540
gagaccgcac cacccgcctc tgggcccag  acagtccaaa caggagcttt acagaaatgc    600
actgtatgag tggccattcc aattttgtat cttgtgtatg catcatacccc tcaagtgaca   660 tctaccctca tggcctaatt gccaccggtg gaaatgacca caatatatgc attttctcac   720
tggacagtcc aatgccactt tatattctaa aaggccacaa aaatactgtt tgtagtctat   780
catctggaaa atttgggaca ttacttagtg gttcatggga caccactgct aaagtctggc   840
tgaatgacaa gtgcatgatg accttgcagg gtcatacagc tgcagtgtgg gcggtaaaga   900
tcttacctga acagggctta atgttgactg gatcagcaga caagactgtt aaactgtgga   960
aggctggaag atgtgagagg acttttttcag ggcatgaaga ctgtgtaaga ggtttggcaa  1020
ttttgagtga aacagaattt ctttcctgtg caaatgatgc tagtattaga aggtggcaaa   1080
tcactggcga gtgtcttgaa gtatattatg gacatacaaa ttatatttat agcatatccg   1140 ttttttccaaa ttgtagagac tttgtgacaa cagcagagga cagatctctg agaatctgga  1200
aacatgggga atgtgctcaa actatccgac ttccagctca gtctatatgg tgctgctgtg   1260
tgctcgacaa tggtgacatt gtggttggtg cgagtgatgg cattattaga gtgtttacag   1320
aatcagaaga tcgaacagca agtgctgaag aaatcaaggc ttttgaaaaa gaactgtctc   1380
acgcaaccat tgattctaaa actggcgatt taggggacat caatgctgag cagcttcctg   1440
ggagggaaca tcttaatgaa cctggtacta gagaaggaca gactcgtcta atcagagatg   1500
gggagaaagt cgaagcctat cagtggagtg ttagtgaagg gaggtggata aaaattggtg   1560
atgttgttgg ctcatctggt gctaatcagc aaacatctgg aaaagttta  tatgaaggga   1620 aagaatttga ttatgttttc tcaattgatg tcaatgaagg tggaccatca tataaattgc   1680
catataatac cagtgatgac ccttggttaa ctgcatacaa cttcttacag aagaatgatt   1740
tgaatcctat gtttctggat caagtagcta aatttattat tgataacaca aaaggtcaaa   1800
tgttgggact tgggaatccc agcttttcag atccatttac aggtggtggt cggtatgttc   1860
cgggctcttc gggatcttct aacacactac ccacagcaga tccttttaca ggtgctggtc   1920
gttatgtacc aggttctgca agtatgggaa ctaccatggc cggagttgat ccatttacag   1980
ggaatagtgc ctaccgatca gctgcatcta aaacaatgaa tatttatttc cctaaaaaag   2040
aggctgtcac atttgaccaa gcaaacccta cacaaatatt aggtaaactg aaggaactta   2100
atggaactgc acctgaagag aagaagttaa ctgaggatga cttgatactt cttgagaaga   2160
tactgtctct aatatgtaat agttcttcag aaaaacccac agtccagcaa cttcagattt   2220
tgtggaaagc tattaactgt cctgaagata ttgtctttcc tgcacttgac attcttcggt   2280
tgtcaattaa acaccccagt gtgaatgaga acttctgcaa tgaaaaggaa ggggctcagt   2340
tcagcagtca tcttatcaat cttctgaacc ctaaaggaaa gccagcaaac cagctgcttg   2400
ctctcaggac ttttttgcaat tgttttgttg gccaggcagg acaaaaactc atgatgtccc   2460
agagggaatc actgatgtcc catgcaatag aactgaaatc agggagcaat aagaacattc   2520
acattgctct ggctacattg gccctgaact attctgtttg ttttcataaa gaccataaca   2580
ttgaagggaa agcccaatgt ttgtcactaa ttagcacaat cttggaagta gtacaagacc   2640
tagaagccac ttttagactt cttgtggctc ttggaacact tatcagtgat gattcaaatg   2700
ctgtacaatt agccaagtct ttaggtgttg attctcaaat aaaaaagtat tcctcagtat   2760
cagaaccagc taaagtaagt gaatgctgta gatttatcct aaatttgctg tagcagtggg   2820
```

```
gaagagggac ggatattttt aattgattag tgttttttc ctcacatttg acatgactga    2880
taacagataa ttaaaaaaag agaatacggt ggattaagta aaattttaca tcttgtaaag    2940
tggtggggag gggaaacaga aataaaattt ttgcactgct gaactgtgag attttcctgt    3000
gtaatttggg tagattttca agagtgtgaa cacaaattta aaataagcta taatcagcaa    3060
caacacaatg acaatgacat cttcccctta ccttagccac taagaagaca agggctgtta    3120
ctcatataac ttgcttttat tacttaatgt acaccaaact gttgttgtca attatctttt    3180
atttaacttc tccaccttca ttgctagatc cttcgaacag cactgataca tttcaaggtc    3240 ttgtttttagg ataactactt taaaatttt taaattatat taaatttata aaataattta    3300
taaattcata tattaaaaca ataagata atttcttgat ttgtcattta taaatcctaa    3360
agtatatttg tttaatggcc tattttaga tgaagaaaaa gccagttggt aagctgtgtt    3420
agtcatgtat cagttcagac agacgaggtc tcaatttaac tccaggctta gatccagttt    3480
cttttgccct tcactatttg aggtaacttc attttcatt ctagttttga tatttggctg    3540 tttattttg tcattttcca ttatttcaaa gggaatttgg aacatgttga attttatcag    3600
gtggttacat aagcaagagt acatcaaact gtattatttg aaagtctaga acctgtcatg    3660
tgaaattact attttttgagc cctctatgtg gtccaggcag aatagtagac acactgatat    3720
ttaatcctta aaaccccttt aaatgagggc cagtattatc tctgctttca gaagtagaca    3780
taataggatg aatcatataa cagaaaaaaa aaagtgaagc caagagggag ttaactactt    3840
aaagtacatg ctatgctata ctttctagag agatcacaga tgtgtgtgaa catcctagca    3900
attaacacaa agaaggaacc atcacattaa ttacacaatt tattgtgtct gaggtaaccc    3960
agtttcttga gagaagcgta actattttca aaagtgggaa agatctttc ataaagacgt    4020 tgccagaaat agcaacattc tcaatactcg tggtgtaaaa accatgaatc ccctggctta    4080
atgccaaatt atagccttag aagaataatt gttccccaaa tgggcaagaa aggttctaat    4140
tgtcaagagt aacccaagta agaacttttg gaatatcaaa aggaaatgag caaaatgtaa    4200
atagagggga tatgtacttt gctgagtatt aaattggaac tacctggtgt gtacctggac    4260
taaatattct gttcactggc tcagttgagt acctatactt ttcgtttttt gattgggttt    4320
aggtggttat gtcaaagtta aatggcaaaa ttaggaattt aacccaggtc tggctggttc    4380
ctttacaata cactgctttc ttaagtacaa ataatttaat tgcaatattt aggaaaagta    4440
ggtacctttg aataatgata agaaacagtc ttggttaaga atatgagttc cctcttcaaa    4500
atgtaagggg tggcaaaatg taaacactgc ttcctattac tgtgcaagtt tttttatgtc    4560
aactttacta tttcatgttt gttgtggaga ttacaaaata tagcttagca aaaggaaaca    4620
atctcacttg aaggatatgt taaataattt aatgatattt taaagatttt ctttttttagt    4680 taaactttcc tatgattctc ttaatgtttt ttctgaatac aaaagtaata aatatttatt    4740
gagtaaaaca cacacacccc aaataaaaat tgcctgtaag gccactatct agagaaaact    4800
attcttaaca tcttgtggca tagtgactat gtatgtaaat gtatttttatt ttattaaaaa    4860 agcgttgtat catacatact ctttgataac ctgattttta aacttatatt tggtacaaag    4920
agctccacat aataaatac aatattctat cata                                  4954
```

<210> SEQ ID NO 38
<211> LENGTH: 342
<212> TYPE: PRT
<213> ORGANISM: Homo sapiens

<400> SEQUENCE: 38

```
Met Ala Pro Leu Asp Leu Asp Lys Tyr Val Glu Ile Ala Arg Leu Cys
1               5                   10                  15

Lys Tyr Leu Pro Glu Asn Asp Leu Lys Val Ser Pro Ile Cys Gly Leu
            20                  25                  30

Ala Pro Ser Gly Cys Gly Ala Pro Ala Gly Arg Pro Phe Leu Ser Pro
        35                  40                  45

Gly Pro Pro Val Phe His Phe Leu Arg Phe Leu Lys Glu Arg Leu
    50                  55                  60

Cys Asp Tyr Val Cys Asp Leu Leu Leu Glu Glu Ser Asn Val Gln Pro
65                  70                  75                  80

Val Ser Thr Pro Val Thr Val Cys Gly Asp Ile His Gly Gln Phe Tyr
                85                  90                  95

Asp Leu Cys Glu Leu Phe Arg Thr Gly Gly Gln Val Pro Asp Thr Asn
            100                 105                 110

Tyr Ile Phe Met Gly Asp Phe Val Asp Arg Gly Tyr Tyr Ser Leu Glu
            115                 120                 125

Thr Phe Thr Tyr Leu Leu Ala Leu Lys Ala Lys Trp Pro Asp Arg Ile
130                 135                 140

Thr Leu Leu Arg Gly Asn His Glu Ser Arg Gln Ile Thr Gln Val Tyr
145                 150                 155                 160

Gly Phe Tyr Asp Glu Cys Gln Thr Lys Tyr Gly Asn Ala Asn Ala Trp
                165                 170                 175

Arg Tyr Cys Thr Lys Val Phe Asp Met Leu Thr Val Ala Ala Leu Ile
            180                 185                 190

Asp Glu Gln Ile Leu Cys Val His Gly Gly Leu Ser Pro Asp Ile Lys
            195                 200                 205

Thr Leu Asp Gln Ile Arg Thr Ile Glu Arg Asn Gln Glu Ile Pro His
210                 215                 220

Lys Gly Ala Phe Cys Asp Leu Val Trp Ser Asp Pro Glu Asp Val Asp
225                 230                 235                 240

Thr Trp Ala Ile Ser Pro Arg Gly Ala Gly Trp Leu Phe Gly Ala Lys
                245                 250                 255

Val Thr Asn Glu Phe Val His Ile Asn Asn Leu Lys Leu Ile Cys Arg
            260                 265                 270

Ala His Gln Leu Val His Glu Gly Tyr Lys Phe Met Phe Asp Glu Lys
            275                 280                 285

Leu Val Thr Val Trp Ser Ala Pro Asn Tyr Cys Tyr Arg Cys Gly Asn
290                 295                 300

Ile Ala Ser Ile Met Val Phe Lys Asp Val Asn Thr Arg Glu Pro Lys
305                 310                 315                 320

Leu Phe Arg Ala Val Pro Asp Ser Glu Arg Val Ile Pro Pro Arg Thr
                325                 330                 335

Thr Thr Pro Tyr Phe Leu
            340

<210> SEQ ID NO 39
<211> LENGTH: 4367
<212> TYPE: DNA
<213> ORGANISM: Homo sapiens

<400> SEQUENCE: 39
gaagcgggct ctcttggggc ctgcagtcgg ggttcagcca gagggggcgc cgggcgtacc      60
gacgtagcgg ggagaaacgg gtcgcgcttt aacggcgctg cgcaggcgcc actcacgggc     120
```

```
cggacgtgac gcagggaaag ttccggcttc ggcctccgcc gctgccgccg ccgctgctac    180
agccgccgcc gccgctgttg ccgcggcttg ttattcttaa aatggcgccg ctagacctgg    240
acaagtatgt ggaaatagcg cggctgtgca agtacctgcc agagaacgac ctgaaggtga    300
gccctatttg cgggctcgcc ccttccggct gtggggcgcc cgccggccgg cccttccttt    360
ctccaggacc cccgccggta tttcattttc ttcgttttct aaaggagcgg ctatgtgact    420
acgtttgtga cctcctctta gaagagtcaa atgttcagcc agtatcaaca ccagtaacag    480
tgtgtggaga tatccatgga cagttttatg acctttgtga actgttcaga actggaggtc    540
aggttcctga cacaaactac atatttatgg gtgattttgt agacagaggt tactatagtt    600
tggagacctt cacttacctt cttgcattaa aggctaaatg gcctgatcgt attacacttt    660
tgcgaggaaa tcatgagagt agacagataa cacaggtcta tggattttat gatgagtgcc    720
aaaccaaata tggaaatgct aatgcctgga gatactgtac caaagttttt gacatgctca    780
cagtagcagc tttaatagat gagcagattt tgtgtgtcca tggtggttta tctcctgata    840
tcaaaacact ggatcaaatt cgaaccatcg aacggaatca ggaaattcct cataaaggag    900
cattttgtga tctggtttgg tcagatcctg aagatgtgga tacctgggct atcagtcccc    960
gaggagcagg ttggcttttt ggagcaaagg tcacaaatga gtttgttcat atcaacaact   1020
taaaactcat ctgcagagca catcaactag tgcacgaagg ctataaattt atgtttgatg   1080
agaagctggt gacagtatgg tctgctccta attactgcta cgttgtgga aatattgctt   1140 cgatcatggt cttcaaagat gtaaatacaa gagaaccaaa gttattccgg gcagttccag   1200
attcagaacg tgttattcct cccagaacga caacgccata tttcctttga ggccttcgcc   1260
catcctgctg acccattttt ctgccctctt cttaccccaa ttttcttgta ttaccctcta   1320
caatatactt tttattgagc actttgctgc tgaaatgctg cctcttgcct ttttttttt   1380 aaattttaaa ttatctaaat ttattgtttg ttgtggtgtc tatagcaaag ttttctatc    1440 aattttcccc catcccatcc ccaccctgga ctcatttgag aagacttgag aaatgtctta   1500
atactcacac tgctgcatgt agctcttgct tatttactgg tctgggaaac aggatgtgtt   1560 tcctttttttt aaaagccaat tgacagatta cacctaaata ctcctccttt tgtatcattc   1620
agccttttgt tttagtttgg taagttttaa gaaatttcag cagcaaagtt gttattcagt   1680
gggcacgatg gactccaaat gcctcaagtt atgtatacct gtcccagatg taaacttcat   1740
tgtcctttgt tggatgatat tttaaatgga tataaaataa attggtctaa agggctgccc   1800
tccttgttgt gttttttaaat tttagttaaa aactgctaca gcttatgact ttgtacttta   1860
agataattgt attgatcttt tttcagattc cttgtatttt ttaataaagt aatcttaaat   1920
aaaactcaga taggttaagt gttagaaatt ttaaacagct tacattgtta gcgtaaagtt   1980 atctttttctt ttttcctaat cagagttctt gacccctttgg ttattgagtt taaaacttca   2040
attgaaattc aatagtattt atttttgaaa aaatcacta aactgtgcct aaagaacata   2100
actgccatat taatgttttg gtttatatcc tctatagtaa tagaaaaaca tttaatactt   2160
gtaatgctga tgtgttaatt tgataccagt tgagtagaat gtgatcaatc cagtttacaa   2220
tctatcatga gtattattaa ctaaaatcta tgtgcttttc aataggaatc attcttctct   2280
tgctgtaaca cttgacccta acttttagaa agtgttcatt tttaaactgc aactggaaag   2340
gttgaaaagt taggactctt gtatttgtga actgtaatct gaagcagatt atttaaagtg   2400
tagaaaaaga aacaagttct tctttttttgc aaaggtctgt gataccatat ttcagctttg   2460
tgtaagtaat ttgaatatcc aaagggttgt gatgatcagt tctgaatatg caactgtcca   2520
```

-continued

```
cttaataagg acaagtattc cagtatctct tatgactgta gtcataaatg atgttggaat    2580
gtacattttg tgaaatagtt ggtatcccct tactatgatt aattttttgtt attccaggaa    2640 atacttgtga agccagccaa ttaataaagc actttagcat ctgttcaggt agttttgaaa    2700
acccactttt cccttcagg  ataagaactt ccaggttacc taaaaatgca ataaaaatct    2760
ttatagtcta agcttcttgg catataattt ttcatcaggg ttttctttta ttaattgagc    2820
acaatactgt tttgatttaa ttttttttccc tcaaaccacc cagctcctta catagttttt    2880
aattatatag ctatatgaaa gaggtggcta agacatttgc tgcacacact tgaactaatg    2940
ttgggtcagt agcttcgtgt tactgccctg atcccagtgt aattcaggtg aaaggtatt    3000 tttatctcac agggatatgt agctatgtat tttactaatt gtgaaacact ggaaattaat    3060
gatgcagaca acttggtgtg gtctttgaac agctctctgc agtatttttt ttttcctgt    3120 taccataaat tgtatttaag tgcttgcttt ccacttaagt tgtactaata gaaccggtaa    3180
ctcccagccc tccctgtttg acactcctta gcttagattg atgtagttgt ttttgttatc    3240
cctataatgt gacttttatt tttaagtcat tgtgtactgc atttgtttgt cactagttgg    3300
gcacgtgcca ataatattct ctccattcct tatctgccat ctctgttttg cctgatttct    3360
cttcaactga ataatggctt tttgcatgga aaaaatagtt tttactatta gacgtgtaaa    3420
gggaagagag agctaatgta ttggactttg tgagcctaca aggaatattt tggatccctc    3480
caataaataa gggctatgta ctatatgtac tatatagagt tatcatgtgg tggaagatac    3540
ttgcaagtca tagatttatg ggcaggagga tttgttactc cctatatcta ggctgaatgt    3600
aaaatccctt atgttgtatc aatgggggta aaaactattt ttatttgcct atgatatact    3660
tggtttctaa taaagtgccc taggctctag tgagaactgt ctactttgaa ttgccattta    3720 ctcccttttcc tcctttggcc gatatgctct tggctagctt tttataagtt aatgtgtttc    3780
cccaaaaagt ttcactactt tatattcatt tgagtgtgat cctaaaacac ctggatcaac    3840
agtacatctc atatgcaatc tgcatcagct cctattctgt ctggatgtct agaactgttg    3900
gaagattttg acgtcttaag ccctaggttt tgctttggga ataaggtttt gaaatattgt    3960
tcattgcatt aagatttgtg tgtgtgtgct ttgtaagccc agaaccaggt tttggaaaat    4020
gcctgtactg tgaaagcaaa ttaggactct ttctgagcct ctttcattgt cagaaataga    4080
atcactttcc atcagcttcc aggaaattgt gtatctggag tcgaagagat ttgacatcaa    4140
gaatccagat ttttaaaatgt aattgttttt taaatgctaa tgtttgtaaa gcaccttcag    4200
ttcttcggat gaaaggtgct atattccctc agtgtaaatt aataaaaaga ttacaggaag    4260
tttgtcaaaa aattcaatgc atagtctgta gtatgtcctg acaagaagtt agcatttttat    4320 ataagaaatt aaaaaatgct tattcctcca aaaaaaaaaa aaaaaaa                 4367
```

<210> SEQ ID NO 40
<211> LENGTH: 271
<212> TYPE: PRT
<213> ORGANISM: Homo sapiens

<400> SEQUENCE: 40

Met Ala Ala Glu Glu Pro Gln Gln Gln Lys Gln Glu Pro Leu Gly Ser
1               5                   10                  15

Asp Ser Glu Gly Val Asn Cys Leu Ala Tyr Asp Glu Ala Ile Met Ala
                20                  25                  30

Gln Gln Asp Arg Ile Gln Gln Glu Ile Ala Val Gln Asn Pro Leu Val
            35                  40                  45

```
Ser Glu Arg Leu Glu Leu Ser Val Leu Tyr Lys Glu Tyr Ala Glu Asp
 50                  55                  60

Asp Asn Ile Tyr Gln Gln Lys Ile Lys Asp Leu His Lys Lys Tyr Ser
 65                  70                  75                  80

Tyr Ile Arg Lys Thr Arg Pro Asp Gly Asn Cys Phe Tyr Arg Ala Phe
                 85                  90                  95

Gly Phe Ser His Leu Glu Ala Leu Leu Asp Asp Ser Lys Glu Leu Gln
                100                 105                 110

Arg Phe Lys Ala Val Ser Ala Lys Ser Lys Glu Asp Leu Val Ser Gln
            115                 120                 125

Gly Phe Thr Glu Phe Thr Ile Glu Asp Phe His Asn Thr Phe Met Asp
130                 135                 140

Leu Ile Glu Gln Val Glu Lys Gln Thr Ser Val Ala Asp Leu Leu Ala
145                 150                 155                 160

Ser Phe Asn Asp Gln Ser Thr Ser Asp Tyr Leu Val Val Tyr Leu Arg
                165                 170                 175

Leu Leu Thr Ser Gly Tyr Leu Gln Arg Glu Ser Lys Phe Phe Glu His
            180                 185                 190

Phe Ile Glu Gly Gly Arg Thr Val Lys Glu Phe Cys Gln Gln Glu Val
        195                 200                 205

Glu Pro Met Cys Lys Glu Ser Asp His Ile His Ile Ala Leu Ala
210                 215                 220

Gln Ala Leu Ser Val Ser Ile Gln Val Glu Tyr Met Asp Arg Gly Glu
225                 230                 235                 240

Gly Gly Thr Thr Asn Pro His Ile Phe Pro Glu Gly Ser Glu Pro Lys
                245                 250                 255

Val Tyr Leu Leu Tyr Arg Pro Gly His Tyr Asp Ile Leu Tyr Lys
            260                 265                 270

<210> SEQ ID NO 41
<211> LENGTH: 2310
<212> TYPE: DNA
<213> ORGANISM: Homo sapiens

<400> SEQUENCE: 41
agttaggtca tgaggctttg gccttgacac caagggatgc tgtctccttg ccggaagcag    60
ctcaccaaag ccggcagaga acccaggttc cgtggggcca cgatgtgggg ctccgcgggc   120
gccccggcgc tggccgactt cctgtctcct gggtcagatg ctgctccgca ctgcagctat   180
ggtcgcatgc agtgcctgcc gaagcccgca gcaggaatgc tgccttcggt gattttaatt   240 tcactttttct acttctctca ataacaaaat ccgcgtttca aactccaggg aaaagaaaac   300
ggaattggct ccaggaggat ctgcaatcac caccggaac tttgggaggc tgggaagatg   360
gagccaaacc aatgtgtggg gtggaggtgc ggatctgggg cggccggcct ctcctacagg   420
tctcaggtcc gcaggcctgg cgtgccagca cctgccacgg gactggaagc ccattccttg   480
acaacgccta aggggatccc gttgctaggg ctgttgccaa ggcggggcaa cgaggagggg   540
ctcgcttccg ggaggacggc aattggcaac ccggaagcgg tcggtagtgc ggcgctgttt   600
aaagatggcg gcggaggaac ctcagcagca gaagcaggag ccgctgggca gcgactccga   660
aggtgttaac tgtctggcct atgatgaagc catcatggct cagcaggacc gaattcagca   720
agagattgct gtgcagaacc ctctggtgtc agacggctg gagctctcgg tcctatacaa   780
ggagtatgct gaagatgaca catctctatca acagaagatc aaggacctcc acaaaaagta   840
```

-continued

| | |
|---|---|
| ctcgtacatc cgcaagacca ggcctgacgg caactgtttc tatcgggctt tcggattctc | 900 |
| ccacttggag gcactgctgg atgacagcaa ggagttgcag cggttcaagg ctgtgtctgc | 960 |
| caagagcaag gaagacctgg tgtcccaggg cttcactgaa ttcacaattg aggatttcca | 1020 |
| caacacgttc atggacctga ttgagcaggt ggagaagcag acctctgtcg ccgacctgct | 1080 |
| ggcctccttc aatgaccaga gcacctccga ctaccttgtg gtctacctgc ggctgctcac | 1140 |
| ctcgggctac ctgcagcgcg agagcaagtt cttcgagcac ttcatcgagg tggacggac | 1200 |
| tgtcaaggag ttctgccagc aggaggtgga gcccatgtgc aaggagagcg accacatcca | 1260 |
| catcattgcg ctggcccagg ccctcagcgt gtccatccag gtggagtaca tggaccgcgg | 1320 |
| cgagggcggc accaccaatc cgcacatctt ccctgagggc tccgagccca aggtctacct | 1380 |
| tctctaccgg cctggacact acgatatcct ctacaaatag gctggctcc agcccgctgc | 1440 |
| tgccctgctg ccccccctctg ccaggcgcta gacatgtaca gaggtttttc tgtggttgta | 1500 |
| aatggtccta tttcaccccc ttcttcctgt cacatgaccc cccccatgt tttattaaag | 1560 |
| ggggtgctgg tggtgagccg tgtgtgcgtg tccctgctct gctgcccgcc tggctgctct | 1620 |
| gtctgctgcc ccctcccccc aggtgggtcc ccctgcttttt cacctatcta ctcctgagct | 1680 |
| tccccaacag gagcaggttt gaggggccag gcctcttgga ggcccctcct gcttcgttgg | 1740 |
| gttctgcttc cttcccttct tagctggctc aggggcttct atgggatcct ggaagttcct | 1800 |
| tagggacttg cccagggtcc cagggccacc cacacttcat ctgctccctc ataggcccca | 1860 |
| cctccacgtc ccggctgggc cccagacccc agcttcctgc cctccaccgg gagtctgcat | 1920 |
| ggttgggagt cctgggtgga ggggcctttg tgaggctgga cccggctcag gcaggtgga | 1980 |
| ggagctgggc ctcccacagg gtgcccgggc agtgccatcc tggtggggga gggcagcctt | 2040 |
| caaacgtgtg gggtctacag tcctcaggtc taggcagggc tgccggttct ccacctcccc | 2100 |
| atccgcccca ggcccctgc ctgtgcctgc cttgcacccc ctctgcttgg gccacggtgt | 2160 |
| ctctgcattg cctgcctttt tgccttcacc tcttttcttc cccgcccct gcacattcgg | 2220 |
| ggtctcagcc cccaggctgt gagctccttg ggggcaggcc ctcaataaat gtgaactgct | 2280 |
| gctgccgcct ctgcaaaaaa aaaaaaaaaa | 2310 |

<210> SEQ ID NO 42
<211> LENGTH: 462
<212> TYPE: PRT
<213> ORGANISM: Homo sapiens

<400> SEQUENCE: 42

Met Ala Ser Asn Ser Ser Ser Cys Pro Thr Pro Gly Gly Gly His Leu
1               5                   10                  15

Asn Gly Tyr Pro Val Pro Pro Tyr Ala Phe Phe Phe Pro Pro Met Leu
            20                  25                  30

Gly Gly Leu Ser Pro Pro Gly Ala Leu Thr Thr Leu Gln His Gln Leu
        35                  40                  45

Pro Val Ser Gly Tyr Ser Thr Pro Ser Pro Ala Thr Ile Glu Thr Gln
    50                  55                  60

Ser Ser Ser Ser Glu Glu Ile Val Pro Ser Pro Pro Ser Pro Pro Pro
65                  70                  75                  80

Leu Pro Arg Ile Tyr Lys Pro Cys Phe Val Cys Gln Asp Lys Ser Ser
                85                  90                  95

Gly Tyr His Tyr Gly Val Ser Ala Cys Glu Gly Cys Lys Gly Phe Phe
            100                 105                 110

```
Arg Arg Ser Ile Gln Lys Asn Met Val Tyr Thr Cys His Arg Asp Lys
            115                 120                 125

Asn Cys Ile Ile Asn Lys Val Thr Arg Asn Arg Cys Gln Tyr Cys Arg
130                 135                 140

Leu Gln Lys Cys Phe Glu Val Gly Met Ser Lys Glu Ser Val Arg Asn
145                 150                 155                 160

Asp Arg Asn Lys Lys Lys Glu Val Pro Lys Pro Glu Cys Ser Glu
            165                 170                 175

Ser Tyr Thr Leu Thr Pro Glu Val Gly Leu Ile Glu Lys Val Arg
            180                 185                 190

Lys Ala His Gln Glu Thr Phe Pro Ala Leu Cys Gln Leu Gly Lys Tyr
            195                 200                 205

Thr Thr Asn Asn Ser Ser Glu Gln Arg Val Ser Leu Asp Ile Asp Leu
210                 215                 220

Trp Asp Lys Phe Ser Glu Leu Ser Thr Lys Cys Ile Ile Lys Thr Val
225                 230                 235                 240

Glu Phe Ala Lys Gln Leu Pro Gly Phe Thr Thr Leu Thr Ile Ala Asp
            245                 250                 255

Gln Ile Thr Leu Leu Lys Ala Ala Cys Leu Asp Ile Leu Ile Leu Arg
            260                 265                 270

Ile Cys Thr Arg Tyr Thr Pro Glu Gln Asp Thr Met Thr Phe Ser Asp
            275                 280                 285

Gly Leu Thr Leu Asn Arg Thr Gln Met His Asn Ala Gly Phe Gly Pro
            290                 295                 300

Leu Thr Asp Leu Val Phe Ala Phe Ala Asn Gln Leu Leu Pro Leu Glu
305                 310                 315                 320

Met Asp Asp Ala Glu Thr Gly Leu Leu Ser Ala Ile Cys Leu Ile Cys
            325                 330                 335

Gly Asp Arg Gln Asp Leu Glu Gln Pro Asp Arg Val Asp Met Leu Gln
            340                 345                 350

Glu Pro Leu Leu Glu Ala Leu Lys Val Tyr Val Arg Lys Arg Pro
            355                 360                 365

Ser Arg Pro His Met Phe Pro Lys Met Leu Met Lys Ile Thr Asp Leu
370                 375                 380

Arg Ser Ile Ser Ala Lys Gly Ala Glu Arg Val Ile Thr Leu Lys Met
385                 390                 395                 400

Glu Ile Pro Gly Ser Met Pro Pro Leu Ile Gln Glu Met Leu Glu Asn
                405                 410                 415

Ser Glu Gly Leu Asp Thr Leu Ser Gly Gln Pro Gly Gly Gly Arg
            420                 425                 430

Asp Gly Gly Leu Ala Pro Pro Gly Ser Cys Ser Pro Ser Leu
            435                 440                 445

Ser Pro Ser Ser Asn Arg Ser Ser Pro Ala Thr His Ser Pro
450                 455                 460

<210> SEQ ID NO 43
<211> LENGTH: 3301
<212> TYPE: DNA
<213> ORGANISM: Homo sapiens

<400> SEQUENCE: 43
gtgcctcttg cagcagccta acccagaagc aggggggaat cctgaatcga gctgagaggg      60
cttccccggt tctcctggga accccatcgg cccctgcca gcacacacct gagcagcatc      120
acaggacatg gcccctcag ccacctagct ggggcccatc taggagtggc atcttttttg      180
```

-continued

```
gtgccctgaa ggccagctct ggaccttccc aggaaaagtg ccagctcaca gaactgcttg    240
accaaaggac cggctcttga gacatccccc aacccacctg gccccagct agggtggggg    300 ctccaggaga ctgagattag cctgccctct tggacagca gctccaggac agggcgggtg    360
ggctgaccac ccaaacccca tctgggccca ggccccatgc cccgaggagg ggtggtctga    420
agcccaccag agcccctgc cagactgtct gcctcccttc tgactgtggc cgcttggcat    480
ggccagcaac agcagctcct gcccgacacc tggggcggg cacctcaatg ggtacccggt    540
gcctccctac gccttcttct tcccccctat gctgggtgga ctctccccgc caggcgctct    600
gaccactctc cagcaccagc ttccagttag tggatatagc acaccatccc cagccaccat    660
tgagacccag agcagcagtt ctgaagagat agtgcccagc cctccctcgc cacccctct    720 accccgcatc tacaagcctt gctttgtctg tcaggacaag tcctcaggct accactatgg    780
ggtcagcgcc tgtgagggct gcaagggctt cttccgccgc agcatccaga gaacatggt    840 gtacacgtgt caccgggaca gaactgcat catcaacaag gtgacccgga accgctgcca    900
gtactgccga ctgcagaagt gctttgaagt gggcatgtcc aaggagtctg tgagaaacga    960
ccgaaacaag aagaagaagg aggtgcccaa gcccgagtgc tctgagagct acacgctgac    1020
gccggaggtg ggggagctca ttgagaaggt gcgcaaagcg caccaggaaa ccttccctgc    1080
cctctgccag ctgggcaaat acactacgaa caacagctca gaacaacgtg tctctctgga    1140
cattgacctc tgggacaagt tcagtgaact ctccaccaag tgcatcatta agactgtgga    1200
gttcgccaag cagctgcccg gcttcaccac cctcaccatc gccgaccaga tcaccctcct    1260
caaggctgcc tgcctggaca tcctgatcct gcggatctgc acgcggtaca cgcccgagca    1320
ggacaccatg accttctcgg acgggctgac cctgaaccgg acccagatgc acaacgctgg    1380
cttcggcccc ctcaccgacc tggtctttgc cttcgccaac cagctgctgc ccctggagat    1440
ggatgatgcg gagacggggc tgctcagcgc catctgcctc atctgcggag accgccagga    1500
cctggagcag ccggaccggg tggacatgct gcaggagccg ctgctggagg cgctaaaggt    1560
ctacgtgcgg aagcggaggc ccagccgccc ccacatgttc cccaagatgc taatgaagat    1620
tactgacctg cgaagcatca gcgccaaggg ggctgagcgg gtgatcacgc tgaagatgga    1680
gatcccgggc tccatgccgc ctctcatcca ggaaatgttg gagaactcag agggctggga    1740
cactctgagc ggacagccgg ggggtggggg cgggacggg ggtggcctgg ccccccgcc    1800 aggcagctgt agccccagcc tcagccccag ctccaacaga agcagcccgg ccacccactc    1860
cccgtgaccg cccacgccac atggacacag ccctcgccct ccgccccggc ttttctctgc    1920
ctttctaccg accatgtgac cccgcaccag ccctgccccc acctgccctc ccgggcagta    1980
ctggggacct tccctggggg acgggagggg aggaggcagc gactccttgg acagaggcct    2040
gggccctcag tggactgcct gctcccacag cctgggctga cgtcagaggc cgaggccagg    2100
aactgagtga ggccctggt cctgggtctc aggatgggtc ctgggggcct cgtgttcatc    2160
aagacacccc tctgcccagc tcaccacatc ttcatcacca gcaaacgcca ggacttggct    2220 ccccatcct cagaactcac aagccattgc tccccagctg ggaacctca acctccccc    2280 tgcctcggtt ggtgacagag ggggtgggac agggggcggg ggttcccct gtacatacccc    2340 tgccatacca accccaggta ttaattctcg ctggttttgt ttttatttta attttttgt    2400 tttgattttt ttaataagaa ttttcatttt aagcacattt atactgaagg aatttgtgct    2460
gtgtattggg gggagctgga tccagagctg gaggggtgg gtccggggga gggagtggct    2520
```

-continued

```
cggaaggggc ccccactctc ctttcatgtc cctgtgcccc ccagttctcc tcctcagcct    2580
tttcctcctc agtttctctc ttaaaactgt gaagtactaa cttccaagg cctgccttcc    2640 cctccctccc actggagaag ccgccagccc ctttctccct ctgcctgacc actgggtgtg    2700
gacggtgtgg ggcagccctg aaaggacagg ctcctggcct tggcacttgc ctgcacccac    2760
catgaggcat ggagcagggc agagcaaggg ccccgggaca gagttttccc agacctggct    2820
cctcggcaga gctgcctccc gtcagggccc acatcatcta ggctcccccag ccccactgt    2880 gaaggggctg gccaggggcc cgagctgccc ccaccccgg cctcagccac cagcaccccc    2940
atagggcccc cagacaccac acacatgcgc gtgcgcacac acacaaacac acacacactg    3000
gacagtagat gggccgacac acacttggcc cgagttcctc catttccctg gcctgccccc    3060 caccccaac ctgtcccacc cccgtgcccc ctccttaccc cgcaggacgg gcctacaggg    3120
gggtctcccc tcacccctgc accccagct gggggagctg gctctgcccc gacctccttc    3180
accaggggtt ggggcccctt ccctggagc ccgtgggtgc acctgttact gttgggcttt    3240
ccactgagat ctactggata aagaataaag ttctatttat tctaaaaaaa aaaaaaaaa    3300 a                                                                   3301
```

<210> SEQ ID NO 44
<211> LENGTH: 132
<212> TYPE: PRT
<213> ORGANISM: Homo sapiens

<400> SEQUENCE: 44

```
Met Asp Val Phe Gln Glu Gly Leu Ala Met Val Val Gln Asp Pro Leu
1               5                   10                  15

Leu Cys Asp Leu Pro Ile Gln Val Thr Leu Glu Glu Val Asn Ser Gln
                20                  25                  30

Ile Ala Leu Glu Tyr Gly Gln Ala Met Thr Val Arg Val Cys Lys Met
            35                  40                  45

Asp Gly Glu Val Met Pro Val Val Val Gln Ser Ala Thr Val Leu
        50                  55                  60

Asp Leu Lys Lys Ala Ile Gln Arg Tyr Val Gln Leu Lys Gln Glu Arg
65                  70                  75                  80

Glu Gly Gly Ile Gln His Ile Ser Trp Ser Tyr Val Trp Arg Thr Tyr
                85                  90                  95

His Leu Thr Ser Ala Gly Glu Lys Leu Thr Glu Asp Arg Lys Lys Leu
                100                 105                 110

Arg Asp Tyr Gly Ile Arg Asn Arg Asp Glu Val Ser Phe Ile Lys Lys
            115                 120                 125

Leu Arg Gln Lys
        130
```

<210> SEQ ID NO 45
<211> LENGTH: 1103
<212> TYPE: DNA
<213> ORGANISM: Homo sapiens

<400> SEQUENCE: 45

```
cagttcctgc gcgtgcgcgc ttggcctccc tagtgcgggc tggcagtgcg ggcagagccc      60
ggctgagagg ggcggccctg gaggagacgg aggccgcggg tgggcccgag cgcaagagg     120 aagatgagga cgaagaagag cgcgctgccgc actccgaggc catggacgtg ttccaggag     180 gtctggctat ggtggtgcag gacccgctgc tctgcgatct gccgatccag gttactctgg     240
```

```
aagaagtcaa ctcccaaata gccctagaat acggccaggc aatgacggtc cgagtgtgca    300
agatggatgg agaagtaatg cccgtggttg tagtgcagag tgccacagtc ctggacctga    360
agaaggccat ccagagatac gtgcagctca agcaggagcg tgaaggggc attcagcaca    420 tcagctggtc ctacgtgtgg aggacgtacc atctgacctc tgcaggagag aaactcacgg    480
aagacagaaa gaagctccga gactacggca tccggaatcg agacgaggtt tccttcatca    540
aaaagctgag gcaaaagtga gcctccagac aggacaaccc tcttcatcac tggtggctga    600
gctttttccc agcaggaatg ggtcctcgaa tcatcgtgcc tctttcacag aaaggacgtt    660
gtggtggcct cacccccaggc atgcccaaca gtaactgtca gcataaacct ggggccctc    720 aggactagga cagggtgagc cagtgctccc tcctttcatg tacttggcct gagactgacc    780
tctccctagg tccaaatgcc ctagtcacat ggcagaccca cggcctggcc cactgtataa    840
aataaacctg tttgcttctt agtttgaaaa gtagaaagcc acagtaacct gggtagcaaa    900
gactgagatt gccccatcac agaggtgagt taagggggaga gaattggtac aggcgagtcc    960
tatagtccaa gatggcgcca caccaccaaa gccttgaggc cacaccactc cccaaaccac   1020
acaactgtgt taccatgatc tccacagcaa ggaggaaata aaagcagagc ggctttaggg   1080
tttgcaaaaa aaaaaaaaaa aaa                                            1103
```

<210> SEQ ID NO 46  
<211> LENGTH: 374  
<212> TYPE: PRT  
<213> ORGANISM: Homo sapiens

<400> SEQUENCE: 46

```
Met Ser Arg Val Pro Ser Pro Pro Pro Ala Glu Met Ser Ser Gly
1               5                   10                  15

Pro Val Ala Glu Ser Trp Cys Tyr Thr Gln Ile Lys Val Val Lys Phe
                20                  25                  30

Ser Tyr Met Trp Thr Ile Asn Asn Phe Ser Phe Cys Arg Glu Glu Met
            35                  40                  45

Gly Glu Val Ile Lys Ser Ser Thr Phe Ser Ser Gly Ala Asn Asp Lys
        50                  55                  60

Leu Lys Trp Cys Leu Arg Val Asn Pro Lys Gly Leu Asp Glu Glu Ser
65                  70                  75                  80

Lys Asp Tyr Leu Ser Leu Tyr Leu Leu Leu Val Ser Cys Pro Lys Ser
                85                  90                  95

Glu Val Arg Ala Lys Phe Lys Phe Ser Ile Leu Asn Ala Lys Gly Glu
            100                 105                 110

Glu Thr Lys Ala Met Glu Ser Gln Arg Ala Tyr Arg Phe Val Gln Gly
        115                 120                 125

Lys Asp Trp Gly Phe Lys Lys Phe Ile Arg Arg Asp Phe Leu Leu Asp
    130                 135                 140

Glu Ala Asn Gly Leu Leu Pro Asp Asp Lys Leu Thr Leu Phe Cys Glu
145                 150                 155                 160

Val Ser Val Val Gln Asp Ser Val Asn Ile Ser Gly Gln Asn Thr Met
                165                 170                 175

Asn Met Val Lys Val Pro Glu Cys Arg Leu Ala Asp Glu Leu Gly Gly
            180                 185                 190

Leu Trp Glu Asn Ser Arg Phe Thr Asp Cys Cys Leu Cys Val Ala Gly
        195                 200                 205

Gln Glu Phe Gln Ala His Lys Ala Ile Leu Ala Ala Arg Ser Pro Val
    210                 215                 220
```

```
Phe Ser Ala Met Phe Glu His Glu Met Glu Ser Lys Lys Asn Arg
225                 230                 235                 240

Val Glu Ile Asn Asp Val Glu Pro Glu Val Phe Lys Glu Met Met Cys
            245                 250                 255

Phe Ile Tyr Thr Gly Lys Ala Pro Asn Leu Asp Lys Met Ala Asp Asp
        260                 265                 270

Leu Leu Ala Ala Ala Asp Lys Tyr Ala Leu Glu Arg Leu Lys Val Met
            275                 280                 285

Cys Glu Asp Ala Leu Cys Ser Asn Leu Ser Val Glu Asn Ala Ala Glu
        290                 295                 300

Ile Leu Ile Leu Ala Asp Leu His Ser Ala Asp Gln Leu Lys Thr Gln
305                 310                 315                 320

Ala Val Asp Phe Ile Asn Tyr His Ala Ser Asp Val Leu Glu Thr Ser
                325                 330                 335

Gly Trp Lys Ser Met Val Val Ser His Pro His Leu Val Ala Glu Ala
            340                 345                 350

Tyr Arg Ser Leu Ala Ser Ala Gln Cys Pro Phe Leu Gly Pro Pro Arg
        355                 360                 365

Lys Arg Leu Lys Gln Ser
        370
```

<210> SEQ ID NO 47
<211> LENGTH: 3105
<212> TYPE: DNA
<213> ORGANISM: Homo sapiens

<400> SEQUENCE: 47

```
ggggaggagg ccgcgcgggg tggggtctgg cggtacgcgc tggctgcgtc gacgtgctga      60
cgccatgacg ccccggctgg tgtgtgtcgg tgtgtatgtg tgtgtgtgag tgtgcgcgct     120
ccgagtgtgt gtgtatttgt gtatcggcgg tcccgcaggt cccggatgtt gcggacagta     180
tgaggcaagc gcaggggggac ggggaccagc agctgtcgcc gccgctctca gatcgagtct     240
tgctctgtca cccaggctgg agtgcagtgg cgcgatctca gctcactgcc acctttgcct     300
cctgggttca agcgattctt ctgcctcagc ctcccgagta gctgggatta caggctctgg     360
gaaccaccct tctactttct gtctctagga atttcactac tctagggtga gagggaaca     420
gaaatctttg ccccctgact ttggaaatct cgtttaacct tcaaactggc gatgtcaagg     480
gttccaagtc ctccacctcc ggcagaaatg tcgagtggcc ccgtagctga gagttggtgc     540
tacacacaga tcaaggtagt gaaattctcc tacatgtgga ccatcaataa ctttagcttt     600
tgccgggagg aaatgggtga agtcattaaa agttctacat tttcatcagg agcaaatgat     660
aaactgaaat ggtgtttgcg agtaaacccc aaagggttag atgaagaaag caaagattac     720
ctgtcacttt acctgttact ggtcagctgt ccaaagagtg aagttcgggc aaaattcaaa     780
ttctccatcc tgaatgccaa gggagaagaa accaaagcta tggagagtca acgggcatat     840
aggtttgtgc aaggcaaaga ctggggattc aagaaattca tccgtagaga ttttctttg     900
gatgaggcca acgggcttct ccctgatgac aagcttaccc tcttctgcga ggtgagtgtt     960
gtgcaagatt ctgtcaacat ttctggccag ataccatga acatggtaaa ggttcctgag    1020
tgccggctgg cagatgagtt aggaggactg tgggagaatt cccggttcac agactgctgc    1080
ttgtgtgttg ccggccagga attccaggct cacaaggcta tcttagcagc tcgttctccg    1140
gttttagtg ccatgtttga acatgaaatg gaggagagca aaaagaatcg agttgaaatc    1200
```

```
aatgatgtgg agcctgaagt tttttaaggaa atgatgtgct tcatttacac ggggaaggct    1260
ccaaacctcg acaaaatggc tgatgatttg ctggcagctg ctgacaagta tgccctggag    1320
cgcttaaagg tcatgtgtga ggatgccctc tgcagtaacc tgtccgtgga gaacgctgca    1380
gaaattctca tcctggccga cctccacagt gcagatcagt tgaaaactca ggcagtggat    1440
ttcatcaact atcatgcttc ggatgtcttg gagacctctg ggtggaagtc aatggtggtg    1500
tcacatcccc acttggtggc tgaggcatac cgctctctgg cttcagcaca gtgcccttt    1560
ctgggacccc cacgcaaacg cctgaagcaa tcctaagatc ctgcttgttg taagactccg    1620
tttaatttcc agaagcagca gccactgttg ctgccactga ccaccaggta gacagcgcaa    1680
tctgtggagc ttttactctg ttgtgagggg aagagactgc attgtggccc cagacttta    1740
aaacagcact aaataacttg ggggaaacgg ggggagggaa aatgaaatga aaccctgtt    1800
gctgcgtcac tgtgttccct ttggcctggc tgagtttgat actgtgggga ttcagtttag    1860
gcgctggccc gaggatatcc cagcggtggt acttcggaga cacctgtctg catctgactg    1920
agcagaacaa atcgtcaggt gcctggagca aaaaggaaaa aaaaaaaga aaggacattg    1980
agttttaaca aagggaaaa ggaaagaaga aaagattttt gcagaatttc tcaaaaatca    2040
gtttgtggat tccagtagta tttatattga gagaaacaaa ttttagtcct tctaactgtg    2100
ctaaaacttg gatatttgtg aaaactcctt accaccatac aagcatcaga agagctctct    2160
tgttgttagc acttattgtt tgcaagaaca gaatacatcc ttttatcctt ttatgaaaaa    2220
tgacaagtga aggcaaaagg ggaaggttat ttgatctgga agatgagtgt ctgatgtgg    2280
tggcttttgc aaaaatcttt attggtgttg aaaactggaa aaaataactc atccagaatt    2340
catattgtct tgacaagaac tatggttctc tgttttaga tattgtggaa aatgttttg    2400
ggcattttc tctgatttta tttcttctcc cccacccctt tttctaaaaa acaaacaaaa    2460
aaaaaacac acaaaacaaa aacagaacaa aagaagagag aaggaaattt tatcaattaa    2520
aaatgctgtg tgataaaatc ccagcccaga ttgctcagct gtttgtacct gacttgccgc    2580
ctgcatagga gccagttctg ttccttctga ctagcccctc ttcctccagg ggagaacttc    2640
caaatgttaa tttttttttt tttgaaaata taaataatta ctattttgta ctgtgtggta    2700
tctctggtct tttgtttcac tcacctgcct tgtctcttgg gtctgagtcc cttgcttaag    2760
ggattttgaa gtcctagttt tcagcttgca gagattatgt ctgaaatgcc taatgagtcg    2820
cagggatttg ttgagactcc gtaatctcaa gttctctttg tgagctatca gcatctgcca    2880
gtctcttgtc ctccctgagt atctcacagt ccatatcctg atgagggatc aggcccctac    2940
ctctgccaag gcaagtaatg gtagtgggct tttaaactgc cccccgtatg ttttaagacc    3000
taatccccac ctcccttctt ctaactaaat ataaaaagat ccaggggaca taaatgtgga    3060
gattaaataa agggaaatta ttgtctctaa aaaaaaaaa aaaaa             3105
```

<210> SEQ ID NO 48
<211> LENGTH: 136
<212> TYPE: PRT
<213> ORGANISM: Homo sapiens

<400> SEQUENCE: 48

Met Val Leu Leu Glu Ser Glu Gln Phe Leu Thr Glu Leu Thr Arg Leu
1               5                   10                  15

Phe Gln Lys Cys Arg Thr Ser Gly Ser Val Tyr Ile Thr Leu Lys Lys
            20                  25                  30

Tyr Asp Gly Arg Thr Lys Pro Ile Pro Lys Lys Gly Thr Val Glu Gly

```
                35                  40                  45
Phe Glu Pro Ala Asp Asn Lys Cys Leu Leu Arg Ala Thr Asp Gly Lys
        50                  55                  60

Lys Lys Ile Ser Thr Val Val Ser Ser Lys Glu Val Asn Lys Phe Gln
65                  70                  75                  80

Met Ala Tyr Ser Asn Leu Leu Arg Ala Asn Met Asp Gly Leu Lys Lys
                85                  90                  95

Arg Asp Lys Lys Asn Lys Thr Lys Thr Lys Ala Ala Ala Ala
            100                 105                 110

Ala Ala Ala Ala Pro Ala Ala Ala Thr Ala Pro Thr Thr Ala Ala
            115                 120                 125

Thr Thr Ala Ala Thr Ala Ala Gln
            130                 135

<210> SEQ ID NO 49
<211> LENGTH: 1140
<212> TYPE: DNA
<213> ORGANISM: Homo sapiens

<400> SEQUENCE: 49
agcggaagtc cgcccagcc taggccgaac ttccggctct cactgctagg ggcttaagcg      60
gagggagtcg agccagcgtc gccgcgatgg tgttgttgga gagcgagcag ttcctgacgg    120
agctgaccag acttttccag aagtgccgga cgtcgggcag cgtctatatc accttgaaga    180
agtatgacgg tcgaaccaaa cccattccaa gaagggtac tgtggagggc tttgagcccg    240
cagacaacaa gtgtctgtta agagctaccg atgggaagaa gaagatcagc actgtggtga    300
gctccaagga agtgaataag tttcagatgg cttattcaaa cctccttaga gctaacatgg    360
atgggctgaa gaagagagac aaaaagaaca aaactaagaa gaccaaagca gcagcagcag    420
cagcagcagc agcacctgcc gcagcagcaa cagcaccaac aacagcagca acaacagcag    480
caacagcagc acagtaaagg gcatacattt cctgctttca ccaattaacc actgaattgc    540 tatttttttcc ttttggccag atagctaggt ttctggttcc cccacagtag gtgttttcac    600
ataagattag ggtccttttg gaaagaatag ttgcagtgtt tataggatag ttgtggtaag    660
aatctagttt attttgcatt tggctaattg gtctgtgctg catggttata tactcctgga    720
ttatagatta aaagtctctg tagacatctc tgtgaagagc aagctatcat taaacatgtc    780
tgtttatcag cactgtctct ttattccttt cccaacccat tttaatagtt ctggcaataa    840
ctactaaatc tagaatgatg tgattaatga ataggcttta gctctataat atcttctagg    900
ttattagaat tgaaacctga cagtttata aaaagtcatg ttatctcatg agctgcttcc      960
cacctggctg tataatttta tcatcatggt tccccagttt cgatgagttc tcacagtcaa   1020
atgagagttt gtttaaccac cttaggagaa acatactaca aagtcatcaa gaataaaggt   1080
tccaaagtaa ttatgatttt tggtttcttt atgccctttg gtttggatat tttcatgtgc   1140

<210> SEQ ID NO 50
<211> LENGTH: 812
<212> TYPE: PRT
<213> ORGANISM: Homo sapiens

<400> SEQUENCE: 50

Met Gln Ala Lys Asn Lys Asp Ala Leu Gln Pro Ile Lys Glu Asp Arg
1               5                   10                  15

Thr Gly Lys Ala Gln Asp Asp Ala Phe Trp Leu Gln Ser Leu Ile Thr
            20                  25                  30
```

```
Asp Ala Phe His Asp Lys Gly Phe Gln Lys Ile Lys Glu Tyr Phe Gln
            35                  40                  45

Gln Lys Glu Ser His Phe Pro Gln Lys Tyr Asn Arg Leu Leu Leu Tyr
 50                  55                  60

Arg Leu Asp Arg Ser Ile Asn Lys Glu Leu Asp Lys Asn Glu Phe Gln
 65                  70                  75                  80

Ser Val Ser Leu Leu Leu Lys Cys Ile Gln Arg Phe Leu Val Asp Gly
                 85                  90                  95

Leu Lys Glu Asp Glu Pro Leu Leu Ile Arg Gln Gly Leu Ile Pro Lys
                100                 105                 110

Leu Val Ser Trp Phe Glu Arg Thr Thr Gly Ile Leu Thr Ser Glu Gly
            115                 120                 125

Leu Ala Ser Asp Thr Ser Leu Ile Cys Val Ile Glu Asp Phe Phe Asp
            130                 135                 140

Thr Ala Leu Ile Ile Ser Arg Ser Ser Ser Glu Gly Lys Ile Gln Met
145                 150                 155                 160

Leu Asp Ser Phe Leu Leu Ser Leu Gly Phe Leu Val Thr Glu Lys Thr
                165                 170                 175

Val Asn His Leu Leu Gln Gln Glu Gly Leu Lys Thr Phe Asn Cys Ile
            180                 185                 190

Leu His Ala Val Pro Arg Glu Glu Arg Lys Lys Phe Pro Leu Ser Glu
            195                 200                 205

Gly Met Cys His Leu Met Lys Asp Leu Ala Arg Thr Leu Leu Thr Val
            210                 215                 220

Gly Asp Tyr Asp Gln Gln Val Ala Ile Ser Glu Ala Leu Cys Arg Leu
225                 230                 235                 240

Thr Ile Lys Lys Ser Arg Asp Glu Leu Val His Lys Trp Phe Asp Asp
                245                 250                 255

Glu Val Ile Ala Glu Ala Phe Lys Glu Ile Lys Asp Arg Glu Phe Glu
            260                 265                 270

Thr Asp Ser Arg Arg Phe Leu Asn His Leu Asn Asn Arg Leu Gly Asp
            275                 280                 285

Gln Arg Arg Val Tyr Ser Phe Pro Cys Ile Ala Ala Phe Ala Asp Glu
            290                 295                 300

His Glu Met Arg Lys Pro Ala Asp Glu Lys Leu Glu Lys Phe Trp Ile
305                 310                 315                 320

Asp Phe Asn Leu Gly Ser Gln Ser Val Thr Phe Tyr Ile Asp Asn Ala
                325                 330                 335

Glu Asn Thr Leu Trp Asp Ser Val Thr Leu Pro Lys Glu Ala Val Met
            340                 345                 350

Asn Phe Ser Ile Thr Glu Thr Glu Lys Ile Lys Ile Phe Ile Ile Tyr
            355                 360                 365

Leu Lys Lys Pro Met Ile Ile Ser Tyr Lys Glu Val Met Lys Ile Glu
            370                 375                 380

Ile His Phe Asp Leu Gln Phe Asn Ile Ser Gln Val Ser Ile Gln Ala
385                 390                 395                 400

Leu Gly Glu Asp Lys Gln Met Leu Pro Asp Gln Thr Lys Ile Ser Ser
                405                 410                 415

Glu Leu Phe Ser Lys Ser Asp Lys Glu Asp Arg Glu Ser Pro Ser Gly
            420                 425                 430

Leu Glu Arg Glu Thr Glu Gln Ala Glu Glu Ser Thr Asn Met Val Glu
            435                 440                 445
```

```
Phe Met Ser Ala Glu Asp Asp Arg Cys Leu Ile Thr Leu His Leu Asn
450                 455                 460

Asp Gln Ser Glu Pro Pro Val Ile Gly Glu Pro Ala Ser Asp Ser His
465                 470                 475                 480

Leu Gln Pro Val Pro Pro Phe Gly Val Pro Asp Phe Pro Gln Gln Pro
            485                 490                 495

Lys Ser His Tyr Arg Lys His Leu Phe Ser Glu Ser Asn Gln Asp Ser
            500                 505                 510

Ser Thr Ser Glu Leu Ser Trp Thr Ser Asn Gln Lys Lys Lys Ser Leu
        515                 520                 525

Lys Ser Tyr Ser Ser Arg Lys Lys Thr Arg Thr Arg Ser Asn Leu Arg
530                 535                 540

Ile Leu Pro Val Phe Pro Pro Ser Ser Gly Ser Gly His Glu Lys Asp
545                 550                 555                 560

Gln Ala Lys Leu Leu Ser Pro Ser Glu Lys Glu Ile Pro Glu Gln Asn
            565                 570                 575

Asn Thr Thr Ser Pro Lys Thr Ser Glu Gln Lys Phe Gln Asp Ser Phe
            580                 585                 590

Ala Phe Leu Thr Ala Glu Asp Ser Ala Gln Lys Thr Glu Leu Gln Asp
        595                 600                 605

Pro His Ser Leu Ser Glu Leu Ser Ser Leu Lys His Ser Glu Asp Glu
610                 615                 620

Glu Lys Pro Lys Ile Val Asn Gln Glu Ser Leu Thr Glu Ser Thr Ser
625                 630                 635                 640

Leu Lys His Lys Leu Arg Asn Leu Glu Asp Lys Asp Ile Pro Glu Gly
            645                 650                 655

Ser Phe Ala Lys Ser Gln Gln Ser Arg Leu Glu Glu Glu Val Ala Pro
            660                 665                 670

Gly Ser Pro Phe Ser Ile Thr Glu Glu Arg Glu Leu Pro Glu Gly Ile
        675                 680                 685

Ser Thr Ser Ser Leu Glu Val Val Pro Glu Asn Leu Asn Gly Ser Ala
690                 695                 700

Ile Leu Pro Thr Phe Glu Asn Phe Thr Lys Lys Arg Lys Arg Lys Tyr
705                 710                 715                 720

Glu Leu Arg Tyr Arg Lys Arg Pro Phe Asn Ser Glu Asn Ala Lys Lys
            725                 730                 735

Ala Pro Asp Cys Leu Ile Lys Leu Leu Asn Gln Met Gln Leu Phe Arg
            740                 745                 750

Leu Asn Lys Leu Glu Arg Phe Gln Asn Leu Val Leu Gly Glu Leu Ser
        755                 760                 765

Ser Leu Lys Gln Asp Ile Gln Ala Leu Glu His Leu Glu Lys Glu Val
770                 775                 780

Leu Glu Phe Trp Gly Lys Gln Ser Ala Asp Leu Gln Ser Phe Cys Asp
785                 790                 795                 800

Leu Gln Val Leu Arg Phe Asn Ser Thr Gln Thr Ser
            805                 810
```

<210> SEQ ID NO 51
<211> LENGTH: 3140
<212> TYPE: DNA
<213> ORGANISM: Homo sapiens

<400> SEQUENCE: 51
gagtgctggc tttctcttaa agggtgagtg cgtgcgccca ggtggtttgg cctgtgtgcg    60

```
ctagttactt gcacgcgctt cttgagtctc aaaacacaga gctctagtaa acttcagggg    120
gcggattcgt caattacagt tgcggaagaa gactcgactc gaagagcggt ccgccaccag    180
ggctctttcg gcagcgcccc cagcgggcgg ggctcttggg cggggaagca ggagagggcc    240
gaccgagcgc aacaaagctg agcggcgcgt cgcttcagga acgaagaagc ctcgttatgc    300
aagcgaaaaa caaagatgct tgcagccta ttaaggaaga caggactggg aaggcccagg    360
atgatgcttt ctggcttcaa tcacttatta cggatgcatt ccatgataaa ggatttcaga    420
aaataaaaga atactttcaa cagaaagaga gccactttcc tcaaaaatat aatcgtcttc    480
tattataccg tcttgacaga tcaataaata aggaactaga taaaaatgaa tttcagtctg    540
tgtcactgtt gctgaaatgt attcagcgat tcctcgtaga tggcctgaaa gaagatgaac    600
ctctgctaat tcggcaggga ctgatcccaa agctagtttc ctggtttgaa agaacaacag    660
gaattctgac ctcggaaggc ctagcctcag acacgtcgct gatttgtgtt atagaagatt    720
tctttgacac tgcattgatt atttccagga gtagtagtga agggaaaatt cagatgttgg    780
attccttcct acttagctta ggattcctgg tgacagaaaa gactgtaaat catttgcttc    840
aacaggaggg cttgaagact tttaactgca ttttgcacgc tgtccctcga agagagaa    900 aaaaattccc tttgtcagaa ggcatgtgtc atcttatgaa agaccttgca aggacactct    960
tgactgtggg tgattatgac cagcaggttg ctatttctga agcgctgtgt agactgacga   1020
ttaaaaaatc aagggatgaa cttgtccata aatggtttga tgatgaagtc attgctgaag   1080
cttccaaaga aattaaggat cgagaatttg agacggacag tagacgtttt ctcaatcacc   1140
taaacaacag acttggtgac caaagaaggg tgtattcatt tccgtgtatt gctgcttttg   1200
ctgatgagca tgagatgaga aaaccagcgg atgaaaaatt agagaaattt tggatcgact   1260
tcaacctagg aagtcagagt gtcactttt atatagacaa tgctgagaat actctatggg   1320
actcagtgac acttccgaag gaagcggtga tgaatttcag cataacagaa acggagaaga   1380
taaagatatt tatcatttac ctgaagaagc ccatgattat cagctacaaa gaagtcatga   1440
aaatagaaat ccattttgat ttgcagttca acatatcaca agtttccatt caagctttag   1500
gagaagacaa acagatgttg cctgaccaga cgaaaatctc ctcagaactt tttagtaagt   1560
ctgataaaga agacagggag agtcccagtg gccttgaaag agaaacagag caggcagaag   1620
aatccactaa catggtggag tttatgagtg ctgaagatga ccgctgccta ataactctcc   1680
acttaaatga ccaatctgag ccacctgtta ttggggaacc tgcctctgat agtcaccttc   1740
agccggtccc tccgttcggg gtccctgact tcccgcaaca acctaagtct cattacagaa   1800
aacatctctt ctctgagagt aatcaagatt caagtaccag tgaactatct tggaccagta   1860
accagaaaaa gaaatcccta aaatcatatt ccagtgaaaa aagacaaga accagaagta   1920 atttgagaat cttgccagtt ttccctccca gtagtggcag tggccatgag aaagaccaag   1980
ctaagcttct atcaccatca gagaaagaaa tacccgagca aaataacacc acatctccaa   2040
agacttctga acaaaaattc caagatagtt ttgcttttt gactgctgaa gattctgccc   2100
agaaaacaga gcttcaagat cctcactcac tgagtgagct ctcttccttg aagcactcag   2160
aagatgaaga aaaacctaag attgtgaacc aagaatcact aacagaaagt actagcttga   2220
aacataagct gagaaacttg gaagacaaag acataccaga aggtagtttt gctaagtcac   2280
aacaatcaag attggaagaa gaggttgctc cgggatcccc tttctcaata acagaagaaa   2340
gagagttgcc agaaggaatt tccacttcat ccctagaagt tgtgccagag aacttgaacg   2400
gttctgccat tctcccaacc tttgaaaact tcactaaaaa acggaaaaga aaatatgagc   2460
```

-continued

```
ttaggtacag aaagcgtccg tttaattcag aaaatgcaaa gaaagcaccg gattgcctaa    2520
taaaactttt aaaccagatg caactgttca gactcaataa actagagcgc tttcaaaatt    2580
tggttcttca agagttgagc agtcttaagc aggatattca ggccctggaa caccttgaga    2640
aggaggttct ggaattctgg gggaaacagt ctgctgatct gcaatctttc tgtgatctgc    2700
aagtgctgag gttcaattca actcagactt cataagaaag ccaaagcctg gttttatgat    2760
tgcagccctc agcctgggct gcctgaagac gaagagaaag agcaaggtta ttgttggctc    2820
aggccttgtt agccagactt cgtgctctgt acgcattcaa tttcctcccc tccaaacatc    2880
atccctggga actgctgagt tcagatagaa tatatgttgg tagtttgcag ttgggttatt    2940
atccatttgt tcataaaaat taacctttg tattaaaatt tggtcagata gtattaatag     3000
aaagttcagg atgttaaaca acttggagtg gtgttgcttt ttttttataa aagtaaaatg    3060 gactttttt tgtttgagaa atgtcttcaa gttttgtgtg aataaaacac tttagcagca    3120
tctgtataaa aaaaaaaaa                                                 3140
```

<210> SEQ ID NO 52
<211> LENGTH: 501
<212> TYPE: PRT
<213> ORGANISM: Homo sapiens

<400> SEQUENCE: 52

```
Met Ala Ala Ser Val Thr Pro Pro Gly Ser Leu Glu Leu Leu Gln
1               5                   10                  15

Pro Gly Phe Ser Lys Thr Leu Leu Gly Thr Lys Leu Glu Ala Lys Tyr
            20                  25                  30

Leu Cys Ser Ala Cys Arg Asn Val Leu Arg Arg Pro Phe Gln Ala Gln
        35                  40                  45

Cys Gly His Arg Tyr Cys Ser Phe Cys Leu Ala Ser Ile Leu Ser Ser
    50                  55                  60

Gly Pro Gln Asn Cys Ala Ala Cys Val His Glu Gly Ile Tyr Glu Glu
65                  70                  75                  80

Gly Ile Ser Ile Leu Glu Ser Ser Ala Phe Pro Asp Asn Ala Ala
                85                  90                  95

Arg Arg Glu Val Glu Ser Leu Pro Ala Val Cys Pro Ser Asp Gly Cys
            100                 105                 110

Thr Trp Lys Gly Thr Leu Lys Glu Tyr Glu Ser Cys His Glu Gly Arg
        115                 120                 125

Cys Pro Leu Met Leu Thr Glu Cys Pro Ala Cys Lys Gly Leu Val Arg
    130                 135                 140

Leu Gly Glu Lys Glu Arg His Leu Glu His Glu Cys Pro Glu Arg Ser
145                 150                 155                 160

Leu Ser Cys Arg His Cys Arg Ala Pro Cys Cys Gly Ala Asp Val Lys
                165                 170                 175

Ala His His Glu Val Cys Pro Lys Phe Pro Leu Thr Cys Asp Gly Cys
            180                 185                 190

Gly Lys Lys Lys Ile Pro Arg Glu Lys Phe Gln Asp His Val Lys Thr
        195                 200                 205

Cys Gly Lys Cys Arg Val Pro Cys Arg Phe His Ala Ile Gly Cys Leu
    210                 215                 220

Glu Thr Val Glu Gly Glu Lys Gln Gln Glu His Glu Val Gln Trp Leu
225                 230                 235                 240

Arg Glu His Leu Ala Met Leu Leu Ser Ser Val Leu Glu Ala Lys Pro
```

```
            245                 250                 255
Leu Leu Gly Asp Gln Ser His Ala Gly Ser Glu Leu Leu Gln Arg Cys
            260                 265                 270

Glu Ser Leu Glu Lys Lys Thr Ala Thr Phe Glu Asn Ile Val Cys Val
        275                 280                 285

Leu Asn Arg Glu Val Glu Arg Val Ala Met Thr Ala Glu Ala Cys Ser
    290                 295                 300

Arg Gln His Arg Leu Asp Gln Asp Lys Ile Glu Ala Leu Ser Ser Lys
305                 310                 315                 320

Val Gln Gln Leu Glu Arg Ser Ile Gly Leu Lys Asp Leu Ala Met Ala
                325                 330                 335

Asp Leu Glu Gln Lys Val Leu Glu Met Glu Ala Ser Thr Tyr Asp Gly
            340                 345                 350

Val Phe Ile Trp Lys Ile Ser Asp Phe Ala Arg Lys Arg Gln Glu Ala
        355                 360                 365

Val Ala Gly Arg Ile Pro Ala Ile Phe Ser Pro Ala Phe Tyr Thr Ser
    370                 375                 380

Arg Tyr Gly Tyr Lys Met Cys Leu Arg Ile Tyr Leu Asn Gly Asp Gly
385                 390                 395                 400

Thr Gly Arg Gly Thr His Leu Ser Leu Phe Phe Val Val Met Lys Gly
                405                 410                 415

Pro Asn Asp Ala Leu Leu Arg Trp Pro Phe Asn Gln Lys Val Thr Leu
            420                 425                 430

Met Leu Leu Asp Gln Asn Asn Arg Glu His Val Ile Asp Ala Phe Arg
        435                 440                 445

Pro Asp Val Thr Ser Ser Ser Phe Gln Arg Pro Val Asn Asp Met Asn
    450                 455                 460

Ile Ala Ser Gly Cys Pro Leu Phe Cys Pro Val Ser Lys Met Glu Ala
465                 470                 475                 480

Lys Asn Ser Tyr Val Arg Asp Asp Ala Ile Phe Ile Lys Ala Ile Val
                485                 490                 495

Asp Leu Thr Gly Leu
            500

<210> SEQ ID NO 53
<211> LENGTH: 2298
<212> TYPE: DNA
<213> ORGANISM: Homo sapiens

<400> SEQUENCE: 53
cttagttccg ggcgcgctgc gaccgttggg gctttgttcg cggggggtcac agctctcatg    60 gctgcagcta gcgtgacccc ccctggctcc ctggagttgc tacagcccgg cttctccaag   120
accctcctgg ggaccaagct ggaagccaag tacctgtgct ccgcctgcag aaacgtcctc   180
cgcaggccct tccaggcgca gtgtggccac cggtactgct ccttctgcct ggccagcatc   240
ctcagctctg ggcctcagaa ctgtgctgcc tgtgttcacg agggcatata tgaagaaggc   300
atttctattt tagaaagcag ttcggccttc ccagataatg ctgcccgcag ggaggtggag   360
agcctgccgg ccgtctgtcc cagtgatgga tgcacctgga aggggaccct gaaagaatac   420
gagagctgcc acgaaggccg ctgcccgctc atgctgaccg aatgtccgc gtgcaaaggc   480 ctggtccgcc ttggtgaaaa ggagcgccac ctggagcacg agtgcccgga gagaagcctg   540
agctgccgga ttgccgggc accctgctgc ggagcagacg tgaaggcgca ccacgaggtc   600
tgccccaagt tcccccttaac ttgtgacggc tgcggcaaga agaagatccc ccgggagaag   660
```

```
tttcaggacc acgtcaagac ttgtggcaag tgtcgagtcc cttgcagatt ccacgccatc    720
ggctgcctcg agacggtaga gggtgagaaa cagcaggagc acgaggtgca gtggctgcgg    780
gagcacctgg ccatgctact gagctcggtg ctggaggcaa agcccctctt gggagaccag    840
agccacgcgg ggtcagagct cctgcagagg tgcgagagcc tggagaagaa gacggccact    900
tttgagaaca ttgtctgcgt cctgaaccgg gaggtggaga gggtggccat gactgccgag    960
gcctgcagcc ggcagcaccg gctggaccaa gacaagattg aagccctgag tagcaaggtg   1020
cagcagctgg agaggagcat tggcctcaag gacctggcga tggctgactt ggagcagaag   1080
gtcttggaga tggaggcatc cacctacgat ggggtcttca tctggaagat ctcagacttc   1140
gccaggaagc gccaggaagc tgtggctggc cgcatacccg ccatcttctc cccagccttc   1200
tacaccagca ggtacggcta caagatgtgt ctgcgtatct acctgaacgg cgacggcacc   1260
gggcgaggaa cacacctgtc cctcttcttt gtggtgatga agggcccgaa tgacgccctg   1320
ctgcggtggc ccttcaacca gaaggtgacc ttaatgctgc tcgaccagaa taaccgggag   1380
cacgtgattg acgccttcag gcccgacgtg acttcatcct cttttcagag gccagtcaac   1440
gacatgaaca tcgcaagcgg ctgccccctc ttctgccccg tctccaagat ggaggcaaag   1500
aattcctacg tgcgggacga tgccatcttc atcaaggcca ttgtggacct gacagggctc   1560
taactgcccc ctactggtgt ctggggggttg ggggcagcca ggcacagccg gctcacggag   1620
gggccaccac gctgggccag ggtctcactg tacaagtggg caggggccgc gcttgggcgc   1680
ttgggagggt gtcggcctgc agccaagttc actgtcacgg gggaaggagc caccagccag   1740
tcctcagatt tcagagactg cggaggggct tggcagacgg tcttagccaa gggctgtggt   1800
ggcattggcc gagggtcttc gggtgcttcc cagcacaagc tgcccttgct gtcctgtgca   1860
gtgaagggag aggccctggg tgggggacac tcagagtggg agcacatccc agcagtgccc   1920
atgtagcagg agcacagtgg atggccttgt gtccctcggg catgacaggc agaaacgagg   1980
gctgctccag gagaagggcc tcctgctggc cagagcaagg aaggctgagc agcttggttc   2040 tccccctctgg cccctggaga gaagggagca ttcctagacc cctgggtgct tgtctgcaca   2100
gagctctggt ctgtgccacc ttggccaggc tggctgtggg agagggtctg gtcccacgcc   2160
gcctctgctc agaccactgt gtgggaggtg cacagcacag cctgcgggta aagtgtgaga   2220
gcttgccatc cagctcacga agacagagtt attaaaccat tcaaatctct gtggtcaaaa   2280
aaaaaaaaaa aaaaaaaa                                                 2298
```

<210> SEQ ID NO 54
<211> LENGTH: 147
<212> TYPE: PRT
<213> ORGANISM: Homo sapiens

<400> SEQUENCE: 54

```
Met Ala Leu Lys Arg Ile Asn Lys Glu Leu Ser Asp Leu Ala Arg Asp
1               5                   10                  15

Pro Pro Ala Gln Cys Ser Ala Gly Pro Val Gly Asp Asp Met Phe His
                20                  25                  30

Trp Gln Ala Thr Ile Met Gly Pro Asn Asp Ser Pro Tyr Gln Gly Gly
            35                  40                  45

Val Phe Phe Leu Thr Ile His Phe Pro Thr Asp Tyr Pro Phe Lys Pro
        50                  55                  60

Pro Lys Val Ala Phe Thr Thr Arg Ile Tyr His Pro Asn Ile Asn Ser
65                  70                  75                  80
```

| | | | | | | | | | | | | |
|---|---|---|---|---|---|---|---|---|---|---|---|---|
|Asn|Gly|Ser|Ile|Cys|Leu|Asp|Ile|Leu|Arg|Ser|Gln|Trp|Ser|Pro|Ala|
| | | | |85| | | | |90| | | | |95| |

Leu Thr Ile Ser Lys Val Leu Leu Ser Ile Cys Ser Leu Leu Cys Asp
            100                 105                 110

Pro Asn Pro Asp Asp Pro Leu Val Pro Glu Ile Ala Arg Ile Tyr Lys
            115                 120                 125

Thr Asp Arg Asp Lys Tyr Asn Arg Ile Ser Arg Glu Trp Thr Gln Lys
        130                 135                 140

Tyr Ala Met
145

<210> SEQ ID NO 55
<211> LENGTH: 3976
<212> TYPE: DNA
<213> ORGANISM: Homo sapiens

<400> SEQUENCE: 55

```
accaagtgag gaaactgggg gacgctgtgg ggaggggcgt ggggctggat cgcgcagcgg      60
ctgcttcctt taccttcctc ccatggtctc cttccggttc tcgatgcttc tctgagccta    120
agggtttccg ccactcgttc accctccccc cagctcatga tcctcctccc tccccgccc    180
tcctggtcca atctccgatc tgtttagtaa gaaggtgctg ttccgagaag aaggaaaagg    240
gcttgacacg tattcactcg gccccggacg tgggaagcaa gccgtctggc ttcggcctca    300
catcggtctt gtgctcggga cggcggcgtt ggcggactga tccgcggcgg tgaagaggcg    360
cctgtgtctg gcagagctgg tgtgagacga gacaatcctg ccccgccgcc gggataatca    420
agagttttgg ccggaccttt gagcatacac cgagagagtg aggagccaga cgacaagcac    480
acactatggc gctgaaacgg attaataagg aacttagtga tttggcccgt gaccctccag    540
cacaatgttc tgcaggtcca gttggggatg atatgtttca ttggcaagcc acaattatgg    600
gacctaatga cagcccatat caaggcggtg tattcttttt gacaattcat tttcctacag    660
actaccccctt caaaccacct aaggttgcat ttacaacaag aatttatcat ccaaatatta    720
acagtaatgg cagcatttgt ctcgatattc taagatcaca gtggtcgcct gctttaacaa    780
tttctaaagt tctttttatcc atttgttcac tgctatgtga tccaaaccca gatgaccccc    840
tagtgccaga gattgcacgg atctataaaa cagacagaga taagtacaac agaatatctc    900
gggaatggac tcagaagtat gccatgtgat gctaccttaa agtcagaata acctgcatta    960
tagctggaat aaactttaaa ttactgttcc tttttttgatt ttcttatccg gctgctcccc   1020
tatcagacct catcttttt aatttattt tttgtttacc tccctccatt cattcacatg    1080
ctcatctgag aagacttaag ttcttccagc tttggacaat aactgctttt agaaactgta   1140
aagtagttac aagagaacag ttgcccaaga ctcagaattt ttaaaaaaaa aaatggagca   1200
tgtgtattat gtggccaatg tcttcactct aacttggtta tgagactaaa accattcctc   1260
actgctctaa catgctgaag aaatcatctg aggggaggg agatggatgc tcagttgtca   1320
catcaaagga tacagcatta ttctagcagc atccattctt gtttaagcct tccactgtta   1380
gagatttgag gttacatgat atgctttatg ctcataactg atgtggctgg agaattggta   1440
ttgaatttat agcatcagca gaacagaaaa tgtgatgtat tttatgcatg tcaataaagg   1500
aatgacctgt tcttgttcta cagagaatgg aaattggaag tcaaacaccc tttgtattcc   1560
aaaatagggt ctcaaacatt ttgtaatttt catttaaatt gttaggaggc ttggagctat   1620
tagttaatct atcttccaat acactgttta atatagcact gaataaatga tgcaagttgt   1680
```

```
caatggatga gtgatcaact aatagctctg ctagtaattg atttatttt cttcaataaa    1740
gttgcataaa ccaatgagtt agctgcctgg attaatcagt atgggaaaca atcttttgta    1800
aatgcaaagc tgtttttgt atatactgtt gggatttgct tcattgtttg acatcaaatg    1860
atgatgtaaa gttcgaaaga gtgaatattt tgccatgttc agttaaagtg cacagtctgt    1920
tacaggttga cacattgctt gacctgattt atgcagaatt aataagctat ttggatagtg    1980
tagctttaat gtgctgcaca tgatactggc agccctagag ttcatagatg gacttttggg    2040
acccagcagt tttgaaatgt gtttatggag tttaagaaat ttatttccca ggtgcagccc    2100
ctgtctaact gaaatttctc ttcaccttgt acacttgaca gctgaaaaaa aacaacatgg    2160
gagtaataat gggtcaaaat ttgcaaaata aagtactgtt ttggtgtggg agttgtcatg    2220
aggctgtgtt gaagtgactt atctatgtgg gatattgagt atccattgaa atggatttgt    2280
tcagccattt acattaatga gcatttaaat gcaacagata tcatttcagg tgacttaaca    2340
tgaatgaata aaagtcaatg ctattggatt gttttttgtt tgacaagtgc tatctgtgcc    2400
actgatttaa cttctgtagt aacaagggca ttaccattct tcacctttcc taattctgat    2460
cccatagttt tacattttc ctgtttattt tgattttgtt cactgcttta tttcttaaag    2520
ttctagcaca tctgtgactc ctccacttcc acattttgc actgcttaca cttacgtgca    2580
atcttattcc ttgtctgcac acacatgtgg aaagctagaa ataaatgtta aaacttactt    2640
tttataaaca ttttaatatg tagtttggac atgatttatt gacttaaggt tcttctctaa    2700
actggaagtg aaatgcatgc cttctgaaga tgttctggct ttgttaattc tgtaatcatt    2760
tcattgggga aaaaaccagc tacgcagttt ttccaatgag tgaattttt catttgtgt    2820
tttgcttaaa acggctcctt cagggtagat gtcatactgc ataacttttt tggattcaaa    2880
ttatgaatga gaaattagtt aacattctgc tccacaaggt aagaaaaact gctcttttggc    2940
tctatttca aaattacttc tgagatgcat atagtctcaa ataacagct ttagtaggca    3000
tatcacttct tgaaagccaa acatgagtgt aagacacttt tatgaaacac ggtggatccc    3060
taactggctt tcaaattgac ctttatagcc ttagacaacc cttaggtatt tacgagatg    3120
acttcttga ttgtcataac aattagtgga tgtgtccagt tctctgtatc tttgacttga    3180
tgctttatac atcatttcat tgttgcttc taagggaata agccatagag gcttctccag    3240
gtttaaaaga acagtaaagt acctggaaaa ccaacatttt tgaatgtatg gacactggac    3300
atgagatatg tacaatgaaa tcttaaaaga atctaagaat ttgccctctt tgccccactc    3360
cacccagtaa tttgacatta ctagtgccat gtataggacc caactgagta ttagaatcag    3420
ttttgactat gtctttgtat ttcctaaatc ttttaatgca taaaccgaat tagggtccag    3480
ttggcctgtt aatggtaaat ttacatttta aatgactcag tttgttttc ctgggcgagt    3540
ttgcaatgtg ataatcagat tttttaaaac tgattaattt gctttcttgt gtgggtgtac    3600
tcacattta aagtatgaac cacagttaac tagtggtctc aggggtagtg aaacactcac    3660
tttttttttt gtttgttttt ttttgtttgt tgaaatggct tagttgaagt atacttaagg    3720
tactgatcat gctgtgttag taatttgggc ggggagggg gtaactcagc catgttttgt    3780
gttggcataa caaaactgtt aatgattgtt gattacactt ttaagtgaat ttgtcttta    3840
tgaggaaccc agtgcaagtc actaaatatt gtctaatagt gacatctgca taagacttgt    3900
aatagctgaa gttaattgag cttaaaggaa ttgttaccat taaagtctgt gtttaaagac    3960
aaaaaaaaaa aaaaaa                                                    3976
```

<210> SEQ ID NO 56
<211> LENGTH: 225
<212> TYPE: PRT
<213> ORGANISM: Homo sapiens

<400> SEQUENCE: 56

```
Pro Ala Ala Arg Arg Ser Arg Arg Leu Ser Pro Ala Phe Leu Gly
1               5                   10                  15

Ser Gly Ala Pro Val Ala Gly Pro Gly Phe Leu Gly Thr Pro Arg Ser
            20                  25                  30

Ser Arg Pro Gln Ser Leu Ser Pro Ala Leu Arg Lys Pro Arg Arg Gln
        35                  40                  45

Pro Gly Pro Ser Ala Gly Arg Met Thr Glu Leu Gln Ser Ala Leu Leu
    50                  55                  60

Leu Arg Arg Gln Leu Ala Glu Leu Asn Lys Asn Pro Val Glu Gly Phe
65                  70                  75                  80

Ser Ala Gly Leu Ile Asp Asp Asn Asp Leu Tyr Arg Trp Glu Val Leu
                85                  90                  95

Ile Ile Gly Pro Pro Asp Thr Leu Tyr Glu Gly Gly Val Phe Lys Ala
            100                 105                 110

His Leu Thr Phe Pro Lys Asp Tyr Pro Leu Arg Pro Pro Lys Met Lys
        115                 120                 125

Phe Ile Thr Glu Ile Trp His Pro Asn Val Asp Lys Asn Gly Asp Val
    130                 135                 140

Cys Ile Ser Ile Leu His Glu Pro Gly Glu Asp Lys Tyr Gly Tyr Glu
145                 150                 155                 160

Lys Pro Glu Glu Arg Trp Leu Pro Ile His Thr Val Glu Thr Ile Met
                165                 170                 175

Ile Ser Val Ile Ser Met Leu Ala Asp Pro Asn Gly Asp Ser Pro Ala
            180                 185                 190

Asn Val Asp Ala Ala Lys Glu Trp Arg Glu Asp Arg Asn Gly Glu Phe
        195                 200                 205

Lys Arg Lys Val Ala Arg Cys Val Arg Lys Ser Gln Glu Thr Ala Phe
    210                 215                 220

Glu
225
```

<210> SEQ ID NO 57
<211> LENGTH: 4208
<212> TYPE: DNA
<213> ORGANISM: Homo sapiens

<400> SEQUENCE: 57

| | |
|---|---|
| gtctcagcgc gcctgcgccg agcggccctg cgcgcagtga ggcagtggcg ggggaaggca | 60 |
| ccggtggggc cgacgggcgg gttgaaggag ggaagcgggc gagcgaagtc ccagtgcgcg | 120 |
| ccgcggcagc ccgggcaccc tcccttccg ggcgtgagtc gctgtgaaaa gagctgaagc | 180 |
| gagcggactc gcaccggcag cgaggcgccg ctcccgccgc ctcagcccgg ccttcctcgg | 240 |
| ctccggcgct ccgtcgcgg ggcccgggtt cctcggcaca cccgctcca gccgccccca | 300 |
| gagcctgtcc ccagcccttc ggaagccccg gcgccagccc gggccctcgg cagggaggat | 360 |
| gacggagctg cagtcggcac tgctactgcg aagacagctg gcagaactca acaaaaatcc | 420 |
| agtggaaggc ttttctgcag gtttaataga tgacaatgat ctctaccgat gggaagtcct | 480 |
| tattattggc cctccagata cactttatga aggtggtgtt tttaaggctc atcttacttt | 540 |

```
cccaaaagat tatcccctcc gacctcctaa aatgaaattc attacagaaa tctggcaccc    600
aaatgttgat aaaaatggtg atgtgtgcat ttctattctt catgagcctg gggaagataa    660
gtatggttat gaaaagccag aggaacgctg gctccctatc cacactgtgg aaaccatcat    720
gattagtgtc atttctatgc tggcagaccc taatggagac tcacctgcta atgttgatgc    780
tgcgaaagaa tggagggaag atagaaatgg agaatttaaa agaaagttg cccgctgtgt    840 aagaaaaagc caagagactg cttttgagtg acatttattt agcagctagt aacttcactt    900
atttcagggt ctccaattga gaaacatggc actgttttc ctgcactcta cccacctatt     960
gctggacttc tgttgtacaa gttggcaaac actggctgga actgggctgc aataaaacat   1020
gccagttatc aatgctgaca gagcctaac aagtgccaac ttacagatga ttacgcattt    1080
tgaattctaa tgaactgttt taaccttcag gaagaattgt aaagacctgt acatagcaca   1140
acatgatccg gataatatat atactgttca tgtacatcca caaatacacc ttgtaccaaa   1200
taatgctttc ttgtagtaga ataagaatcg tgtaaattct aagagatttt agcaggtttt   1260 cttcctatt cattgtttct tatcagttta aaaggattcc tttaagcatg tcagatgaaa    1320
agcaattagg attaaaagtt tccatttaat ttcccttaaa cccttgaggc ttcattaaac   1380
tcttttcact tactaaactt ttgtatcttc tttgttttga cacactcccc tttgctttta   1440
tctcttacct gccagaatgt tctcaaatga tttagttcaa atactgaaat acttaatgag   1500
caattacttg attttaatg atgacttcga aggagtcatc actaggtgct ttgtcctttt    1560
tgtattctag ttgcacccac ctcttggatt ggatatagca ataacattta ttggccgttg   1620
tgagctcttg atcccagtca ttaccctga gaactaaaaa tagatggttc ttaattcaac    1680
ttactgaaaa tttccccaaa caatagcaaa tctgactttt ccctcttcag ttgcctggta   1740
ttaaggttgg ataaatgaag catgcacagc tacaggcttt ctacttaact tctgggtttg   1800
ctattacaaa tcctatttac tctcataccc ttctccttag tccttcatat ttctctgcct   1860
ctattcttct atactgcaga ttttttctcac ctattgtaca aagaaattgc gatgtatatt  1920
ttcatgtaat ttgattttgg aattctgtca ccttatgtag tgagttcttc caaaatataa   1980
ttttttttca ataattgtca agttgttggc ttttattgta ttgaatgaag gctataatac   2040
tgagtgccag agaagtggtt taggaaaatc tcaggttgat tccttatgca aatgaacttt   2100
taatacttga aaatcacatg gccatggcag tatatgtatt tggttctatc tagattcttc   2160
tgtgaatcta aaagcattac agggtaaat gctttgctat ttgacgtata gatcccgtca    2220
ctaacaatag tacacttgga tgtgattaat gtttgagctt caatatattt catatcatac   2280
agttttctaa aacaacttca gcaaatggta aaatgaacat gtgcagtgtt aaaggcaggc   2340
cttaggctcc ttcatgtttg ttgtgaggtt gtgtgtggga agtagtcttt ggcttataag   2400
ggatagaact tgagacagta gcagatggga catggtgttt gattgtgaga atcagtgaga   2460
attcgtgcat ctctgctctg tggggtttgg agaaatgctt tggcagaaga gtgaaagaac   2520
tcctgccaag agcccagacc tctacaaacg ttgtatgtcc ttttttaagc agaaataaaa   2580
tggttgagga tgtagtcaca gtagagagtg attttttttct aagtccctgt cctctactct   2640
gaagcgttat aaaaacctgt aaacattata caaacccaca aaccttatag aaactcgtaa   2700
gtgtgttgtg actggaaatt gattcattag aacccagttt tctttaagaa ctttgtgact   2760
tggttttttt tttcctttc caaagactgt aaaaatagtt gccccaaaat gtcagcactg    2820
cacaccctcc agggacttgg aatacaatcc ttttactttt ttttttttt ttttaagaa     2880 actgggtctc tctgtcaccc aggctggagt gcagtggcaa cgatcatagc taactgcagc   2940
```

-continued

```
tttgacctcc tgggctcaag tgatcctcct gcctcagcct cctgagtagc taggactaca    3000
ggtgtatgcc accatgcctg gctaatacaa aaaaattctt ttaagagatg ggatccctcc    3060
cttttaaaat cagaacttgt tcacatggtg gttgcttgtg gcaaaacgga gttcaaattt    3120
tgctctccta ttgctataat tctgctagca atctgttgag gtgaaacttg gatctgact     3180
cttcagcaag cagcaaatga cctagtaact cagggacaac tatttttgaa ctttaagtgc    3240
cactttaatg cagttagttt gataaaacca tgtgggtttt ttttttaggg ctagctctac    3300
gggagtggaa gtgagagcca ggcatgagtg cgtctccaca tgcttttcca cctgccctga    3360
gtgtgttaca tactgaaaca ggcctacata gatgttacaa cttcccttcc tctgtcggag    3420
atgtcatctg tgcctttctc agtgttcatc tgataatgta aatttaaatg cctctacatt    3480
tgatacgaaa cccacattca ggtgacactg aacgaggtgg cttttgtccc accagtgcct    3540
catcagtgtg aggcgattcc tctctgcttt aggaaaatga ttttcccc taaacttgtg      3600
ccaaccatca acaacatctc catagatctt atggattgta gaactgttgg ctgtttccta    3660
aatttattcc aagttctcgt agaggcatat agatttcagt ctgtgcttgt atgggataga    3720
tgatctgagt ggctttctgg cctcttttt gagtttaaaa tccatatgag gttgacgtgt     3780
catactaagg taacatgttt gtgaggttat tccactagta ctgtgatcac gtgggtgtca    3840
gtatctttaa cggccttcat tcttggttgt gagattttat ttgatatgcc cactcaccct    3900
cgacgaatct gcccgctttg ggctgtggtg cctgtgtatc tttgcccgtc tggtctccag    3960
ttggtggaat taccttttt gtactgccac ttctcagcat cttttgaaatt tgacataatg    4020
ttgcttcatt tcagttttt tagttctgta atttgttgat tgtatttaac tatgtgagtt     4080
ctgttgtgat gtttactgta ttgtaaagca cctcattcat gtgatgagtg ctctataaat    4140
caataaatga tgacttagag gctgtatcac gagctatttt ggttttagga tgcaggtctc    4200
aaaagcaa                                                             4208
```

<210> SEQ ID NO 58
<211> LENGTH: 183
<212> TYPE: PRT
<213> ORGANISM: Homo sapiens

<400> SEQUENCE: 58

```
Met Ile Lys Leu Phe Ser Leu Lys Gln Gln Lys Glu Glu Ser
1               5                   10                  15

Ala Gly Gly Thr Lys Gly Ser Ser Lys Lys Ala Ser Ala Ala Gln Leu
            20                  25                  30

Arg Ile Gln Lys Asp Ile Asn Glu Leu Asn Leu Pro Lys Thr Cys Asp
        35                  40                  45

Ile Ser Phe Ser Asp Pro Asp Asp Leu Leu Asn Phe Lys Leu Val Ile
    50                  55                  60

Cys Pro Asp Glu Gly Phe Tyr Lys Ser Gly Lys Phe Val Phe Ser Phe
65                  70                  75                  80

Lys Val Gly Gln Gly Tyr Pro His Asp Pro Lys Val Lys Cys Glu
                85                  90                  95

Thr Met Val Tyr His Pro Asn Ile Asp Leu Glu Gly Asn Val Cys Leu
            100                 105                 110

Asn Ile Leu Arg Glu Asp Trp Lys Pro Val Leu Thr Ile Asn Ser Ile
        115                 120                 125

Ile Tyr Gly Leu Gln Tyr Leu Phe Leu Glu Pro Asn Pro Glu Asp Pro
    130                 135                 140
```

Leu Asn Lys Glu Ala Ala Glu Val Leu Gln Asn Asn Arg Arg Leu Phe
145                 150                 155                 160

Glu Gln Asn Val Gln Arg Ser Met Arg Gly Gly Tyr Ile Gly Ser Thr
            165                 170                 175

Tyr Phe Glu Arg Cys Leu Lys
            180

<210> SEQ ID NO 59
<211> LENGTH: 1540
<212> TYPE: DNA
<213> ORGANISM: Homo sapiens

<400> SEQUENCE: 59

| | | | | | |
|---|---|---|---|---|---|
| aggcgcacaa | cgcaggccgg | gcgggaagag | ccaaagcggg | caggcggcgg | aaatatccga | 60 |
| agcggcgggg | cgcccgaggc | cgttgccgac | ctccgcgcta | aagccgctgc | tgccgcggaa | 120 |
| gacgatcctc | cagtacccgc | ccgccgtcac | cgcagctgcc | gtgtcctcct | cccaccccta | 180 |
| gccgcacccc | ctcgcggagg | gatcagctga | gcggccaaac | ggcacggtcg | ggggagcccc | 240 |
| gagtccgcag | ctgcagcggg | gcctgagacc | agagttggcg | agggcaagga | aggagcggcc | 300 |
| ccgggcagtg | ggggcgggc | cgggcgggcc | cgagaacagc | cgaatttggc | cgagcgctgc | 360 |
| cgagcgagtc | cgaggcgctg | gccaggccg | gagccggact | acgggagccg | aggcgggccg | 420 |
| cgcggtgggc | gcggagagga | cggagcggc | gcggcaggcc | gggcgggtgg | cggcagcagc | 480 |
| ggaggaggcc | gcagctgcgg | gtccgaggag | cggaggcgac | gcgggcggcg | gcgggggggcc | 540 |
| gggtggccgg | ggtccgggc | cccgcggcgg | cggcagcggc | ggcggcggcg | gcaggatgat | 600 |
| caagctgttc | tcgctgaagc | agcagaagaa | ggaggaggag | tcggcgggcg | gcaccaaggg | 660 |
| cagcagcaag | aaggcgtcgg | cggcgcagct | gcggatccag | aaggacataa | acagctgaa | 720 |
| cctgcccaag | acgtgtgata | tcagcttctc | agatccagac | gacctcctca | acttcaagct | 780 |
| ggtcatctgt | cctgatgagg | gcttctacaa | gagtgggaag | tttgtgttca | gttttaaggt | 840 |
| gggccagggt | tacccgcatg | atccccccaa | ggtgaagtgt | gagacaatgg | tctatcaccc | 900 |
| caacattgac | ctcgagggca | acgtctgcct | caacatcctc | agagaggact | ggaagccagt | 960 |
| ccttacgata | aactccataa | tttatggcct | gcagtatctc | ttcttggagc | ccaaccccga | 1020 |
| ggacccactg | aacaaggagg | ccgcagaggt | cctgcagaac | aaccggcggc | tgtttgagca | 1080 |
| gaacgtgcag | cgctccatgc | ggggtggcta | catcggctcc | acctactttg | agcgctgcct | 1140 |
| gaaatagggt | tggcgcatac | ccaccccgc | cacggccaca | agccctggca | tcccctgcaa | 1200 |
| atatttattg | ggggccatgg | gtaggggttt | ggggggcggc | cggtggggga | atcccctgcc | 1260 |
| ttggccttgc | ctccccttcc | tgccacgtgc | ccctagttat | tttttttttt | ttaacaccat | 1320 |
| gtgattaagg | tcggcgctgc | ctcccccgac | ccactcagcg | atgggaaatg | aattggcttg | 1380 |
| tctagccccc | ctgctgggtg | cttgttcagc | ccccactctg | ggctgtggag | tgggtgggca | 1440 |
| acgggcctgg | gtagctgggc | ccaggcaacc | caccccctcca | cctctggagg | tcccaccagg | 1500 |
| ctattaaagg | ggaatgttac | tgcaaaaaaa | aaaaaaaaa | | | 1540 |

<210> SEQ ID NO 60
<211> LENGTH: 1706
<212> TYPE: PRT
<213> ORGANISM: Homo sapiens

<400> SEQUENCE: 60

Met Gly Val Pro Lys Phe Tyr Arg Trp Ile Ser Glu Arg Tyr Pro Cys

-continued

```
1               5                   10                  15
Leu Ser Glu Val Val Lys Glu His Gln Ile Pro Glu Phe Asp Asn Leu
                20                  25                  30
Tyr Leu Asp Met Asn Gly Ile Ile His Gln Cys Ser His Pro Asn Asp
                35                  40                  45
Asp Val His Phe Arg Ile Ser Asp Lys Ile Phe Thr Asp Ile
 50                  55                  60
Phe His Tyr Leu Glu Val Leu Phe Arg Ile Ile Lys Pro Arg Lys Val
 65                  70                  75                  80
Phe Phe Met Ala Val Asp Gly Val Ala Pro Arg Ala Lys Met Asn Gln
                85                  90                  95
Gln Arg Gly Arg Arg Phe Arg Ser Ala Lys Glu Ala Glu Asp Lys Ile
                100                 105                 110
Lys Lys Ala Ile Glu Lys Gly Glu Thr Leu Pro Thr Glu Ala Arg Phe
                115                 120                 125
Asp Ser Asn Cys Ile Thr Pro Gly Thr Glu Phe Met Ala Arg Leu His
130                 135                 140
Glu His Leu Lys Tyr Phe Val Asn Met Lys Ile Ser Thr Asp Lys Ser
145                 150                 155                 160
Trp Gln Gly Val Thr Ile Tyr Phe Ser Gly His Glu Thr Pro Gly Glu
                165                 170                 175
Gly Glu His Lys Ile Met Glu Phe Ile Arg Ser Glu Lys Ala Lys Pro
                180                 185                 190
Asp His Asp Pro Asn Thr Arg His Cys Leu Tyr Gly Leu Asp Ala Asp
                195                 200                 205
Leu Ile Met Leu Gly Leu Thr Ser His Glu Ala His Phe Ser Leu Leu
210                 215                 220
Arg Glu Glu Val Arg Phe Gly Gly Lys Lys Thr Gln Arg Val Cys Ala
225                 230                 235                 240
Pro Glu Glu Thr Thr Phe His Leu Leu His Leu Ser Leu Met Arg Glu
                245                 250                 255
Tyr Ile Asp Tyr Glu Phe Ser Val Leu Lys Glu Lys Ile Thr Phe Lys
                260                 265                 270
Tyr Asp Ile Glu Arg Ile Ile Asp Asp Trp Ile Leu Met Gly Phe Leu
                275                 280                 285
Val Gly Asn Asp Phe Ile Pro His Leu Pro His Leu His Ile Asn His
                290                 295                 300
Asp Ala Leu Pro Leu Leu Tyr Gly Thr Tyr Val Thr Ile Leu Pro Glu
305                 310                 315                 320
Leu Gly Gly Tyr Ile Asn Glu Ser Gly His Leu Asn Leu Pro Arg Phe
                325                 330                 335
Glu Lys Tyr Leu Val Lys Leu Ser Asp Phe Asp Arg Glu His Phe Ser
                340                 345                 350
Glu Val Phe Val Asp Leu Lys Trp Phe Glu Ser Lys Val Gly Asn Lys
                355                 360                 365
Tyr Leu Asn Glu Ala Ala Gly Val Ala Ala Glu Glu Ala Arg Asn Tyr
                370                 375                 380
Lys Glu Lys Lys Lys Leu Lys Gly Gln Glu Asn Ser Leu Cys Trp Thr
385                 390                 395                 400
Ala Leu Asp Lys Asn Glu Gly Glu Met Ile Thr Ser Lys Asp Asn Leu
                405                 410                 415
Glu Asp Glu Thr Glu Asp Asp Leu Phe Glu Thr Glu Phe Arg Gln
                420                 425                 430
```

```
Tyr Lys Arg Thr Tyr Tyr Met Thr Lys Met Gly Val Asp Val Ser
        435             440             445

Asp Asp Phe Leu Ala Asp Gln Ala Ala Cys Tyr Val Gln Ala Ile Gln
450             455             460

Trp Ile Leu His Tyr Tyr Tyr His Gly Val Gln Ser Trp Ser Trp Tyr
465             470             475             480

Tyr Pro Tyr His Tyr Ala Pro Phe Leu Ser Asp Ile His Asn Ile Ser
                485             490             495

Thr Leu Lys Ile His Phe Glu Leu Gly Lys Pro Phe Lys Pro Phe Glu
            500             505             510

Gln Leu Leu Ala Val Leu Pro Ala Ala Ser Lys Asn Leu Leu Pro Ala
            515             520             525

Cys Tyr Gln His Leu Met Thr Asn Glu Asp Ser Pro Ile Ile Glu Tyr
        530             535             540

Tyr Pro Pro Asp Phe Lys Thr Asp Leu Asn Gly Lys Gln Gln Glu Trp
545             550             555             560

Glu Ala Val Val Leu Ile Pro Phe Ile Asp Glu Lys Arg Leu Leu Glu
                565             570             575

Ala Met Glu Thr Cys Asn His Ser Leu Lys Lys Glu Arg Lys Arg
        580             585             590

Asn Gln His Ser Glu Cys Leu Met Cys Trp Tyr Asp Arg Asp Thr Glu
            595             600             605

Phe Ile Tyr Pro Ser Pro Trp Pro Glu Lys Phe Pro Ala Ile Glu Arg
        610             615             620

Cys Cys Thr Arg Tyr Lys Ile Ile Ser Leu Asp Ala Trp Arg Val Asp
625             630             635             640

Ile Asn Lys Asn Lys Ile Thr Arg Ile Asp Gln Lys Ala Leu Tyr Phe
            645             650             655

Cys Gly Phe Pro Thr Leu Lys His Ile Arg His Lys Phe Phe Leu Lys
                660             665             670

Lys Ser Gly Val Gln Val Phe Gln Gln Ser Ser Arg Gly Glu Asn Met
        675             680             685

Met Leu Glu Ile Leu Val Asp Ala Glu Ser Asp Glu Leu Thr Val Glu
        690             695             700

Asn Val Ala Ser Ser Val Leu Gly Lys Ser Val Phe Val Asn Trp Pro
705             710             715             720

His Leu Glu Glu Ala Arg Val Val Ala Val Ser Asp Gly Glu Thr Lys
                725             730             735

Phe Tyr Leu Glu Glu Pro Pro Gly Thr Gln Lys Leu Tyr Ser Gly Arg
            740             745             750

Thr Ala Pro Pro Ser Lys Val Val His Leu Gly Asp Lys Glu Gln Ser
            755             760             765

Asn Trp Ala Lys Glu Val Gln Gly Ile Ser Glu His Tyr Leu Arg Arg
770             775             780

Lys Gly Ile Ile Ile Asn Glu Thr Ser Ala Val Tyr Ala Gln Leu
785             790             795             800

Leu Thr Gly Arg Lys Tyr Gln Ile Asn Gln Asn Gly Glu Val Arg Leu
                805             810             815

Glu Lys Gln Trp Ser Lys Gln Val Val Pro Phe Val Tyr Gln Thr Ile
            820             825             830

Val Lys Asp Ile Arg Ala Phe Asp Ser Arg Phe Ser Asn Ile Lys Thr
835             840             845
```

```
Leu Asp Asp Leu Phe Pro Leu Arg Ser Met Val Phe Met Leu Gly Thr
850                 855                 860

Pro Tyr Tyr Gly Cys Thr Gly Glu Val Gln Asp Ser Gly Asp Val Ile
865                 870                 875                 880

Thr Glu Gly Arg Ile Arg Val Ile Phe Ser Ile Pro Cys Pro Asn
            885                 890                 895

Leu Asp Ala Leu Ile Gln Asn Gln His Lys Tyr Ser Ile Lys Tyr Asn
                900                 905                 910

Pro Gly Tyr Val Leu Ala Ser Arg Leu Gly Val Ser Gly Tyr Leu Val
            915                 920                 925

Ser Arg Phe Thr Gly Ser Ile Phe Ile Gly Arg Gly Ser Arg Arg Asn
930                 935                 940

Pro His Gly Asp His Lys Ala Asn Val Gly Leu Asn Leu Lys Phe Asn
945                 950                 955                 960

Lys Lys Asn Glu Glu Val Pro Gly Tyr Thr Lys Val Gly Ser Glu
                965                 970                 975

Trp Met Tyr Ser Ser Ala Ala Glu Gln Leu Leu Ala Glu Tyr Leu Glu
                980                 985                 990

Arg Ala Pro Glu Leu Phe Ser Tyr Ile Ala Lys Asn Ser Gln Glu Asp
            995                 1000                1005

Val Phe Tyr Glu Asp Asp Ile Trp Pro Gly Glu Asn Glu Asn Gly
    1010                1015                1020

Ala Glu Lys Val Gln Glu Ile Ile Thr Trp Leu Lys Gly His Pro
    1025                1030                1035

Val Ser Thr Leu Ser Arg Ser Ser Cys Asp Leu Gln Ile Leu Asp
    1040                1045                1050

Ala Ala Ile Val Glu Lys Ile Glu Glu Val Glu Lys Cys Lys
    1055                1060                1065

Gln Arg Lys Asn Asn Lys Lys Val Arg Val Thr Val Lys Pro His
    1070                1075                1080

Leu Leu Tyr Arg Pro Leu Glu Gln Gln His Gly Val Ile Pro Asp
    1085                1090                1095

Arg Asp Ala Glu Phe Cys Leu Phe Asp Arg Val Val Asn Val Arg
    1100                1105                1110

Glu Asn Phe Ser Val Pro Val Gly Leu Arg Gly Thr Ile Ile Gly
    1115                1120                1125

Ile Lys Gly Ala Asn Arg Glu Ala Asp Val Leu Phe Glu Val Leu
    1130                1135                1140

Phe Asp Glu Glu Phe Pro Gly Gly Leu Thr Ile Arg Cys Ser Pro
    1145                1150                1155

Gly Arg Gly Tyr Arg Leu Pro Thr Ser Ala Leu Val Asn Leu Ser
    1160                1165                1170

His Gly Ser Arg Ser Glu Thr Gly Asn Gln Lys Leu Thr Ala Ile
    1175                1180                1185

Val Lys Pro Gln Pro Ala Val His Gln His Ser Ser Ser Ser Ser
    1190                1195                1200

Val Ser Ser Gly His Leu Gly Ala Leu Asn His Ser Pro Gln Ser
    1205                1210                1215

Leu Phe Val Pro Thr Gln Val Pro Thr Lys Asp Asp Glu Phe
    1220                1225                1230

Cys Asn Ile Trp Gln Ser Leu Gln Gly Ser Gly Lys Met Gln Tyr
    1235                1240                1245

Phe Gln Pro Thr Ile Gln Glu Lys Gly Ala Val Leu Pro Gln Glu
```

-continued

```
             1250                1255                1260
Ile Ser Gln Val Asn Gln His His Lys Ser Gly Phe Asn Asp Asn
    1265                1270                1275
Ser Val Lys Tyr Gln Gln Arg Lys His Asp Pro His Arg Lys Phe
    1280                1285                1290
Lys Glu Glu Cys Lys Ser Pro Lys Ala Glu Cys Trp Ser Gln Lys
    1295                1300                1305
Met Ser Asn Lys Gln Pro Asn Ser Gly Ile Glu Asn Phe Leu Ala
    1310                1315                1320
Ser Leu Asn Ile Ser Lys Glu Asn Glu Val Gln Ser Ser His His
    1325                1330                1335
Gly Glu Pro Pro Ser Glu Glu His Leu Ser Pro Gln Ser Phe Ala
    1340                1345                1350
Met Gly Thr Arg Met Leu Lys Glu Ile Leu Lys Ile Asp Gly Ser
    1355                1360                1365
Asn Thr Val Asp His Lys Asn Glu Ile Lys Gln Ile Ala Asn Glu
    1370                1375                1380
Ile Pro Val Ser Ser Asn Arg Arg Asp Glu Tyr Gly Leu Pro Ser
    1385                1390                1395
Gln Pro Lys Gln Asn Lys Lys Leu Ala Ser Tyr Met Asn Lys Pro
    1400                1405                1410
His Ser Ala Asn Glu Tyr His Asn Val Gln Ser Met Asp Asn Met
    1415                1420                1425
Cys Trp Pro Ala Pro Ser Gln Ile Pro Pro Val Ser Thr Pro Val
    1430                1435                1440
Thr Glu Leu Ser Arg Ile Cys Ser Leu Val Gly Met Pro Gln Pro
    1445                1450                1455
Asp Phe Ser Phe Leu Arg Met Pro Gln Thr Met Thr Val Cys Gln
    1460                1465                1470
Val Lys Leu Ser Asn Gly Leu Leu Val His Gly Pro Gln Cys His
    1475                1480                1485
Ser Glu Asn Glu Ala Lys Glu Lys Ala Ala Leu Phe Ala Leu Gln
    1490                1495                1500
Gln Leu Gly Ser Leu Gly Met Asn Phe Pro Leu Pro Ser Gln Val
    1505                1510                1515
Phe Ala Asn Tyr Pro Ser Ala Val Pro Pro Gly Thr Ile Pro Pro
    1520                1525                1530
Ala Phe Pro Pro Pro Thr Gly Trp Asp His Tyr Gly Ser Asn Tyr
    1535                1540                1545
Ala Leu Gly Ala Ala Asn Ile Met Pro Ser Ser His Leu Phe
    1550                1555                1560
Gly Ser Met Pro Trp Gly Pro Ser Val Pro Val Pro Gly Lys Pro
    1565                1570                1575
Phe His His Thr Leu Tyr Ser Gly Thr Met Pro Met Ala Gly Gly
    1580                1585                1590
Ile Pro Gly Gly Val His Asn Gln Phe Ile Pro Leu Gln Val Thr
    1595                1600                1605
Lys Lys Arg Val Ala Asn Lys Lys Asn Phe Glu Asn Lys Glu Ala
    1610                1615                1620
Gln Ser Ser Gln Ala Thr Pro Val Gln Thr Ser Gln Pro Asp Ser
    1625                1630                1635
Ser Asn Ile Val Lys Val Ser Pro Arg Glu Ser Ser Ser Ala Ser
    1640                1645                1650
```

```
Leu Lys Ser Ser Pro Ile Ala Gln Pro Ala Ser Ser Phe Gln Val
    1655            1660                1665

Glu Thr Ala Ser Gln Gly His Ser Ile Ser His His Lys Ser Thr
    1670            1675                1680

Pro Ile Ser Ser Ser Arg Arg Lys Ser Arg Lys Leu Ala Val Asn
    1685            1690                1695

Phe Gly Val Ser Lys Pro Ser Glu
    1700            1705

<210> SEQ ID NO 61
<211> LENGTH: 10143
<212> TYPE: DNA
<213> ORGANISM: Homo sapiens

<400> SEQUENCE: 61
atggtcggcc gggcggtgtg ttgtcatccg cggagcgacg accggaggct gcggcggagc      60
cccggcgggg cgtttggttt cggtttggcc ctgactggga ttagtgttga cgatcgaaat     120
gggagtcccc aagttttaca gatggatctc agagcggtat ccctgtctca gcgaagtggt     180
gaaagagcat cagattcctg aatttgacaa cttgtacctg gatatgaatg gaattataca     240
tcagtgctcc catcctaatg atgatgatgt tcactttaga atttcagatg ataaaatctt     300
tactgatatt tttcactacc tggaggtgtt gtttcgcatt attaaaccca ggaaagtgtt     360
ctttatggct gtagatggtg tggctcctcg agcaaaaatg aaccagcagc gtgggaggcg     420
ttttaggtca gcaaaggagg cagaagacaa aattaaaaag gcaatagaga agggagaaac     480
tcttcctaca gaggccagat tgattccaa ctgtatcaca ccaggaactg aatttatggc     540
caggttacat gaacatctga gtattttgt aaatatgaaa atttccacag acaagtcatg     600
gcaaggagtt accatctact ctcaggcca tgagactcct ggagaaggag agcataaaat     660
catggaattt atcagatccg agaaagcaaa gccagatcat gatccaaaca ccagacactg     720
tctttatggt ttagatgctg acttgattat gcttggatta acaagtcatg aggcacattt     780
ttctctctta agagaagaag ttcgatttgg tggcaaaaaa acacaacggg tatgtgctcc     840
agaagaaact acatttcacc ttctacactt gtctttaatg agagagtata ttgactatga     900 gtttcagta ttaaaagaaa agatcacatt taaatatgat attgaaagga atagatgaa     960 ttggattttg atggggtttc ttgttggtaa tgattttatc cctcatctac ctcatttaca    1020
tattaatcat gatgcactgc ctcttcttta tggaacatat gttaccatcc tgccagaact    1080 tggggttat attaatgaaa gtgggcacct caacttacct cgatttgaga ataccttgt     1140 gaaactatca gattttgatc gggagcactt cagtgaagtt tttgtggacc taaaatggtt    1200
tgaaagcaaa gttggtaaca agtacctcaa tgaagcagca ggtgtcgcag cagaagaagc    1260
caggaactac aaggaaaaga aaagttaaa gggccaggaa aattctctgt gttggactgc    1320
tttagacaaa aatgaaggcg aaatgataac ttctaaggat aatttagaag atgagactga    1380
agatgatgac ctatttgaaa ctgagtttag acaatataaa gaacatatt acatgacgaa    1440 gatgggggtt gacgtagtat ctgatgactt tctggctgat caagctgcat gttatgttca    1500
ggcaatacag tggattttgc actattacta tcatggagtt cagtcctgga gctggtatta    1560
tccttatcat tatgcacctt cctgtctga tatacacaac atcagtacac tcaaaatcca    1620
ttttgaacta ggaaaacctt ttaagccatt tgaacagctt cttgctgtac ttccagcagc    1680
cagcaaaaat ttacttcctg catgctacca gcatttgatg accaatgaag actcaccaat    1740
```

```
tatagaatat tacccacctg attttaaaac tgacctaaat gggaaacaac aggaatggga   1800
agctgtggtg ttaatccctt ttattgatga gaagcgatta ttggaagcca tggagacatg   1860
taaccactcc ctcaaaaagg aagagaggaa aagaaaccaa catagtgagt gcctaatgtg   1920
ctggtatgat agagacacag agtttatcta tccttctcca tggccagaaa agttccctgc   1980
catagaacga tgttgtacaa ggtataaaat aatatcctta gatgcttggc gtgtagacat   2040
aaacaaaaac aaaataacca gaattgacca gaaagcatta tatttctgtg gatttcctac   2100
tctgaaacac atcagacaca aattttttt gaagaaaagt ggtgttcaag tattccagca   2160
aagcagtcgt ggagaaaaca tgatgttgga atcttagtg gatgcagaat cagatgaact   2220
taccgtagaa aatgtagctt catcagtgct tggaaaatct gtctttgtta attggcctca   2280
ccttgaggaa gctagagtcg tggctgtatc agatggagaa actaagtttt acttggaaga   2340
acctccagga acacagaagc tttattcagg aagaactgcc ccaccatcta aagtggttca   2400
tcttggagat aaagaacaat ctaactgggc aaaagaagta caaggaattt cagaacacta   2460
cctgagaaga aaggaataa taataaatga acatctgca gttgtgtatg ctcagttact   2520
cacaggtcgt aaatatcaaa taatcaaaa tggtgaagtt cgtctagaga aacagtggtc   2580
aaaacaagtt gttccttttg tttatcaaac tattgtcaag gacatccgag ctttcgactc   2640
ccgtttctcc aatatcaaaa cattggatga tttgtttcct ctgagaagta tggtctttat   2700
gctgggaact cccctattatg gctgcactgg agaagttcag gattcaggtg atgtgattac   2760
agaaggtagg attcgtgtga ttttcagcat tccatgtgaa cccaatcttg atgctttaat   2820
acagaaccag cataaatatt ctataaagta caacccagga tatgtgttgg ccagtcgcct   2880
tggagtgagt ggataccttg tttcaaggtt tacaggaagt attttttattg gaagaggatc   2940 taggagaaac cctcatggag accataaagc aaatgtgggt ttaaatctca aattcaacaa   3000
gaaaaatgag gaggtacctg gatatactaa gaaagttgga agtgaatgga tgtattcatc   3060
tgcagcagaa caacttctgg cagagtactt agagagagct ccagaactat ttagttatat   3120
agccaaaaat agccaagagg atgtgttcta tgaagatgac atttggcctg agaaaaatga   3180
gaatggtgct gaaaaagttc aagaaattat tacttggcta aaaggacatc ctgtcagtac   3240
tttatctcgt tcttcttgtg atttacaaat tctggatgca gctattgttg agaaaattga   3300
ggaagaagtc gaaagtgca agcaaagaaa gaataataag aaggtgcgag taacagtgaa   3360 acccccatttg ctatacagac ctttagaaca gcaacatgga gtcattcctg atcgggatgc   3420
agaattttgt cttttttgacc gtgttgtaaa tgtgagagaa aacttctcag ttccagttgg   3480
ccttcgaggc accatcatag gaataaaagg agctaataga gaagccgatg tactatttga   3540
agtattattt gatgaagaat ttcctggagg gttaacaata agatgctcac ctggtagagg   3600
ttatcgactg ccaacaagtg ccttggtgaa cctttctcat gggagtcgct ctgaaactgg   3660
aaatcagaag ttgacagcca tcgtaaaacc acaaccagct gtacatcaac atagctcaag   3720
ttcatcagtt tcctctgggc atttgggagc cctcaaccat tcccctcaat cacttttgt   3780 tcctactcaa gtacctacta aagatgatga tgaattctgc aacatttggc agtccttaca   3840
gggatctgga aagatgcaat actttcagcc aactatacaa gagaagggtg cagttctacc   3900
tcaagaaata agccaagtaa atcaacatca taaatctggc tttaatgaca acagtgttaa   3960
atatcagcaa agaaaacatg accctcacag aaaatttaaa gaagagtgta agagtcctaa   4020
agctgagtgt tggtcccaaa aaatgtccaa taagcagcct aactctggaa ttgagaactt   4080
tttagcatct ttgaatatct ccaaagaaaa tgaagtacag tcatctcatc atggggagcc   4140
```

```
tccaagtgaa gagcatttgt caccacagtc atttgccatg ggaacacgga tgcttaaaga    4200
aattctaaaa attgatggct ctaacactgt ggaccataag aatgaaatca aacagattgc    4260
taatgaaatc cctgtttcct ctaacagaag agatgaatat ggattaccct ctcagcctaa    4320
acaaataag aaattagcat cttatatgaa caagcctcac agtgctaatg agtaccataa     4380
tgttcagtct atggacaata tgtgttggcc tgcccccagc cagatccctc ctgtatccac    4440
accagtaact gaactttctc gaatttgttc ccttgttgga atgccacaac ctgatttctc    4500
ctttcttagg atgccacaga caatgaccgt tgccaagta aaattatcta atggcttact     4560
ggtacatggg ccacagtgcc actctgaaaa tgaagccaaa gagaaagctg cacttttttgc   4620
tttacaacag ttgggctcct taggcatgaa tttcccttttg ccttcacaag tatttgcaaa   4680
ttatccttca gctgtaccac ctggaaccat tcctccagcc tttcccccac ctactggctg    4740
ggatcactat ggaagcaact atgcattggg ggcagctaat ataatgcctt cgtcgtctca    4800
tctctttggc tcaatgccat ggggaccatc ggtgccagtt cctgggaagc ccttccatca    4860
tactttatat tctgggacca tgcccatggc tgggggaata ccaggggggtg tgcacaatca    4920
gtttataacct ctgcaggtta ctaaaaaaag ggttgcaaac aaaaagaact ttgagaataa   4980
ggaagcccag agttctcaag ccactccagt tcagactagc cagccagatt cttccaacat    5040
tgtcaaagta agtccacggg agagctcatc agcttctttg aagtcctctc cgattgctca    5100
acctgcatct tcttttcaag ttgaaactgc ctctcaaggc catagtatat ctcaccataa    5160
gtcaacacca atctcttctt caagaagaaa atcaagaaaa ctggctgtta attttggtgt    5220
ttctaaacct tctgagtaaa tttggctctt agaattaagt taatttcttc tctttccatc    5280
tacctttta taaatacata tctatgtctc ataaaaatta gaatgtacta ttttaaaata     5340
atatgtgtaa attgaaattt ttttcatttt taagttatca ggcacttttc atgctgttta    5400
aaagactgtg tatcaaattg tgcactttaa gtatgtgcag tttgttgtat gtcaattata    5460
cctcaataaa tctgtaataa aaaactaaat taaaccttgc attaaaataa tatcacagta    5520
tcagtggact aaacattaaa atgtaccact ctaatcattg gcctcatgat tgaagcatcc    5580
tgaactatga attagacatc agttagcaat aataagcatt ttttacacta tcattgagga    5640
ataattacat ggagcatgaa atttgggcct ccagtataac ttactgaatg tggattttat    5700
ttctcttttt aatgatgtaa gaaaattgtc aggagaatgg ctcttattta tgtgtgtttt    5760
aacttatgct tgttgcctc tgagggtctt tagacctgct gtgaaaggat cacatttgtt     5820
gtggtgctgc cagttttgct ttattctaaa ttttgtacca aagcaacttt agaataatca    5880
gaatatttca tctaactgct tagaactata aatagcattc taaatttgag taaatacaat    5940
tttttaggtt actcaagaac cagcattagt aatttctagt aaaattgttt caaaatctac    6000
agggtacaat gattacaaat taatcttcta acaaaataaa atatgaaata ttagtcatgt    6060
taattaataa actgtattat tttgtatagc tttttatttg cttacctgac attttatgag    6120
agcttcatag ttggtcggta tgtagtgctt cttgggactg aagaaattct aattgttgtt    6180
taagttccaa ggtgtgctac aatataggag gcacagtcat cagtttgtga catacattat    6240
ttactgccta tttcattctg attctatatt tttagcttta tgctgaactg ttcaatgatg    6300
ctgggattct ctcttttgcat gtcatatgtg aatgtgtggt tcaagctgta actgttgaaa    6360
ttattttaga atttatgacg atttctcagc agggcctatg tttatatata tatatatatt    6420
tattctttag tttttgtgat atgcttatat ttttaaggaa gtaagttata gcatactttt    6480
```

```
ttaaaagtag gaaccacaat ctttatatgg agcagcttgt tatatctgat tttcatgtaa    6540
ctcattggaa actctgccat gactcttaaa gtagtcttac ttgttttta  aaatgctggt    6600
attaaactaa atggactcct ttcactaact gctgatttca gagtttaaat gttagcagga    6660
tatttgtgta ttagcagtgc cttcagtata agagagaaat attcattatc tgtcatttat    6720
catagtcgta taagtttcca tgattttatt ttctgttatt ttcataagtt cagatgttta    6780
tcagttccca acattgtttc tttatctgta gtgggatctt gagtaatgag gctcaagtaa    6840
atcctcaatg tgtataatta ttgcctcata aactctctct ttgttttaa  aggaaacatc    6900
tattatggta atacaaagaa aagttaaatt gtgacagtaa tgttatatta acctcttcct    6960
actttaaagt gtgaaatgtt tcacctcagc tgtacaaact ccagcattga aatttgcct     7020
cactcattac tcctgtgtga cagttatata aatagcatgc agctcacatc tgttttagag    7080
catagaagaa gcggcacctg ccatcttctg aaaactccaa agggaaattt cagtagacat    7140
agtgcactaa acccataagg atacttgacc aatatttgag cacagcaagc tgacagttct    7200
atacagatag gcagtgaaag agttttattt tccagccagg cgcagtggct caaatcccag    7260
cacttcggga ggctaaggca ggcggatcac ttgaggtccg gagttccaga caagcctggc    7320
caacatgatg aagccctgtc tctactaaaa atacaaaaat tagccgggcg tgatggcaca    7380
tgcctttagt cccagctact cgggaggctg aggcatgaga atcatttgaa cccgcgaggc    7440
agagtctgca gtgagccgag attgcaccac tgcactccag cctggagagc agagcaagac    7500
tctgtctcaa aaaaagaaa  aaagttttat tatccttact tttttttaa  cattattatt    7560
ctaaaggtca aaactgagaa gagattaaga taggagagag ctccataatg gctggatagt    7620
ggtcaggcat tctctattct tttcccctg  tagacccatt ctaaatgtgg gcctgaggtc    7680
aatgggagat gtgccctccc tatggaggat gtaagaagca gaggccattt ctgccccatg    7740
ttgaggaaac aatctgttga tagacctgga atttagagta tatctgaaaa gcagttggac    7800
ttcaagaaat ttaaaattct ctcttttgaga tggggtggac taagaccacc cccaaagttt    7860
aaaaatatgc tcattcaact tgaatcttct gaggactttt tgtgaaaatg gtggactgtt    7920
tagggcatag gacagattcc ccaaattgct ttatgcttcc acataactag agcacttcaa    7980
tctatttaag cctttgtctc ctaactgaaa cattatttct aaatatttct attcaataag    8040
tttttttctt tttgagcaac ttaagtgaat tttgaagatt gctccttcca gtctcgttcc    8100
ttttcacatt ttcctgcatt acctaataat tacctcagcg ttagaatttg aatgtattaa    8160
ttgatttaaa catcatgtag actaaagtct taaacatcta agactcagtt gtagttgcag    8220
aaaaaaatta aagtcacctc tactgaacct tggtttcaat ttaagatttt tcttgctttt    8280
caaagggta  actaataaag attgaagggt ttttttcccg attggtggag gaatgaagaa    8340
ctattgatgc aagttttttt attgtttctt tctatgatca ggtacctgct ttcattttag    8400
actgctactt ccaaactaag ctagattctt ggttttaatg agaggaggca gagagaggga    8460
ggcagatgga agaagaaaaa cagttaaata agacatacccc agtcactgca tttttggact    8520
ataccgtatc tttctagcac aaggaaatag ataaactgta aggtcttttt tactcacttt    8580
ttatttatgt gttctatttg tgttagtcat aactgtttat agtggttgtc taattttttac   8640
ttttattata tgagatagag ctgtgcagat cttcactcaa gttagttctg tcacgcttct    8700
tcccattatt tagagcacag ttttttaaag caactgtaca atttctcagc cttatgagct    8760
tgctgtattt cttggtatca tgttgcttcc aaatttgtt  tttactgtag aagacaatta    8820
atttattgta gagaagtggc tgtgaaagtc gttctctgtc tttaaaaatc aattgcagaa    8880
```

```
gttcatttgt cattttcta gagataaatt atagtactca aactggcagt gctcagtata    8940
tacattttgt aagctttgtc agtgaaacca tcagttttgc aggagcttcc tttcctagtc   9000
aagataaagc ttaaaattcc agaaattaat gtcgttcgga ctgactttat tcatatttcc   9060
atcaaacttc tccaatacag taagagatag tgttgaacca gcatcaagtc tccagaaaca   9120
tggcagagca gacaggccgt taagtttcac agacatcata gatcctttc ttaaagaaga    9180 aaaacatgta taaatagtt ttagtagtcc aaaatgtcaa ctatctgtag ctgcttttgt    9240
gtgtgtgtca gtgaacaaat aataatgcct tgctcaatca atgcattcag ccatctcaag   9300
tgcaatttgt gaaggagact atggtttcca aaagatacat tttttttacaa agttaaacct  9360 gtaaaaagtc tttttttttt tccctccagc cgtacaccaa ctgcacttgg ttgtttcagc   9420
agttggtata ctattaaatt gtccaggcca aataggtttc tgtagctgtt ttagtaattt   9480
gaagccaaat tctcatgctg tttctcatta aaagaatga gaatttggtc catagttagc    9540
tttaagttct ctcttccttt ctttccctta cagttaaggg tttggtgggg gatggggagg   9600
ttgttttcgt ttttggatt tttttgtctt ttggctttaa gtatcatatt ttctttttgcc   9660 tgtatccaac tgcttctttg agtattttca tctagtttaa tgtgagtaat agatgctgtg   9720
ctgtcattga agtgttcaac attttgttca tttaaacaaa agtgtaattc atacatatat   9780
agatacatat cttaattgat ttctcaacta tttataagt aactggaatt tttcattaga    9840
tcttatacag agaagtattt tattaaaat tcaaaaggga agactttat gtgctcattt      9900 tgtaattttt gattttaaat atctttcact tgtctgccaa ttaaagtgtt ttaaacttgc   9960
attggaatgg actccgaatg tattttttgtg gtgttacgtt atccgtagat ttctagcatg 10020
aagttagcct cacgatgctg tgcaaaggat tttaaaatat gagagtcact gaaagagttt  10080
aaacatctgt tcatgttaaa tgctctatgg attttaatta aagacttgag aatgatttta  10140
taa                                                                10143
```